United States Patent
Aharoni et al.

(10) Patent No.: US 8,338,663 B2
(45) Date of Patent: Dec. 25, 2012

(54) ISOPRENOID SYNTHASES

(75) Inventors: Asaph Aharoni, Tel-Aviv (IL); Maarten Anthonie Jongsma, Wageningen (NL); Henricus Adrianus Verhoeven, Schijndel (NL); Hendrik Jan Bouwmeester, Renkum (NL)

(73) Assignee: Monsanto Invest N.V., Amstelveen (NL)

( * ) Notice: Subject to any disclaimer, the term of this patent is extended or adjusted under 35 U.S.C. 154(b) by 550 days.

(21) Appl. No.: 12/272,329

(22) Filed: Nov. 17, 2008

(65) Prior Publication Data

US 2010/0144893 A1 Jun. 10, 2010

Related U.S. Application Data

(62) Division of application No. 10/635,223, filed as application No. PCT/NL02/00089 on Feb. 12, 2002, now Pat. No. 7,453,024.

(30) Foreign Application Priority Data

Feb. 12, 2001 (EP) .................................... 01200488

(51) Int. Cl.
*A01H 5/00* (2006.01)
*C12N 15/29* (2006.01)
*C12N 15/52* (2006.01)
*C12N 15/82* (2006.01)

(52) U.S. Cl. ....................................... 800/279; 800/298

(58) Field of Classification Search ........... 800/278–320
See application file for complete search history.

(56) References Cited

U.S. PATENT DOCUMENTS

| 4,041,185 | A | | 8/1977 | Parliment ...................... 426/534 |
| 5,196,200 | A | | 3/1993 | Wilson et al. .................. 424/411 |
| 5,849,526 | A | * | 12/1998 | Pichersky .................... 435/69.1 |
| 6,190,895 | B1 | | 2/2001 | Croteau et al. |

FOREIGN PATENT DOCUMENTS

| EP | 0420630 | 4/1991 |
| WO | 97/15584 | 5/1997 |
| WO | 99/37139 | 7/1999 |
| WO | 00/22150 A3 | 4/2000 |

OTHER PUBLICATIONS

Pattnaik, S. et al. Microbios 1997 vol. 89; pp. 39-46.*
Donath, J., Phytochemistry 1995; vol. 39, No. 4, pp. 785-790.*

(Continued)

*Primary Examiner* — Russell Kallis
(74) *Attorney, Agent, or Firm* — Ladas & Parry LLP

(57) ABSTRACT

The invention relates to the field of genetic engineering of flavor, fragrance and biocontrol agent development. More specifically it relates to a process for production of natural flavors, fragrances or bio-control agents by the control of one or more genes implicated in that process. The invention provides an isolated or recombinant nucleic acid or functional fragment thereof encoding a proteinaceous molecule essentially capable of flavor, fragrance and/or bio-control agent synthesis when provided with a suitable substrate under appropriate reaction conditions. The invention further provides a nucleic acid or functional fragment thereof encoding a proteinaceous molecule essentially capable of synthesizing at least a monoterpene alcohol linalool when contacted with geranyl diphosphate (GPP) and/or at least a sesquiterpene alcohol nerolidol when contacted with farnesyl diphosphate (FPP) under appropriate reaction conditions.

2 Claims, 34 Drawing Sheets

OTHER PUBLICATIONS

Bohlmann Jorg, et al. XP002171015 "Terpenoid-Based Defenses in Conifers: cDNA Cloning, Characterization, and Functional Expression of Wound-Inducible (El-Alpha-Bisabolene Synthase From Grand Fir (*Abies grandis*)" Proceedings of the National Academy of Sciences of the United States vol. 95, No. 12, Jun. 9, 1998 pp. 6756-6761 ISSN: 0027-8424.

Marty I: XP002171017 "Fragaria Vesca Partial mRNA for Putative Sesquiterpene Cyclase" and Nam Young-Woo, et al. XP001007177 "Isolation and Characterization of mRNAs Differentially Expressed During Ripening of Wild Strawberry (*Fragaria vesca* L.) Fruits" Plant Molecular Biology, vol. 39 No. 3 Feb. 1999 pp. 629-636.

Bohlmann Jorg, et al. XP002171016 "Plant Terpenoid Synthases: Molecular Biology and Phylogenetic Analysis" Proceedings of the National Academy of Sciences of the United States; vol. 95, No. 8 Apr. 14, 1998 pp. 4126-4133 ISSN: 0027-8424.

Tittiger, C., et al. Insect Biochemistry and Molecular Biology (2000) vol. 30, pp. 1203-1211.

Hohn, T, et al. Plant Physiology (1991) vol. 97, pp. 460-462.

* cited by examiner

SOSV → [Wild (1), Wild (2), Cultivated (1), Cultivated (2)]

Fig. 16

| CONSTRUCT (C#) | 5'REGION | LOCALIZATION |
|---|---|---|
| H64NORL | | |
| C1- | M2 MID GFP | Cytosol |
| C2- | M1 SC M2 MID GFP | Cytosol |
| H64TAR4 | | |
| C3- | M1 SC M2 MID GFP | Mitochondria + Plastids |
| C4- | M1 M2 GFP | Cytosol |
| C5- | M2 MID GFP | Cytosol |
| CITRUS- LIMONENE SYNTHASE | | |
| C6- | M 240 Bp GFP | Plastids |
| H64VES | | |
| C7- | M1 M2 MID GFP | Plastids |
| C8- | M1 M2 GFP | Cytosol |
| C9- | M2 MID GFP | Cytosol |
| HYBRID | | |
| C10- | M1 M2 MID GFP<br>←H64VES→←H64NORL→ | Plastids |

ISOPRENOID SYNTHASES

This application is a divisional of application Ser. No. 10/635,223 filed on Aug. 5, 2003, (now U.S. Pat. No. 7,453,024 issued Nov. 18, 2008) which is a 371 of International Application No.: NL2002/000089 filed on Feb. 12, 2002, which designated the U.S., claims the benefit thereof and incorporates the same by reference.

The invention relates to the field of genetic engineering of flavor, fragrance or bio-control agent development. More specifically it relates to a process for production of bioactive isoprenoid compounds by the control or modulation of one or more genes implicated in that process.

Isoprenoids are the largest and most diverse group of plant secondary compounds. At least 20,000 isoprenoids have been described and without doubt many more will be discovered in the future. By definition isoprenoids are made up of so called isoprene (C5) units. This can be recognized in the number of C-atoms present in the isoprenoids which usually can be divided by five (C5, C10, C15, C20, C25, C30 and C40), although also irregular isoprenoids and polyterpenes have been reported. Important members of the isoprenoids a.o. are the carotenoids, gibberellins, abscisic acid, some cytokinins, sterols, and the terpenoids, consisting of a.o. monoterpenes, sesquiterpenes, diterpenes, triterpenes, tetraterpenes and polyterpenes (rubbers), etc. Most of these compounds occur free but they can also be modified, or derivatized as esters and glycosides, or attached to proteins. Among the isoprenoids there are many compounds with biological activity, for example as plant growth regulator (gibberellins, abscisic acid, cytokinins), and in the interaction between plants and other organisms (for example as anti-microbials, infochemicals and as the isoprenoid germination stimulants that are exuded by the roots of some plant species and induce the germination of parasitic weed seeds).

Mono- and sesquiterpenes, the C10 and C15 branch of the isoprenoid family, were investigated for their economically interesting value as flavor and fragrance compounds in foods and cosmetics and their anti-carcinogenic and antimicrobial properties. Mono- and sesquiterpenes have also been shown to be of ecological significance, for instance in the interaction between plants, plants and insects/spider mites and plants and microorganisms. Therefore, plants producing mono- and sesquiterpenes have been investigated by many authors and this has resulted in a better understanding of the biochemical pathways leading to the formation of these compounds and their derivatives.

Linalool is an acyclic monoterpene alcohol that has a peculiar creamy floral, sweet taste. In *Clarkia breweri* (Onagraceae) linalool, amongst other compounds, is responsible for the attraction of pollinating moths. Linalool is one of the volatile compounds released as a semiochemical after herbivore attack in some plants and as such may attract predators of the herbivores. The sweet taste of linalool makes it suitable to enhance the blueberry flavor of foodstuffs especially of beverages (U.S. Pat. No. 4,041,185). Furthermore, linalool is known to have a broad-spectrum antimicrobial activity. It is reported by Pattnaik et al. (*Microbios* 89: 39-46, 1997) to display antibacterial activity against Gram-positive and Gram-negative bacteria as well as antifungal activity against yeast-like and filamentous fungi.

Nerolidol, the sesquiterpene analogue of the monoterpenoid linalool, is a component of many essential oils and flower headspaces (Bauer et al., Common Fragrance and Flavor Materials. Preparations, Properties and Uses, VCH Verlaggesellschaft, Weinheim, Germany, 1990; Knudsen et al., Phytochemistry 33: 253-280, 1993). Nerolidol has been reported to have anti-microbial activity. EP 0420630A2 describes the use of nerolidol in an antiplaque oral composition. Bouwmeester et al (Plant Physiol. 121: 173-180, 1999) for cucumber and Lima bean and Degenhardt and Gershenzon (Planta 210: 815-822, 2000) for maize showed that nerolidol biosynthesis is induced upon respectively spider mite or *Spodoptera* feeding. The enzyme responsible for the formation of nerolidol catalyses the regulatory step in the formation of the important signalling molecule 4,8-dimethyl-1,3(E),7-nonatriene. Both nerolidol and 4,8-dimethyl-1,3(E),7-nonatriene are important constituents of the volatile blend produced in maize upon feeding of beet army worm larvae (Turlings et al., Science 250: 1251-1253, 1990; Degenhardt and Gershenzon, 2000) and in gerbera in response to feeding of spider mites (Krips et al., J. Chem Ecol 1999). Also in the headspace of several flowers, nerolidol is an important constituent often together with 4,8-dimethyl-1,3(E),7-nonatriene (Kaiser, In: Perfumes: Art, Science and Technology, Elsevier Science Publishers, Essex, UK, pp 213-250, 1991; Knudsen et al., 1993). Nerolidol has also been reported as a constituent of pheromone mixtures of a number of insects and spider mites (Aldrich-J R; Lusby-W R; Kochansky-J P, Experientia. 1986, 42: 5, 583-585; Regev-S; Cone-W W. Environmental-Entomology 1976, 5: 1, 133-138) and has been described as being miticidal if formulated in a controlled release substrate (U.S. Pat. No. 4,775,534). Also, nerolidol has been reported to be an extremely effective repellent of mosquitoes.

From a number of plants, several cDNAs encoding enzymes involved in the biosynthesis of monoterpenoids have been isolated such as S-linalool and R-linalool synthases (Cseke et al., Mol. Biol. Evol. 15: 1491-1498, 1998; Jia et al., Arch Biochem Biophys 372: 143-149, 1999), (−)-4S limonene synthase (Colby et al., J Biol Chem 268: 23016-23024, 1993; Bohlmann et al., J Biol Chem 272: 21784-21792, 1997).

WO 9715584 describes the use of S-linalool synthase, an acyclic monoterpene synthase, in the genetic engineering of scent production. The use of the limonene (monoterpene) cyclase in the control of corn rootworm, by inserting a nucleotide sequence coding for limonene cyclase into the plants is described in WO 9637102. In WO 0022150 the use of a limonene synthase, linalool synthase and combination of limonene and carveol synthase (actually called limonene hydroxylase) for the control of insects is described. However, terpenoid products were only formed in combination with a GPP synthase.

The enzymes involved in the production of precursors for the synthesis of the primary monoterpene skeletons are all active in the plastids, since all cloned genes of this pathway until now have plastid targeting signals. Recently, for one enzyme, (4S)-limonene synthase, localisation in the leucoplasts of the secretory cells in *Mentha spicata* has been demonstrated with immunogold labeling. The plastid targeting signals indicate that isoprenoid precursors for monoterpene metabolism are formed in the plastids, although some partitioning of these precursors between the different cellular compartments in plants has been shown to occur. Unlike other monoterpene (and diterpene) cyclases that bear cleavable transit peptides of 50-70 amino acids, the S-linalool synthase cDNA isolated by Pichersky and co-workers encodes a protein with an apparent cleavable peptide of maximally only eight amino acids long. Nevertheless, typical plastid targeting signal characteristics were found in the first 60 amino acids of the cDNA, supporting that the linalool synthase enzyme, as expected for a monoterpene synthase, is indeed targeted to the plastids. Two independent cDNA clones encoding 5-epi-aristolochene synthase (EAS) from tobacco have been isolated and characterised by Facchini and Chappell (*Proc Natl Acad. Sci. USA*, 89:11088-11092, 1992). Back and Chappell described the cloning and bacterial expression of vetispiradiene synthase found in *Hyoscyamus muticus* (*J. Biol. Chem.*, 270(13):7375-7381, 1995). The cDNA encoding amorpha-4,11-diene synthase, an intermediate in the biosynthesis of the anti-malarial artemisinin, was isolated and characterised by Mercke et al. (*Arch. Biochem. Biophys.*, 381(1):173-180, 2000). Sesquiterpene biosynthesis is compartmentalised to the cytosol, and none of the sofar isolated sesquiterpene synthases bear any targeting signal. Farnesyl diphosphate (FPP) is present in every living organism and it is the precursor of a large number of primary and secondary metabolites. It has been established that FPP is the precursor of all sesquiterpenoids. There are several thousands of different sesquiterpenoid compounds identified in many living organisms. Examples are the bitter sesquiterpene lactones such as sonchuside A and C, and cichorilide A in chicory (De Kraker et al., *Plant Physiol* 117: 1381-1392, 1998). The first committed step in the biosynthesis of these compounds is catalysed by a germacrene A synthase which was cloned from chicory (PCT/EP 0002130). Other examples are the cloning of three sesquiterpene synthases ((E)-α-bisabolene, δ-selinene, and γ-humulene synthase) from grand fir (WO 99/37139; Bohlmann et al., *proc Natl Acad Sci, USA*, 95: 6756-6761), and a germacrene C synthase from tomato (Colby et al., *Proc Natl Acad Sci, USA*, 95: 2216-2221). The use of the amorpha-4,11-diene synthase in the engineering of artemisinin biosynthesis is described in EP 0 982 404 A1. However, the putative sesquiterpene synthase responsible for the formation of the biologically important nerolidol has never been cloned.

The use of recombinant DNA technology to introduce resistance based on secondary metabolites in plants has had only limited success. For example, Hain et al (Nature 361, 153-156, 1993) succeeded in introducing fungal resistance in a number of plant species by the introduction of the resveratrol synthase cDNA, that they isolated from grape. Although there are reports on the anti-microbial and insecticidal effects of specific terpenoids, resistance against fungi as a result of the expression of a terpene synthase in plants has not been reported sofar.

The invention provides an isolated or recombinant nucleic acid or functional fragment thereof encoding a proteinaceous molecule essentially capable of isoprenoid bioactive compound (herein also identified as flavor, fragrance and/or bio-control agent) synthesis when provided with a suitable substrate under appropriate reaction conditions. Presently, the main way to produce plant flavor (for ease of reference with flavor also fragrances are generally meant) compounds is by the synthetic route. Synthetic organic chemicals constitute more than 80-90% (by weight and value) of the raw materials used in flavor and fragrance formulations. However, problems often exist concerning production. Extraction from intact plants and conventional fermentation are currently providing alternative routes for the commercial production of flavor/aroma chemicals. However, the demand for natural flavors by the consumer has been steadily increasing, and demand often outstrips supply. In many cases sought after flavor compounds can not easily be isolated. An understanding of the precursors and characterization of genes encoding enzymes involved in diverse pathways leading to the formation of flavors is essential for the production of natural flavors. The nucleic acids and their encoded proteinaceous molecules of the present invention are involved in the biosynthetic pathway for terpenoid production and as such they provide new means and methods for the in-vivo and in-vitro biotechnological production of bio-flavours, natural flavor chemicals and bio-control compounds.

In addition the nucleic acids and their encoded proteinaceous molecules of the present invention and products synthesized are essentially capable acting as potent bio-control agents alone or in combination.

Fungi and bacteria have become an increasing threat to humans. Opportunistic microbial infections have increased dramatically in the last two decades and have become a significant cause of morbidity and mortality. Over recent years, the frequency of life-threatening fungal infections has increased dramatically, making fungal infections now responsible for nearly 40% of all deaths from hospital-acquired infections. Increased numbers of patients with an impaired immune system (such as due to ageing, severe burns, AIDS, chemotherapy against cancer, or immunosuppressive therapy for organ transplants), together with a growing list of potential pathogenic fungi and bacteria are recognized as factors contributing to this rising public health-hazard. There is only a limited set of bio-control compounds available, and resistance to existing bio-control drugs is becoming a problem of increasing concern. Also clinically used antimycotics may show harmful side effects.

Fungi are responsible for substantial economic losses due to food spoilage caused by highly dangerous toxins (mycotoxins). To add to this problem food additives to prevent fungal contamination may also be potentially carcinogenic. Additionally plant pathogenic micro-organisms cause huge crop losses and this has promoted the extensive use of pesticides all over the world. Some pesticides have deleterious effects on other organisms than the pests they are intended to control, on water quality, and on the environment in general. Current antimicrobials are often not specific enough, and several microbial species exhibit increasing resistance to these pesticides. There is a need to develop new and more advanced bio-control agents with novel modes of action and broad spectra directed against plant and animal pathogens. The nucleic acids and their encoded proteinaceous molecules of the present invention involved in terpenoid biosynthesis, as such provide a new method for the in-vivo and in-vitro biotechnological production of natural and more specific antimicrobials or bio-control agents, for example antifungals.

The nucleic acid as used herein refers to an oligonucleotide, nucleotide or polynucleotide, and fragments or portions thereof, and to DNA or RNA of genomic or synthetic origin which may be single- or double-stranded, and represents the sense or antisense strand. A proteinaceous molecule as used herein refers to a molecule comprising peptide or protein. Natural flavor synthesis as used herein refers to flavor and fragrance compounds synthesized that are identical to their natural counterparts. Natural counterpart as used herein refers to products that are obtained directly from plants and sometimes from animal sources by physical procedures. Synthetic flavors refers to nature identical compounds that are produced synthetically but are chemically identical to their natural counterpart. Nature-identical compounds are with few exceptions the only synthetic compounds used in flavors in addition to natural products. Artificial flavor synthesis refers to flavor compounds that have not been identified in plant or animal products for human consumption. The nucleic acids of the present invention pave the way for the production of artificial flavors using techniques known in the art such as for example combinatorial biosynthesis, metabolic pathway engineering, gene shuffling, directed evolution of proteins etc. Bio-control synthesis as used herein refers to bio-control compounds synthesized which can act as an bio-control agent. A bio-control agent as used herein refers to a compound, which can at least in part suppress or inhibit or restrict the growth of a pathogenic organism (e.g. fungi, bacteria etc.), that is a compound that has anti-pathogenic activity.

The invention further provides for a nucleic acid or functional fragment thereof wherein said nucleic acid encodes a proteinaceous molecule essentially capable of synthesizing at least a monoterpene alcohol linalool when contacted with geranyl diphosphate (GPP) and/or at least a sesquiterpene alcohol nerolidol when contacted with farnesyl diphosphate (FPP) under appropriate reaction conditions. The definition 'functional fragment thereof' means that a particular subject sequence may vary from the reference sequence by one or more substitutions, deletions, or additions, the net effect of which does not result in an adverse functional dissimilarity between the reference and the subject sequence. It may be advantageous to produce a nucleic acid according to the invention or derivatives thereof possessing a substantially different codon usage. It is known by those skilled in the art that as a result of degeneracy of the genetic code, a multitude of gene sequences, some bearing minimal homology to the nucleotide sequences of any known and any naturally occurring genes may be produced. The invention includes possible variation of the nucleic acid sequence that could be made by selecting combinations based on possible codon choices. In addition deliberate amino acid substitution may be made on the basis of similarity in polarity, charge, solubility, hydrophobicity, and/or the amphipathetic nature of the residues as long as the biological activity of the polypeptide is retained.

In a preferred embodiment said nucleic acid encodes a terpene cyclase which has a combined nerolidol and linalool synthesizing capacity. Nerolidol is a sesquiterpene analog of the monoterpenoid linalool. The enzymes involved in the production of precursors for the synthesis of the primary monoterpene skeletons have been shown to be active in the plastids. The ability of said terpene cyclase to synthesize linalool appears to be influenced by the presence of a plastid targeting signal sequence that is rich in hydroxylated and basic residues. Sesquiterpene biosynthesis is compartmentalised to the cytosol, and none of the sofar isolated sesquiterpene synthases bear any targeting signal. However, the present invention shows that monoterpenes can also be produced by cytosolic monoterpene synthases. Apparently the substrate GPP is present in the cytosol. The invention shows that the production of sesquiterpenes in the cytosol is hampered by a lack of substrate. The co-expression of a cytosolic FPP-synthase or the transformation with a fusion construct of sesquiterpene synthase and FPP synthase is now provided to overcome this problem. An additional solution is the targeting of sesquiterpene biosynthesis to other cell compartments by adding or changing a targeting signal to/of the sesquiterpene synthase and/or co-transformation of an FPP synthase with the same targeting or transformation with a targeted fusion construct of sesquiterpene synthase and FPP synthase. In addition to FPP synthase, other enzymes catalyzing committed steps in the biosynthesis of GPP and FPP through the mevalonate and non-mevalonate pathway can be coupled to or co-expressed with monoterpene and sesquiterpene synthases to increase the levels of monoterpenes and/or sesquiterpenes produced. These enzymes can be directed (by adding, changing and removing targeting signals) to different compartments (i.e. mitochondria, chloroplasts, chromoplasts, leucoplasts, peroxisomes (see also example 7).

The invention thus provides a nucleic acid according to the invention encoding a proteinaceous molecule provided with a targeting signal, such as a plastid targeting or a mitochondrial targeting signal, or a targeting signal to any other organel or a nucleic acid according to the invention encoding a proteinaceous molecule without such signal, depending on where synthesis is required. The invention thus provides a nucleic acid according to the invention encoding a proteinaceous molecule essentially capable of isoprenoid bio-active compound synthesis in the cytosol in a cell when provided with a suitable substrate under appropriate reaction conditions. Similarly, it provides a nucleic acid according to the invention encoding a proteinaceous molecule essentially capable of isoprenoid bio-active compound synthesis in a plastid in a cell or in a mitochondrium in a cell when provided with a suitable substrate under appropriate reaction conditions.

In a preferred embodiment said nucleic acid as provided herein is provided with a nucleic acid encoding a targeting signal and/or remnants of a targeting signal. Preferably said targeting signal is a plastid targeting signal. Said plastid targeting signal is preferably located in the N terminus (N-terminal transit peptide) and may have a high abundance of serine residues and/or threonine and/or a low number of acidic residues and/or rich in hydroxylated and basic residues. In one preferred embodiment said targeting signal has a F (Phe), K (Lys), V (Val), F (Phe), N (Asn) motif and/or a D (asp) S (Ser), L (Leu), L (Leu), Xaa, S (Ser), S (Ser) motif, where Xaa is preferably P (pro) or S (Ser). In another, the target signal RRxxxxxxxxW is preferred. In particular the invention provides a nucleic acid encoding an essentially sesquiterpene synthase bioactive fragment, said nucleic acid provided with a targeting signal to provide the encoded gene product with monoterpene synthase activity, or a nucleic acid encoding an essentially monoterpene synthase bioactive fragment, said nucleic acid deprived from an essentially plastid targeting signal to provide the encoded gene product with sesquiterpene synthase activity, and thus provides the various enzymes with a different activity as would be expected.

It is understood that through convergent or divergent evolution new proteins with altered functions may be created by this route. The mutations that lead to divergence are mostly single base substitutions that engender individual amino acid replacements, although other events leading to deletions or insertions also occur. The mutations may be in a nucleic acid comprising the transit peptide and/or the open reading frame (ORF). The new protein usually contains many of the pre-existing features. The original biological function may be restored by reversing mutations (e.g. single base substitutions) using techniques known in the art (e.g. site directed mutagenesis).

In a preferred embodiment through a single base substitution in a predecessor sequence of said nucleic acid sequence (e.g. H64NORL) the N-terminal transit peptide is restored. Restored as used herein means that a stop codon in the target signal is removed, for example through a single base substitution, so that translation begins at the first ATG (Met) upstream of the target signal/transit sequence or target signal remnant. The predecessor sequence of said nucleic sequence is a sequence (common ancestor sequence) which has a stop codon in the target signal or the target signal remnant so that the translation of the protein begins at a second ATG (Met) truncating the target signal or the target signal remnant. It is conjectured that the presence of the restored target signal or target signal remnant influences the synthesis of linalool and/or nerolidol.

The invention provides for a nucleic acid according to the invention wherein said proteinaceous molecule comprises a terpene synthase/cyclase. Preferably said proteinaceous molecule comprises a terpene synthase (cyclase), the properties of which should resemble those of other terpene synthases (cyclases). The invention further provides a nucleic acid according to the invention wherein said proteinaceous molecule comprises a sesquiterpenoid synthase/cyclase. Sesquiterpenoid synthases/cyclases participate in the biosynthesis of most sesquiterpenoids. Ionization of FPP to the farnesyl cation is the first step in the biosynthesis of a large number of sesquiterpenes. The products of many of the sesquiterpenoid synthases/cyclases catalyzing the formation of a terpenoid skeleton from the respective diphosphate substrates (FPP) are mostly cyclic hydrocarbons, with a few exceptions such as for example the acyclic sesquiterpene alcohol nerolidol. None of the sofar isolated sesquiterpene synthases bear any targeting signal.

The invention further comprises a nucleic acid according to the invention wherein said proteinaceous molecule comprises a nerolidol synthase/cyclase protein or functional fragment thereof. The nerolidol synthase/cyclase protein is essentially capable of the synthesis of the acyclic sesquiterpene alcohol nerolidol.

The invention provides a nucleic acid wherein said nerolidol synthase/cyclase comprises (3S)-(E)-nerolidol synthase. The invention further comprises a nucleic acid according to the invention wherein said sesquiterpene alcohol nerolidol comprises trans-nerolidol. The invention further comprises a nucleic acid according to the invention wherein said monoterpene alcohol linalool comprises S-linalool.

The invention provides for a nucleic acid according to the invention wherein said nucleic acid encodes a proteinaceous molecule comprising an amino acid sequence or functional fragment thereof that is at least 50% identical to H64MUT sequence, more preferred 53 or 60% homologous, and even more preferred 70, 80, 90, 95 or 99% homologous to the sequence as shown in FIG. 2 or functional fragment thereof.

Homology is generally over the full-length of the relevant sequence shown herein. As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Deliberate amino acid substitution may be made on the basis of similarity in polarity, charge, solubility, hydrophobicity, and/or the amphipathetic nature of the residues as long as the biological activity of the polypeptide is retained. In a preferred embodiment, all percentage homologies referred to herein refer to percentage sequence identity, e.g. percent (%) amino acid sequence identity with respect to a particular reference sequence can be the percentage of amino acid residues in a candidate sequence that are identical with the amino acid residues in the reference sequence, after aligning the sequences and introducing gaps, if necessary, to achieve the maximum percent sequence identity, without considering any conservative substitutions as part of the sequence identity. Amino acid similarity or identity can be determined by genetic programs known in the art.

The invention further provides a nucleic acid or functional fragment thereof according to the invention wherein said nucleic acid encodes a proteinaceous molecule essentially capable of the synthesis of at least one monoterpenoid when contacted with geranyl diphosphate (GPP) under appropriate reaction conditions. The invention further provides a nucleic acid according to the invention wherein said nucleic acid encodes a proteinaceous molecule essentially capable of the synthesis of at least one monoterpenoid, wherein said monoterpenoid comprises α-pinene and/or β-pinene (bicyclic terpene hydrocarbons) and/or sabinene and/or β-myrcene (acyclic monoterpene) and/or α-phellandrene and/or β-phellandrene and/or α-terpinolene and/or α-terpineol and/or γ-terpinene. Preferably said proteinaceous molecule comprises a terpene synthase (cyclase), the properties of which should resemble those of other terpene synthases (cyclase). Even more preferred said proteinaceous molecule comprises a monoterpenene synthase/cyclase. Preferably said monoterpenoid comprises an olefinic monoterpenoid.

The invention further comprises a nucleic acid according to the invention wherein said nucleic acid encodes a proteinaceous molecule comprising an amino acid sequence or functional fragment thereof that is at least 50% identical to SOSV sequence (see FIG. 6), more preferred 53 or 60% homologous, and even more preferred 70, 80 or 90% homologous to the sequence as shown in FIG. 6 or functional fragment thereof. Preferably said nucleic acid does not contain an insertion of two cytosine residues causing a frame-shift followed by a stop codon giving rise to a truncated open reading frame (ORF), as depicted in FIGS. 6 and 7.

The invention further comprises a nucleic acid encoding a proteinaceous molecule according to the invention obtainable from a eukaryote. A eukaroyte as used herein comprises a cell or organism with a membrane-bound, structurally discrete nucleus and other well-developed subcellular compartments. Eukaryotes as used herein include all organisms except viruses, bacteria, and cyanobacteria (blue-green algae). Preferably said nucleic acid is obtainable from strawberry and/or maize and/or tea and/or cucumber and/or lima bean and/or cotton and/or thyme species and/or citrus species and/or eucalypt species and/or grapefruit and/or fungi and/or yeasts.

The invention further comprises a nucleic acid encoding a proteinaceous molecule according to the invention obtainable from a prokaroyte. A prokaryote as used herein comprises a cell or organism lacking a membrane-bound, structurally discrete nucleus and other subcellular compartments e.g. bacteria, including archaebacteria and cyanobacteria (blue green algae).

The invention further comprises a nucleic acid encoding a proteinaceous molecule according to the invention obtainable from invertebrate animals. An arthropod is a member of a phylum of invertebrate animals that includes insects, arachnids (spiders and mites e.g. spider mites (*Tetranychus urticae*), aphids (e.g. *Aphis gossypii, Myzus persicae*), and thrips (*Frankliniella occidentalis*) and crustaceans (crabs, lobsters, pillbugs, shrimp, etc.).

In a preferred embodiment said nucleic acid encoding a proteinaceous molecule according to the invention is obtainable from strawberry. The invention further provides a nucleic acid according to the invention wherein said nucleic acid expression is repressed by auxin during fruit maturation. Indole-3-acetic acid or auxin is a plant hormone that plays key roles in regulating cell division, extension, and differentiation.

The invention provides a proteinaceous molecule encoded by a nucleic acid according to the invention. The invention further provides a vector comprising a nucleic acid according to the invention. Preferably said vector is a recombinant expression vector comprising a coding sequence which is operably linked to a promoter sequence capable of directing expression of said coding sequence in a host cell for said vector, and a transcription termination sequence, in which the coding sequence is a nucleic acid according to the invention. Preferably said nucleic acid has been provided with means for nuclear targeting and/or integration in a host genome.

Methods which are well known in the art can be used to construct expression vectors containing the nucleic acid of the invention, and appropriate transcriptional and translational controls. These methods include in-vitro recombinant techniques. Exogenous transcriptional elements and initation codons can be used and also can be of various origins, both natural and synthetic. The efficiency of expression may be enhanced by the inclusion of enhancers appropriate to the cell system in use. In the case of plant expression vectors, the expression of a nucleic acid of the invention may be driven by a number of previously defined and yet to be defined promoters, including inducible and developmentally regulated promoters. The invention further contemplates the use of the individual promoters of the nucleic acid of the present invention for this purpose. In particular any promoters particularly responsive to ripening events, wound-inducible or specific inducible promoters (e.g. spider mite, insect etc. inducible promoters, which can be isolated from plants that were fed upon by for example spider mites or insects), may be used to drive the tissue specific expression of said nucleic acid. In addition, viral promoters such as the 35S and the 19S promoters of CaMV may be used alone or in combination with the omega leader sequence from TMV. Promoters or enhancers derived from the genomes of plant cells, tissue specific promoters i.e fruit specific promoters, Fbp7 (Columbo et al. 1997; Plant Cell 9; 703-715), 2A11 promoter (Pear et al., 1989, *Plant Molecular Biology*, 13:639-651), small subunit of Rubisco (Corruzzi et al., 1984; *EMBO J.* 3:16; Broglie et al., 1984 Science 224:838-843) or timing specific promoters such as ripening specific promoters (the E8 promoter, Diekman and Fisher, 1988, *EMBO J,* 7:3315-3320) may be used. Suitable terminator sequences include that of the *Agrobacterium tumefaciens* nopaline synthase gene (Nos 3' end), the tobacco ribulose bisphosphate carboxylase small subunit termination region; and other 3' regions known in the art. Methods known in the art can be used to construct recombinant vectors which will express 'sense' or 'antisense' nucleic acid. Antisense or partial sense or other techniques may also be used to reduce the expression of said nucleic acid leading to the production of a flavour, fragrance and/or bio-control compound. Full length sense techniques may be used to increase or reduce the expression of said nucleic acid leading to the production of a flavor and bio-control compound.

The invention further provides a replicative cloning vector comprising a nucleic acid according to the invention and a replicon operative in a host cell for said vector. The invention contemplates the use of yet non-described biological and non biological based expression systems and novel host(s) systems that can be can be utilized to contain and express the nucleic acid of the invention. The definition host cell as used herein refers to a cell in which an foreign process is executed by bio-interaction, irrespective of the cell belongs to a unicellular, multicellular, a differentiated organism or to an artificial cell, cell culture or protoplast.

The invention further provides a host comprising a nucleic acid according to the invention or a vector according to the invention. A variety of vector/host expression systems can be utilized to contain and express the nucleic acid of the invention. These include micro-organisms such as bacteria (e.g. *E coli, B subtilis, Streptomyces*, Pseudomonads) transformed with recombinant bacteriophage, plasmid or cosmid DNA expression systems, yeast (e.g *S. cerevisiae, Kluyveromyces lactis, Pichia pastoris, Hansenula polymorpha, Schizosacch. Pombe, Yarrowia*) transformed with yeast expression vectors; filamentous fungi (*Aspergillus nidulans, Aspergillus orizae, Aspergillus niger*) transformed with filamentous fungi expression vectors, insect cell systems transfected with virus expression vectors (eg baculovirus, adenovirus, herpes or vaccinia viruses); plant cell systems transfected with virus expression vectors (e.g. cauliflower mosaic virus, CaMV, tobacco mosaic virus, TMV) or transformed with bacterial expression vectors (e.g Ti or Pbr322 plasmid); or mammalian cell systems (chinese hamster ovary (CHO), baby hamster kidney (BHK), Hybridoma's, including cell lines of mouse, monkey, human and the like. A host strain may be chosen for its ability to modulate the expression of the nucleic acid or to process the expressed proteinaceous molecule in the desired fashion. Such modifications of said proteinaceous molecule include acylation, carboxylation, glycosylation, phosphorylation and lipidation. Post translation processing which cleaves a 'prepro' form of said proteinaceous molecule may also be important for correct insertion, folding and/or function. Different host cells which have the correct cellular machinery and characteristic mechanisms for such post-translational activities maybe chosen to ensure correct modification and processing of the introduced, foreign proteinaceous molecule.

The invention further provides a host comprising a nucleic acid according to the invention or a vector according to the invention wherein said host comprises a prokaroytic cell. The invention further provides a host comprising a nucleic acid according to the invention or a vector according to the invention wherein said host comprises a eukaryotic cell.

The invention further provides a host comprising a nucleic acid according to the invention or a vector according to the invention wherein said host comprises a plant and propagating material thereof. The invention is particularly useful for enabling plants to produce linalool, nerolidol or a combination of the two. This enables breeding of plants with improved flavor/fragrance as described for linalool alone in WO 9715584, or improved resistance against micro-organisms or insects as described in Examples 8, 9, 12, 13 and 14 and WO 0022150 for linalool that had however to be co-expressed with a GPP synthase.

The bacterial diseases to which resistance is provided herein include but are not limited to:

*Erwinia* spp. (e.g. *E. amylovora* (fire blight) and *E. carotovora*), *Clavibacter* spp. (e.g. *C. michiganense* pv. *Sepedonicum* (bacterial ringspot potato), *Corynebacterium* spp., *Pseudomonas* spp. (e.g. *P. syringae* pv. tomato), *Xanthomonas* spp. (*X. campestris* and *X. vesicatoria*), and *Agrobacterium* spp.

The fungal diseases to which resistance is provided herein include but are not limited to:

Powdery mildew fungi (*Sphaerotheca* spp. (e.g. *S. pannosa* var. *rosa*. (rose), *S. humuli* (hop), *S. fuliginea* (cucurbits)), *Podosphaera leucotricha* (apple), *Uncinula necator* (grape), *Erysiphe* spp. (e.g. *E. cichoracearum* (cucurbits, tomato), *E. polygoni* (beet)), *Leveillula taurica* (tomato), *Microsphaera euonymi* (squash)), *Botrytis* spp. (e.g. *B. cinerea* (grey mold)), *Cladosporium* spp. (e.g. *C. fulvum* (in tomato)), *Sphaeropsis* spp. (e.g. *Sphaeropsis sapinea* (tip blight of pine), *Cercospora* spp. (*C. beticola* in beet, *C. zeae-maydis* in corn, *C. sorghi* in sorghum), *Fusarium* spp. (e.g. *F. oxysporum f. niveum* (wilt on watermelon) *F. graminearum* and *F. moniliforme* (scab on wheat) *F. moniliforme, F. oxysporum, F. subglutinans, F. proliferatum*), anthracnose diseases (*Apiognomonia veneta* (in Sycamore, ash, oak, maple, and walnut), *Colletotrichum trifolii* (Alfalfa anthracnose), *Colletotrichum coccodes* (black dot in potato)), rust diseases (e.g. *Puccinia recondita* (leaf rust in wheat) and *Uromyces appendiculatus* (rust in bean)), *Phytophtora* spp. (*P. infestans* (late blight on potato), *P. sojae* (blight on soybean), *P. megasperma* f. sp. *medicaginis* (root rot in alfalfa)), spoilage fungi (*Gibberella* spp., *Diplodia* spp., *Penicillium, Aspergillus* spp. *Penicillium* spp., *Peacilomyces* spp.), *Verticillium* spp. (e.g. *V. albo-atrum* (black root rot in strawberry), *Septoria* spp. (e.g. *S. tritici* and *S. avenae* f. sp. *triticea* (*Sep-*

*toria* in wheat), *S. lycopersici* (*Septoria* leaf spot in tomato)), *Sclerotinia* spp. (e.g. *S. sclerotiorum* (white mold of beans), *Aphanomyces* spp. (e.g. *A. cochlioides* (root rot in sugar beet), *Alternaria* spp. (e.g. *A. solani* (early blight in tomato), *Magnaporthe* spp. (e.g. *M. grisea* (blast in rice))

Insects

The insects to which resistance is provided herein include but are not limited to *Lepidoptera, Orthoptera, Homoptera, Hemiptera*, especially squash bugs (*Anasa tristis*); green stink bug (*Acrosternum hilare*); *Riptortus clavatus*; *Coleoptera*, especially, Colorado potato beetle (*Leptinotarsa decemlineata*); three-lined potato beetle (*Lema trilineata*); asparagus beetle (*Criceris asparagi*); Mexican bean beetle (*Epilachna varivestis*); red flour beetle (*Tribolium castaneum*); confused flour beetle (*Tribolium confusum*); the flea beetles (*Chaetocnema* spp., *Haltica* spp. and *Epitrix* spp.); corn rootworm (*Diabrotica* Spp.); cowpea weevil (*Callosobruchus maculatus*); boll weevil (*Anthonomus grandis*); rice weevil (*Sitophilus oryza*); maize weevil (*Sitophilus zeamais*); granary weevil (*Sitophilus granarius*); Egyptian alfalfa weevil (*Hypera postica*); bean weevil (*Acanthoscelides obtectus*); lesser grain borer (*Rhyzopertha dominica*); yellow meal worm (*Tenebrio molitor*); *Thysanoptera*, especially, western flower thrips (*Frankliniella occidentalis*); Diptera, especially, leafminer spp. (*Liriomyza trifolii*); plant parasitic nematodes especially the potato cyst nematodes (*Globodera* spp.), the beet cyst nematode (*Heterodera schachtii*) and root knot nematodes (*Meloidogyne* spp.).

Resistance can also be conferred by the invention in a tritrofic manner. That is, the invention can be used to have (transgenic) plants produce volatiles such as linalool, nerolidol and dimethylnonatriene—which is derived in planta from nerolidol—constitutively upon feeding of insects or spider mites. These volatiles are known, as shown in the present invention, to be attractive to predators of insects and spider mites and these predators can efficiently exterminate the attacking herbivores thus protecting the crop against its enemies.

Resistance can de determined by performing the appropriate test with the particular organism but can be predicted as well by determining terpene content such as demonstrated in FIG. 30 and example 13 herein. Plant as used herein refers to eukaryotic, autotrophic organisms. They are characterized by direct usage of solar energy for their primary metabolism, their permanent cell wall and in case of multicellular individuals their open unlimited growth. In case of heterotrophic plants, the organisms are in an evolutionary context essentially derived from autotrophic plants in their structure and metabolism. The invention provides a plant or a part, such as a stem, leave, tuber, root, fruit or seed or propagating material thereof transformed with the expression vector according to the invention.

The invention further provides a plant or part thereof which contains within its genome a vector according the invention.

The invention provides a host comprising a nucleic acid according to the invention or a vector according to the invention wherein said host comprises a plant cell. 'Plant cell' as used herein is any self-propagating cell bounded by a semi permeable membrane and containing one or more plastids. Such a cell requires a cell wall if further propagation is required. Plant cell as used herein may be part of a whole plant or may be an isolated cell or part of a tissue which may be regenerated into a whole plant and includes for example, seeds, suspension cultures, embryos, meristematic regions, callous tissues, protoplasts, leaves, roots, shoots, gametophytes, sporophytes, pollen and microspores. The vector constructs according to the invention can be introduced into plant cells by direct DNA transformation, or pathogen mediated transfection. The procedure or method for preparing a transformant can be performed according to the conventional technique used in the fields of molecular biology, biotechnology and genetic engineering. Manipulation of nucleic acid in plant cells may be carried out using the Cre/lox site specific recombination system as outlined in patent application WO9109957. The target plant may be selected from any monocotyledonous or dicotyledonous plant species. Exemplary plants include potato, tomato, petunia, maize, sorghum, cotton, soybean, beans, rape, alfalfa, asparagus, sweet potato and chrysanthemum. However, it is not to be construed as limiting, in as much as microbes and insects may infest many other crops. Thus, the methods of the invention are readily applicable to numerous plant species, if they are found to be susceptible to the microbes or insect species listed hereinabove, including without limitation, species from the genera *Medicago, Trifolium, Vigna, Citrus, Daucus, Arabidopsis, Brassica, Raphanus, Sinapis, Capsicum, Lycopersicon, Nicotiana, Solanum, Helianthus, Bromus, Asparagus, Panicum, Pennisetum, Cucumis, Glycine, Lolium, Triticum* and *Zea*.

The invention further provides a host comprising a nucleic acid according to the invention or a vector according to the invention wherein said host comprises an insect cell. Insect cells such as silkworm cells or larvae themselves may be used as a host. For example in one such system, *Autographa californica* nuclear polyhedrosis virus (AcNPV) is used as a vector to express foreign nucleic acid in *Spodoptera frugiperda* cells or in *Trichoplusia* larvae. The nucleic acid of the invention may be cloned into the nonessential region of the virus, such as the polyhedrin gene, and placed under control of a polyhedrin promoter. Successful insertion of the nucleic acid will render the polyhedrin gene inactive and produce recombinant virus lacking coat protein coat. The recombinant viruses are then used to infect *S frugiperda* cells or *Trichoplusia larvae* in which the nucleic acid is expressed [Smith et al. (1993) J Virol 46:584; Engelhard et al. (1994) *Proc. Natl. acad Sci*, 91: 3224-7].

The invention further provides a host wherein said vector according to the invention and said host expresses a nerolidol synthase/cyclase protein or polypeptide. Preferably said host exhibits suitable glycosyltransferase activity, whereby the produced linalool and nerolidol is converted and accumulated or stored in said host as its respective linaloylglycoside and nerolidylglycoside. Preferably said host contains the appropriate (inducible) glycosidase enzyme suitable for the release of the respective linalool and nerolidol. Alternatively said host is provided with a nucleic acid coding for a suitable (inducible) glycosidase enzyme. Host which contain a nucleic acid encoding a proteinaceous molecule according to the invention may be identified by a variety of procedures known in the art. These procedures include, but are not limited to DNA-DNA, DNA-RNA hybridisation, amplification using probes (portions or fragments of said nucleic acid), protein bioassay or immunoassay techniques which include membrane, solution or chip based technologies for the detection and/or quantification of said nucleic acid and encoded proteinaceous molecule.

The invention further provides a host wherein said vector according to the invention and said host expresses a monoterpenene synthase/cyclase protein or polypeptide.

The invention provides a method for producing a flavor, fragrance and/or biocontrol compound comprising a) transforming or transfecting a suitable host with at least one nucleic acid encoding a proteinaceous molecule according to the invention b) expressing said nucleic acid in the presence of a suitable substrate c) optionally isolating the formed product. In a preferred embodiment said nucleic acid includes a restored target signal or a target signal remnant, i.e. in those case where plastid targeting is required. In a preferred embodiment of the invention is a method to produce nerolidol and/or linalool and/or α-pinene and/or β-pinene (bicyclic terpene hydrocarbons) and/or sabinene and/or β-myrcene (acyclic monoterpene) and/or α-phellandrene and/or β-phellandrene and/or α-terpinolene and/or α-terpineol and/or γ-terpinene or mixtures thereof by a) transforming/transfecting a suitable host b) expressing at least one nucleic acid of the invention in the presence of a suitable substrate and c) isolating the formed products. In a preferred embodiment said host exhibits suitable glycosyltransferase activity, whereby the produced linalool and/or nerolidol is converted and accumulated or stored in said host as its respective linaloylglycoside and nerolidylglycoside. It is most easy when said host already contains the appropriate (inducible) glycosidase enzyme suitable for the release of the respective linalool and nerolidol. This is however not required, expression without said glycosyltransferase and/or glycosidase activity is perfectly well suitable for most purposes and alternatively said host may even be provided with a nucleic acid coding for a suitable glycosidase enzyme, when deemed required. For bio-control activity, it is even provided to express the compounds according to the invention without said glycosyltransferase and/or glycosidase activity, and let the bio-control activity partly depend on said activity in the target organism, e.g. after uptake by an insect the insects saliva, or on the induction of said activity after herbivory or fungal infection.

A method for producing a compound according to the invention is provided comprising a) transforming or transfecting a suitable host with at least one nucleic acid encoding a proteinaceous molecule according to the invention b) expressing said nucleic acid in the presence of a suitable substrate c) optionally isolating the formed product, wherein said host comprises a microorganism, plant cell or plant. Micro-organism as used herein refers to microscopic organisms such as for example Archaea, Bacteria, Cyanobacteria, Microalgae, Fungi, Yeast, Viruses, Protozoa, Rotifers, Nematodes, Micro-Crustaceans, Micro-Molluscs, Micro-Shellfish, Micro-insects etc.

The invention provides a method for producing a flavor, fragrance and or bio-control compound in a cell-free lysate expression system comprising expressing at least one nucleic acid encoding a proteinaceous molecule according to the invention in the presence of a suitable substrate and optionally isolating the formed product, wherein said free lysate system contains all the components necessary for expression and processing. Cell-free lysate expression system as used herein refer to cell-free translation/translocation systems known in the art, such as for example rabbit reticulocyte lysate translation system.

The invention further provides a flavor and/or bio-control compound obtainable by a method according to the invention. Preferably said flavor and/or bio-control compound comprises at least a nerolidol and/or linalool and/or α-pinene and/or β-pinene (bicyclic terpene hydrocarbons) and/or sabinene and/or β-myrcene (acyclic monoterpene) and/or α-phellandrene and/or β-phellandrene and/or α-terpinolene and/or α-terpineol and/or γ-terpinene or mixtures thereof.

The invention further provides use of a flavor compound according to the invention in the processed food industry as an additive. Preferably as a food additive to enhance the flavor of syrups, ice-creams, ices, frozen desserts, yogurts, pastries, sauces, sweets, confectionery, baked goods etc., and like products, for example the enhancement of blueberry flavor (U.S. Pat. No. 4,041,185). Strawberry is a popular fruit for natural flavor ingredients because of its flavor, fragrance, aroma and scent. The invention provides the use of the nucleic acid according to the invention, for the industrial production of 'fruit' flavors which are natural to match the odor fidelity of the natural fruit. The invention provides for the production of novel flavors, fragrances and/or bio-control agents by the use of the nucleic acid according to the invention, alone or in combination, to provide novel avenues for production. For example, the natural or the stereochemically pure nerolidol may be used as a substrate for the semi-synthesis of flavor and fragrance compounds or insect repellents as described in U.S. Pat. No. 5,196,200A). The compounds of the present invention may be used to replace potentially carcinogenic synthetic food additives currently used. The invention provides use of a flavor and/or bio-control compound according to the invention as a disinfectant additive for example to obtain natural formulations and compositions such as antiplaque oral compositions as described in EP 0420630). The invention further provides use of a flavor and/or bio-control compound according to the invention as a degreasing solvent and/or plasticiser and/or dye carrier.

The invention further provides use of a flavor and/or bio-control compound according to the invention as a flavoring and/or bio-control agent for oral medications and vitamins. The invention further provides use of a flavor compound according to the invention for providing additional flavor/aroma in beverages, including alcoholic and non-alcoholic beverages.

The invention further provides use of a flavor compound according to the invention for enhancing or reducing plant flavor/aroma/fragrance/scent.

The invention further provides use of a flavor compound according to the invention for enhancing the flavor/aroma of natural products and/or synthetic products and/or artificial products. The invention further provides use of a flavor compound according to the invention for the industrial synthesis of nature identical flavor/aroma substances. In a preferred embodiment said flavor compound of the present invention is used for the production of novel combinations of artificial flavor substances.

The invention provides use of a flavor and/or bio-control compound according to the invention as a pest control agent. Pest as used herein is a general term for organisms (rats, insects, mites, micro-organisms etc.) which may cause illness or damage or consume food crops and other materials important to humans/animals. The nucleic acid of the present invention pave the way through plant breeding to produce crops at least more capable of controlling or even eliminating detrimental pest infestations by enabling them to produce more terpenoid volatiles (plant volatile allelochemicals) to repel the attacking pest and/or to attract natural pest enemies to the crop. Preferably said terpenoid volatiles comprise nerolidol and/or linalool. The flavor and/or bio-control compounds of the present invention can be used as insecticides, insect repellents, insect pheromones, miticides, scabicides, antimicrobial agents, anti-fungals, anti-herbivore feeding agents etc. For example, nerolidol has been reported to be an extremely effective repellent of mosquitoes. Formulations containing natural nerolidol, produced according to the present invention, may therefore be used in mosquito control.

In a preferred embodiment said compound according to the invention is used for control of the a) interaction between plants and insects b) interaction between plants and micro-organisms c) interaction between one plant and another.

The invention provides use of a flavor and/or bio-control compound according to the invention as an anti-microbial agent. Anti-microbial agent as used herein refers to a compound which can at least in part suppress or inhibit or restrict the growth of a pathogenic organism (e.g. fungi, bacteria, yeast etc.).

Preferably said compound may be used together with at least one other compound having anti-microbial activity to augment or supplement said anti-microbial activity (e.g. said compound can act synergistically with at least one other anti-microbial compound). The use of synergistic combinations of anti-microbial agents has many advantages. One such advantage is that it minimizes the known risk associated with the use of potentially deleterious anti-microbial agents which can be used in lower dosages to achieve the same effect. It also lowers risks associated with the use of non specific/non-selective anti-microbial agents, for example as additives in food and non food products. Preferably said compound can be used for crop treatment programs to reduce or eliminate the use of harmful pesticides/biocides [e.g. spray treatments]. It can be incorporated into products as an bio-control agent [e.g. household materials, detergents, food products etc.] or applied to products [e.g. as an external coating to leather products etc.] to reduce risk of spoilage or contamination.

The invention further provides use of a flavor compound according to the invention for providing flavor/aroma in cosmetics (inc. soap perfumes, perfume specialties and bases), creams, sun-protectant products, hair conditioners, cleaning products, personal care products, health care products (inc. all mammalian health care products). The invention further provides use of a flavor compound according to the invention as a lengthening agent and fixative in perfumes or as a suspension aid for aluminium salts in anti-perspirants pharmaceuticals (e.g. deodorants).

The invention provides use of a nucleic acid according to the invention as a molecular marker or diagnostic tool. Preferably as a molecular marker for flavor formation [for example nerolidol and/or linalool and/or α-pinene and/or β-pinene (bicyclic terpene hydrocarbons) and/or sabinene and/or β-myrcene (acyclic monoterpene) and/or α-phellandrene and/or β-phellandrene and/or α-terpinolene and/or α-terpineol and/or γ-terpinene production] in plant breeding. Even more preferred as a molecular marker for fruit. ripening (for example fruit ripening of strawberry and grapefruit). The nucleic acid according to the invention can be used as markers for the selection of crop species, such as for example maize, cotton, apple, and cucumber, and any other crops employing a volatile release defense mechanism, with improved production of volatile terpenoids (e.g. a predator attracting flavor (terpenoid) compound according to the invention) in response to feeding pests.

The invention further provides use of a flavor and/or bio-control compound according to the invention in the preparation of a composition. Suitable basis for compositions are known in the art. Preferably said composition comprises at least nerolidol and/or linalool and/or α-pinene and/or β-pinene and/or sabinene and/or β-myrcene and/or α-phellandrene and/or β-phellandrene and/or α-terpinolene and/or α-terpineol and/or γ-terpinene, or mixtures thereof.

The invention further provides a composition comprising a flavor and/or bio-control compound according to the invention. Preferably said compositions are anti-fungal, miticidal, or pesticidal. For example a miticidal composition is useful for controlling spider mite populations. Preferably said compositions comprise slow-release formulations which can be employed for fumigation purposes. For example fumigation in agriculture for the protection of crops against micro-organisms and pests e.g. insects, mites etc. Preferably said composition is in a form that can be administered to a plant, animal (including human), food or non-food product, industrial product etc.

The invention provides a composition comprising a flavor and/or bio-control compound according to the invention which is a pharmaceutical. Suitable pharmaceutical compositions are known and they may be in dosage forms such as tablets, pills, powders, suspensions, capsules, suppositories, injection preparations, ointments, eye drops etc. The invention provides a composition comprising a flavor and/or bio-control compound according to the invention which is a neutraceutical.

The invention provides for use of a composition comprising a flavor and/or bio-control compound according to the invention for augmenting or enhancing the aroma and/or taste of food or non food products and/or protection of food or non food products against fungal contamination and/or pest infestation. For example chewing gums, medicinal products, detergents, cosmetics, confectionery etc. Preferably said composition will enhance the shelf life/preservation of food and non-food products (inc. industrial products).

The invention provides for use of a composition comprising a flavor and/or bio-control compound according to the invention for the biological control of pests. For example administrating said composition to a plant. Modes of administration can readily be determined by conventional protocols and may take the form of sprays, dissoluble pellets etc.

The invention provides for use of a composition comprising a flavor and/or bio-control compound according to the invention for the protection of stored products. For example for the protection of stored products against micro-organisms, insects and other pests. For example the protection of potatoes, flowerbulbs, onions etc. against *Phytophtora* spp, *Phoma* spp, *Fusarium*, *Botrytis* spp and other stored product pathogens.

The invention provides for use of a composition comprising a flavor and/or bio-control compound according to the invention for the prevention or treatment of disease. For example for the treatment of dental caries and/or dental plaque and/or skin disorders (dermatological formulations) and/or immunosuppressive, anti-leukaemia and anti-retroviral treatment. A preferred embodiment is that said composition is suitable for human consumption or external application.

The invention provides for a method of treatment of disease comprising administering a composition according to the invention with a carrier to a suitable recipient. Preferably said carrier is a pharmaceutically acceptable carrier (e.g. drug carrier system) or inert carrier, such as a glycoside.

BRIEF DESCRIPTION OF THE DRAWINGS

FIG. 2: Sequence alignment of H64 proteins H64NORS (SEQ ID NO: 19), H64MUT is (SEQ ID NO: 21), H64VES (SEQ ID NO: 23). H64MUT nucleic acid sequence after the stop codon in H64NORL (SEQ ID NO: 17) (location marked) was changed into a Leucine residue. Black background corresponds to identical residues in all three sequences and gray background corresponds to identity between two out of the three sequences.

A. Protein sequence alignment of the different H64 fragments obtained by PCR on genomic DNA and the same regions in cDNAs isolated. Arrows indicate which one of the sequences do not have a stop codon in this region. The RR motif is common in targeting signals of monoterpene synthases. Black background corresponds to identical residues in all seven sequences and gray background corresponds to identity between at least three out of the seven sequences. In FIG. 3A, the following sequences identifiers identify the sequences as they are listed in the Sequence Listing (infra):
SEQ8C (H64NORU3/UP16) SEQ ID NO: 35
SEQ Q9C (H64NORU4/UP1) SEQ ID NO: 38
SEQ 4B (H64VES) SEQ ID NO: 23 (1-89)
SEQ 6C (H64NORU1/W151) SEQ ID NO: 29 (1-81)
SEQ7C (H64NORU2/UP3 SEQ ID NO: 32
SEQ3B (H64MUT) SEQ ID NO: 21 (1-61)
B. Site directed mutagenesis and constructing H64MUT from H64NORL. The 5'region of H64NORL and H64MUT is aligned between the two ATG codons and the position of directed mutagenesis is marked by the gray background. The stop codon T(U)GA in H64NORL was converted to a codon encoding a leucine residue (CTA). In FIG. 3B, the following sequences identifiers identify the sequences as they are listed in the Sequence Listing (infra):
SEQ3A (H64MUT5') SEQ ID NO: 20 (145-247)
SEQ1A (H64NORL5') SEQ ID NO: 16 (244-346), FIG. 4: Expression of H64 genes analyzed by RNA gel blots and H64NORL cDNA as a probe.
A. Expression in vegetative (leaves) and reproductive (4 stages of fruit development) tissues.
B. Expression in ripe fruit of two wild cultivars (1, Plant Research International line H1 and 2 Plant Research International line 92189) and two cultivated cultivars (1, cultivar Calypso and 2, cultivar Gorrella.
C. Expression in fruits treated with or without the synthetic auxin NAA. Strawberry fruit (cultivar *Elsanta*) at the white stage of development were treated with lanolin paste containing 100 mM NAA. Treated and control berries (paste with no NAA) were treated, left on the vine for 7 days and then picked and used for RNA isolation.

FIG. 6: Nucleic acid sequence alignment of the two cultivated SOSA cDNAs cloned (MA and WS) and their homolog from the wild strawberry (SOSV). Black background corresponds to identical residues in all three sequences and gray background corresponds to identity between two out of the three sequences. The location of the CC insertion causing the frame shift and the stop codon following it is depicted. The stop codon at the 3' is the end of the ORF. In FIG. 6, the following sequences identifiers identify the sequences as they are listed in the Sequence Listing (infra):
SEQ10A (SOSA/WS) SEQ ID NO: 39
SEQ11A (SOSA/MA SEQ ID NO: 42
SEQ12A (SOSV) SEQ ID NO: 45.

FIG. 7: Alignment of the protein sequence of the different SOS cDNAs isolated. Black background corresponds to identical residues in all five sequences and gray background corresponds to identity between at least three out of the five sequences. The insertion of CC in SEQ11B(SOSA/MA) and SEQ10B(SOSA/WS) forms a proline residue and a stop codon after. In SEQ11C(SOSA/MA) and SEQ10C(SOSA/WS) the two cytosine nucleotides were removed and allowed further translation of the protein. In FIG. 7, the following sequences identifiers identify the sequences as they are listed in the Sequence Listing (infra):
SEQ11B (SOSA/MA) SEQ ID NO: 43
SEQ12B (SOSV) SEQ ID NO: 46
SEQ10B (SOSA/WS) SEQ ID NO: 40
SEQ10C (SOSA/WS) SEQ ID NO: 41

In FIG. 8, the following sequences identifiers identify the sequences as they are listed in the Sequence Listing (infra):
DNA SEQ23B (SOSA5/W74) SEQ ID NO:75
DNA SEQ23B (SOSA6/256) SEQ ID NO:78
DNA SEQ24B (SOSA7/W61) SEQ ID NO: 81
DNA SEQ21B (SOSA4/W59) SEQ ID NO: 72
DNA SEQ19B (SOSA2/W68) SEQ ID NO: 66
DNA SEQ15B (SOSV3/W90) SEQ ID NO: 54
DNA SEQ17B (SOSV5/W84) SEQ ID NO: 60
DNA SEQ20B (SOSA3/W 46) SEQ ID NO: 69
DNA SEQ13B (SOSV1/W76) SEQ ID NO: 48
DNA SEQ16B (SOSV4/W79) SEQ ID NO: 57
DNA SEQ18B (SOSA1/W66) SEQ ID NO: 63
DNA SEQ10A (SOS/WS) SEQ ID NO: 39 (629-833)
DNA SEQ11A (SOSA/MA) SEQ ID NO: 42 (1322-1526)
DNA SEQ14B (SOSV2/W93) SEQ ID NO: 51
DNA SEQ12A (SOSV) SEQ ID NO: (635-839).

FIG. 9: Expression of SOS genes analyzed by RNA gel blots and SOSV cDNA as a probe
Expression in ripe fruit of two wild cultivars (1, Plant Research International line H1 and 2 Plant Research International line 92189) and two cultivated cultivars (1, cultivar Calypso and 2, cultivar Gorrella.

FIG. 16: Schematic representation of the different constructs used for GFP transient expression assays in tobacco protoplasts. Fragments derived from the 5'-end of the cDNAs described in the invention were used for a translational fusion with the GFP gene. The MID motif is present in most sesquiterpene synthase genes described up to date. SC, stop codon. M1 and M2 are the two methionine residues at the N-termini of the various proteins (see also FIG. 3A).

The short genomic DNA sequence obtained (H64W149) contains an RW motif instead of an RR motif and it might be of importance for the formation of the monoterpene linalool. In the wild cultivars (diploid) only one variant encoding a protein with a targeting signal could be identified (both by PCR on either DNA and RNA) which may only catalyze the formation of the low levels of linalool detected.

Headspace analysis. Samples of ripe or ripening fruits were enclosed in 1-L glass jars that were closed with a teflon-lined lid equipped with an in- and outlet, and placed in a climate room at 25° C. and 210 μmol.m$^{-2}$.s$^{-1}$ provided by 400-W HPI-T lights (Philips, Eindhoven, the Netherlands). A vacuum pump was used to draw of air through the glass jars at approximately 100 mL min$^{-1}$, with the incoming air being purified through a glass cartridge (140×4 mm) containing 150 mg Tenax TA (20/35 mesh, Alltech, Breda, the Netherlands). At the outlet the volatiles emitted by the fruits were trapped on a similar Tenax cartridge. Volatiles were sampled during 24 h. Cartridges were eluted using 3×1 mL of redistilled pentane-diethyl ether (4:1). Of the (non-concentrated) samples, 2 μL were analysed by GC-MS using an HP. 5890 series II gas chromatograph equipped with an HP-5MS column (30 m×0.25 mm i.d., 0.25 μm df) and an HP 5972A Mass Selective Detector. The GC was programmed at an initial temperature of 45° C. for 1 min, with a ramp of 10° to 280° C. and final time of 5 min. The injection port (splitless mode), interface and MS source temperatures were 250, 290 and 180° C., respectively, and the He inlet pressure was controlled by electronic pressure control to achieve a constant column flow of 1.0 mL min$^{-1}$. Ionization potential was set at 70 eV, and scanning was performed from 48-250 amu.

Figure 1:
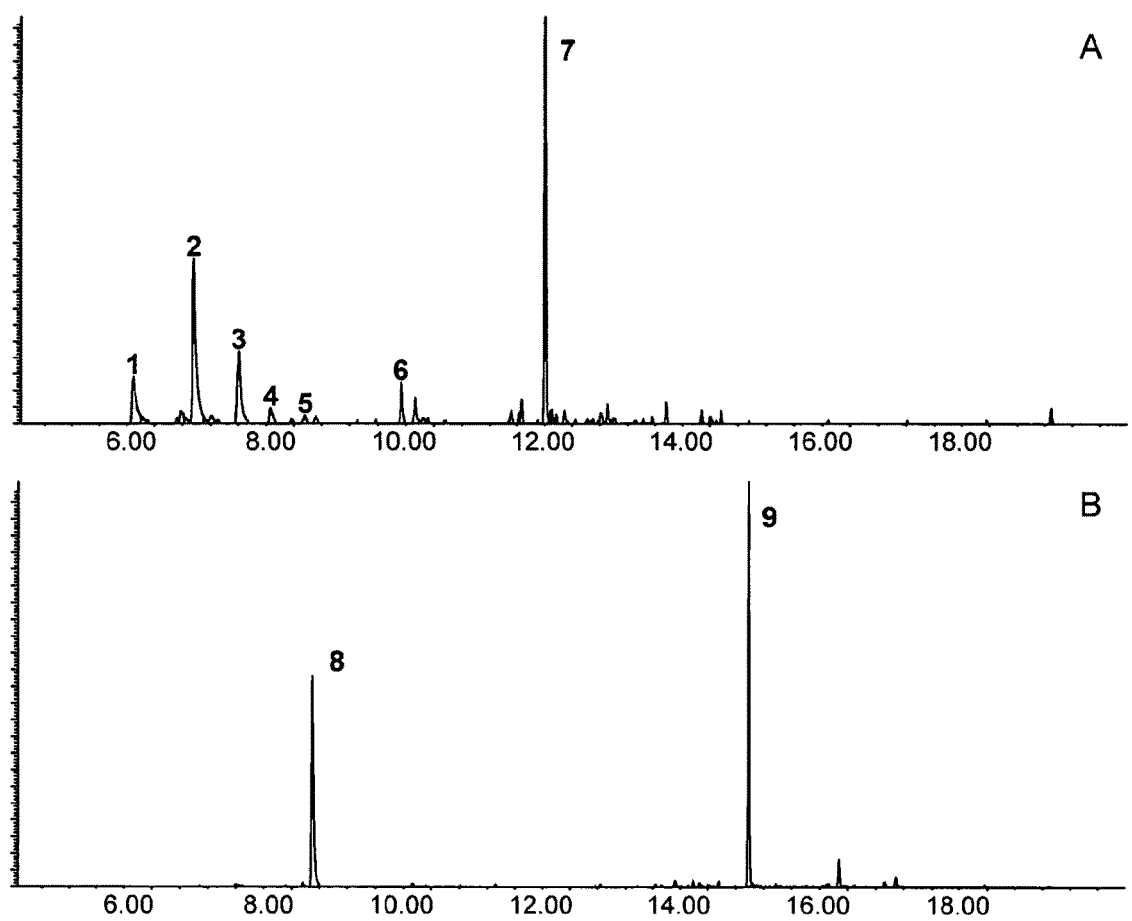
FIG. 1: Headspace analysis using GC-MS of wild (A) and cultivated strawberry (B). Chromatograms are of m/z 93 (obtained in SCAN mode). Peaks:
1, α-pinene; 2, β-myrcene; 3, β-phellandrene; 4, γ-terpinene (tentative); 5, α-terpinolene (tentative); 6, α-terpineol; 7, carvylacetate; 8, linalool; 9, trans-nerolidol.

The analysis of the headspace profiles was focused on terpenoids by only showing the ion 93 chromatogram (although samples were analysed using the SCAN mode). In that way, remarkable differences can be seen between cultivated and wild strawberry: the headspace profile of the wild strawberry contains carvylacetate and a number of olefinic monoterpenes such as α-pinene, myrcene, α-phellandrene, and α-terpinolene, α-terpineol and γ-terpinene (the last three tentatively identified) (FIG. 1A), whereas the cultivated is dominated by two major peaks only: linalool and trans-nerolidol (FIG. 1B).

Example 2

General Molecular Techniques

DNA was isolated from young strawberry leaves as described by Marty et al., [Theor. Appl. Genet. (2000) 100: 1129-1136].

RNA gel blots experiments were performed as described by Aharoni et al., [The Plant Cell, (2000) 12, 647-661].

Cloning full length cDNAs was performed by using the SMART RACE cDNA Amplification Kit (Clontech) according to the manufacturer instructions with slight modifications either to annealing temperatures (normally reduced by 5 to 10° C. compared to the one recommended) or amount of cycles (up to 35 cycles).

PCR, restriction digests, plasmid DNA isolation and gel electrophoresis were performed using standard protocols. All fragments were purified out of gel using the GFX purification kit (Amersham). Cloning of PCR fragments was either done to the PCR SCRIPT (Stratagene) or pCR 4Blunt-TOPO (Invitrogen) vectors (for blunt end products generated when using pfu polymerase) or to the pGEM-T Easy (Promega) vector (when A tailed PCR products were generated by the use of taq polymerase). Throughout the text the following construct/cDNA names will be used (also see sequence listing):

H64VES: wild strawberry, full length cDNA (with targeting signal)
H64NORL: original cultivated strawberry cDNA starting from Met 1, including stopcodon between Met 1 and Met 2 (non-functional targeting signal)
H64NORS: derived from H64NORL starting from Met 2 (no targeting signal)
H64MUT: derived from H64NORL; stopcodon repaired
H64TAR: used for transformation of plants: composed of H64VES Met1 to Met 2 region and H64NORS (with targeting signal)
H64NOR: used for transformation of plants: H64NORS including intron Example 3

Construction of a Strawberry Red Fruit Stage cDNA Library, Mass Excision and Random Sequencing Messenger RNA Isolation and cDNA Library Construction Total RNA was isolated from strawberry fruit red stage of development using the method described by Manning K. [Analytical Biochemistry (1991) 195, 45-50]. The cultivar used was *Fragaria×ananassa Duch*. cv. Elsanta. The cDNA library was produced as a custom service by (Stratagene) in the lambda zap vector. Messenger RNA was isolated from total RNA using the polyA+ isolation kit (Pharmacia).

Mass Excision and Random Sequencing

The ExAssist™/SOLR™ system (Stratagene) was used for mass excision of the pBluescript SK(–) phagemid. The excision was done according to the manufacturer instructions using 20×10³ pfu from the non-amplified library for each excision. High quality plasmid DNA from randomly picked colonies was extracted using the QIAGEN BioROBOT 9600. Colonies were grown overnight in 3 ml Luria Broth medium (10 g/l tryptone, 5 g/l yeast extract, 5 g/l NaCl) supplemented with 100 mg/l ampicillin, centrifuged at 3000 RPM for 10 min. and the pellet was used directly for plasmid DNA isolation by the robot. Each DNA isolation round consisted of 96 cultures.

Insert size was estimated by agarose gel electrophoresis after restriction enzyme digestion of the pBlueScript (SK–) vector with EcoRI and XhoI. Inserts with length above 500 bp were used for sequencing. Plasmid DNA from the selected samples were used for polymerase chain reaction (PCR) sequencing reactions using the ABI PRISM™ Dye Terminator Cycle Sequencing Ready Reaction Kit and the MJ Research PTC-200 DNA Engine™ thermal cycler. The T3 and T7 universal primers were used for sequencing from the 5' and 3' ends respectively. PCR program was according to the Dye Terminator manufacture's protocol (ABI PRISM). The ABI 373, 370A and 310 sequencers (Applied Bio-systems) were used. Sequences were edited manually to remove vector and non reliable sequences and submitted to the BLAST homology search (Altschul et al. J. Mol. Biol. 215, 403-410, 1990) provided by the National Center for Biotechnological Information on the world wide web (info@ncbi.nlm.nih.gov). Search was performed against all non-redundant data bases available by the program.

Example 4

Cloning and Characterization of H64 Genes from Wild and Cultivated Strawberry

Cloning of the H64 cDNA from Cultivated Strawberry (H64NORL) and its Homologue from the Wild Strawberry (H64VES)

Figure 2:
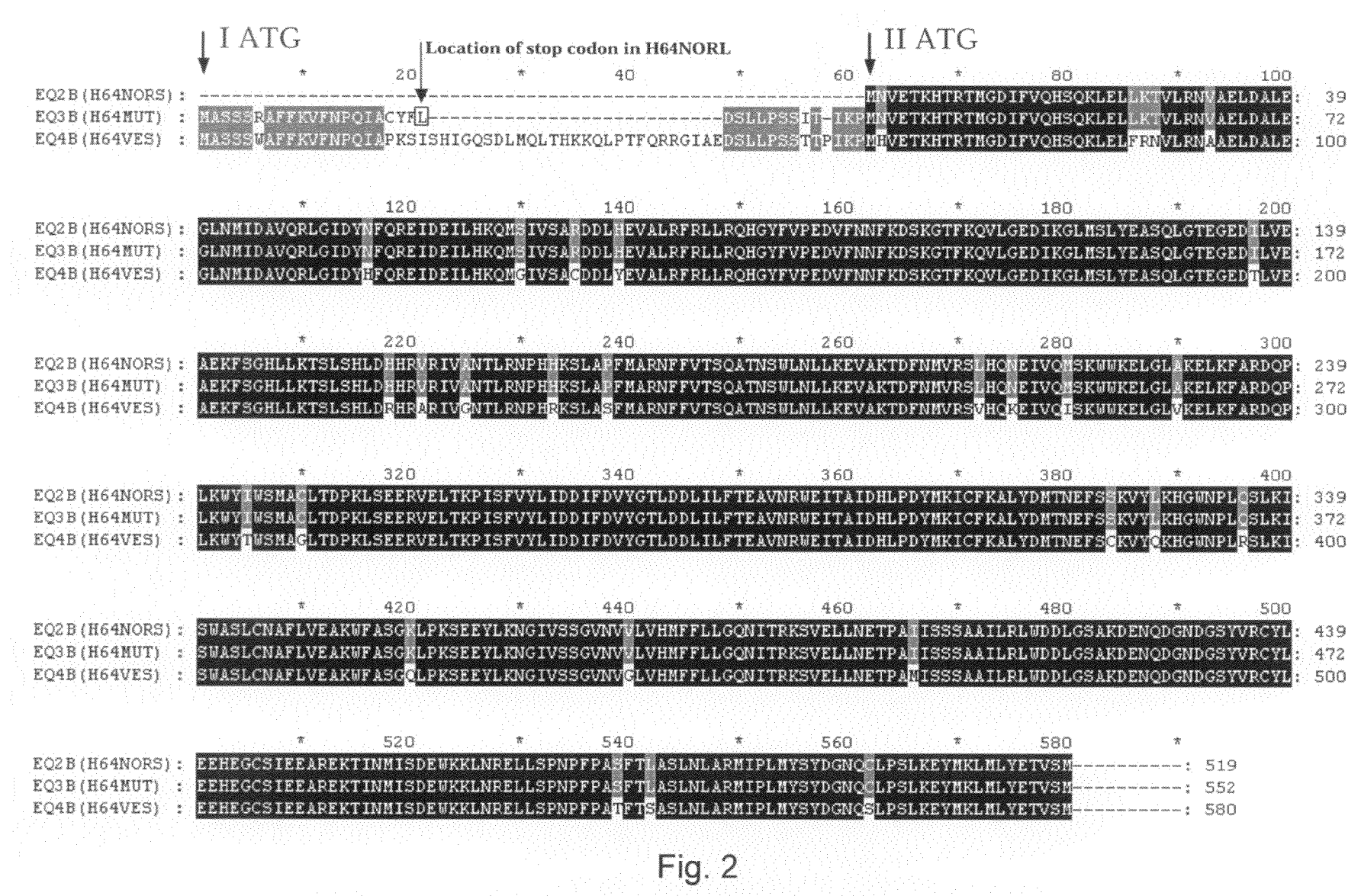

We primarily identified the H64 cDNA out of our randomly sequenced clones originating from the cultivated strawberry cultivar *Elsanta* (ripe red fruit) cDNA library. Homology search results using the BLAST program indicated that the cDNA might encode a terpene synthase protein. The entire H64 cDNA is 1874 bp long [(termed H64Normal Long (H64NORL)] and contains a open reading frame (ORF) encoding a 519 amino acids (aa) long protein [we termed the part of the cDNA forming the 519 aa ORF as H64Normal Short (H64NORS), see FIG. 2].

Cloning of the wild strawberry homolog of the cultivated H64 cDNA was accomplished by the use of the SMART RACE kit (Clontech) using RNA from the Plant Research International collection of wild strawberries (line 92189). Oligonucleotides primarily used for sequencing the H64NORL cDNA were used for 3' RACE amplification (AAP291 - 5'-CTTCATGAGGTTGCACTTCG-3' (SEQ ID NO: 2) and the nested oligonucleotide AAP 293 -5'-AATG-GTGGAAGGAGCTTGGATTGG- 3' (SEQ ID NO: 3). The full length wild strawberry cDNA [H64 Vesca (H64VES)] was obtained by designing an oligonucleotide on the 3' untranslated region (UTR) based on the 1000 bp fragment obtained in the 3' RACE and using it to RACE for the 5' side (5'GTTCAACTCCACTTCCAGCAGTC 3' (SEQ ID NO: 4). The H64VES cDNA is 1894 bp long and contains a open reading frame encoding a 580 amino acids (aa) long protein.

Figure 3:
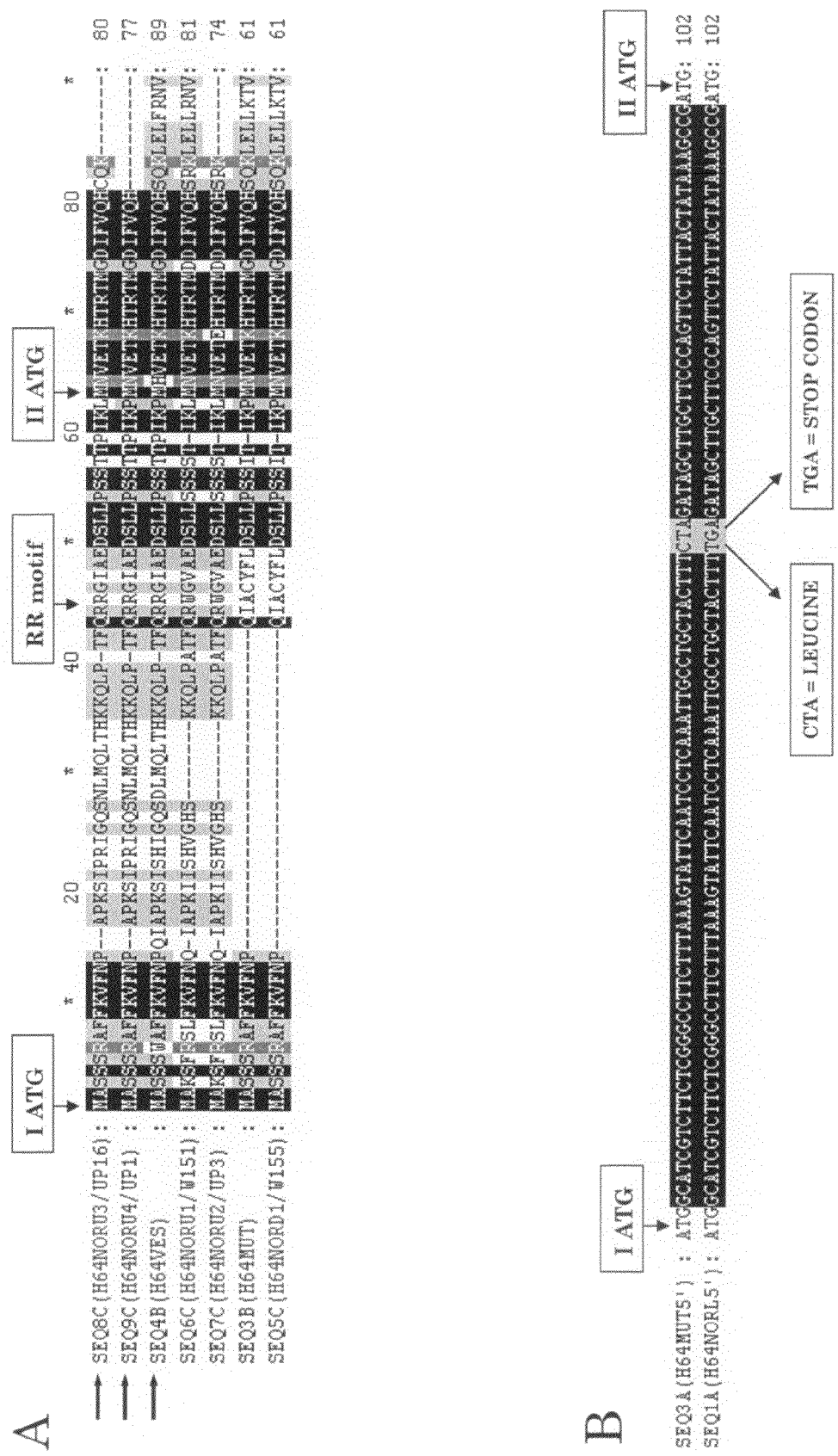
FIG. 3: targeting signals in the different H64 genes.

Sixty one amino acids downstream of the first methionine residue of the 580 aa protein we could identify an additional methionine residue. This 61 amino acids resemble the characteristic plastidic targeting signal of monoterpene synthases since it contains the two arginines motif and a large number of serine residues [Williams et al. (Biochemistry, 37 12213-12220, 1998); see FIG. 3A). The H64NORL and H64VES cDNAs share 96% identity at the nucleic acid level and if the stop codon is eliminated and the rest of the sequence translated, 92.4% at the amino acid level (from the ATG located at nucleotide 145 up to the end of the coding region). H64VES and H64NORS share 97.2% identity at the nucleic acid level and 94.2% at the amino acid level (when the part starting from the beginning of H64NORS from H64NORVES is used for the alignment up to the end of the coding region).

Figure 4:
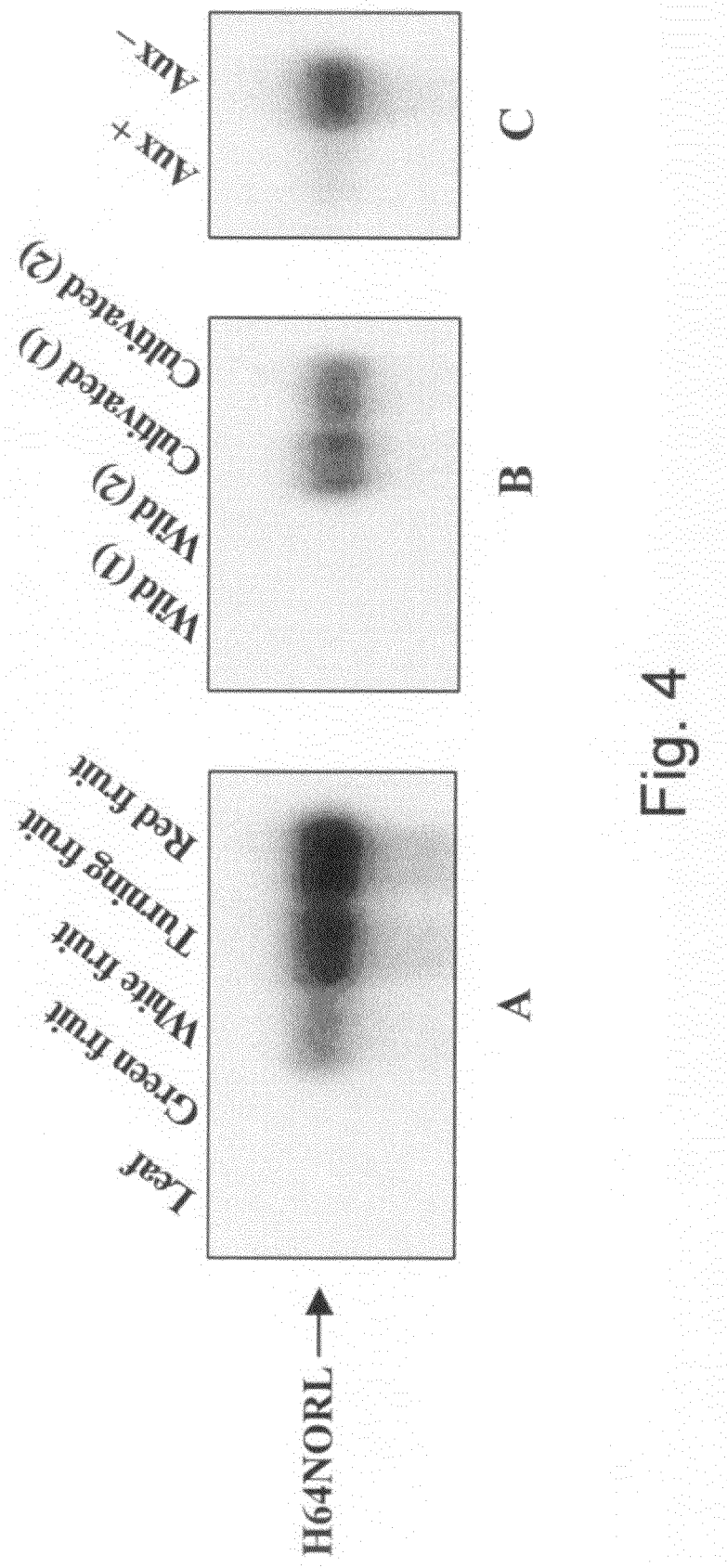

Analysis of H64 Expression During Development, in Cultivated and Wild Cultivars and in Response to Auxin Treatment RNA gel blot analysis using H64NORL as a probe revealed that it is upregulated during the cultivated strawberry fruit ripening (FIG. 4). No expression could be detected in the leaf and green fruit tissues. H64 expression increased from the white to red stage of fruit development. Analysis of H64 expression in ripe fruits of two wild, and two cultivated cultivars showed that H64 is strongly expressed in the cultivated cultivars and hardly any expression could be detected in the wild cultivars (slight signal was detected in the wild cultivars after long exposure of the film, data not shown). Another RNA gel blot showed that H64 is repressed by auxin. This correlates with the fact that also other ripening up-regulated genes in strawberry are repressed by auxin.

Site Directed Mutagenesis of H64NORL

A more thorough analysis of the H64 cDNA (termed H64NORL) revealed that it might contain an additional ATG start codon, 99 by upstream of the original ATG we identified (proposed to be the beginning of the ORF encoding the 519 aa H64NORS protein). The two ATG codons were located in frame but no peptide could be formed between them since a stop codon located 39 bp before the down stream ATG was evident. We suspected that the part between the two ATG is actually part of the protein and for some reason it might be mutated so a shorter protein starting for the downstream ATG might be formed. Additional support to this idea was the high abundance of serine residues identified in the translated area between the two ATGs. It resembled N-termini of other monoterpenoid synthases which contain relatively high abundance of serine residues. We therefore employed site directed mutagenesis in order to modify the stop codon and construct a non truncated H64NORL protein [termed H64 Mutagenized (H64MUT)]. By changing the stop codon (TGA) into a leucine residue (CTA) the H64MUT cDNA is 1659 bp long containing a 552 aa long protein (see FIG. 3B). The site directed mutagenesis was performed using the QuikChange kit as described by the manufacturer (Stratagene). The oligonucleotide used for the exchange was, 5'-GGGAAGCAAGCTATCTAGAAAGTAGCAG-GCAA TT- 3' (SEQ ID NO: 5).

PCR on Cultivated Strawberry Genomic DNA

In order to verify whether the sequence we obtained for H64NORL was not a PCR artifact and the stop codon between the two ATGs exists, we performed PCR on the cultivated strawberry genomic DNA. We designed two oligonucleotides one upstream the first ATG (5'- CTCCCA-CAGCTTCTTAGTTGC- 3' (SEQ ID NO: 6)) and the other downstream of the second ATG (the beginning of H64NORS) (5'-CTAGCTCTGCTACATTCCTCAAGAC-3' (SEQ ID NO: 7)). Amplification with these two oligonucleotides was expected to amplify a fragment of approximately 200 bp. We obtained two clear fragments of 300 bp and 400 bp each. Sequencing four clones of the 300 bp length fragments revealed them to be similar to the original H64NORL cDNA. Sequencing and aligning 20 of the larger clones identified several isoforms which were different from the original cultivated H64NORL cDNA. All fragments (including the short ones) contained an intron of approximately 100 bp. Four unique different clones out of the 20 sequenced were identified. Two of them [SEQ6C(H64NORU1/w151) and SEQ7C (H64NORU2/UP3)] had an additional 20 aa (compared to H64MUT) but still contained a stop codon located immediately at the beginning of the peptide they formed. Other two fragments [SEQ8C(H64NORU3/UP16) and SEQ9C (H64NORU4/UP1)] did not contain any stop codon and were most similar to the sequence of H64VES. These fragments added 26 aa to the H64MUT sequence and they both contain the two arginine residues as in H64VES which are most often found in the plastidic targeting signal of monoterpene synthases (see FIG. 3A).

Cloning H64MUT/H64NORS for Expression in E. coli

Figure 5:
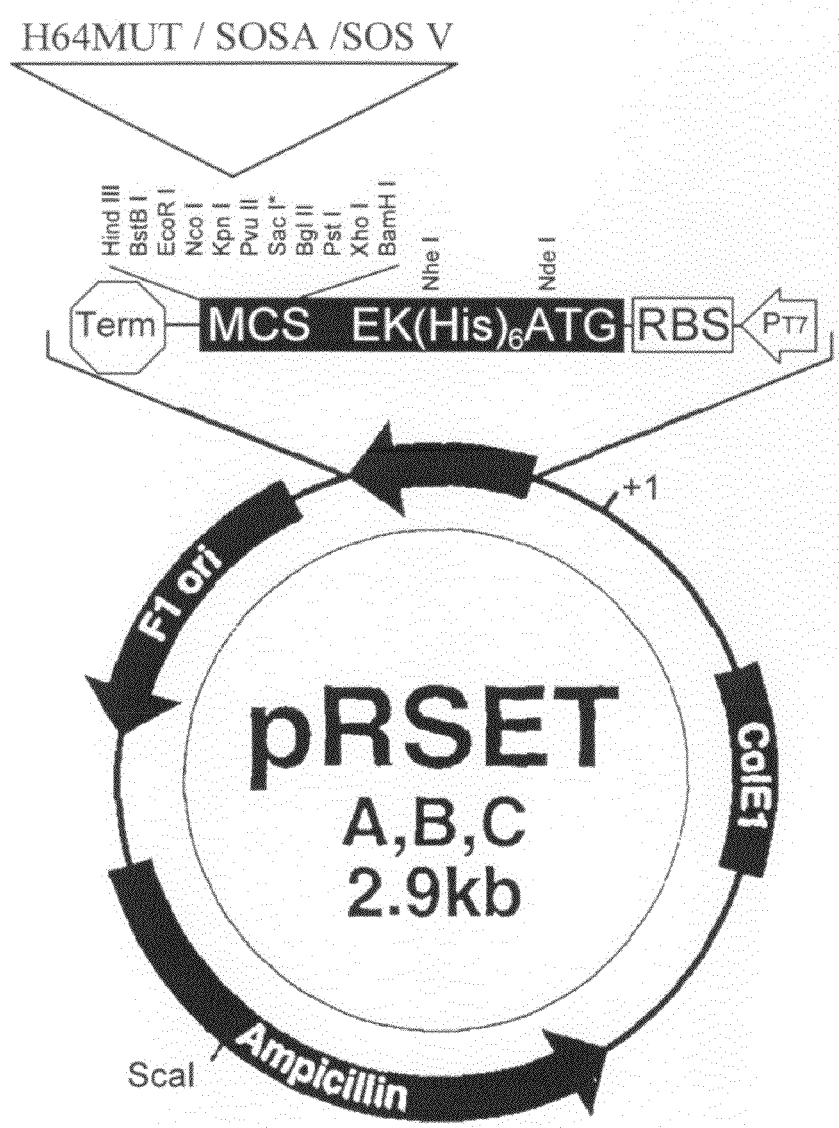
FIG. 5: The pRSET B expression vector used for cloning and expression of H64MUT/, SOSA and SOSV in *E. Coli* cells.

The E. coli expression vector pRSETB (Invitrogen) was used for heterologous expression of strawberry terpene synthases (see FIG. 5). The pRSETB vector contains the T7 promoter which can be induced by isopropyl-β-D-thiogalactopyranoside (IPTG) and therefore by inserting the desired gene downstream of this promoter, the gene can be expressed in E. coli. In addition, DNA inserts were positioned downstream and in frame with a sequence that encodes an N-terminal fusion peptide. This sequence includes (in 5' to 3' order from the N-terminal to C-terminal), an ATG translation initiation codon, a series of six histidine residues that function as a metal binding domain in the translated protein, the Anti-Xpress epitope, and the enterokinase cleavage recognition sequence.

The original pRSETB was primarily used for the insertion of the gene encoding the Green Fluorescent Protein (GFP). The GFP gene was fused to the pRSETB vector using the BamHI and HindIII restriction sites located at the multiple cloning site (MCS) as can be seen in FIG. 5. This construct for the expression of GFP served as control for the experiments together with the empty pRSETB vector.

Cloning the GFP gene to the pRSETB vector inserted an additional SalI restriction site at the 3' of the GFP gene and together with the BamHI site located at the 5' of the GFP gene served as sites for cloning H64MUT. The BamHI and SalI sites were introduced to the 5' and 3' respectively of the H64MUT coding sequence by the use of PCR. The 552 amino acid open reading frame of the H64MUT clone was amplified with the pfu DNA polymerase (Stratagene) and oligonucleotides (containing the BamHI and SalI sites) AAP339 (5'-CGGATCCGGCATC-GTCTTCTCGGGC- 3'(SEQ ID NO: 8)) and AAP334 (5'-CGTCGACCAACTCCACTTCCGG-TAGTC- 3' (SEQ ID NO: 9)) according to the manufacturers instructions. The PCR product was cloned into PCR-script vector (Stratagene), cut out with BamHI and SalI and further inserted (as a translation fusion) into the corresponding restriction sites in the pRSETB vector. H64NORS was cloned in a similar way.

Bacterial Expression and Partial Purification Using the His Tag Columns.

The pRSETB vector harboring the H64MUT or H64NORS was used to transform E. coli strain BL21 Gold DE3 pLysE (Stratagene) as described by the manufacturer. For bacterial expression typically 1 ml of overnight liquid culture grown at 37° C. in Luria Broth (LB) medium (10 g/l tryptone, 5 g/l yeast extract, 5 g/l NaCl) supplemented with 100 mg/l ampicillin was diluted 50 times in the same medium and grown until the $OD_{600}$ reached 0.4 (at 37° C.). At this stage IPTG was added to a final concentration of 1 mM in order to induce expression. After overnight growth at 16° C. the cells were harvested by centrifugation at 4000×g for 15 min. Pellet and a sample from the supernatant were kept for SDS gel analysis. The cells were further processed as described by the Ni-NTA Spin Columns manufacturers (QIAGEN) for protein purification under native conditions. First elute from the column (200 µl) was further used for enzymatic activity assays.

Example 5

Cloning and Characterization of SOS Genes from Wild and Cultivated Strawberry

Cloning of the SOS cDNA from Cultivated Strawberry (SOSA) and its Homolog from the Wild Strawberry (SOSV)

Figure 6:
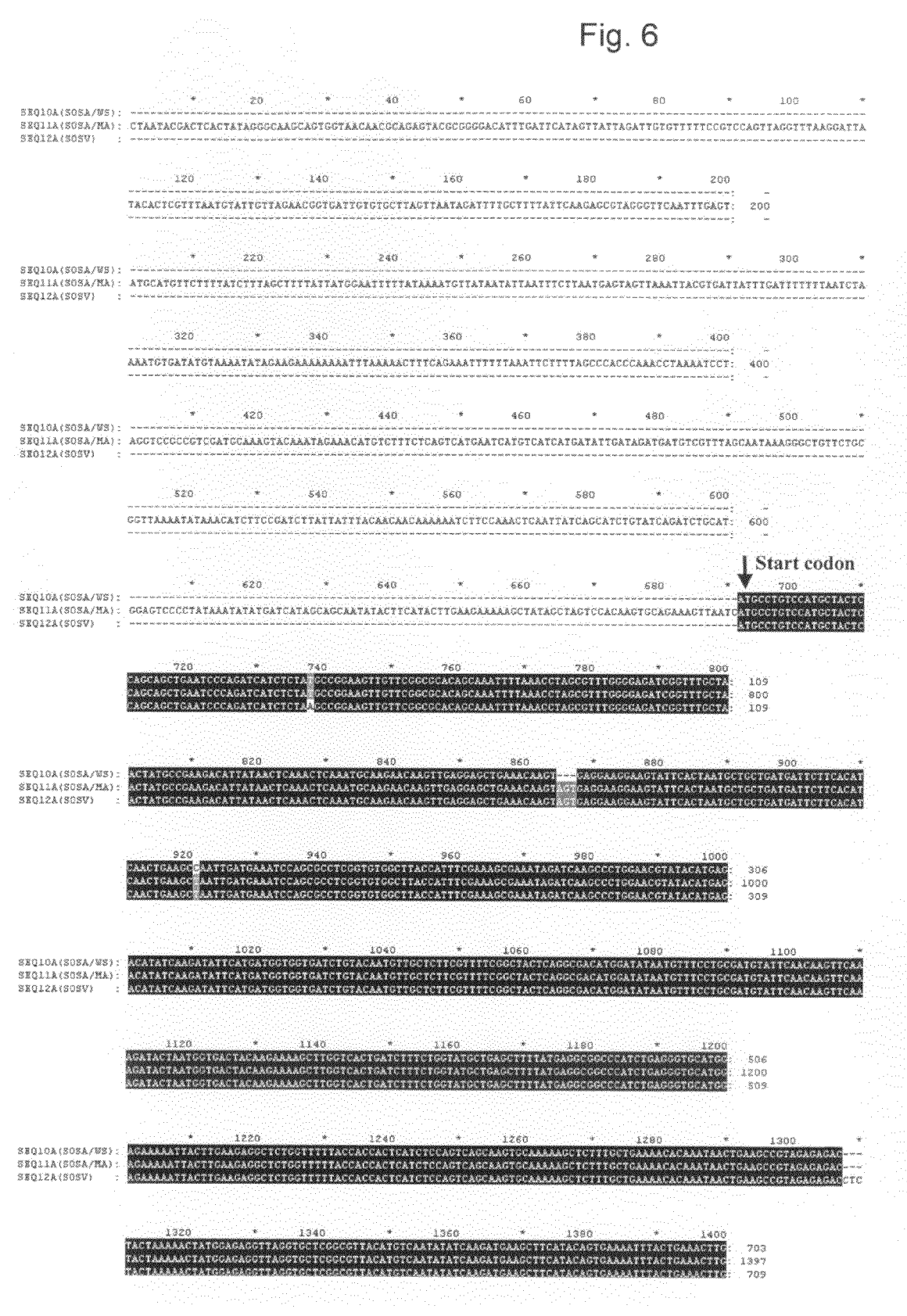
Figure 6:
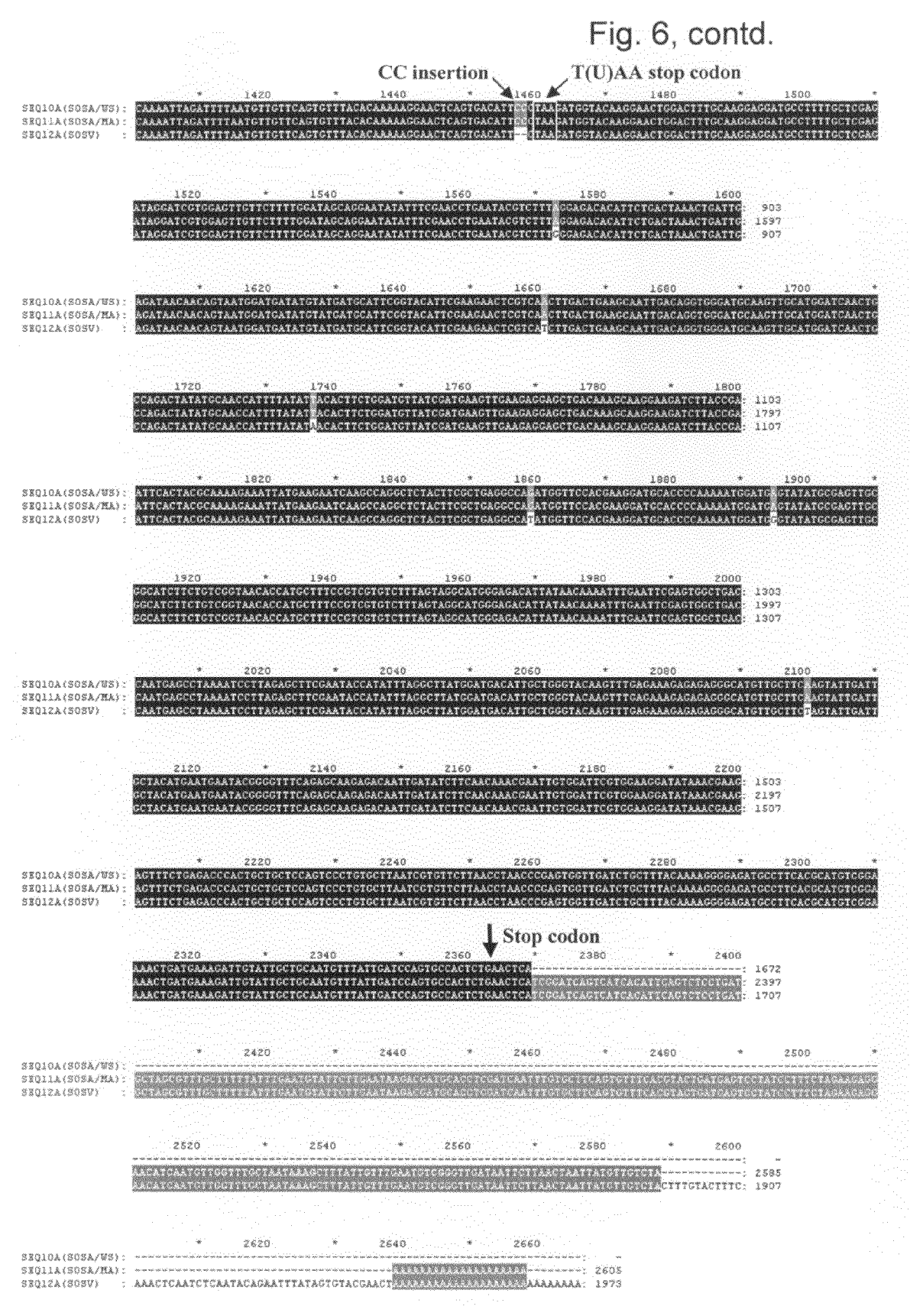
Figure 7:
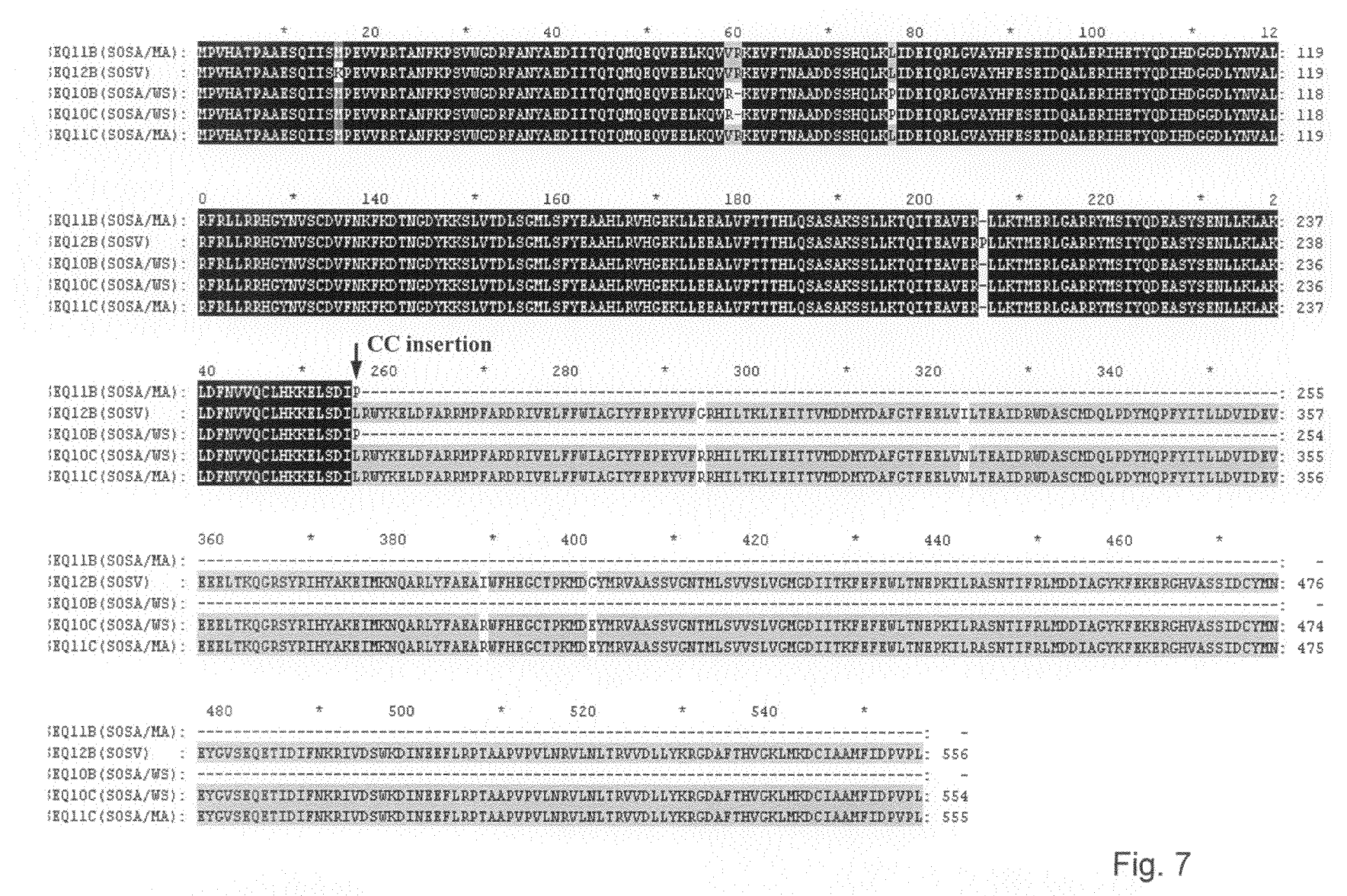

For cloning the SOSA(MA) cDNA from the cultivated strawberry CV Elsanta, we designed an oligonucleotide on a published sequence of a sesquiterpene cyclase from the wild strawberry (Nam et at. Plant Mol. Biol. 39: 629-636, 1999). The oligonucleotide (AAP 272, 5'- GATGATATGTATGAT-GCATTCGG- 3' (SEQ ID NO: 10)) was used to perform a 3' RACE reaction using the RACE kit (Clontech) and a 991 bp fragment was cloned. For cloning the full length cDNA we performed a 5'RACE reaction using an oligonucleotide designed on the 3' UTR of the cDNA (AAP283, 5'-GAAAG-GATAGGCTCATCAGTACGTG-3') (SEQ ID NO: 11)). The entire SOSA(MA) cDNA cloned is 2605 bp long. We however could not identify an ORF encoding a protein longer then 255 aa, which is less then a half of a typical terpene synthase. Therefor a second attempt to clone a cDNA with a longer ORF was performed. Using oligonucleotides based on the SOSA(MA) sequence, one located on the beginning of the ORF (AAP325, 5'-CGGATCCGCCTGTCCATGC-TACTCC- 3' (SEQ ID NO: 12)) and the other on the UTR (AAP341, 5'CGTCGACTGAGTTCAGAGTGGCACTGG-3' (SEQ ID NO: 13)), a second full-length SOSA cDNA was isolated by the means of PCR on the cultivated strawberry cDNA [termed SOSA(WS)]. Sequencing SOSA(WS) revealed that as for SOSA(MA) it contains a truncated ORF. We decided to clone the full length SOS homolog from the wild strawberry in order to identify the cause for such a truncation in the cultivated genes ORF. Cloning of the wild SOS homolog was performed by 3'RACE reaction using an oligonucleotide designed on the SOSA(MA) ORF (AAP325, see above). The full length SOS homolog from the wild strawberry (SOSV) is 1973 bp long and contains a ORF encoding a 556 aa long protein. Aligning SOSA(MA), SOSA (WS) and SOSV nucleic acid sequences revealed minor changes in the ORF (see FIG. 6). We could however identify the basis of the truncation in the cultivated SOS genes which was an insertion of two cytosine nucleotides causing a frame shift followed by a stop codon (see FIG. 6). Removing the CC insertion from the SOSA(WS) and SOSA(MA) genes results in the formation of ORFs encoding 554 and 555 aa respectively (FIG. 7).

PCR on Cultivated and Wild Strawberry Genomic DNA

Figure 8:
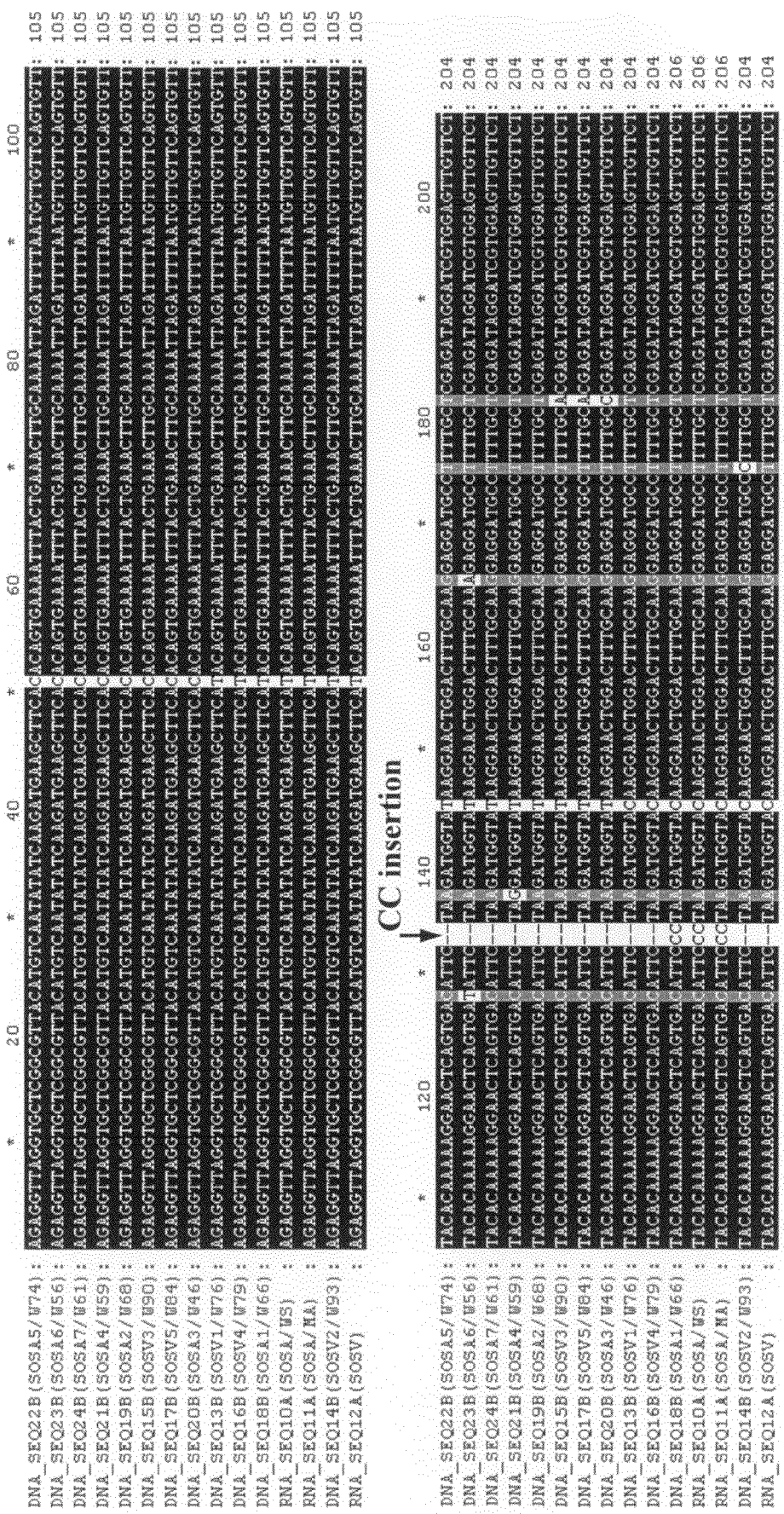
FIG. 8: Nucleic acid sequence alignment of the different SOS fragments obtained by PCR on genomic DNA and the same regions in cDNAs isolated from wild and cultivated strawberry. The source of the fragment is marked in the left side of each sequence name. Black background corresponds to identical residues in all fifteen sequences and gray background corresponds to identity between at least twelve out of the fifteen sequences.

In order to confirm the presence of the CC frame shift, causing a truncation in the cultivated strawberry SOS genes we analyzed the existence of the insertion at the DNA level. PCR on both wild and cultivated strawberry genomic DNA was performed using two oligonucleotides located from both sides of the place of insertion (AAP345, 5'-AGAGGTTAG-GTGCTCGGCGTTAC- 3' (SEQ ID NO: 14)) and the reverse oligonucleotide, AAP346, 5' GAACAACTCCACGATC-CTATCTC- 3' (SEQ ID NO: 15). The expected amplified DNA fragment was 200 bp. PCR products at the size of 300 bp were obtained from both reactions using the wild and cultivated DNA. We sequenced 20 and 15 fragments from the cultivated and wild strawberry reactions respectively. All fragments contained an intron of approximately 100 bp. Sequence alignment of all fragments revealed 7 different sequences from the cultivated and 5 from the wild. FIG. 8 shows an alignment of all fragments of the SOS genes both from the wild and cultivated strawberry obtained either from RNA (the different cDNAs) or from DNA. Among the cultivated fragments we could identify 2 fragments which showed the CC insertion while the other 5 did not contain it. On the other hand no fragment in the wild strawberry could be detected that contained the frame shift mutation.

Analysis of SOS Expression in Ripe Cultivated and Wild Strawberry Fruit

Figure 9:
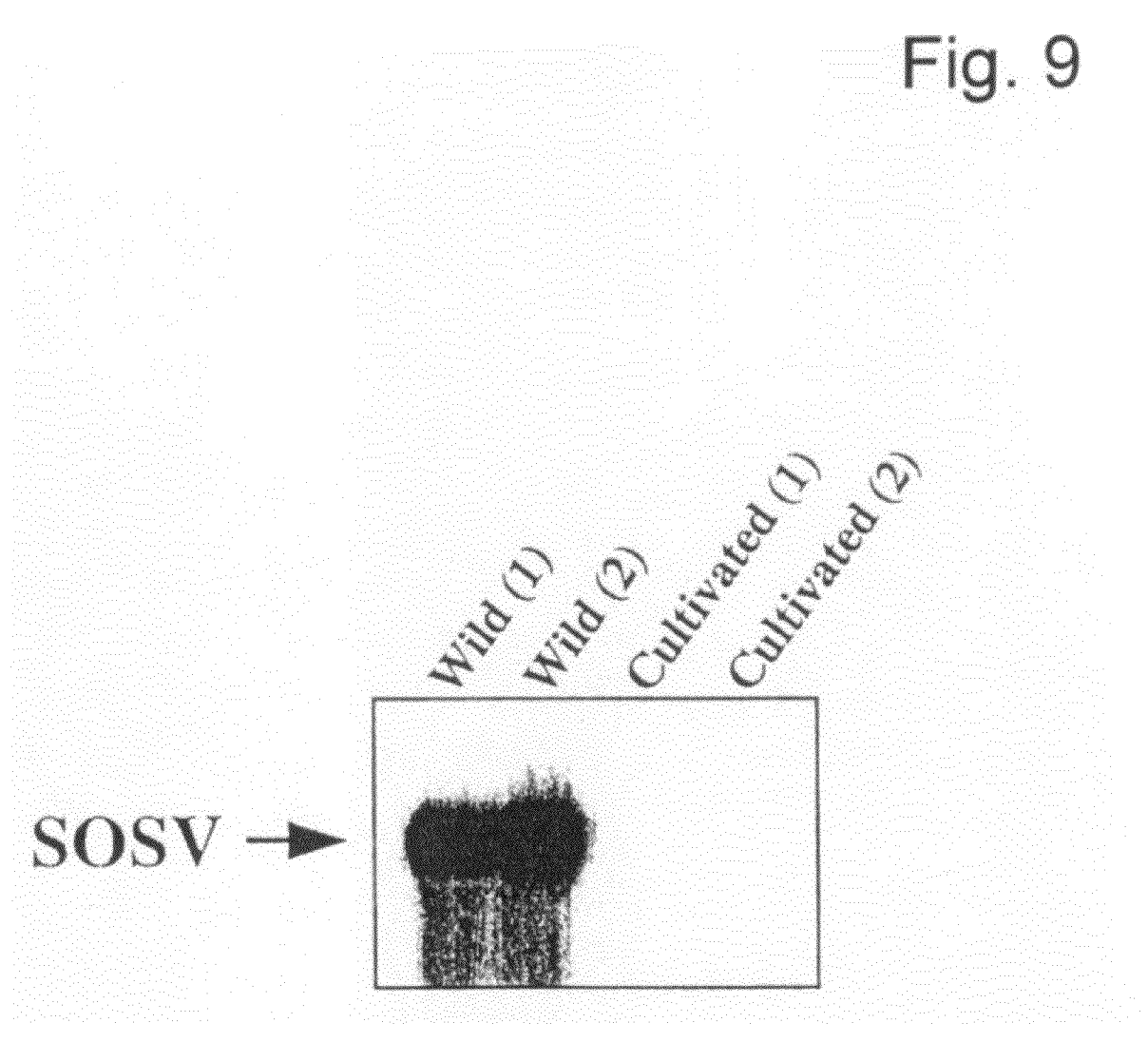

Using the SOSV cDNA as a probe we analyzed SOS gene expression in two different wild and cultivated cultivars (FIG. 9). The SOSV cDNA could be used for hybridization with blots containing RNA from both wild and cultivated cultivars since the SOSA genes and SOSV share nearly 99% identity at the nucleic acid level (in the ORF region). Hardly any expression could be detected in the cultivated cultivars while strong expression could be detected in the wild cultivars. The SOSA probe was also used for hybridizing blots with RNA extracted from different cultivated (*Elsanta*) fruit developmental stages, but just weak signal could be detected after long exposure. Nam et al., (1999) were also not able to detect expression of the partial cDNA homolog of SOS with RNA derived from different fruit developmental stages of the cultivated strawberry. Expression in different wild strawberry plant tissues was restricted to the fruit, specifically to the red ripe stage.

Cloning and Expression of SOSV and SOSA in *E. coli*

Both the SOSA and SOSV coding regions were used for the formation of a recombinant protein in *E.Coli* cells. The entire ORF of SOSA cDNA although truncated was expressed in order to serve as a negative control for the enzymatic assays. Similar to the cloning of H64MUT the BamHI and SalI restriction sites at the 5' and 3'of the GFP gene respectively served as sites for the cloning of SOSA and SOSV ORFs into the pRSETB expression vector. The BamHI and SalI sites were introduced to the 5' and 3' respectively of the wild and cultivated SOS genes coding sequence by the use of PCR. The restriction sites were added to the oligonucleotides used for PCR reaction (AAP325, 5'-CGGATCCGC-CTGTCCATGCTACTCC- 3' (SEQ ID NO: 12) and the reverse primer AAP341, 5'CGTCGACTGAGTTCA-GAGTGGCACTGG-3' (SEQ ID NQ: 13)). The PCR product was cloned into PCR-script vector (Stratagene), cut out with BamHI and SalI and further inserted (as a translation fusion) into the corresponding restriction sites in the pRSETB vector. Expression of SOSA and SOSV in *E.Coli* was performed parallel to the expression of H64MUT and under identical experimental conditions.

Example 6

Analysis of SOSA, SOSV, H64MUT and H64NORS Recombinant Enzymes

For determination of terpene synthase identity, the His-tag purified enzymes (prepared as described above under Example 4.6) were diluted 10-fold with buffer A containing 15 mM MOPSO (pH 7.0), 10% glycerol, 10 mM $MgCl_2$, 1 mM sodium ascorbate and 2 mM DTT. To 1 mL of this enzyme preparation, 40 μM of either [$^3$H]-geranyl diphosphate (GPP) or [$^3$H]-farnesyl diphosphate (FPP) were added. Assays with GPP as substrate were also supplemented with 1 mM $MnCl_2$. After the addition of a 1-mL redistilled pentane overlay, the tubes were carefully mixed and incubated for 1 h at 30° C. After the assay, the tubes were vortexed, the pentane layer was removed and passed over a short column of aluminum oxide overlaid with anhydrous $Na_2SO_4$. The assay was re-extracted with 1 mL of diethyl ether, which was also passed over the aluminum oxide column, and the column washed with 1.5 mL of diethyl ether. 100 μL of the organic extract was removed for liquid-scintillation counting in 4.5 mL of scintillation cocktail (Ultima Gold, Packard Bioscience, The Netherlands). Radio-labelled products were present in the organic extracts of:

|  | H64MUT | H64NORS | SOSV | SOSA |
|---|---|---|---|---|
| [$^3$H]-GPP | + | + | + | − |
| [$^3$H]-FPP | + | + | − | − |

Figure 10:
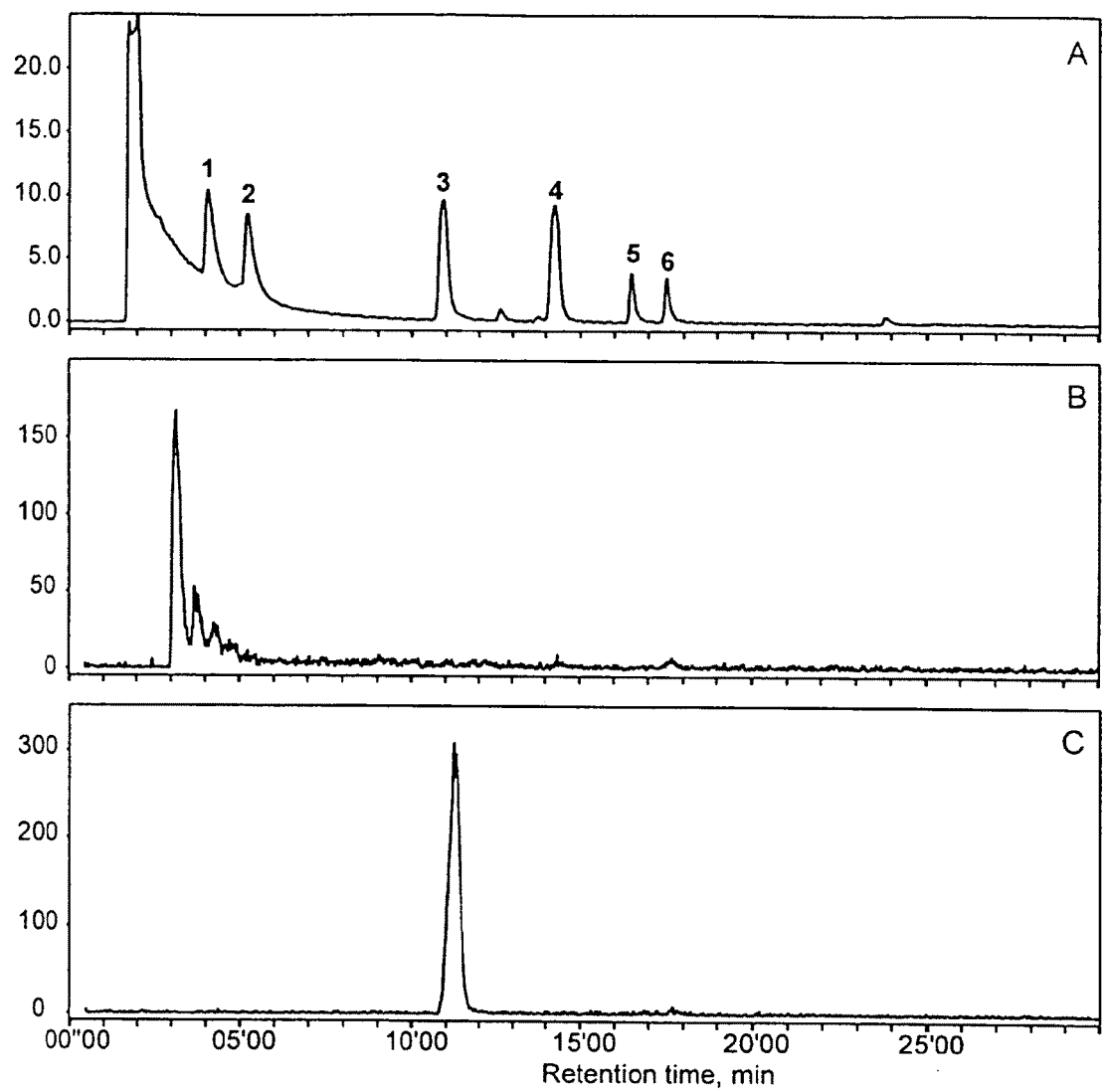
FIG. 10: Radio-GLC analysis of radio-labelled products formed from [$^3$H]-geranyl diphosphate in assays with recombinant proteins. A, FID signal showing unlabelled authentic standards of 1, β-myrcene; 2, trans-ocimene; 3, linalool; 4, α-terpineol; 5, nerol; 6, geraniol. B,C, radio-traces showing enzymatic products of recombinant proteins SOSV (B) and H64MUT (C).
Figure 11:
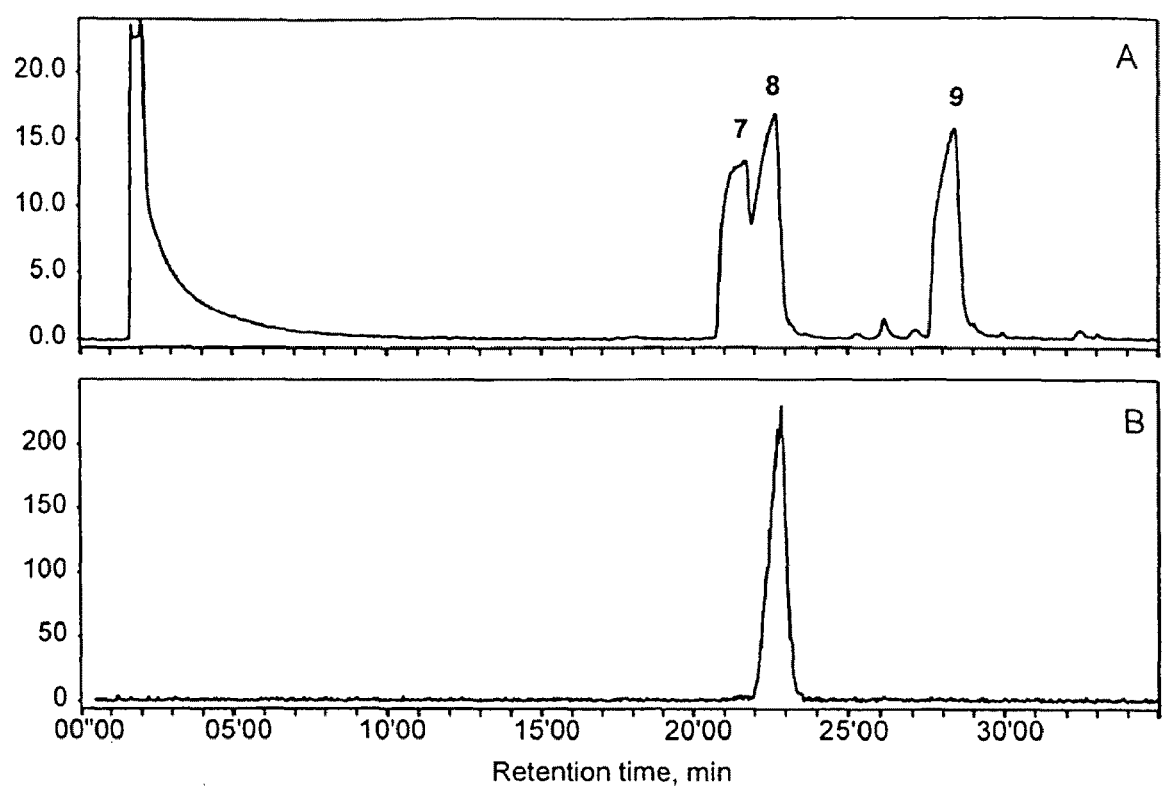
FIG. 11: Radio-GLC analysis of radio-labelled products formed from [$^3$H]-farnesyl diphosphate in assays with recombinant protein. A, FID signal showing unlabelled authentic standards of 7, cis-nerolidol; 8, trans-nerolidol; 9, trans-trans-farnesol. B, radio-trace showing enzymatic products of recombinant protein H64MUT.

Subsequently, the extracts were carefully concentrated under a stream of N2 before analysis using radio-GLC and GC-MS. Radio-GLC was performed on a Carlo-Erba 4160 Series gas chromatograph equipped with a RAGA-90 radio-activity detector (Raytest, Straubenhardt, Germany). Sample components eluting from the column were quantitatively reduced before radioactivity measurement by passage through a conversion reactor filled with platinum chips at 800° C. Samples of 1 μL were injected in the cold on-column mode. The column was a fused silica capillary (30 m×0.32 mm i.d.) coated with a film of 0.25 μm of polyethylene glycol (EconoCap EC-WAX, Alltech Associates) and operated with a He-flow of 1.2 mL $min^{-1}$. The oven temperature was programmed to 70° C. for 1 min, followed by a ramp of 5° $min^{-1}$ to 210° C. and a final time of 10 min. About 20% of the column effluent was split with an adjustable splitter to an FID (temperature 270° C.). The remainder was directed to the conversion reactor and radio detector. $H_2$ was added prior to the reactor at 3 mL $min^{-1}$, and $CH_4$ as a quench gas prior to the radioactivity detector (5 mL counting tube) to give a total flow of 36 mL $min^{-1}$. Radio-GLC analysis gave the following results:

the SOSV and H64MUT and H64NORS recombinant proteins catalysed the formation of radio-labelled products from [$^3$H]-GPP (FIG. 10). For the SOSV protein a number of radio-labelled product peaks were visible in the retention time area of olefinic monoterpenes (FIG. 10B). The major radio-labelled product did not co-elute with any of the added unlabelled reference compounds, but one of the minor radio-labelled peaks seemed to co-elute with the reference β-myrcene. For the H64MUT recombinant enzyme the single radio-labelled product co-eluted with linalool (FIG. 10C).

with [$^3$H]-FPP as substrate scintillation counting showed that neither the SOSA nor the SOSV recombinant protein catalysed any radio-labelled product formation. The H64MUT protein catalysed the formation of a radio-labelled product which radio-GC analysis showed to be one single product, co-eluting with trans-nerolidol (FIG. 11).

Figure 12:
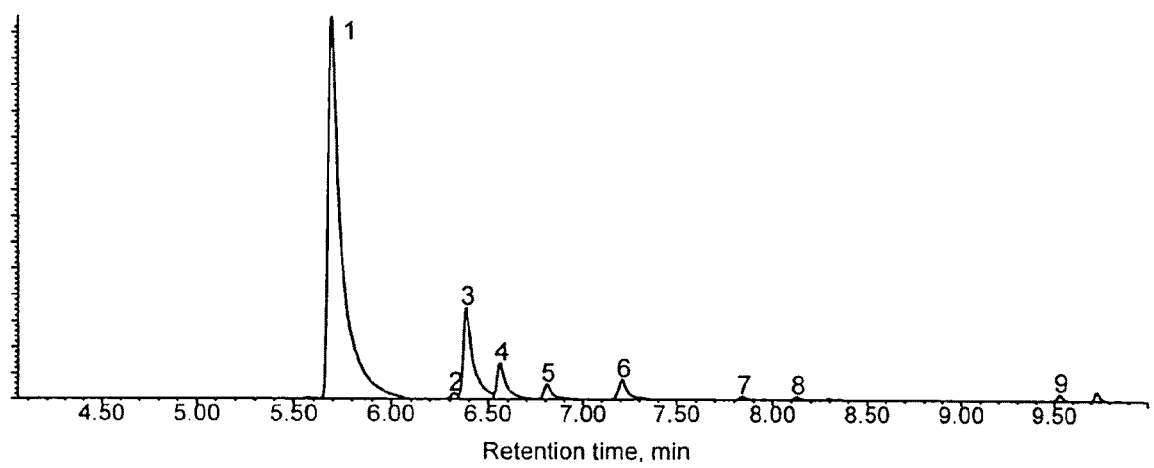
FIG. 12: GC-MS analysis on an HP5-MS column of products formed from geranyl diphosphate in assays with recombinant SOSV protein. Peaks: 1, α-pinene; 2, β-pinene; 3, sabinene; 4, β-myrcene; 5, α-phellandrene; 6, β-phellandrene; 7, dihydromyrcenol (tentative); 8, α-terpinolene (tentative); 9, α-terpineol (tentative).
Figure 13:
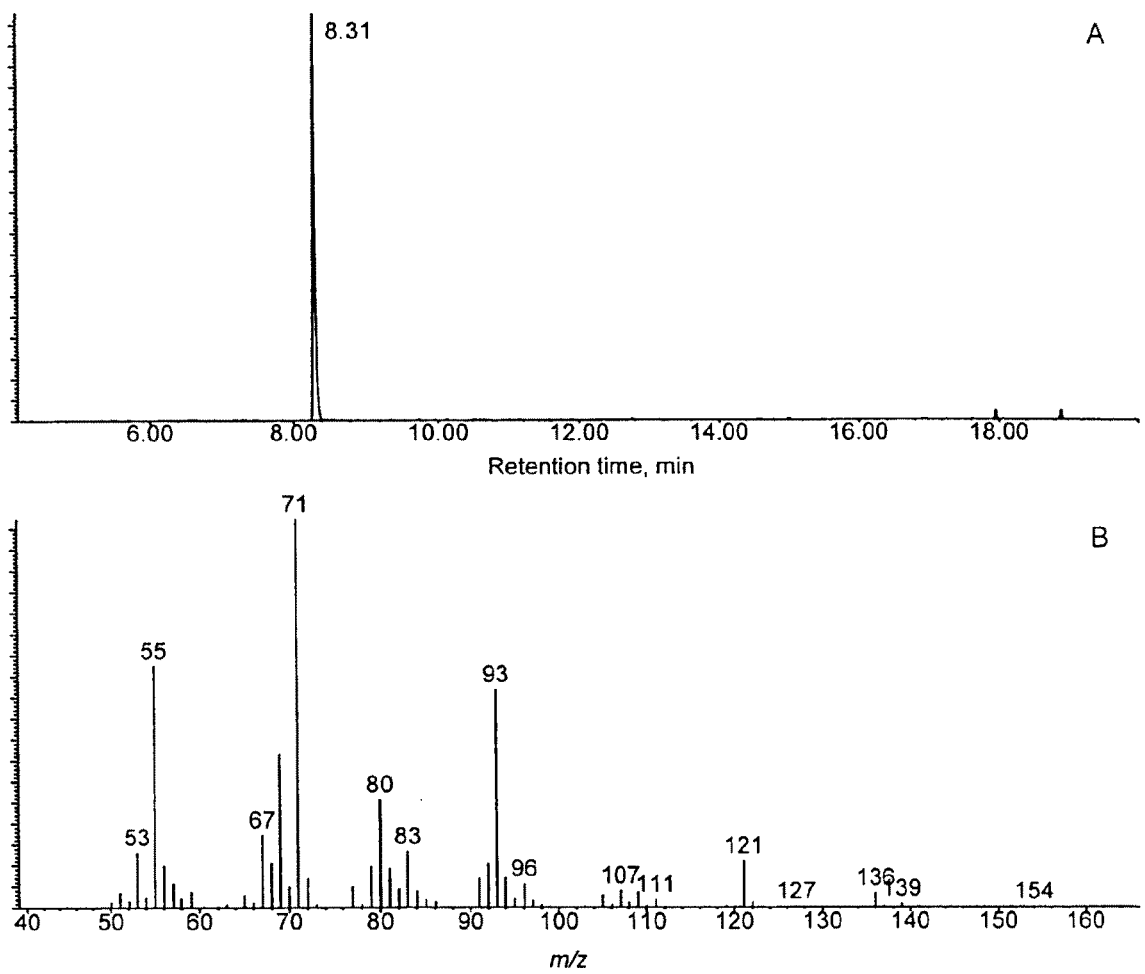
FIG. 13: GC-MS analysis on an HP5-MS column of the product formed from geranyl diphosphate in an assay with recombinant H64MUT protein. A, m/z 93 chromatogram. B, mass spectrum of the major product peak (linalool).
Figure 14:
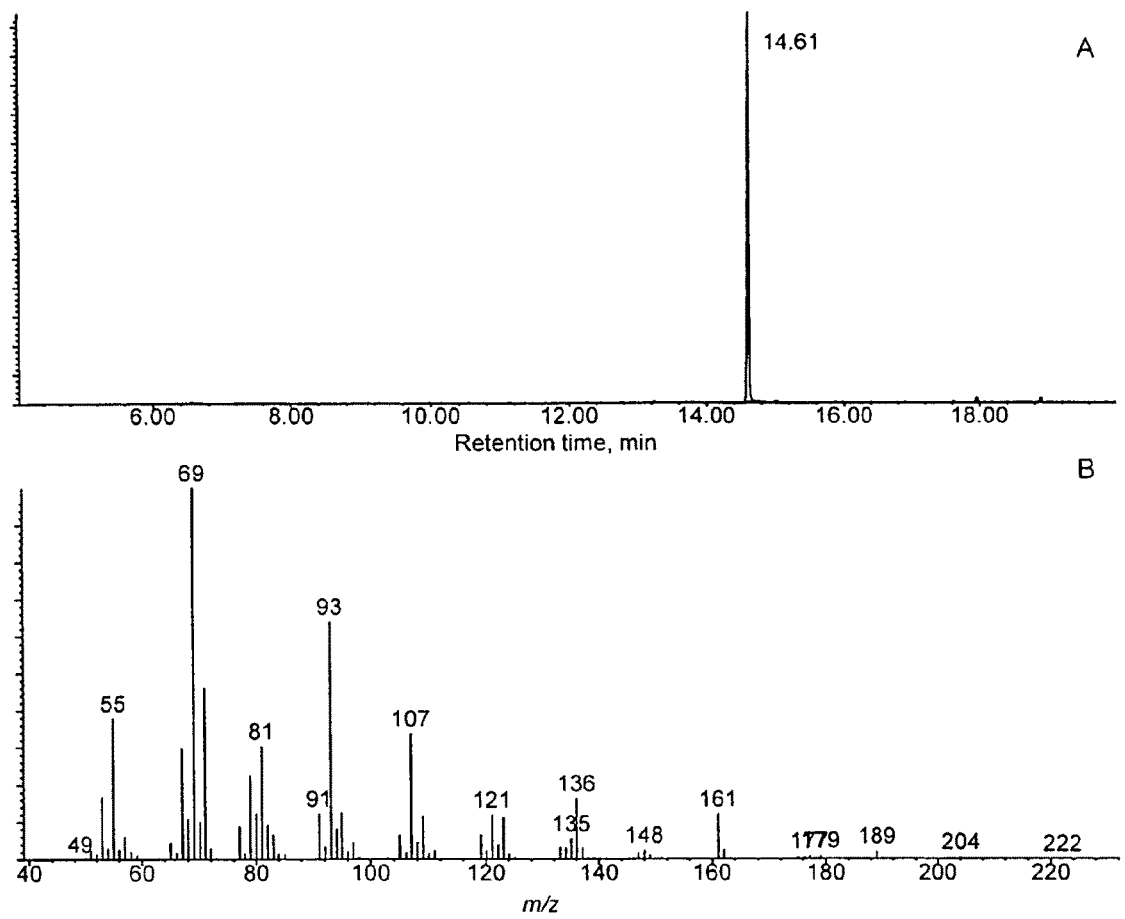
FIG. 14: GC-MS analysis on an HP5-MS column of the product formed from farnesyl diphosphate in an assay with recombinant H64MUT protein. A, m/z 93 chromatogram. B, mass spectrum of the major product peak (nerolidol).

The samples were also analysed by GC-MS using a HP 5890 series II gas chromatograph equipped with an HP5-MS column (30 m×0.25 mm i.d., 0.25 μm df) and HP 5972A Mass Selective Detector (Hewlett-Packard). The oven was programmed at an initial temperature of 45° C. for 1 min, with a ramp of 10° C. min$^{-1}$ to 280° C. and final time of 5 min. The injection port (splitless mode), interface and MS source temperatures were 250, 290 and 180° C., respectively, and the He inlet pressure was controlled by electronic pressure control to achieve a constant column flow of 1.0 mL min$^{-1}$. Ionization potential was set at 70 eV, and scanning was performed from 48-250 amu. The m/z 93 chromatogram of SOSV recombinant protein catalysed products from [$^3$H]-GPP again shows several peaks (FIG. 12) as was also seen in the radio-GC chromatogram (FIG. 10B). The compounds were identified as α-pinene (major compound), β-pinene, sabinene, β-myrcene, α-phellandrene, β-phellandrene, dihydromyrcenol (tentative), α-terpinolene (tentative) and α-terpineol (tentative). This shows that SOSV is not a sesquiterpene synthase as is claimed for a fragment nucleic acid isolated by Nam et al (*Plant Mol Biol*, 39: 1999-2002, 1999) and Marty (EMBL Database, Accession number AJ001452), but a monoterpene synthase, viz. an α-pinene synthase. Nam et al and Marty had isolated just a fragment of the cDNA and for example missed the 5'-side. Hence, the authors were also not able to functionally express the protein and identified it wrongly as a sesquiterpene synthase. The GC-MS chromatograms of the incubations of the H64MUT protein with [$^3$H]-GPP or [$^3$H]-FPP show the presence of one terpene product for each substrate and comparison of the retention times and mass spectra with authentic standards confirmed that from [$^3$H]-GPP linalool was produced (FIG. 13) and from [$^3$H]-FPP trans-nerolidol (FIG. 14). Analysis using enantioselective columns showed that both linalool and nerolidol were of the S configuration, so (3S)-(E)-nerolidol and S-linalool. Characterisation. The H64NORS encoded and his-tag purified protein was shown to have an optimum pH of around 7 for both GPP and FPP. For both substrates there was no preference for Mn$^{2+}$ (at 1 mM) or Mg$^{2+}$ (at 10 mM) and therefore a combination of the two was routinely used. The affinity of the enzyme for the two substrates strongly differed. The Km for FPP was 3.2 µM which is in the expected range for sesquiterpene synthases. However, for GPP the Km was >50 µM which is highly unusual. However, the apparent Vmax for GPP was much higher than for FPP.

Example 7

Analysis of Targeting

Figure 15:
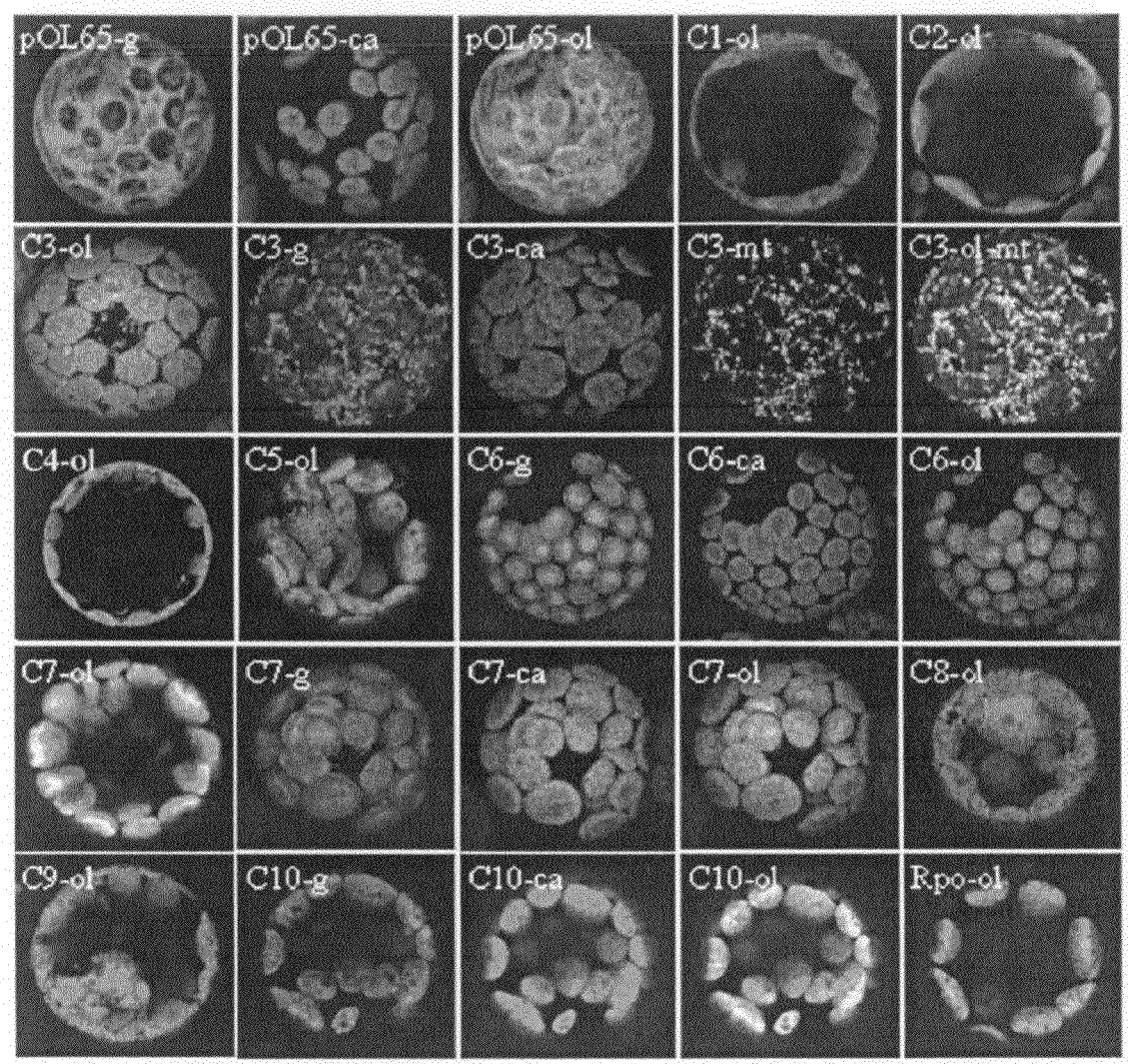
FIG. 15: Transient GFP expression of fusion proteins in tobacco protoplasts. g, GFP; ca, chlorophyll auto-fluorescence; mt, MitoTracker (mitochondrial stain); ol, overlay of chlorophyll auto-fluorescence image and GFP image; ol-mt, overlay of chlorophyll auto-fluorescence image, GFP image and Mitotracker image. 10 different constructs were made (C1-C10) to study fragments derived from H64NORL (C1, C2), H64TAR4 (C3, C4, C5) and H64VES (C7, C8, C9). See FIG. 16 for a schematic representation of the different constructs made and used for the localization studies. C6 shows localization of fusion of a citrus limonene synthase 5' end with GFP. C10 is a fusion of the H64VES region between the two Methionine residues and the region down stream of the second Methionine from H64NORL. pOL65 is the original vector, containing only GFP and was used to insert all fragments for fusion with the GFP. Rpo-ol is a positive control for plastidic targeting signal. Chloroplasts are on average 5 micrometer in size while mitochondria are 1 micrometer in size. pOL65, C1, C2, C4, C5, C8 and C9 all show cytosolic localization. C3 shows dual plastidic and mitochondrial localization. C6, C7, C10 and Rpo-ol show plastidic subcellular localization.
Figure 17:
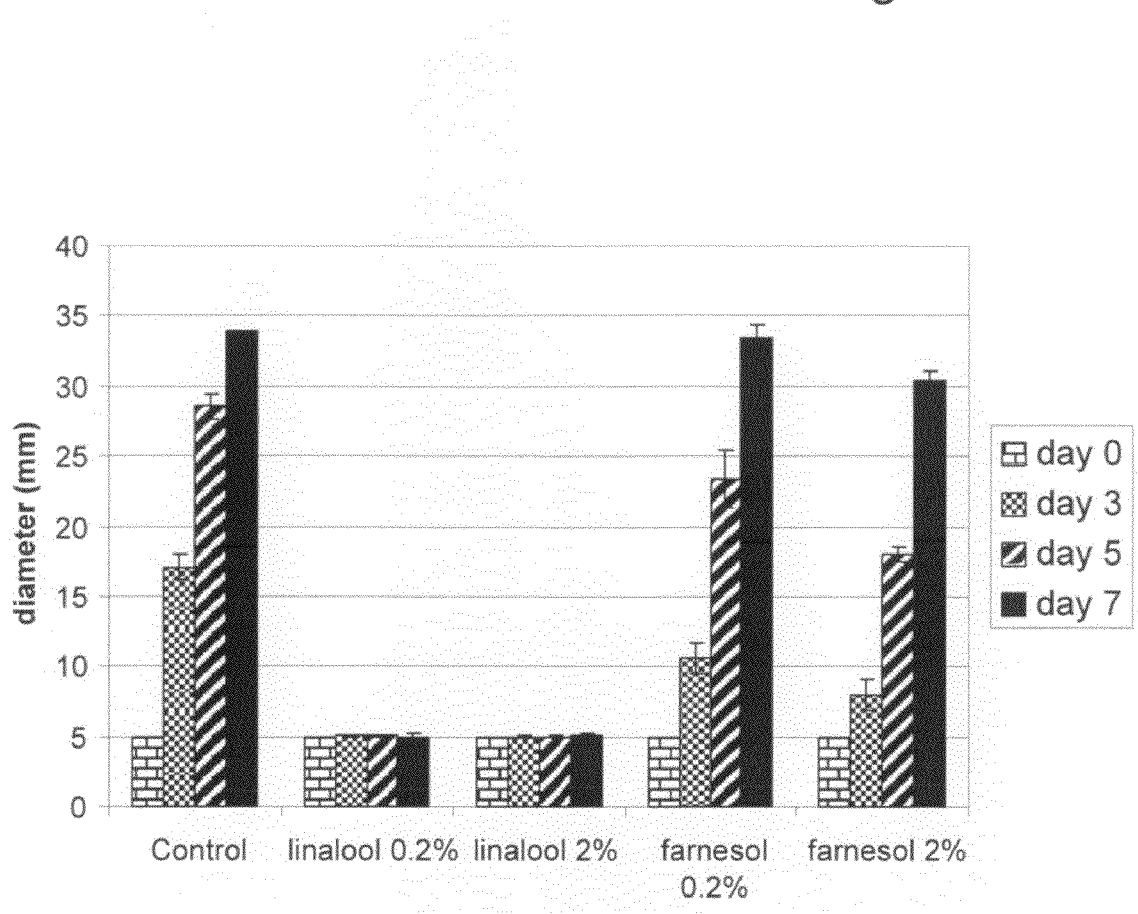
FIG. 17: Comparison of effects of farnesol and linalool present in the growth medium on mycelium growth of *Phytophthora infestans*.
Figure 18:
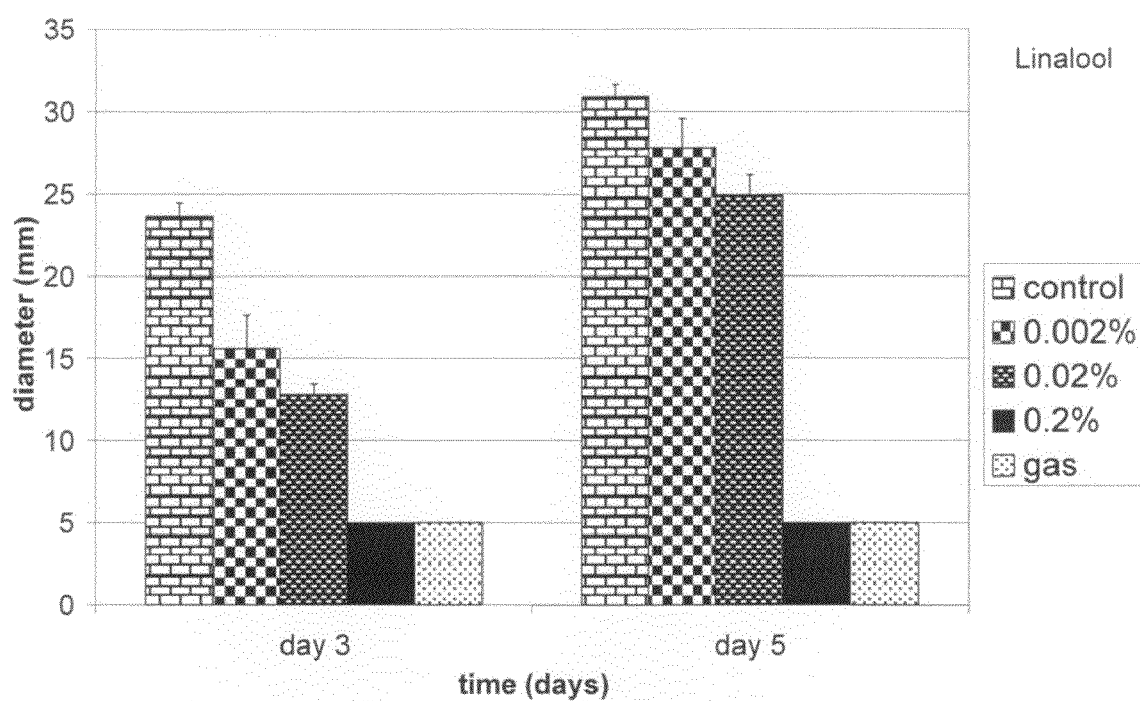
FIG. 18: Dose-response data of effects of linalool present in the growth medium or the vapour phase on mycelium growth of *Phytophthora infestans*.
Figure 19:
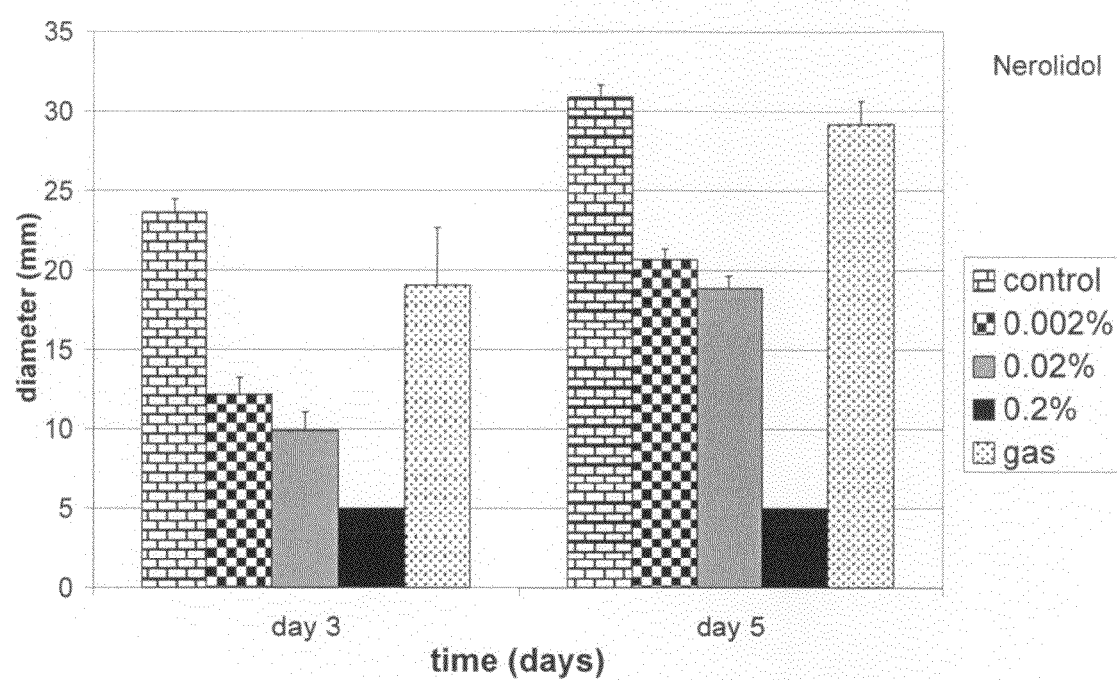
FIG. 19: Dose-response data of effects of nerolidol present in the growth medium or the vapour phase on mycelium growth of *Phytophthora infestans*.
Figure 20:
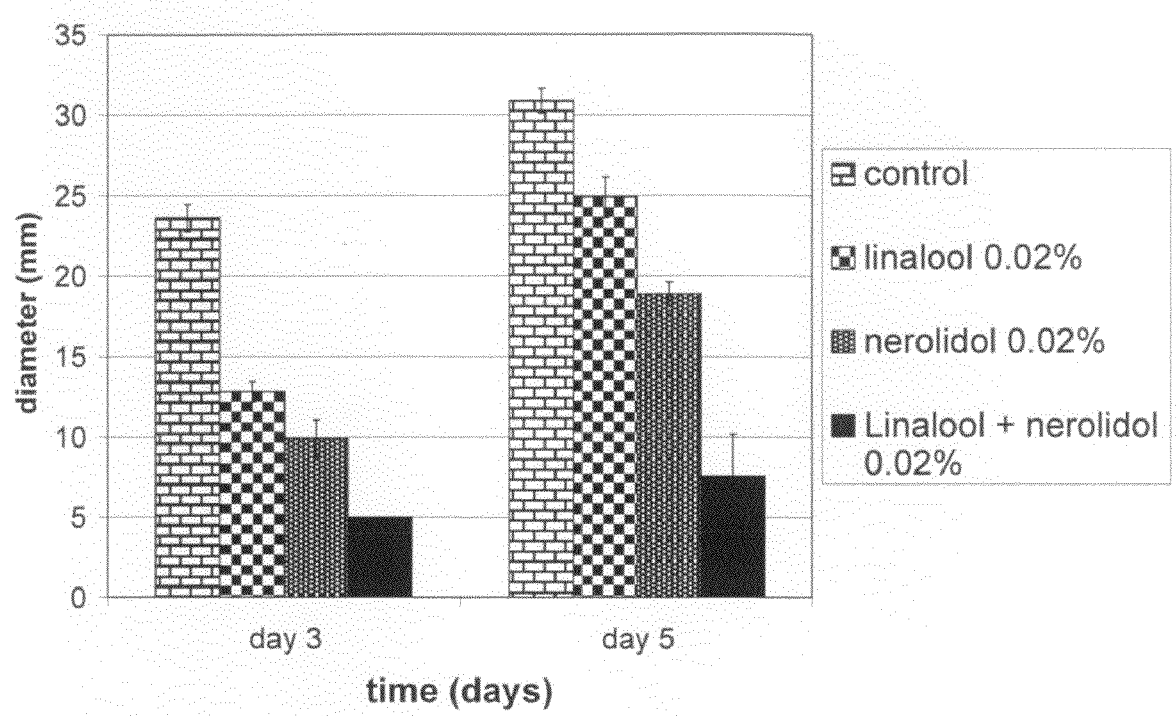
FIG. 20: Dose-response data of effects of linalool and nerolidol present in the growth medium alone and in combination on mycelium growth of *Phytophthora infest using the recombinant enzymes produced in *E.coli* show that the capability of the cultivated variety to form nerolidol was acquired by removing (by deletions and translation stop) the targeting signal to the plastid [were the substrate for monoterpene biosynthesis is available (GPP)] and by directing the translation start to the downstream AUG codon. However, linalool in the cultivated varieties may also be formed by enzymes encoded by genes similar to H64TAR2, H64TAR4 and H64TAR6 which contain a proper targeting signal with no stop and therefore their protein products are directed to the plastid for forming linalool. If GPP is present in the cytosol, then linalool could also be produced there by an enzyme encoded by a cytosolically expressed eDNA. We can not exclude that translation in H64TAR2, H64TAR4 and H64TAR6 may also start from the downstream AUG codon (the one downstream from the RR motif and not the additional AUG codon present just prior the RR motif) and this will result in the formation of nerolidol as well. However, since cultivated varieties like the ones used in this study are mostly octaploids it is likely that evolutionary processes as polyploidity allows the plant to form an additional (mutated) gene from an existing gene and to produce an additional beneficial compound such as nerolidol for flavour and defense. Williams et al., (Biochemistry 1998, 37, 12213-12220) described a role for the tandem arginines present in the N-terminal of monoterpene synthases in the unique diphosphate migration step accompanying formation of the intermediate 3-s-linalyl diphosphate and preceding the final cyclization reaction catalyses by the monoterpene synthases. This RR motif is present in H64TAR2, H64TAR6, and H64VES and this might explain the formation of linalool by this genes encoding enzymes. However, the H64MUT recombinant protein does not contain the RR motif but catalyses the formation of both nerolidol and linalool. This might implicate other residues between the RR motif location and the down stream AUG as functioning to determine whether monoterpene will be formed. This motif contain 12 amino acids: N-termini-DSLLPSSITIKP (SEQ ID NO: 1).
Figure 21:
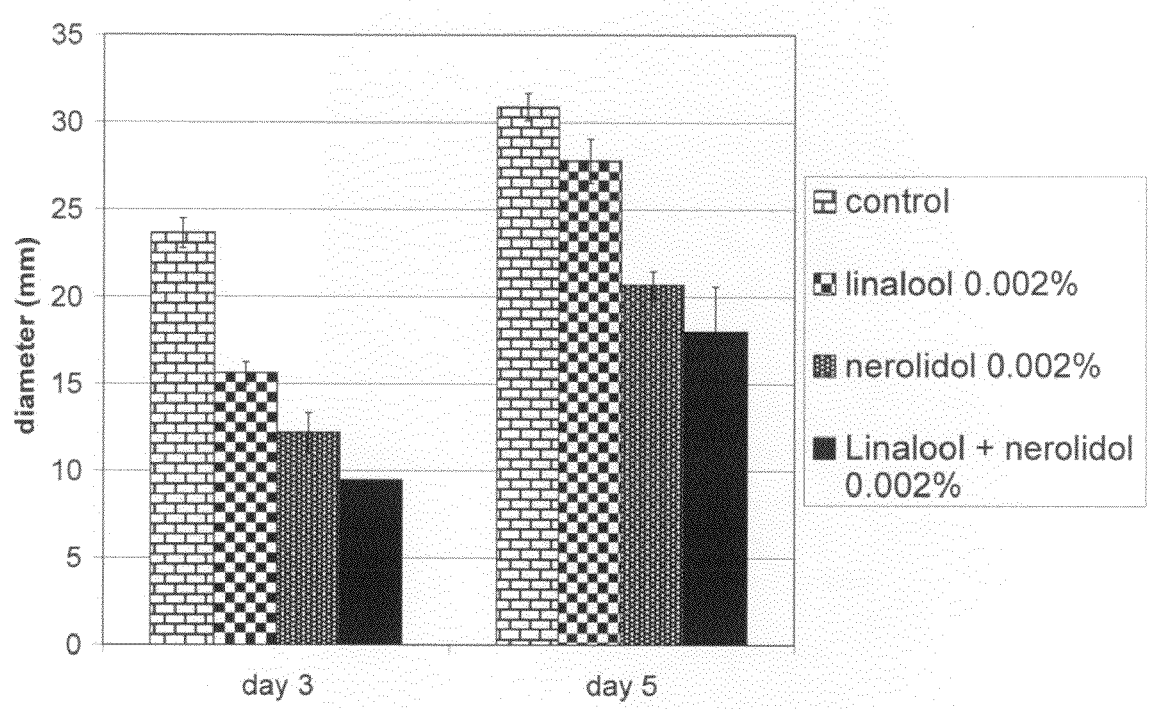
Figure 22:
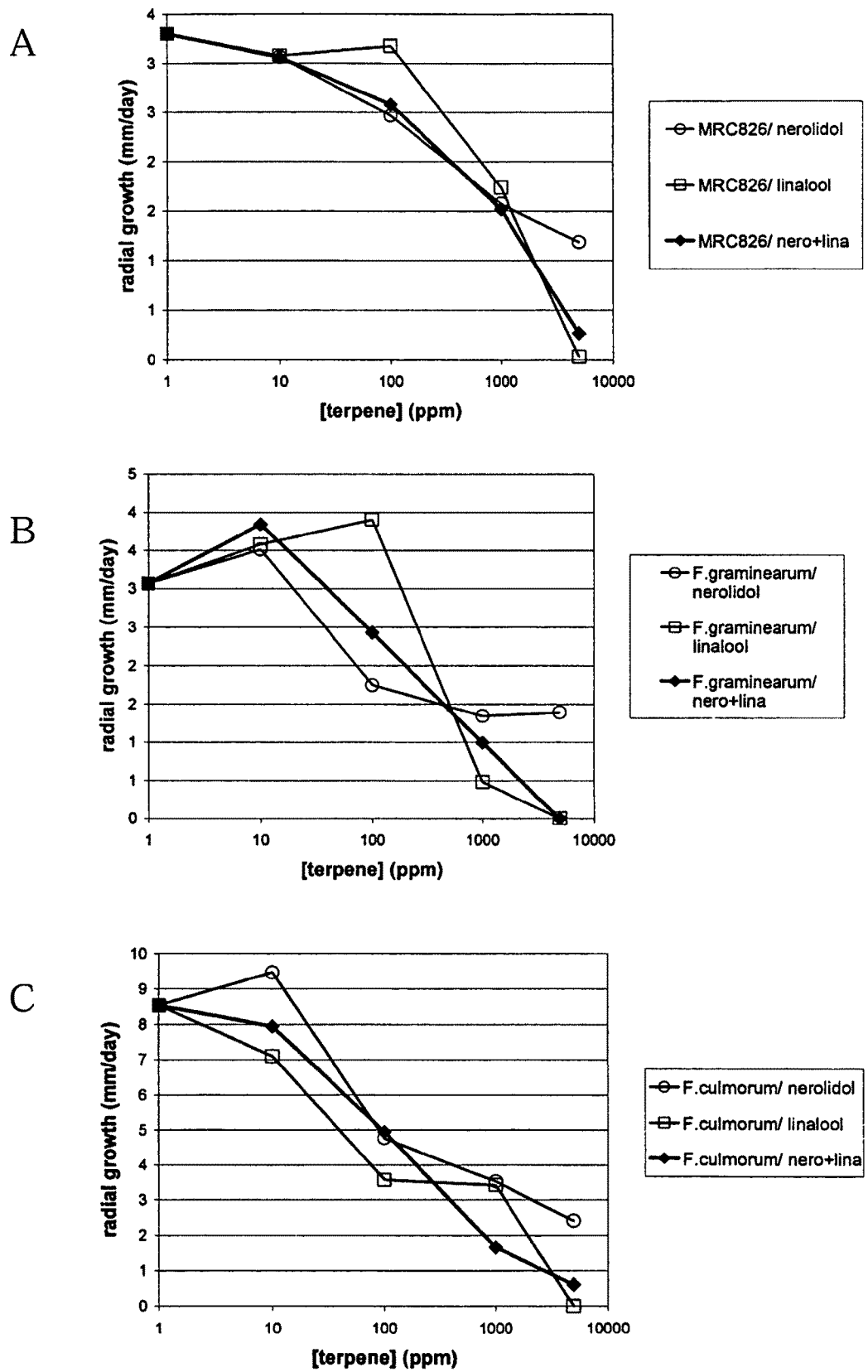
Figure 23:
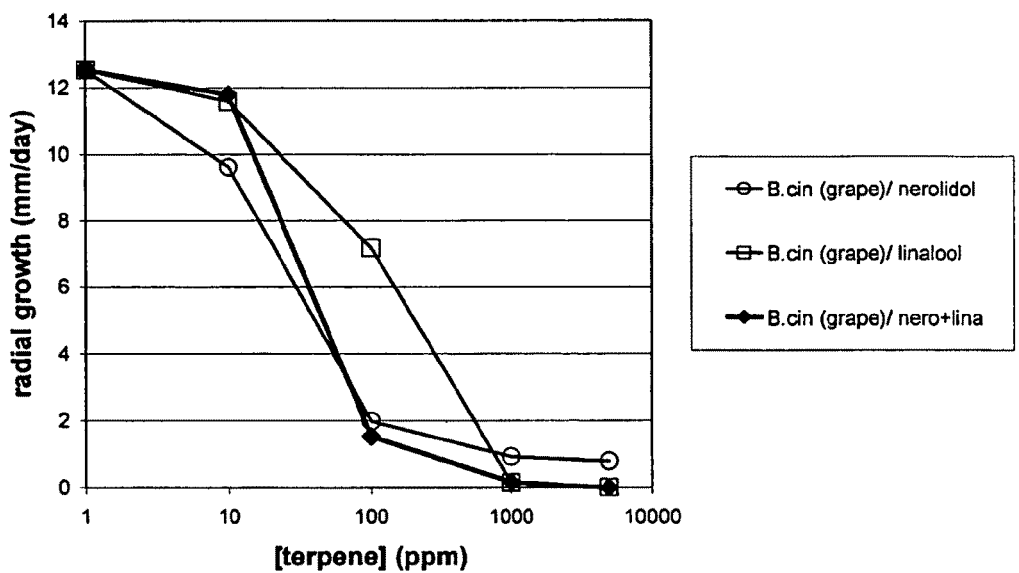
Figure 23:
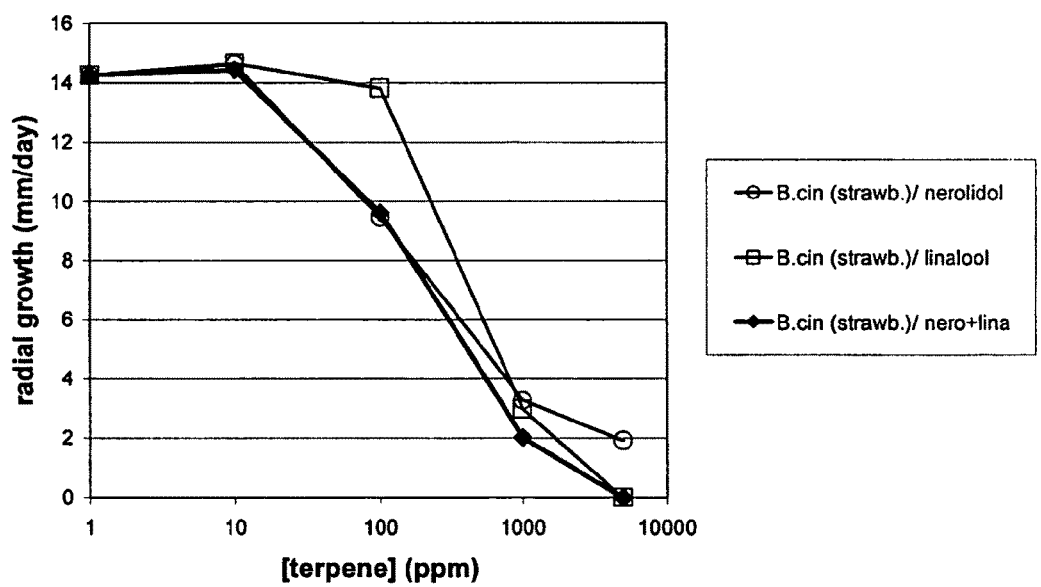
Figure 24:
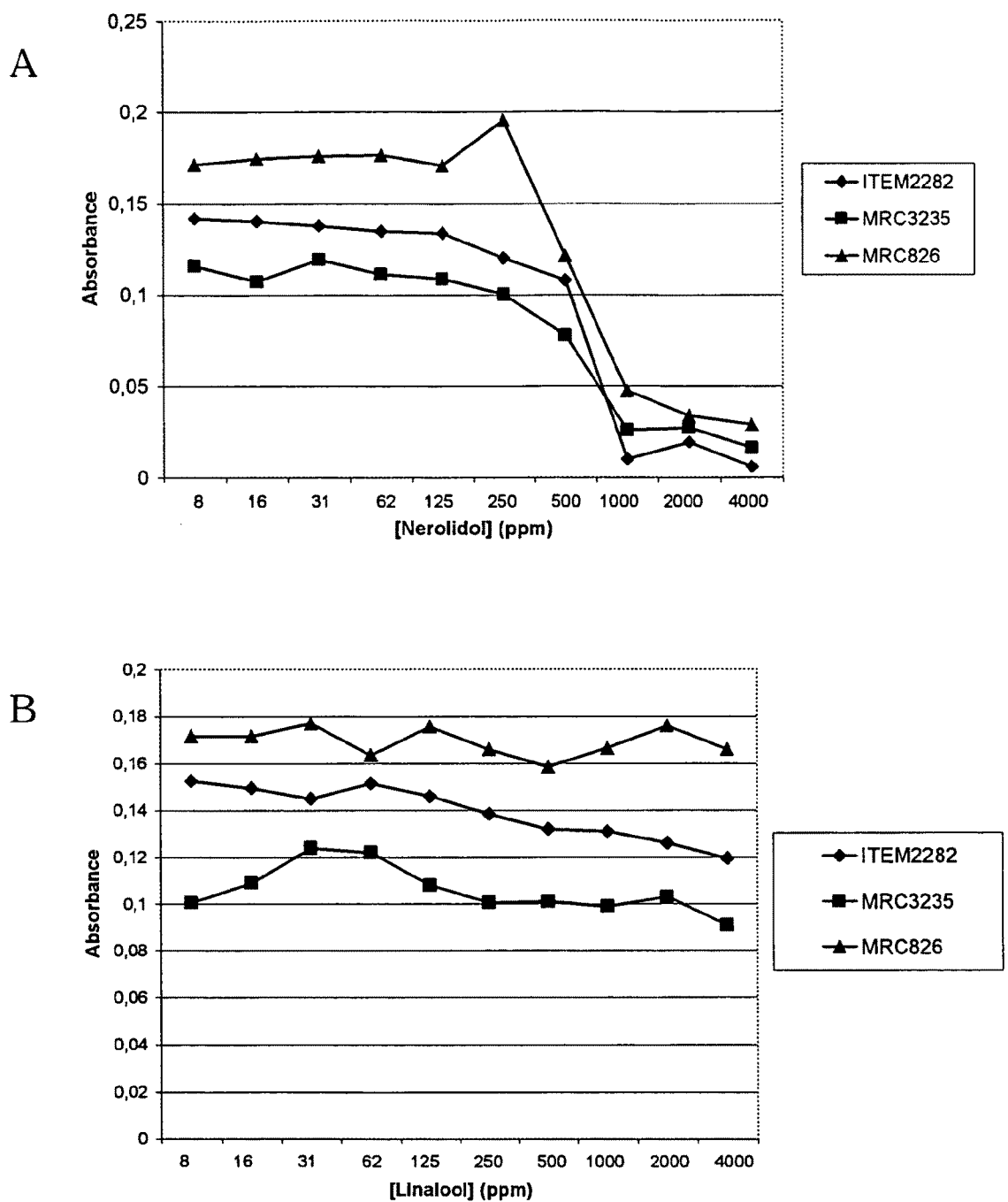

We used transient expression assays using the Green Fluorescent Protein (GFP) to identify the sub-cellular localization of the proteins encoded by the different nucleic acid fragments described in this invention (FIG. 15). We first constructed 13 different constructs which fused in-frame the 5'-end parts of the different genes (H64NORL, H64NORS, H64TAR4, H64VES, SOSV) to the GFP gene (FIG. 16). Different regions of the 5'-ends were used part of them included a portion from the protein itself (up to the MID motif). Expression in plants was driven by the 35S cauliflower mosaic virus promoter. Plasmid DNA from constructs was used to transform tobacco protoplasts. After transformation the protoplasts were incubated for 24 hr at 28° C. in the dark and thereafter used for the analysis of GFP transient expression and subcellular localization using confocal laser scanning microscopy. The results demonstrated that the 5'-ends of both H64TAR4 and H64VES encode a targeting signal (FIG. 15). The protein encoded by H64TAR4 is targeted to the plastids (e.g. chloroplasts) and mitochondria while the H64VES protein is targeted to the plastids (e.g. chloroplasts). H64NORL and H64NORS, which are most active in the ripe cultivated strawberry, are targeted to the cytosol. SOSV is also targeted to the cytosol, in-contrast to all monoterpene synthases described to date which are plastid localized. Thus, according to this experiment for monoterpene synthases the cytosol and not only the plastids are a possible location and in the cytosol there are high levels of GPP to synthesize the monoterpenes. For sesquiterpene synthases normally reported to be localized in the cytosol other sub-cellular localization may be possible such as in the mitochondria and chloroplasts and they may use FPP in these compartments and produce high levels of the sesquiterpene. We also demonstrated by the same method that the different targeting signals of the terpene synthases could be easily swapped by the use of site-directed mutagenesis. For example the plastidic targeting signal encoded by the H64VES N-terminal part could be modified to dual targeting to mitochondria and chloroplasts by a change in 2 amino acid residues (Tryptophan-W6 changed to Arginine-R6 and deletion of Isoleucine-I16).

Example 8

Effects of Nerolidol on *Agrobacterium tumefaciens*

FPP, the precursor for sesquiterpene biosynthesis is a most common metabolite and exists in every living organism. Thus, the expression of a protein encoding a nerolidol synthase will result in the conversion of endogenous FPP to nerolidol in most living organisms. We constructed a binary vector (plasmid used for the transformation of plants cells, which lacks the virulent genes present on the Ti plasmid of the virulent strain of *Agrobacterium tumefaciens*) containing the H64NORS gene flanked by a 35S CaMV promoter (5'-end) and a Nopaline Synthase (NOS) terminator (3'-end) and used it to transform 2 different strains of *Agrobacterium*. In both cases no colonies were obtained after plating the transformation reaction on Luria Broth (LB) medium containing 50 mg/l kanamycin and Rifampicin. Thus, the H64 NORS gene was expressed in *Agrobacterium* and the protein encoded by it converted the bacterial endogenous FPP to nerolidol, which is highly toxic to the *Agrobacterium* cells, and therefore no transformants were obtained. Thus, transgenic plants expressing a nerolidol synthase will have an anti-microbial effect and could be used for the protection against *Agrobacterium* crown-gall disease. In order to be able to introduce a plasmid containing such a terpene synthase having toxic effects on the bacteria one can introduce one or more introns into the coding sequence of the gene. These introns can not be spliced by the bacteria and hence no functional protein is formed by the micro-organism. In the plant, the normal eukaryotic splicing process will lead to a functional protein. The introduction of suitable, organ-specific and/or inducible promoters in the appropriate construct will allow the directed expression of linalool and/or nerolidol at the appropriate site to control crown-gall disease in plants such as fruits, rose, etc. Also, slow release formulations or other compositions containing linalool and/or nerolidol may be useful to control crown-gall disease.

Example 9

Effects of Linalool and Nerolidol on Spore Germination, Lesion Growth and Sporulation of *Phytophthora infestans, Fusarium* spp. and *Botrytis* spp Comparison of Effects of Farnesol and Linalool on Mycelium Growth of *Phytophthora infestans* on Growth Medium Farnesol and linalool were tested in two concentrations (2% and 0.2% (v/v)) through the addition to Plich medium in 6 well plates (3 ml per well). One 6 well plate per compound was used with two different concentrations in triplicate. All wells were inoculated with a plug of *Phytophthora infestans* mycelium (isolate VK98014, 1 month old) and incubated at 20° C. On day 3, 5 and 7 the radial growth of the mycelium was measured. An overview of the results is given in FIG. 17. The mycelium growth of *Phytophthora infestans* was inhibited completely 3, 5 and 7 days after the experiment by both the high and the low concentrations of linalool. Farnesol resulted in a partial inhibition of mycelium growth at both the high and the low concentration. The experiment demonstrates that linalool is more active than farnesol for the inhibition of mycelium growth of *Phytophthora infestans*.

Comparison of the Effects of Linalool and Nerolidol on Mycelium Growth of *Phytophthora infestans* Alone and in Combination on Growth Medium Linalool and nerolidol were tested in three concentrations (0.2%, 0.02% and 0.002% (v/v)) through the addition to Plich medium in 6 well plates (3 ml per well). One 6 well plate per compound was used with two different concentrations in triplicate. To study whether the compounds acted directly or through the vapour phase in one plate mycelia were grown on control medium with the compounds (0.2%) added to the medium in the adjacent wells. Free exchange of the compounds through the vapour phase was possible this way. All wells were inoculated with a plug of *Phytophthora infestans* mycelium (isolate VK98014, 1 week old) and incubated at 20° C. On day 3 and 5 the radial growth of the mycelium was measured. The results are shown in FIGS. 18-21.

FIG. 18 shows that linalool is active even at the lowest concentration of 0.002% (=20 ppm). Remarkably, the effects of linalool are equally effective through the vapour phase as through the medium. Apparently this monoterpene is so volatile that the active concentrations in the vapour and medium phase are similar. This high activity in the vapour phase makes linalool an attractive compound for the protection of stored products against micro-organisms e.g. the protection of potato to *Phytophthora, Phoma*, and *Fusarium*.

FIG. 19 shows that nerolidol is slightly more effective than linalool (compare FIG. 18) in inhibiting *Phytophthora infestans* mycelium growth and that it is a strong inhibitor of mycelium growth even at the lowest concentration of 20 ppm. In contrast to linalool the effects through the vapour phase are negligible. This can be explained by the fact that the sesquiterpene nerolidol is much less volatile than the monoterpene linalool.

FIGS. 20 and 21 show that the action of linalool and nerolidol is stronger in combination than when taken alone. This suggests that the simultaneous production of these compounds in plants could result in more effective fungal control compared to a situation when only one of the two compounds is present.

The Effect of Nerolidol Infiltrated in Potato Leaves on the Germination of *Phytophthora infestans* Spores, Lesion Formation and Sporulation.

Leaves of potato cultivar Bintje were vacuum-infiltrated with a 0.05% (v/v) solution of nerolidol. This was done by placing 6 leaflets at a time in a 50 ml bluecap with the nerolidol solution or a water control. The tubes were placed for 15-30 min under vacuum which was then suddenly released. Good infiltration was visible by the dark green color of the leaves. The leaves had gained about 25% weight this way so that the actual concentration in the leaves was in the range of ca. 0.0125%. The leaves were placed on water agar (1.5%) and inoculated with 250-500 spores of the 4 different *Phytophthora infestans* isolates (race-0, IPO-c, 428-2, VK98014). The leaves were incubated one night in the dark at 15° C. and then moved to normal lighting conditions (15° C., 16 h light, 8 h dark). After 7 days the leaves were scored for the formation of lesions and sporulation. The results demonstrate that also when infiltrated in potato leaves nerolidol strongly inhibits mycelium growth, lesion formation and sporulation at a low concentration. The effects appear to be not race-specific but equally affecting the four different isolates showing that also nerolidol provides broad resistance against this fungus.

Effects of Linalool and Nerolidol on *Fusarium* and *Botrytis* Mycelial Growth

*Fusarium*. Nerolidol and linalool were tested in a range of concentrations (10-5000 ppm) alone and in combination through the addition to Plich medium in 6 well plates (3 ml per well). In the case of comparing the application of nerolidol and linalool alone to the combination of the two compounds, 100 ppm of the single compound was for example compared to 50+50 ppm of the two compounds together. One 6 well plate per compound was used with two different concentrations in triplicate. All wells were inoculated with a mycelium plug of *Fusarium graminearum, Fusarium culmorum* or *F. verticillioides* strain MRC826 and incubated at 20° C. Each day the radial growth of the mycelium was measured. The results of day 7 are given in FIG. 22. The mycelium growth of all *Fusarium* spp. was inhibited at concentrations above 10 ppm. At low concentrations nerolidol was slightly more effective than linalool in the case *F. graminearum* and MRC826. At very high concentrations linalool was more effective. The combined use of nerolidol and linalool is at least as effective as either individual compound and appears to provide a more robust inhibition against all *Fusarium* species.

*Botrytis*. Nerolidol and linalool were tested in a range of concentrations (10-5000 ppm) alone and in combination through the addition to Plich medium in 6 well plates (3 ml per well). In the case of comparing the application of nerolidol and linalool alone to the combination of the two compounds, 100 ppm of the single compound was for example compared to 50+50 ppm of the two compounds together. One 6 well plate per compound was used with two different concentrations in triplicate. All wells were inoculated with a mycelium plug of *Botrytis cinerea* isolated from grape and strawberry and incubated at 20° C. Each day the radial growth of the mycelium was measured. The results of day 7 are given in FIG. 23. The mycelium growth of all *Botrytis* isolates was inhibited at concentrations above 10 ppm. At low concentrations nerolidol was more effective than linalool. At very high concentrations linalool or the combination of linalool and nerolidol was most effective. The combined use of nerolidol and linalool is at least as effective as either individual compound and appears to provide the most robust inhibition against all *Botrytis* isolates.

Effects of Linalool and Nerolidol on *Fusarium* Spore Germination.

A spectrophotometric assay was used to monitor the onset of germination of *Fusarium verticillioides* spores (isolates: ITEM2282, MRC3235, MRC826, MRC826-2) in solution. The spores were diluted to a concentration of $10^5$ spores/ml in Czapek Dox medium and mixed with 8-4000 ppm of linalool or nerolidol. Linalool did not affect the germination of the spores at all (FIG. 24B). Nerolidol, however, showed strong inhibition of germination at concentrations above 250 ppm (FIG. 24A). This suggests that nerolidol provides an additional mode of control of *Fusarium verticillioides* at the level of spore germination in comparison to linalool and that for the most effective control at all stages of fungal development of *Fusarium* spp a combined use of nerolidol and linalool is most appropriate.

Example 10

Transformation and Characterization of *Arabidopsis*, Potato, Tomato and Petunia Preparation of Constructs for the Transformation of Plants.

Constructs with the H64 cDNAs are prepared for the transformation of plants in order to yield plants that will produce linalool and/or nerolidol in various compartments:

The cDNAs are placed under the control of either the 35S promoter or the Rubisco promoter, both separately and in combination in order to obtain plants producing linalool or nerolidol alone or in combination. It is also contemplated that for some purposes glycosylation or deglycosylation of the terpene-alcohol is required for the mode of action against fungi or insects. For this reason also constructs are made containing glycosyl-transferases or glycosidases in conjunction with the linalool and/or nerolidol synthase cDNAs.

Construction of Binary Vectors.

The appropriate sequences were ligated into a pFlap10 vector. The ligation product was transformed to *E. coli* DH5α competent cells, and transformed colonies were grown O/N at 37° C. and 250 rpm. The expression cassette was removed from the resulting vector by using Pad and AscI restriction enzymes (NEB, England) and ligated into the binary vector pBINPLUS, containing a kanamycin resistance selection marker (nptII), after digestion with PacI and AscI. Colonies were checked after transformation by back-transformation to *E. coli* DH5α competent cells.

Transformation of *Arabidopsis*

We used the floral-dip transformation method to transform *Arabidopsis* plants ecotype Columbia according to Marsh-Martinez et al. (2002). After collecting the seeds they were let to dry for several days and then sown on MS medium containing 50 mg/l kanamycin and 400 mg/l cefotaxime. Green shoots, 1 cm in size were transferred to the green house and grown to maturity.

Transformation of Potato

On day 1 an *Agrobacterium tumefaciens* culture of AGL0 containing a BINPLUS derived binary vector was started in 50 ml LB-medium containing 50 mg/l kanamycin and shaken for 2 days at 28° C. On day 2 internodes from an in vitro culture of the potato cultivar Desiree were cut into 0.5-1 cm pieces and placed on R3B medium (30 g/l sucrose, 4.7 g/l Murashige and Skoog salts, pH 5.8 (KOH), 8 g/l purified agar, 2 mg/l NAA and 1 mg/l BAP) which was covered with 2 sterile filterpapers that had previously been soaked in 2 ml PACM medium (30 g/l sucrose, 4.7 g/l Murashige and Skoog salts, 2 g/l casein hydrolysate, pH 6.5 (KOH), 1 mg/ml 2,4-D and 0.5 mg/l kinetine). The dishes were taped with parafilm and incubated overnight at 24° C. under a regime of 16 h light. At day 3 the *A. tumefaciens* culture was poured in a sterile petridish containing the explants. After 5-10 min explants are removed from the culture, placed on a sterile filter paper to remove excess *Agrobacteria* and placed back on the R3B medium containing dishes after first removing the top filter paper (leaving one behind). Dishes with explants were further incubated at 24° C. and 16 h light until day 5, when the explants were transferred to dishes containing ZCVK medium (20 g/l sucrose, 4.7 g/l Murashige and Skoog salts, pH 5.8 (KOH), 8 g/l purified agar, 1 mg/l zeatine, 200 mg/l vancomycin, 100 mg/l kanamycin, 200 mg/l claforan). On day 19 and subsequently every 3-4 weeks explants were transferred to new ZCVK medium. When shoots appeared shoots were transferred to Murashige and Skoog medium containing 20% sucrose (MS20). After rooting plants were transferred to the green house Petunia Transformation.

Leaf cuttings of Petunia W115 were transformed with *Agrobacterium tumefaciens* strain LBA4404 using a standard plant transformation protocol (Lücker et al., *The Plant Journal* 27: 315-324, 2001). As a control leaf cuttings were also transformed with LBA4404 containing the pBINPLUS vector. Furthermore some non-transformed leaf cuttings were carried through the regeneration process. Rooting plants, arising from the *Agrobacterium* transformation were tested with PCR for the presence of the respective gene construct. Positive plants were transferred to the greenhouse. All transgenic plants were phenotypically normal and showed a normal development compared with non-transformed control plants, which had gone through the same regeneration process.

Tomato Transformation.

The tomato cultivar 'Micro-Tom' (*Lycopersicon flavour*) was used (Scott and Harbaugh, 1989). The plants were grown from seeds provided by a seed company (Beekenkamp seed, Holland). Micro-Tom seeds were first sterilised. A rinse in 70% ethanol followed by a two hour bleaching in 1.5% $HClO_4$. After bleaching, the seeds were quickly rinsed in water twice and then washed in water for ten and sixty minutes. After sterilisation, seeds were sowed in pots, containing 80 ml vermiculite and 70 ml of germination medium containing 4.4 g/l MS salts with vitamins and 0.5% sucrose (pH 5.8).

After 7 days of growth in a culture room (25° C.), covered with 2 folds of filter paper, the cotyledons were cut under water near the petiole and the tip with a rolling action of the scalpel, to minimize damage. The explants were placed on their backs on filter paper on feederlayers to incubate overnight in the culture room (25° C.), covered with 4 folds of filter paper, under low light conditions. After incubation, the explants were immersed in the *Agrobacterium* suspension for 20 minutes. After immersion, the explants were placed back on feederlayers for co-cultivation, following a rinse in a solution containing 400 mg/l carbenicillin and 100 mg/l tricarcillin. The explants were placed in callus inducing medium (4.4 g/l MS salts with Nitsch vitamins, 3% sucrose, 0.8% purified agar (Oxoid), pH 6.0, 2 mg/l zeatin, 400 mg/l carbenicillin, 100 mg/l tricarcillin, 100 mg/l kanamycin). The plates were covered with 2 folds of filter paper and set to grow in a culture room (25° C.) under low light conditions for 3 weeks. Formed callus was transferred to shoot inducing medium (as callus inducing medium, but with 1 mg/l zeatin, 200 mg/l carbenicillin, 50 mg/l tricarcillin).

These plates were set to grow under the same conditions as the callus-inducing plates. Shoots formed were transferred to rooting medium in pots (4.4 g/l MS salts with Nitsch vitamins, 3% sucrose, 0.5% agargel (Sigma), pH 6.0, 0.25 mg/l IBA, 50 mg/l kanamycin, 400 mg/l carbenicillin. The growing conditions remained the same. Fully-grown plants were subsequently transferred to the greenhouse.

Analysis of the Transgenic Plants with Capillary Gas Chromatography-Mass Spectrometry (GC-MS).

The tissues to be analyzed were collected in the greenhouse and frozen in liquid nitrogen. In general, 200 mg frozen material was homogenized and transferred to a mortar containing 1.5 mL 5M $CaCl_2$ and a small amount of purified sea sand. These tissues were mixed with 0.75 mL 5M $CaCl_2$. The material was ground rapidly and thoroughly with a pestle, inhibiting enzymatic reactions. 0.75 mL of the material was introduced into a 1.8 mL GC vial containing a small magnetic stirrer. The vial was then closed with an aluminum cap with a PTFE/Butylrubber septum. Subsequently the vial was placed in a 50° C. waterbath and preheated for 20 minutes while stirring. The headspace sampled during 30 minutes with a 100μ PDMS SPME fiber (Supelco, Belfonte Pa. USA).

Figure 25:
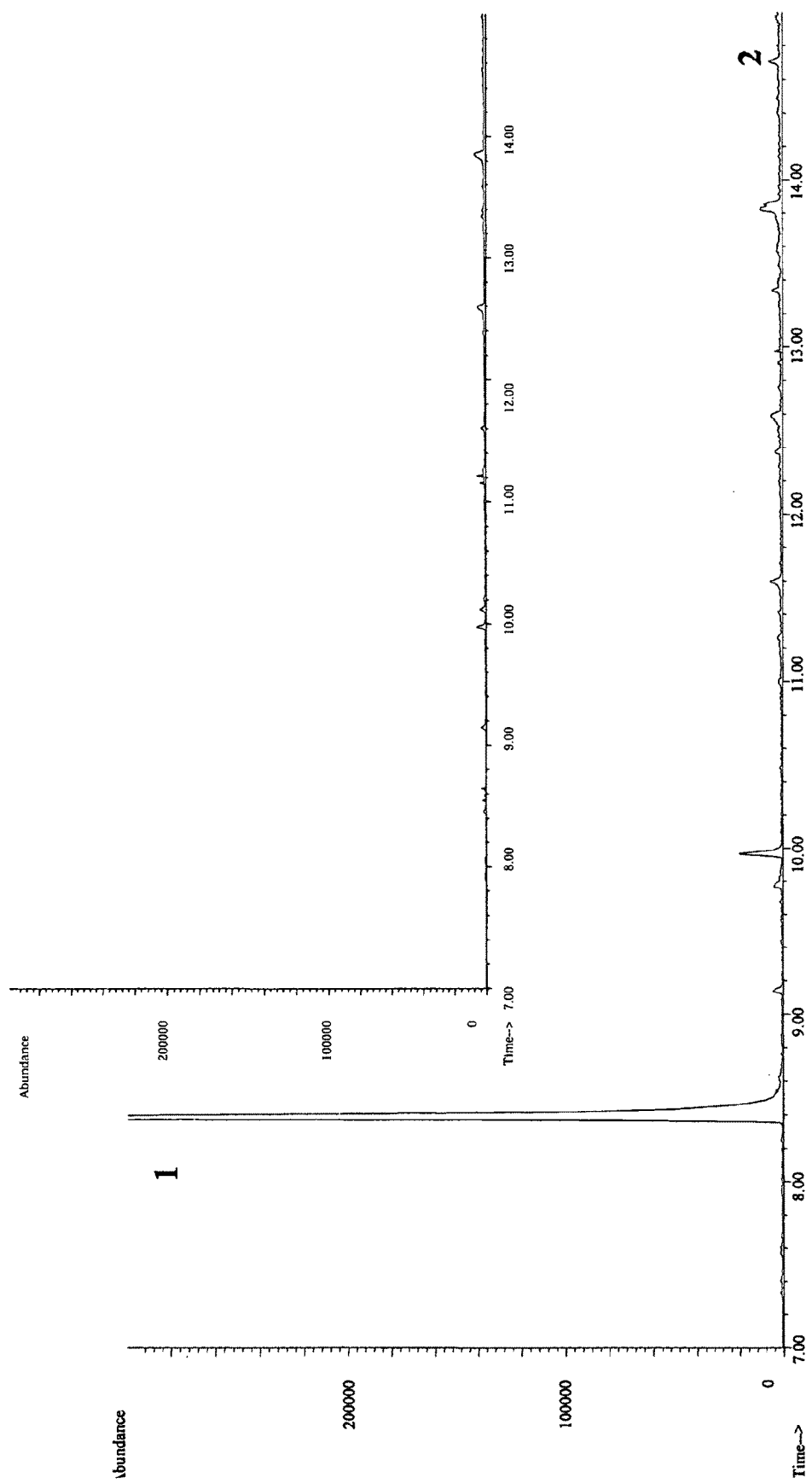
Figure 26:
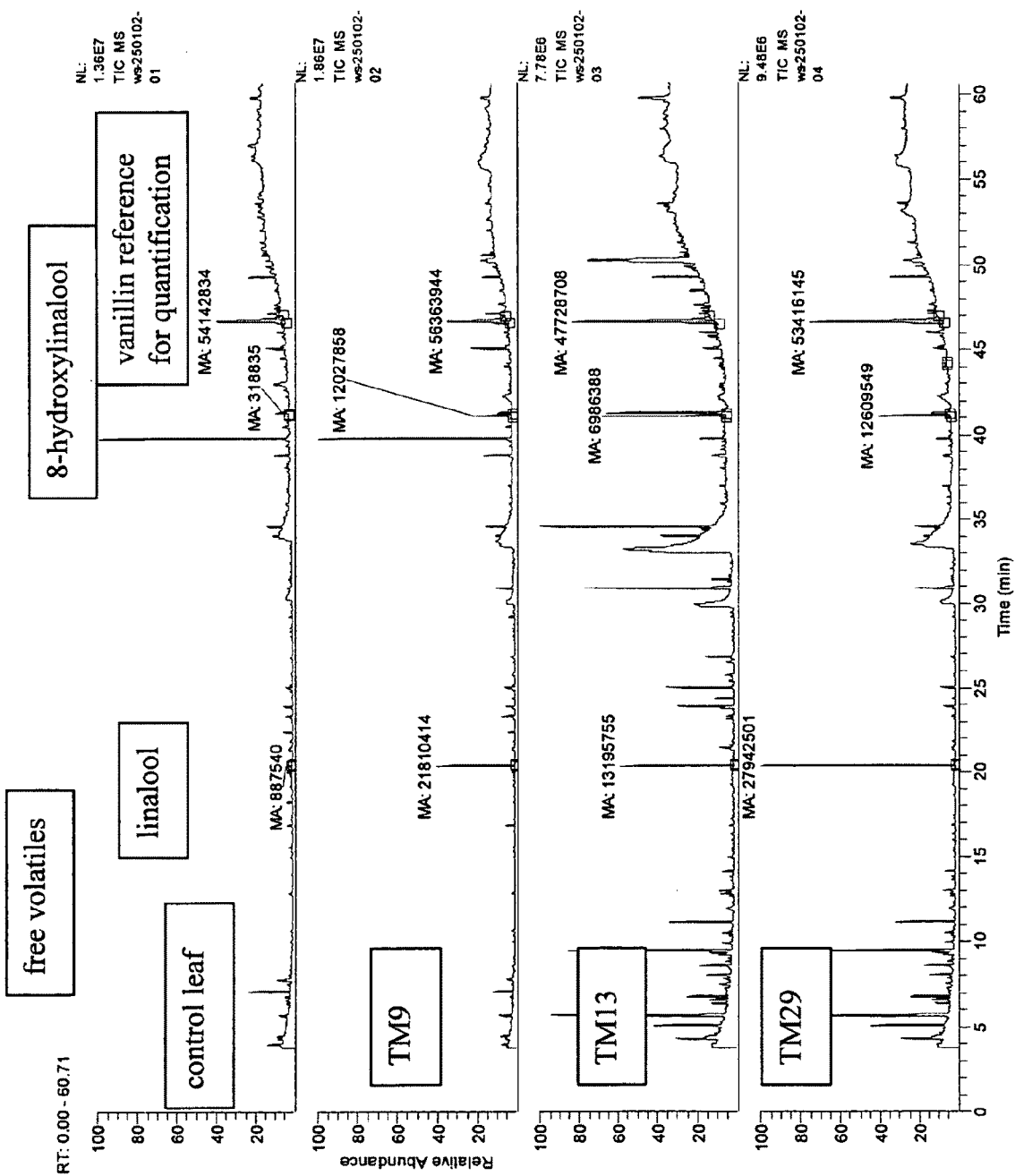

GC-MS analysis was performed using a Fisons 8060 gas chromatograph directly coupled to a MD 800 mass spectrophotometer (Interscience, Breda, the Netherlands). A HP-5 column (50 m×0.32 mm, film thickness 1.05 μm) was used with He (37 kPa) as carrier gas. GC oven temperature was programmed as follows: 2 min 80° C., ramp to 250° C. at 8° min$^{-1}$ and 5 min 250° C. Mass spectra in the electron impact mode were generated at 70 eV. The compounds were identified by comparison of GC retention indices and mass spectra with those of authentic reference compounds. Injection was performed by thermal desorption of the SPME fiber in the injector at 250° C. during 1 min using the splitless injection mode with the split valve being opened after 60 sec. Alternatively, volatiles were trapped on cartridges containing Tenax, eluted using pentane/ether and analysed using GC-MS essentially as described by Bouwmeester et al (1998). Transgenic *Arabidopsis* plants expressing H64TAR, for example, produced large amounts of linalool and smaller amounts of nerolidol (FIG. 25). Transgenic potato lines also produced substantial amounts of linalool, but also the hydroxy-derivative 8-hydroxylinalool (FIG. 26). Interestingly, the native linalool of potato, which can also be detected, had a different stereochemistry as the transgenic linalool (FIG. 26), which allowed a clear distinction between native and transgenic product.

Because it was suspected that in some of the plant species these compounds were present in a bound form, leaf material of Petunia (transgenic and control samples) was harvested and frozen in liquid nitrogen, and ground to a fine powder in a cooled mortar and pestle. In total 60 mg of the powdered leaf material was transferred to 0.5 ml of citrate buffer at pH 4.5, to which 140 i.u. β-glucosidase were added. The vial was capped and incubated during 12 h at 25° C. Subsequently, the headspace of the vial was sampled during 30 minutes with 100 micron PDMS solid phase microextraction device and analysed using GC-MS as described above. No linalool or nerolidol was detectable in samples from the untransformed control plants, whereas in the transgenic plants both linalool and nerolidol were detected. The sample of transgenic leaf material without beta-glucosidase present during the incubation did not show any detectable linalool or nerolidol, indicating that all linalool and nerolidol is stored in the petunia leaves in the form of its glucoside, instead of continuous emission as was described for linalool in the flowers of *Clarkia breweri*.

Identification of Glycosides in Transgenic Plants

High-performance-liquid-chromatography electrospray-ionization tandem mass spectrometry (HPLC-ESI-MS-MS) analysis of methanol extracts was performed on a triple stage quadrupole TSQ 7000 LC-MS-MS system with an electrospray ionization (ESI) interface (Finnigan MAT, Bremen, Germany). The temperature of the heated capillary was 240° C. The ESI capillary voltage was set to 3.5 kV, resulting in a 3.4 μA current. Nitrogen served as both the sheath (70 psi) and auxiliary gas (10 L/min). Data acquisition and evaluation were carried out on a Personal DECstation 5000/33 (Digital Equipment, Unterföhring, Germany) and ICIS 8.1 software (Finnigan MAT). HPLC separation was carried out on an Eurospher 100 C-18 column (100×2 mm, 5 μm, Knauer, Berlin, Germany) using a linear gradient with a flow rate of 200 μL min$^{-1}$. Solvent A was 5 mM ammonium acetate in water, and solvent B was 5 mM ammonium acetate in methanol. The gradient program was as follows: 0-30 min 5 to 100% B. Mass spectra were acquired in the negative mode. Product ion spectra were available by collision-induced dissociation (CID) (1.5 mTorr of Argon; −20 eV). For preparation of extracts plant leaves (3 to 7 g) were homogenized in 50 ml of 80% methanol and centrifuged (2000 g for 5 min). The residue was washed with 50 ml of 80% methanol and the supernatants were combined. Methanol was removed in vacuum and the remaining aqueous solution was extracted with 2×20 ml diethyl ether. The extract was subjected to XAD-2 (20 cm, 1 cm inner diameter) solid phase extraction. The column was successively washed with 50 ml water and 50 ml diethyl ether. Glycosides were eluted with 80 ml methanol. The extract was concentrated in vacuum. The residue was dissolved in 1 ml of 50% methanol in water and analyzed by HPLC-ESI-MS-MS.

Figure 27:
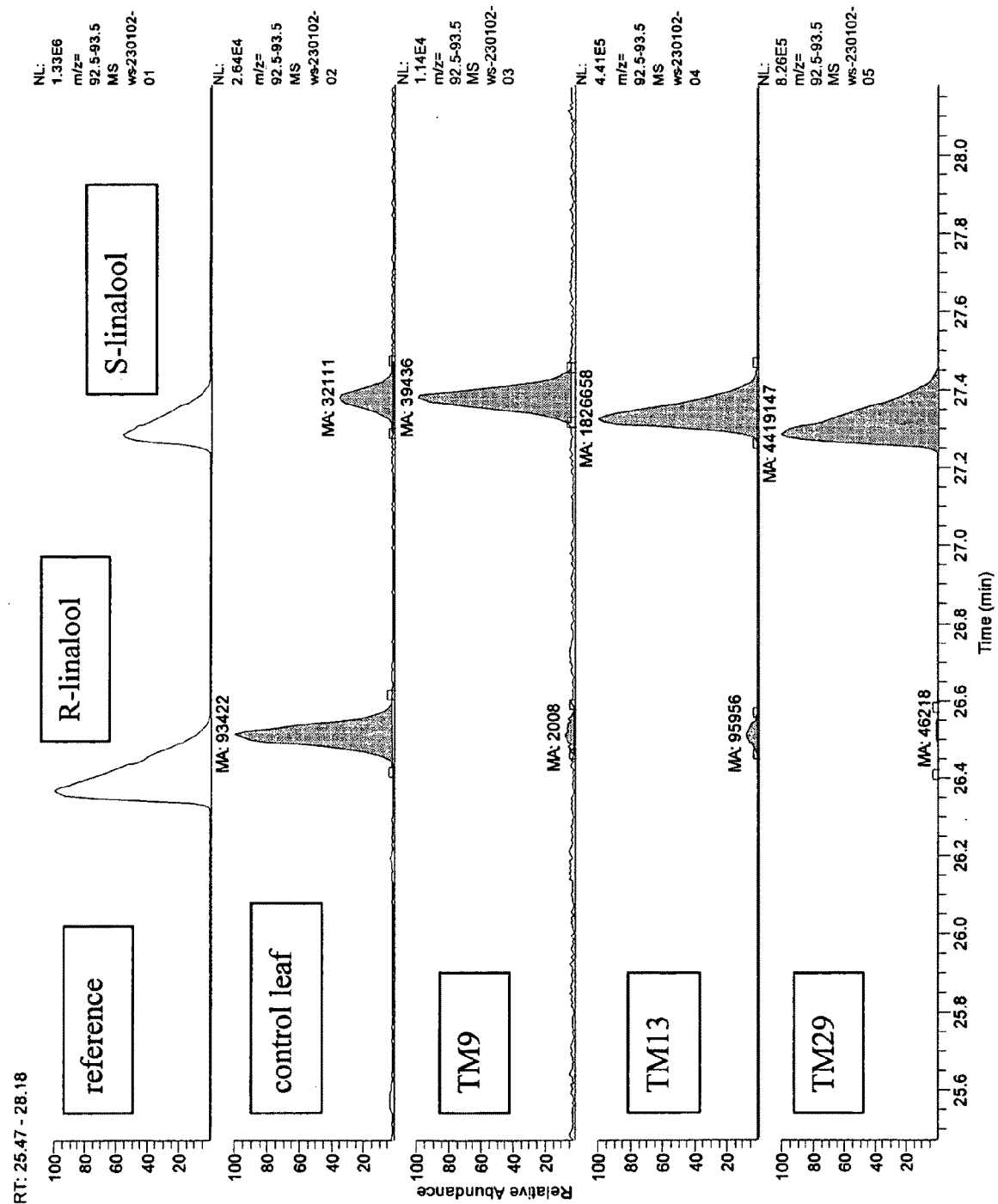
Figure 28A:
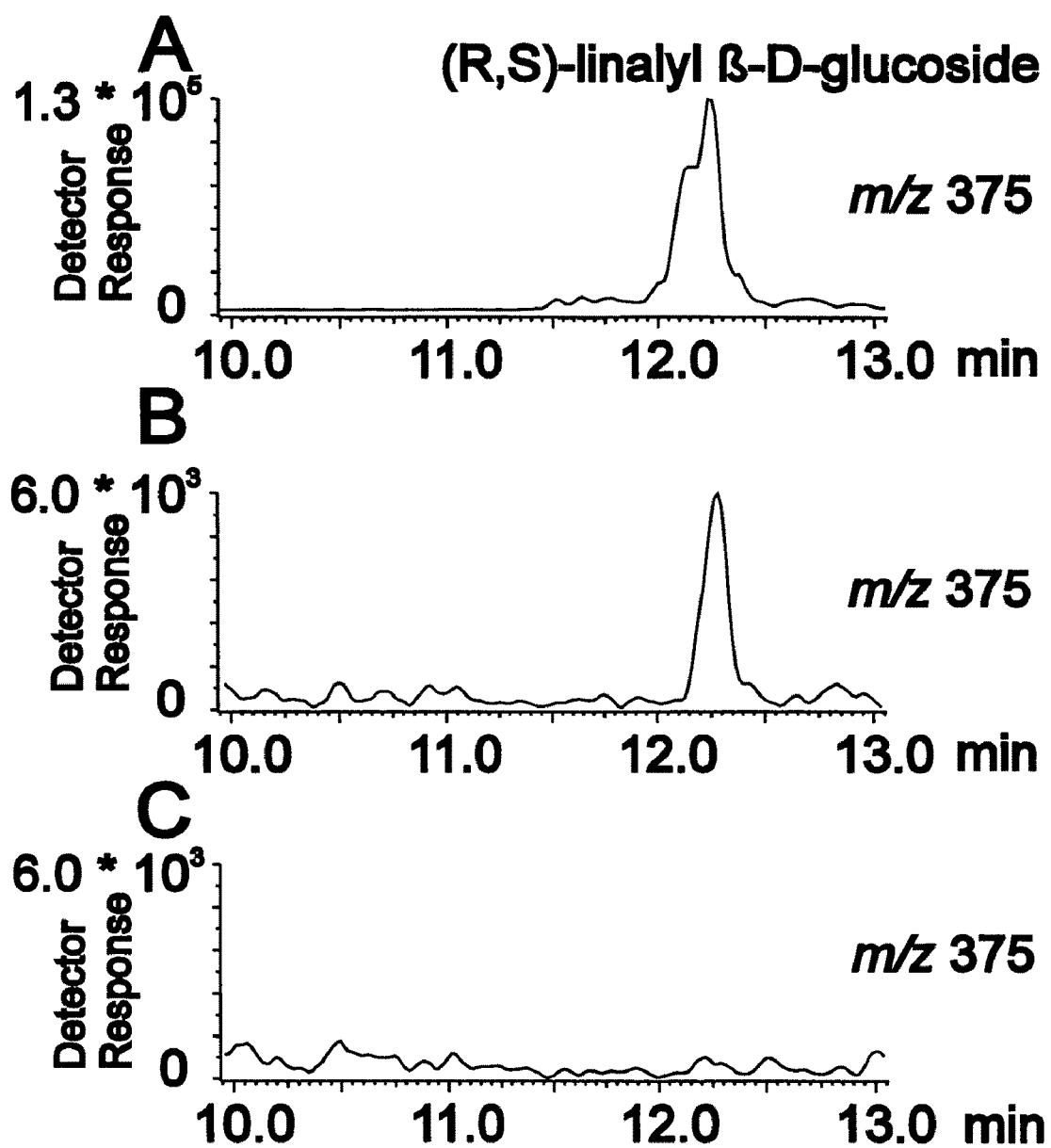
Figure 28B:
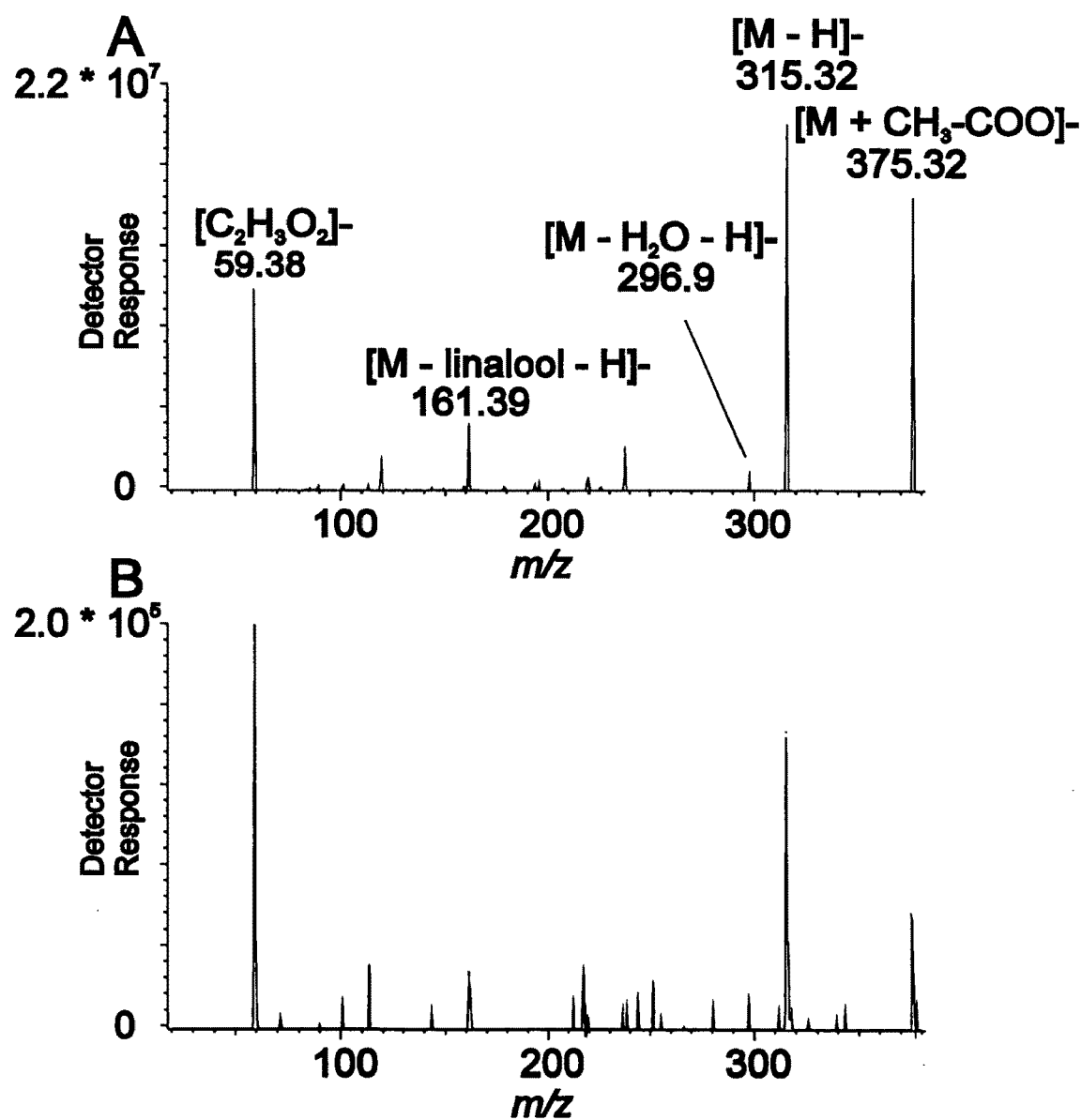
Figure 29:
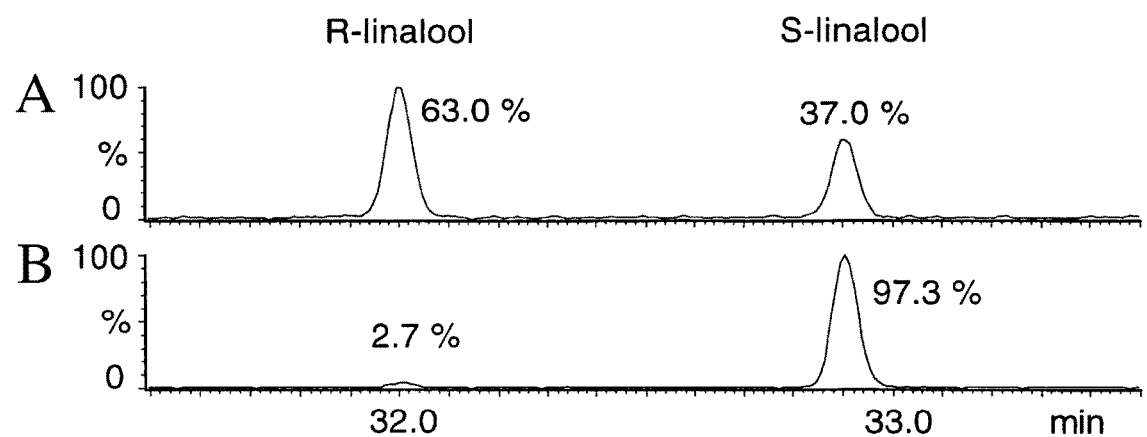
Figure 30A:
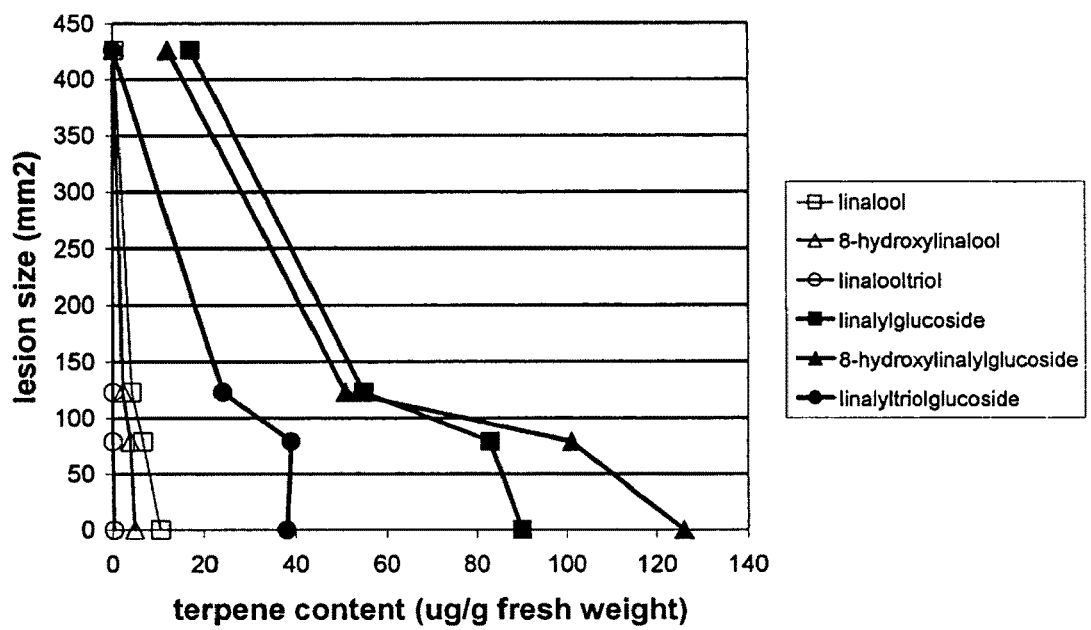
Figure 30B:
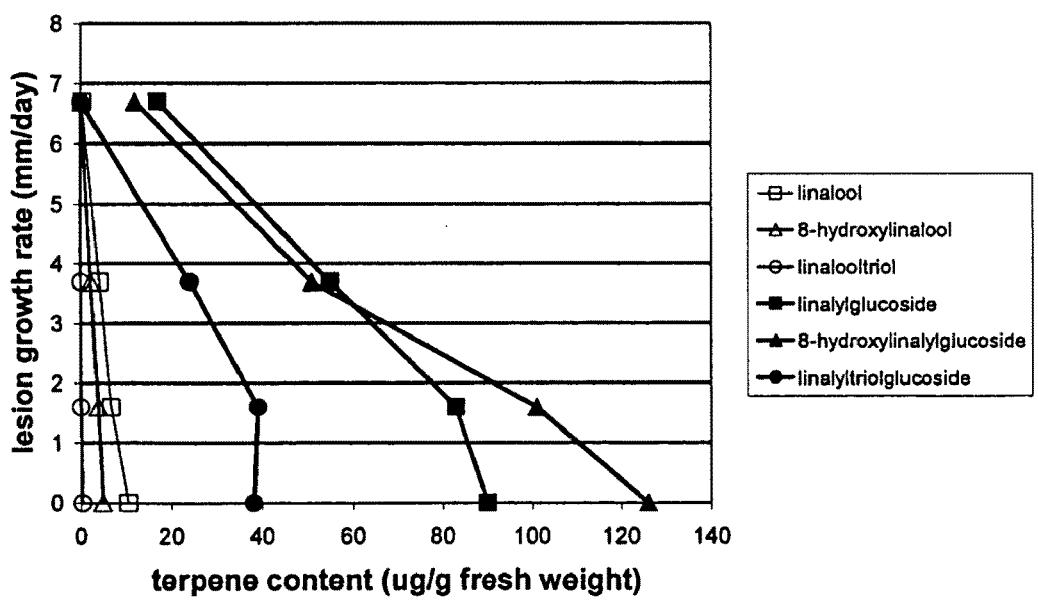
Figure 30C:
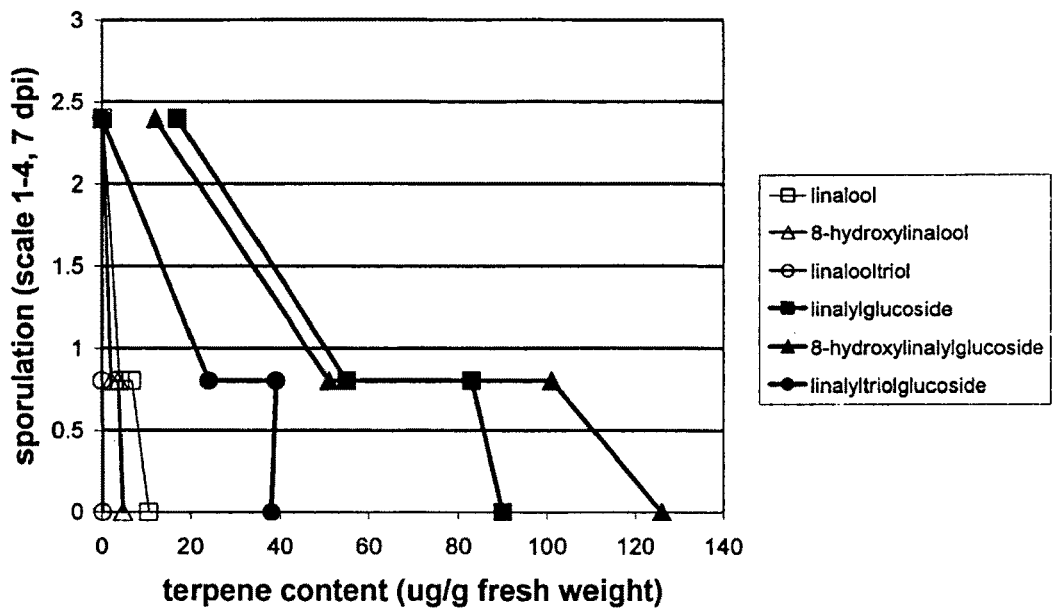
Figure 30D:
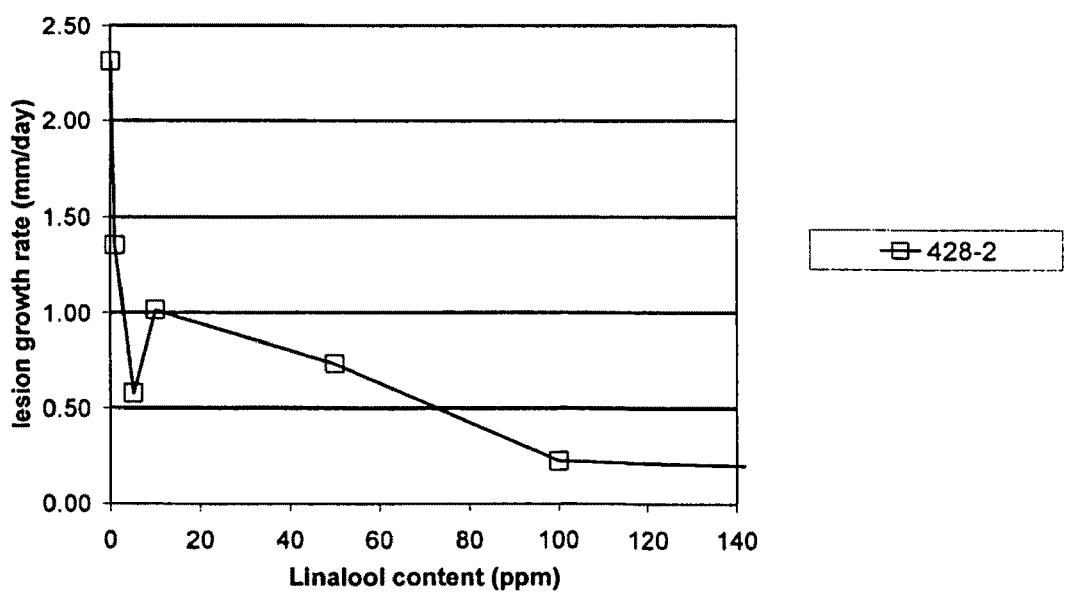

R,S-Linalyl β-D-glucopyranoside was synthesized from R,S-linalool and 2,3,4,6-tetra-O-acetyl-beta-D-glucopyranosyl bromide according to a modified Koenigs-Knorr synthesis. For enzymatic hydrolysis an aliquot of the methanol extract was dissolved in 2 ml of 0.2 M phosphate buffer (pH 5.5), and 200 μl of Rohapect D5L (Röhm, Darmstadt, Germany), a pectinolytic enzyme preparation exhibiting glycosidase activity was added. After an incubation period of 24 h at 37° C., the liberated aglycons were extracted two times by 1 ml of diethyl ether each. The combined organic layers were dried over $Na_2SO_4$ and concentrated. Multidimensional gas chromatography mass spectrometry (MDGC-MS) analyses were performed with tandem Fison 8160 GC connected to a Fison 8130 GC and a Fisons MD 800 quadrupole mass spectrometer equipped with Fisons MassLab software (Version 1.3). The first GC was fitted with a split injector (1:10, at 230° C.) and a flame ionization detector (at 250° C.). The first GC employed a 25 m×0.25 mm i.d. fused silica capillary column coated with a 0.25 μm film of DB-Wax 20 M (J & W Scientific) for the pre-separation of the target molecule. Separation of enantiomers was achieved with the second GC using a 25 m×0.25 mm i.d. fused silica capillary column coated with a 0.15 μm film of 2,3-di-β-ethyl-6-O-tert. Butyl dimethylsilyl-β-cyclodextrin/PS086. The column in GC1 was connected by a multicolumn switching system (Fisons) to the column in GC2. The retention time of the compound of interest was determined by GC separation while the column in GC1 was connected to the FID. Separation of the enantiomers was achieved in the second GC after transfer of the compound of interest from the capillary column in GC1 to the column in GC2 via the switching device. The fused silica capillary column in GC1 was maintained at 60° C. then programmed to 240° C. at 10° C. min$^{-1}$ with He gas flow at 3 ml min$^{-1}$. The fused silica capillary column in GC2 was maintained at 60° C. (15 min) then programmed to 200° C. at 2° C. min$^{-1}$ with He gas flow at 3 ml min$^{-1}$. The compound of interest was transferred from GC1 to GC2 from 9.8 min to 10.3 min. The MS operating parameters were ionization voltage, 70 eV (electron impact ionization); ion source and interface temperature, 230° C. and 240° C., respectively. Linalyl-β-D-glucopyranoside was synthesised in order to verify the identity of the glycoside present in the transgenic petunia tissue transformed with S-linalool synthase. HPLC-MS/MS analysis on control and transgenic Petunia tissue as shown in FIG. 28, revealed that the m/z 375 ion trace (FIG. 27A) of the compound detected in the transgenic Petunia tissue had the same retention time as one of the two diastereomers of (R,S)-linalyl β-D-glucoside that are slightly resolved in ion trace A. Also the product ion spectrum of the synthesised reference compound fits the spectrum of the peak detected in the transgenic petunia tissue nicely (FIG. 28B). The control Petunia tissue ion trace m/z 375 showed only a slight elevation above background level at the retention time of the linalyl β-D-glucoside indicating that there is also a basal level of linalyl-β-D-glucoside present in the plant before transformation (FIG. 28A). Following Chiral phase Multidimensional Gas Chromatography Mass Spectrometry (MDGC-MS) analysis, after enzymatic hydrolysis of the glucoside fraction of leaf tissue, revealed that the transgenic Petunia leaf contains highly enriched (S)-linalyl-β-D-glucoside. The control plant however contains slightly enriched (R)-linalyl-β-D-glucoside. Since no tissue-specific promoter for expression was used, the enzyme can be formed in all plant organs and will give a product in all cells where GPP is present. By the action of a highly active endogenous glucosyltransferase of Petunia that is able to efficiently bind the S-linalool produced by the transgenic plants as (S)-linalyl-β-D-glucoside, cellular damage is prevented. Such a highly active glycosyltransferase was also reported in transgenic Kiwi fruit expressing stilbene synthase, that accumulated picied (resveratrol-glucoside) in stead of resveratrol. Large-scale volatilisation of linalool from the transgenic plants could be excluded, since only traces of linalool were detectable when the headspace of the transformed plants was analysed. Volatilisation only occurred from the flowers and not from leaves. This in contrast to Arabidopsis where large amounts of linalool were emitted from the leaves (FIG. 25). Therefore we conclude that most of the linalool in Petunia is directly bound as a β-D-glucoside.

Further analysis of potato-leaf extracts also showed the presence of glucosides, not only of linalool itself but also of 8-hydroxylinalool. In addition, more derivatives of linalool were found such as linalool-triol, including the corresponding glucoside (Table 1).

In conclusion, transgenic plants expressing the inserted transgenes are shown to produce the expected terpenoid compounds. Their amounts, release, oxidation to polyols, and derivatization to glycosides vary from species to species and can be influenced by the co-expression of other sequences (see Example 11). When these compounds are not stored in any bound intermediates such as glycosides, the plants have altered olfactory characteristics.

TABLE 1

| sample weight (g) | control 3.5 | TM9 3.5 | TM13 4.1 | TM29 3.0 |
|---|---|---|---|---|
| linalool (µg/g fresh weight) by GC-MS | 0.3 | 6.6 | 4.0 | 10.5 |
| 8-hydroxylinalool (µg/g fresh weight) by GC-MS | 0.1 | 3.7 | 2.1 | 4.7 |
| linalooltriol (µg/g fresh weight) by GC-MS | <0.1 | <0.1 | <0.1 | 0.3 |
| glycosidically bound linalool (µg/g fresh weight) by GC-MS | 0.4 | 3.3 | 0.6 | 1.0 |
| glycosidically bound 8-hydroxylinalool (µg/g fresh weight) by GC-MS | 1.6 | 18.7 | 8.9 | 27.2 |
| glycosidically bound linalooltriol (µg/g fresh weight) by GC-MS | <0.1 | 3.3 | 1.4 | 5.8 |
| linalylglucoside (µg/g fresh weight) by LC-MS | 17 | 83 | 55 | 90 |
| 8-hydroxylinalylglucoside tentatively (µg/g fresh weight) by LC-MS | 12 | 101 | 51 | 126 |
| linalyltriolglucoside tentatively (µg/g fresh weight) by LC-MS | <1 | 39 | 24 | 38 |
| linalool enantiomeric ratio (R:S) by MDGC-MS | 74:26 | 5:95 | 5:95 | 1:99 |
| glycosidically bound linalool enantiomeric ratio by MDGC-MS | 96:4 | 1:99 | 2:98 | 1:99 |

Example 11

Effects of Changes in Targeting of Sesquiterpene Synthases to Achieve High Level Expression of Sesquiterpene Compounds in Mitochondria It is commonly accepted that sesquiterpene biosynthesis in plants occurs in the cytosol and not in any other cell compartment (Bick and Lange (2003) ABB 415: 146-154). It is also the current knowledge and this has been described in several publications that the only isoprenoids produced by plants in the mitochondria are the prenyl chains of ubiquinones. The state of the art did not contain any teaching which would reliably predict that the expression of a cytosolic sesquiterpene synthase in mitochondria would result in high expression of sesquiterpene compounds. Indeed, the literature which did predict that constitutive sesquiterpene production could be achieved by expression of cytosolic sesquiterpene synthases in the native location of the cytosol proved to be unreliable with absent or very low levels (this application, Wallaart et al., Planta 212: 460-465, 2001; Hohn and Ohlrogge, Plant Physiol 97: 460-462, 1991). Because of the presence of a mitochondrial targeted FPP synthase in the Arabidopsis genome, we expected that FPP, the substrate for the nerolidol synthase, would be present in the mitochondria of Arabidopsis, but it did not provide any clue as to whether the substrate pool would be available to sesquiterpene synthases which are normally expressed in the cytosol, nor to which quantity the sesquiterpenes would be produced.

Figure 31:
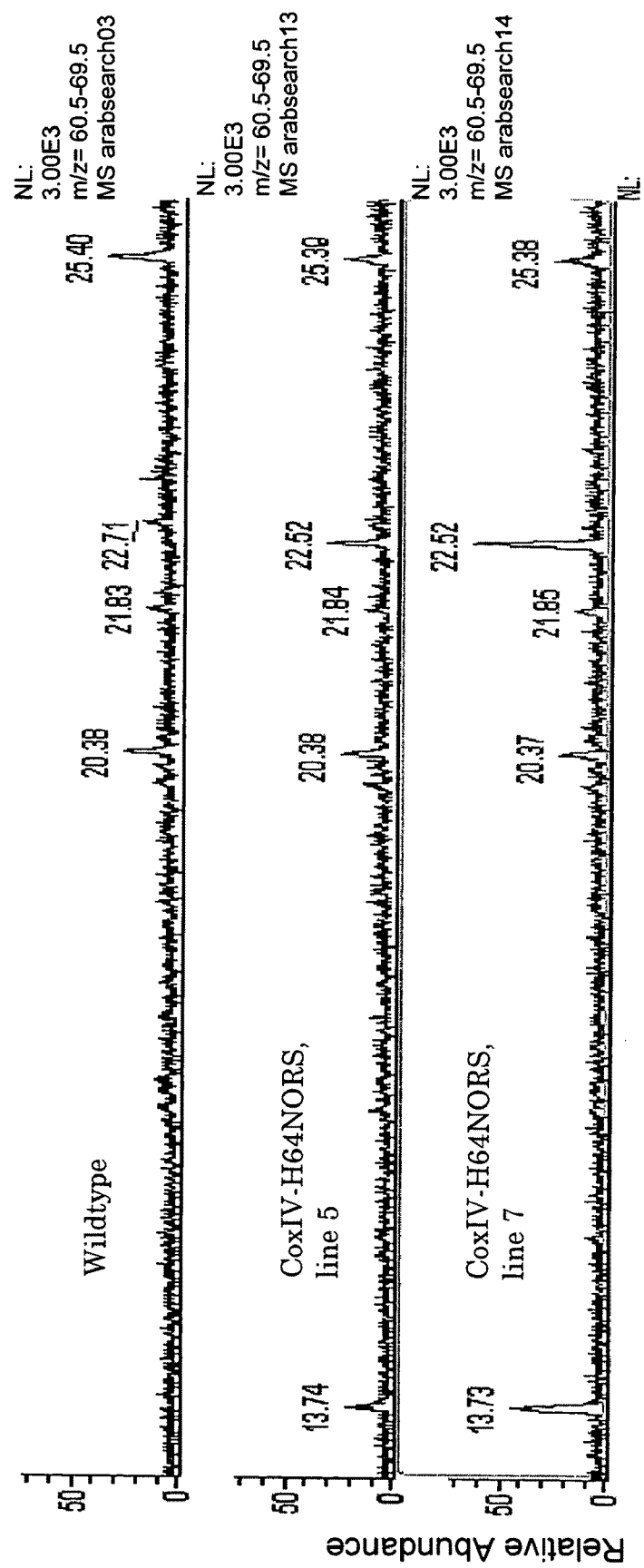

In this example we present a method which depends on overexpressing a cytosolic sesquiterpene synthase in mitochondria through the fusion to a mitochondrial targeting sequence using Arabidopsis thaliana plants (ecotype Columbia) as a model plant. To study this we used the published CoxIV targeting signal (Kohler et al. Plant J 11: 613-621 (1997)) fused to H64NORS. The construct was transformed to Arabidopsis as described in Example 10. Volatile production was determined using SPME-headspace sampling on intact Arabidopsis leaves (2-4 leaves per vial) and GC-MS analysis using the Fisons 8060 GC-MS as described in Example 10. Nine out of twelve CoxIV-transgenic plants produced (E)-nerolidol and/or dimethylnonatriene to high levels. FIG. 31 shows representative GC-MS chromatograms for a number of transgenic lines and a wildtype.

This shows that it is possible to obtain high constitutive (and inducible) sesquiterpene biosynthesis by changing the subcellular location of expression of sesquiterpene genes to the mitochondria.

Example 12

Increasing the Pool of Sesquiterpene Precursors in the Mitochondria by Inducing or Repressing Any of the Genes or the Corresponding Enzymatic Steps of Either the Cytosolic or the Plastidic or the Mitochondrial Isoprenoid Biosynthetic Pathway The production of sesquiterpenes in different transgenic plant species, using their native signal sequences, has proved to be largely unsuccessful in our hands, as has also been reported by several other authors (Wallaart et al., Planta 212: 460-465, 2001; Hohn and Ohlrogge, Plant Physiol 97: 460-462, 1991). We investigated how to enhance the level of sesquiterpene production further complementary to the method described in Example 11.

This second method depends on overexpressing an IPP isomerase or any other gene encoding the proteins which catalyze the production of isoprenoid precursors (i.e. DXP synthase, DXP reductoisomerase, 2-C-methyl-D-erythritol 4-phosphate cytidyltransferase, 4-(cytidine 5' diphospho)-2-C-methyl-D-erythritol kinase, 2-C-methyl-D-erythritol 2,4-C-cyclodiphosphate synthase, (E)-4-hydroxy-3-methyl but-2-enyl diphosphate synthase, (E)-4-hydroxy-3-methyl but-2-enyl diphosphate reductase, acetoacetyl CoA thiolase, 3-hydroxy-3-methyl-glutaryl-CoA synthase, 3-hydroxy-3-methyl-glutaryl-CoA reductase, MVA kinase, phosphomevanolate kinase, MVA diphosphate decarboxylase, FPP synthase) in wild-type plants or in transgenic plants, which already over-express a sesquiterpene synthase in mitochondria using *Arabidopsis thaliana* plants (ecotype Columbia) as a model plant. Activity of the genes and enzymes mentioned above could either be induced or repressed to achieve higher substrate pools in the mitochondria. Since exchange of isoprenoid precursors between different cellular compartments might occur, the above mentioned proteins could be localized in cellular compartments other than mitochondria and still contribute to the overall precursor pool in mitochondria.

As an example of the above method of enhancing the pool of isoprenoid precursors in mitochondria two genes from the above mentioned set were introduced in two ways, either by co-transformation of two binary vectors harboring the different genes or by retransformation of a plant already transformed with a single gene, and selecting using a new selectable marker (hygromycin instead of kanamycin that was used in the first genetic transformation). Apart from the terpenoid synthase genes described elsewhere, the genes used included an IPP isomerase from strawberry encoding a mitochondrial protein (mitoIPPI), and a cytosolic IPP isomerase (cytoIPPI) Co-transformation was performed with the following combinations of genes: mitoIPPI and a mitochondrial localized H64NORS cytoIPPI and mitochondrial localised H64NORS

Example 13

Transgenic Plants with Improved Biological Control of Pests

Linalool and nerolidol, and its derivative 4,8-dimethyl-1,3 (E),7-nonatriene have been reported to play an important role in the attraction of predators of a variety of insect and spider mite pests by a large number of crops. The sequences described in the present invention can be used as markers for the selection of crop species, such as for example maize, cotton, apple, and cucumber, and any other crops employing this indirect defense mechanism, with improved production of volatile, predator attracting, compounds in response to feeding herbivores. In addition, the present invention can be used to make transgenic plants with improved signalling capacity. Hereto the DNA sequences could be placed under the control of an inducible promoter, such as wound-inducible or specific inducible promoters. These promoters are isolated from plants that were fed upon by for example spider mites or insects. Spider mite inducible promoters can for example be isolated from cucumber or lima bean. These plant species have been shown to strongly react to spider mite feeding with the production of volatile signalling compounds (Bouwmeester et al., 1999). Subtractive (up- and down-regulated) libraries are made from non-infested (control) and infested plant material using the PCR-Select™ cDNA Subtraction Kit (Clontech), and the expression of the cDNAs in these subtractive libraries checked using cDNA micro-array technology (see for example Aharoni et al., 2000) using mRNA from control, spider-mite infested and JA-treated plant materials as probes for hybridisation. Many induced cDNAs are detected. The full-length cDNAs of interesting, strongly regulated genes are obtained using the RACE PCR technology, or by screening a cDNA library. Promoters of strongly (up-) regulated genes are isolated using the Genome Walker™ kit (Clontech).

As mentioned above, the DNA sequences from the invention can be placed under the control of wound-inducible or the isolated suitable (tissue-) specific (inducible) promoters and used for transformation of crops in which biological control is enabled by the production of inducible volatile signalling compounds, such as cucumber, maize and cotton, using published protocols. As an example for the power of this approach we have expressed the nucleic acid from the invention with a mitochondrial targeting signal in *Arabidopsis*. The state of the art did not contain any teaching which would predict that the expression of a cytosolic sesquiterpene synthase in mitochondria would result in high expression of sesquiterpene compounds. Indeed, the literature which predicted that constitutive sesquiterpene production could be achieved by expression of cytosolic sesquiterpene synthases in the cytosol was proved to be unreliable. Because of the presence of a mitochondrial targeted FPP synthase in the *Arabidopsis* genome, we expected that FPP, the substrate for the nerolidol synthase, would be present in the mitochondria of *Arabidopsis*, but it did not provide any clue as to whether the substrate pool would be available to sesquiterpene synthase which are normally expressed in the cytosol nor to which quantity the sesquiterpenes would be produced.

To study this we used the published CoxIV targeting signal (Kohler et al. Plant J 11: 613-621 (1997)) fused to H64NORS. Both constructs were transformed to *Arabidopsis* as described in Example 10. Volatile production was determined using SPME-headspace sampling on intact *Arabidopsis* leaves (2-4 leaves per vial) and GC-MS analysis using the Fisons 8060 GC-MS as described in Example 10. Nine out of twelve CoxIV-transgenic plants produced (E)-nerolidol and/or dimethylnonatriene to very high levels, comparable to the levels of linalool, when the gene was expressed in the chloroplast. FIG. 31 shows representative GC-MS chromatograms for a number of transgenic lines and a wildtype. Boland and cowokers have shown that a number of plant species are able to convert exogenously applied nerolidol to dimethylnonatriene (J. Donath, W. Boland [1995] Phytochemistry 39: 785-790). Apparently, also *Arabidopsis* is able to convert nerolidol to dimethylnonatriene also when nerolidol biosynthesis is catalysed by a transgene. Feeding of nerolidol to wildtype *Arabidopsis* leaves confirmed that nerolidol is transformed to dimethylnonatriene by endogenous *Arabidopsis* enzymes. The response of predatory mites (*Phytoseiulus persimilis*) to the transgenic plants was determined using a Y-tube olfactometer (e.g. Takabayashi et al., J. Chem. Ecol. 20(2), 373-385, 1994). In a series of three replicated experiments, the dimethylnonatriene (and nerolidol) producing *Arabidopsis* plants were highly significantly more attractive to starved predatory mites than wildtype *Arabidopsis* (P<0.001; determined using a $X^2$ test) (Table 6).

TABLE 6

Results of a two-choice Y-tube experiment in which 4 or 5 CoxIV-H64NORS transformed and 4 or 5 wildtype *Arabidopsis* plants were offered to 20 predatory mites. Results were analysed using a $X^2$-test. $X^2 = 13.42$; P < 0.001.

| Transgenic line | Number of predatory mites going to | | |
|---|---|---|---|
| | CoxIV-H64NORS | wildtype | no choice |
| 9 | 18 | 2 | |
| 8* | 13 | 5 | 2 |
| 2 | 16 | 3 | |

*According to GC-MS analysis this was a lower expressing transgenic line

Example 14

Effects of Linalool and Nerolidol Expression on Resistance to Micro-Organisms

Several plant species expressing the H64NORS gene and producing elevated levels of linalool and nerolidol were analyzed for resistance to microbial infections of powdery mildew and *Phytophthora infestans*. Clear effects were observed on leaves and fruits showing that the in vitro data presented in Example 7 are predictive of the in vivo data in transgenic plants.

Petunia and Powdery Mildew

Transformed tomato plants (control (empty vector) and transgenic homozygous for the trait) were grown from seed in a small greenhouse under identical controlled conditions (n=30). The plants were inoculated with powdery mildew (*Erysiphe cichoracearum*) spores. After 4 weeks plants were scored for infection. The results indicate that the presence of linalool protected the plants from infection by mildew (Table 2).

TABLE 2

Infection of wildtype and transgenic linalool producing *Petunia* plants with powdery mildew

| | Heavily infected | Moderately infected (lower, older leaves) | Clean |
|---|---|---|---|
| Control empty vector | 75% | — | 25% |
| Homozygous for linalool | — | 10% | 90% |

Tomato and *Phytophthora infestans*

Green fruits were harvested from various homozygous transgenic Microtom tomato lines. Earlier these lines had been characterized for linalool content by steam destillation and GC-MS. Ten different berries from each transgenic line were inoculated by pricking the top of the fruit with a tooth pick dipped in a suspension of 10,000 sporangia/ml of *Phytophthora infestans* IPO428-2. After 7 days the fruits were scored for infection level (Table 3). Nearly all diseased fruits had turned completely grey/black just below the skin. Fruits were scored clean if they had no infection at all. A strong correlation was observed between a high linalool expression level and a low percentage of diseased berries. The transgenic fruits with high linalool levels largely remained free of infection

TABLE 3

Relationship between linalool production and *Phytophthora infestans* infection of green fruits for different transgenic lines.

| Tomato line | % diseased berries | quantity of linalool (arbitrary units) |
|---|---|---|
| control | 60 | 465 |
| 1A | 70 | 2,000 |
| 1C | 50 | 3,778 |
| 1B | 30 | 22,989 |
| 1BA | 10 | 18,125 |

Potato and *Phytophthora infestans*

Transgenic potato lines expressing the H64NORS gene in two different constructs (H64NOR and H64TAR) were analyzed for production of linalool and nerolidol in the headspace using an SPME fiber and GC-MS. The H64NOR construct did not yield nerolidol or linalool production above the background present in potato, while the H64TAR construct gave very high levels of linalool and low levels nerolidol in the headspace. Both sets of plants were tested for *Phytophthora infestans* resistance by inoculating 5 detached leaves in 2 replicates with spore suspensions and scoring lesion area, lesion growth and sporulation (Table 4). A very strong correlation was observed between high linalool expression levels and strongly repressed or absent lesion growth and sporulation.

TABLE 4

Effect of different constructs on linalool production and *Phytophthora infestans* lesion growth and sporulation

| Construct | Potato genotype Transgenic line | [1]Lesion area (mm$^2$) | [1]Lesion growth rate (LGR: mm/day) t5-7 dpi | [1]Sporulation (7 dpi) | Linalool (×10$^2$ arb. units) (5 min/ measurement) |
|---|---|---|---|---|---|
| H64NOR | I5 | 271 | 4.2 | 1.4 | 625 |
| | I12 | 506 | 7.7 | 2.8 | 1125 |
| | I20 | 294 | 5.2 | 2 | 1275 |
| | I23 | 456 | 8.0 | 2.6 | 1150 |
| | I27 | 574 | 8.5 | 3.4 | 3750 |
| | I30 | 458 | 7.0 | 2.3 | 1675 |

TABLE 4-continued

Effect of different constructs on linalool production and *Phytophthora infestans* lesion growth and sporulation

| Construct | Potato genotypeTransgenic line | [1]Lesion area ($mm^2$) | [1]Lesion growth rate (LGR: mm/day) t5-7 dpi | [1]Sporulation (7 dpi) | Linalool ($\times 10^2$ arb. units) (5 min/ measurement) |
|---|---|---|---|---|---|
| H64TAR | T1 | 0 | 0 | 0 | 163000 |
| | T9 | 79 | 1.6 | 0.8 | 390000 |
| | T13 | 123 | 3.7 | 0.8 | 152000 |
| | T24 | 143 | 2.3 | 0.8 | 390000 |
| | T29 | 0 | 0 | 0 | 157000 |
| | T31 | 0 | 0 | 0 | 229000 |

[1]Five leaves per genotype were each inoculated with 1 drop of 10 microliter inoculum per leaf (IPO428-2, 50.000 sporangia/ml) and scored for lesion area, growth and sporulation (visual score on a scale of 0-4) at the indicated days post infection (dpi)

FIG. 30 combines the data of table 1 and 4. FIGS. 30A, B and C provide the correlation in lesion size, lesion growth rate, and sporulation respectively of *Phytophthora infestans* isolate IPO 428-2 plotted against the content of linalool, 8-hydroxylinalool, linalooltriol, lynalylglucoside, 8-hydroxylinalylglucoside and linalyltriolglucoside content of the potato transgenic lines T or TM-9, -13, -29 and a control line. The control data from table 4 on fungal growth and sporulation were taken to be the average values of the H64NOR plants (I-lines) with negligible increased levels of either linalool, nerolidol or derivatives. The linalool (derivative) data provided in table 1 are known to the art to be much more reliable and quantitative than the SPME data on linalool in table 4, which justifies their preferred use. FIG. 30 demonstrates a strong dose-effect correlation of the levels of linalool (derivatives) produced in potato to the levels of resistance. With high levels of terpene expression clearly complete resistance to *Phytophthora infestans* infection was obtained. Furthermore, FIG. 30D provides the in vitro data on the sensitivity of *Phytophthora infestans* isolate IPO428-2 which was used for the in planta experiments to pure linalool in the medium as described in Example 9. From the comparison of the in vitro data with the in planta data of FIG. 30 it is clear that the quantities produced in planta are in the same range as the quantities required in vitro to affect the mycelial growth. It is not clear, however, whether the naturally formed alcohol and glucoside derivatives of linalool are similarly active to inhibit fungal growth as the free underived linalool forms and may contribute to the effect of free linalool in a major way.

Example 15

Effect of Linalool and Nerolidol Expression on Insect Resistance

*Arabidopsis thaliana* and *Myzus persicae*

A line of *Arabidopsis thaliana* transformed with the H64TAR construct was characterized to have a single gene insertion by Southern blot, high headspace levels of linalool and lower headspace levels of nerolidol (Example 10). This line was selected and selfed. Selfed seeds were sown and young, non-flowering plants were analysed for levels of linalool in the headspace using SPME GC-MS analysis (Example 10). Homo- and heterozygous plants with high levels of linalool were used in a bioassay with *Myzus persicae* female adults to observe repellent or deterrent effects of linalool expression (Table 5). For each experiment two leaves were taken from the plant, one from a control and one from a linalool plant and embedded next to each other in gelling wateragar of a small petridish. Ten adult females were placed on the inside of the lid of the petridish. After preset times the number of adults on each of the leaves was recorded. A deterrent effect was visible over time. Initially the aphids did not display any preference but after 2 days a very significant distribution was observed in which 62% were on control plants and 38% were on linalool plants. This indicates that linalool and/or nerolidol are potential insect deterrents or repellents in plants that can express high levels of these compounds.

TABLE 5

Effect of linalool production in transgenic *Arabidopsis* on choice of aphids.

| Time after inoculation (hours) | Aphids on control *A. thaliana* (%) | Aphids on linalool expressing *A. thaliana* line (%) | Significance (P-value, t-test) |
|---|---|---|---|
| 0.25 | 50 | 50 | 0.47 |
| 1 | 52 | 47 | 0.31 |
| 4 | 58 | 41 | 0.05 |
| 20 | 56 | 43 | 0.09 |
| 24 | 57 | 42 | 0.2 |
| 26 | 59 | 40 | 0.11 |
| 45 | 62 | 37 | 0.003 |

Note: Nucleic acid sequence (A); Translation of nucleic acid sequence of A (B) or if sequence contains an intron: (A) Nucleic acid sequence including intron; (B) Nucleic acid sequence from (A) excluding intron; (C) Translation of nucleic acid from (B).

```
INFORMATION FOR NO: 1A (H64NORL)
SEQUENCE CHARACTERISTICS:
LENGTH: 1874
TYPE: cDNA
STRANDNESS: Single
TOPOLOGY: Linear
OTHER INFORMATION: CULTIVATED STRAWBERRY
LINALOOL/NEROLIDOL SYNTHASE
SEQUENCE DISCRIPTION FOR NO: 1A
CTAATACGACTCACTATAGGGCAAGCAGTGGTAACAACGCAGAGTACGCG

GGGACAACTTAAGTTCTTAATTCGCAAACAAAGATCAAGAAGAGCGAAAG

AAATATCATCTCCCACAGCTTCTTAGTTGCTGATCATAGATCAGATGGCA

TCGTCTTCTCGGGCCTTCTTTAAAGTATTCAATCCTCAAATTGCCTGCTA

CTTTTGAGATAGCTTGCTTCCCAGTTCTATTACTATAAAGCCGATGAACG
```

```
TTGAAACCAAGCATACTAGAACTATGGGTGACATTTTTGTCCAACATTCT
CAGAAGTTGGAACTATTGAAAACTGTCTTGAGGAATGTAGCAGAGCTAGA
TGCCCTTGAAGGTTTGAATATGATCGATGCTGTTCAAAGGCTAGGCATCG
ATTACAACTTTCAACGAGAAATCGACGAAATCCTGCACAAGCAAATGAGT
ATTGTGTCTGCCCGTGATGATCTTCATGAGGTTGCACTTCGCTTTCGACT
ACTGAGACAACATGGTTACTTCGTGCCTGAAGATGTGTTTAACAACTTCA
AGGACAGCAAAGGAACGTTCAAGCAAGTTCTGGGTGAAGACATCAAGGGA
TTGATGAGCTTATACGAAGCTTCGCAGCTAGGTACAGAAGGAGAAGATAT
ACTTGTTGAAGCTGAAAAGTTTAGCGGCCATCTGCTAAAGACTTCTCTGT
CACATCTTGATCATCATCGAGTCAGAATTGTTGCAAATACATTGAGGAAT
CCTCATCACAAAAGCTTGGCCCCATTCATGGCCAGGAACTTTTTCGTTAC
TTCTCAAGCCACCAATTCATGGTTAAATTTGCTAAAAGAAGTAGCAAAAA
CAGATTTCAATATGGTCCGGTCTCTGCACCAGAATGAAATAGTTCAAATG
TCCAAATGGTGGAAGGAGCTTGGATTGGCTAAGGAACTGAAGTTTGCAAG
AGATCAACCACTGAAATGGTACATTTGGTCCATGGCATGCCTGACAGATC
CAAAGTTATCAGAGGAGAGGGTTGAGCTCACAAAACCCATCTCTTTTGTC
TATTTGATAGATGACATTTTCGATGTTTATGGAACCCTTGATGACCTCAT
TCTCTTCACAGAAGCTGTTAATCGATGGGAAATTACTGCTATAGACCACT
TACCAGACTATATGAAGATATGCTTCAAGGCTCTCTATGATATGACTAAT
GAATTCAGCAGCAAGGTCTATCTGAAGCATGGATGGAACCCCTTACAATC
TTTGAAAATTTCGTGGGCGAGTCTTTGCAATGCATTTTTGGTGGAAGCAA
AATGGTTCGCCTCTGGGAAGCTGCCGAAGTCAGAAGAGTACTTGAAGAAT
GGCATCGTTTCTTCTGGGGTAAATGTGGTTCTAGTCCACATGTTTTTTCT
CTTGGGTCAGAACATAACCAGAAAGAGTGTGGAGTTGTTGAATGAAACTC
CAGCCATTATATCGTCCTCAGCAGCAATTCTTCGACTCTGGGACGATTTA
GGAAGTGCAAAGGATGAGAACCAGGATGGGAACGATGGGTCGTATGTAAG
GTGCTACTTAGAGGAACATGAAGGCTGTTCCATTGAGGAGGCACGAGAAA
AGACGATTAATATGATTTCAGATGAATGGAAGAAACTGAACAGAGAACTG
CTCTCTCCAAATCCATTTCCAGCATCATTCACATTGGCTTCTCTTAATCT
CGCAAGAATGATCCCCTTGATGTATAGCTACGATGGCAACCAATGCCTTC
CATCTCTTAAAGAGTATATGAAACTGATGTTGTATGAGACTGTATCAATG
TAATTAATAATAAGACTACCGGAAGTGGAGTTGAACTTCAAAGGTGGGTG
GTCAAGAGAAACAAGAAGCCTAAG
INFORMATION FOR NO: 1B (H64NORL)
SEQUENCE CHARACTERISTICS:
LENGTH: 519
TYPE: Peptide
STRANDNESS: Single
TOPOLOGY: Linear
OTHER INFORMATION: CULTIVATED STRAWBERRY
LINALOOL/NEROLIDOL SYNTHASE
SEQUENCE DISCRIPTION FOR NO: 1B
MNVETKHTRTMGDIFVQHSQKLELLKTVLRNVAELDALEGLNMIDAVQRLG
IDYNFQREIDEILHKQMSIVSARDDLHEVALRFRLLRQHGYFVPEDVFNNF
KDSKGTFKQVLGEDIKGLMSLYEASQLGTEGEDILVEAEKFSGHLLKTSLS
HLDHHRVRIVANTLRNPHHKSLAPFMARNFFVTSQATNSWLNLLKEVAKTD
FNMVRSLHQNEIVQMSKWWKELGLAKELKFARDQPLKWYIWSMACLTDPKL
SEERVELTKPISFVYLIDDIFDVYGTLDDLILFTEAVNRWEITAIDHLPDY
MKICFKALYDMTNEFSSKVYLKHGWNPLQSLKISWASLCNAFLVEAKWFAS
GKLPKSEEYLKNGIVSSGVNVVLVHMFFLLGQNITRKSVELLNETPAIISS
WSAAILRLDDLGSAKDENQDGNDGSYVRCYLEEHEGCSIEEAREKTINMIS
DEWKKLNRELLSPNPFPASFTLASLNLARMIPLMYSYDGNQCLPSLKEYMK
LMLYETVSM
INFORMATION FOR NO: 2A (H64NORS)
SEQUENCE CHARACTERISTICS:
LENGTH: 1631
TYPE: cDNA
STRANDNESS: Single
TOPOLOGY: Linear
OTHER INFORMATION: CULTIVATED STRAWBERRY
LINALOOL/NEROLIDOL SYNTHASE
SEQUENCE DISCRIPTION FOR NO: 2A
ATGAACGTTGAAACCAAGCATACTAGAACTATGGGTGACATTTTTGTCCAA
CATTCTCAGAAGTTGGAACTATTGAAAACTGTCTTGAGGAATGTAGCAGAG
CTAGATGCCCTTGAAGGTTTGAATATGATCGATGCTGTTCAAAGGCTAGGC
ATCGATTACAACTTTCAACGAGAAATCGACGAAATCCTGCACAAGCAAATG
AGTATTGTGTCTGCCCGTGATGATCTTCATGAGGTTGCACTTCGCTTTCGA
CTACTGAGACAACATGGTTACTTCGTGCCTGAAGATGTGTTTAACAACTTC
AAGGACAGCAAAGGAACGTTCAAGCAAGTTCTGGGTGAAGACATCAAGGGA
TTGATGAGCTTATACGAAGCTTCGCAGCTAGGTACAGAAGGAGAAGATATA
CTTGTTGAAGCTGAAAAGTTTAGCGGCCATCTGCTAAAGACTTCTCTGTCA
CATCTTGATCATCATCGAGTCAGAATTGTTGCAAATACATTGAGGAATCCT
CATCACAAAAGCTTGGCCCCATTCATGGCCAGGAACTTTTTCGTTACTTCT
CAAGCCACCAATTCATGGTTAAATTTGCTAAAAGAAGTAGCAAAAACAGAT
TTCAATATGGTCCGGTCTCTGCACCAGAATGAAATAGTTCAAATGTCCAAA
TGGTGGAAGGAGCTTGGATTGGCTAAGGAACTGAAGTTTGCAAGAGATCAA
CCACTGAAATGGTACATTTGGTCCATGGCATGCCTGACAGATCCAAAGTTA
TCAGAGGAGAGGGTTGAGCTCACAAAACCCATCTCTTTTGTCTATTTGATA
GATGACATTTTCGATGTTTATGGAACCCTTGATGACCTCATTCTCTTCACA
GAAGCTGTTAATCGATGGGAAATTACTGCTATAGACCACTTACCAGACTAT
ATGAAGATATGCTTCAAGGCTCTCTATGATATGACTAATGAATTCAGCAGC
AAGGTCTATCTGAAGCATGGATGGAACCCCTTACAATCTTTGAAAATTTCG
TGGGCGAGTCTTTGCAATGCATTTTTGGTGGAAGCAAATGGTTCGCCTCT
GGGAAGCTGCCGAAGTCAGAAGAGTACTTGAAGAATGGCATCGTTTCTTCT
GGGGTAAATGTGGTTCTAGTCCACATGTTTTTTCTCTTGGGTCAGAACATA
ACCAGAAAGAGTGTGGAGTTGTTGAATGAAACTCCAGCCATTATATCGTCC
TCAGCAGCAATTCTTCGACTCTGGGACGATTTAGGAAGTGCAAAGGATGAG
AACCAGGATGGGAACGATGGGTCGTATGTAAGGTGCTACTTAGAGGAACAT
GAAGGCTGTTCCATTGAGGAGGCACGAGAAAAGACGATTAATATGATTTCA
GATGAATGGAAGAAACTGAACAGAGAACTGCTCTCTCCAAATCCATTTCCA
```

```
GCATCATTCACATTGGCTTCTCTTAATCTCGCAAGAATGATCCCCTTGATG

TATAGCTACGATGGCAACCAATGCCTTCCATCTCTTAAAGAGTATATGAAA

CTGATGTTGTATGAGACTGTATCAATGTAATTAATAATAAGACTACCGGAA

GTGGAGTTGAACTTCAAAGGTGGGTGGTCAAGAGAAACAAGAAGCCTAAG

INFORMATION FOR NO: 2B (H64NORS)
SEQUENCE CHARACTERISTICS:
LENGTH: 519
TYPE: Peptide
STRANDNESS: Single
TOPOLOGY: Linear
OTHER INFORMATION: CULTIVATED STRAWBERRY
LINALOOL/NEROLIDOL SYNTHASE
SEQUENCE DISCRIPTION FOR NO: 2B
MNVETKHTRTMGDIFVQHSQKLELLKTVLRNVAELDALEGLNMIDAVQRLG

IDYNFQREIDEILHKQMSIVSARDDLHEVALRFRLLRQHGYFVPEDVFNNF

KDSKGTFKQVLGEDIKGLMSLYEASQLGTEGEDILVEAEKFSGHLLKTSLS

HLDHHRVRIVANTLRNPHHKSLAPFMARNFFVTSQATNSWLNLLKEVAKTD

FNMVRSLHQNEIVQMSKWWKELGLAKELKFARDQPLKWYIWSMACLTDPKL

SEERVELTKPISFVYLIDDIFDVYGTLDDLILFTEAVNRWEITAIDHLPDY

MKICFKALYDMTNEFSSKVYLKHGWNPLQSLKISWASLCNAFLVEAKWFAS

GKLPKSEEYLKNGIVSSGVNVVLVHMFFLLGQNITRKSVELLNETPAIISS

SAAILRLWDDLGSAKDENQDGNDGSYVRCYLEEHEGCSIEEAREKTINMIS

DEWKKLNRELLSPNPFPASFTLASLNLARMIPLMYSYDGNQCLPSLKEYMK

LMLYETVSM

INFORMATION FOR NO: 3A (H64MUT)
SEQUENCE CHARACTERISTICS:
LENGTH: 1874
TYPE: cDNA
STRANDNESS: Single
TOPOLOGY: Linear
OTHER INFORMATION: CULTIVATED STRAWBERRY
LINALOOL/NEROLIDOL SYNTHASE
SEQUENCE DISCRIPTION FOR NO: 3A
CTAATACGACTCACTATAGGGCAAGCAGTGGTAACAACGCAGAGTACGCGG

GGACAACTTAAGTTCTTAATTCGCAAACAAAGATCAAGAAGAGCGAAAGAA

ATATCATCTCCCACAGCTTCTTAGTTGCTGATCATAGATCAGATGGCATCG

TCTTCTCGGGCCTTCTTTAAAGTATTCAATCCTCAAATTGCCTGCTACTTT

CTAGATAGCTTGCTTCCCAGTTCTATTACTATAAAGCCGATGAACGTTGAA

ACCAAGCATACTAGAACTATGGGTGACATTTTTGTCCAACATTCTCAGAAG

TTGGAACTATTGAAAACTGTCTTGAGGAATGTAGCAGAGCTAGATGCCCTT

GAAGGTTTGAATATGATCGATGCTGTTCAAAGGCTAGGCATCGATTACAAC

TTTCAACAGAGAAATCGACGAAATCCTGCACAAGCAAATGAGTATTGTGTCT

GCCCGTGATGATCTTCATGAGGTTGCACTTCGCTTTCGACTACTGAGACAA

CATGGTTACTTCGTGCCTGAAGATGTGTTTAACAACTTCAAGGACAGCAAA

GGAACGTTCAAGCAAGTTCTGGGTGAAGACATCAAGGGATTGATGAGCTTA

TACGAAGCTTCGCAGCTAGGTACAGAAGGAGAAGATATACTTGTTGAAGCT

GAAAAGTTTAGCGGCCATCTGCTAAAGACTTCTCTGTCACATCTTGATCAT

CATCGAGTCAGAATTGTTGCAAATACATTGAGGAATCCTCATCACAAAAGC

TTGGCCCCATTCATGGCCAGGAACTTTTTCGTTACTTCTCAAGCCACCAAT

TCATGGTTAAATTTGCTAAAAGAAGTAGCAAAAACAGATTTCAATATGGTC

CGGTCTCTGCACCAGAATGAAATAGTTCAAATGTCCAAATGGTGGAAGGAG

CTTGGATTGGCTAAGGAACTGAAGTTTGCAAGAGATCAACCACTGAAATGG

TACATTTGGTCCATGGCATGCCTGACAGATCCAAAGTTATCAGAGGAGAGG

GTTGAGCTCACAAAACCCATCTCTTTTGTCTATTTGATAGATGACATTTTC

GATGTTTATGGAACCCTTGATGACCTCATTCTCTTCACAGAAGCTGTTAAT

CGATGGGAAATTACTGCTATAGACCACTTACCAGACTATATGAAGATATGC

TTCAAGGCTCTCTATGATATGACTAATGAATTCAGCAGCAAGGTCTATCTG

AAGCATGGATGGAACCCCTTACAATCTTTGAAAATTTCGTGGGCGAGTCTT

TGCAATGCATTTTTGGTGGAAGCAAAATGGTTCGCCTCTGGGAAGCTGCCG

AAGTCAGAAGAGTACTTGAAGAATGGCATCGTTTCTTCTGGGGTAAATGTG

GTTCTAGTCCACATGTTTTTTCTCTTGGGTCAGAACATAACCAGAAAGAGT

GTGGAGTTGTTGAATGAAACTCCAGCCATTATATCGTCCTCAGCAGCAATT

CTTCGACTCTGGGACGATTTAGGAAGTGCAAAGGATGAGAACCAGGATGGG

AACGATGGGTCGTATGTAAGGTGCTACTTAGAGGAACATGAAGGCTGTTCC

ATTGAGGAGGCACGAGAAAAGACGATTAATATGATTTCAGATGAATGGAAG

AAACTGAACAGAGAACTGCTCTCTCCAAATCCATTTCCAGCATCATTCACA

TTGGCTTCTCTTAATCTCGCAAGAATGATCCCCTTGATGTATAGCTACGAT

GGCAACCAATGCCTTCCATCTCTTAAAGAGTATATGAAACTGATGTTGTAT

GAGACTGTATCAATGTAATTAATAATAAGACTACCGGAAGTGGAGTTGAAC

TTCAAAGGTGGGTGGTCAAGAGAAACAAGAAGCCTAAG

INFORMATION FOR NO: 3B (H64MUT)
SEQUENCE CHARACTERISTICS:
LENGTH: 552
TYPE: Peptide
STRANDNESS: Single
TOPOLOGY: Linear
OTHER INFORMATION: CULTIVATED STRAWBERRY
LINALOOL/NEROLIDOL SYNTHASE
SEQUENCE DISCRIPTION FOR NO: 3B
MASSSRAFFKVFNPQIACYFLDSLLPSSITIKPMNVETKHTRTMGDIFVQH

SQKLELLKTVLRNVAELDALEGLNMIDAVQRLGIDYNFQREIDEILHKQMS

IVSARDDLHEVALRFRLLRQHGYFVPEDVFNNFKDSKGTFKQVLGEDIKGL

MSLYEASQLGTEGEDILVEAEKFSGHLLKTSLSHLDHHRVRIVANTLRNPH

HKSLAPFMARNFFVTSQATNSWLNLLKEVAKTDFNMVRSLHQNEIVQMSKW

WKELGLAKELKFARDQPLKWYIWSMACLTDPKLSEERVELTKPISFVYLID

DIFDVYGTLDDLILFTEAVNRWEITAIDHLPDYMKICFKALYDMTNEFSSK

VYLKHGWNPLQSLKISWASLCNAFLVEAKWFASGKLPKSEEYLKNGIVSSG

VNVVLVHMFFLLGQNITRKSVELLNETPAIISSSAAILRLWDDLGSAKDEN

QDGNDGSYVRCYLEEHEGCSIEEAREKTINMISDEWKKLNRELLSPNPFPA

SFTLASLNLARMIPLMYSYDGNQCLPSLKEYMKLMLYETVSM

INFORMATION FOR NO: 4A (H64VES)
SEQUENCE CHARACTERISTICS:
LENGTH: 1894
TYPE: cDNA
STRANDNESS: Single
TOPOLOGY: Linear
```

OTHER INFORMATION: WILD STRAWBERRY LINALOOL/
NEROLIDOL SYNTHASE
SEQUENCE DISCRIPTION FOR NO: 4A
AAGCAGTGGTAACAACGCAGAGTACGCGGGGACAACTGAAGTTCTTAATTC

GCAAACAAAGATCAAGAAGAGCGAAAGAAGTATCATCTCCCGCCTTAGGTG

CTGATCATAGATCAGATGGCATCGTCTTCTTGGGCCTTCTTTAAAGTATTC

AATCCCCAAATTGCTCCAAAAAGTATCTCACATATTGGCCAGTCTGACCTC

ATGCAGCTTACACATAAGAAGCAGCTGCCTACTTTTCAAAGACGGGGCATT

GCCGAAGATAGCTTGCTTCCCAGTTCTACTACTCCCATAAAGCCGATGCAC

GTTGAAACCAAGCATACTAGAACTATGGGTGACATTTTTGTCCAACATTCT

CAGAAGTTGGAACTATTCAGAAATGTCTTGAGGAATGCAGCAGAGCTAGAT

GCCCTTGAAGGTTTGAATATGATCGATGCCGTTCAAAGGCTAGGCATCGAT

TACCACTTTCAACGAGAAATCGACGAAATTCTGCACAAGCAAATGGGTATT

GTATCTGCCTGTGATGATCTTTATGAGGTTGCACTTCGTTTTCGACTACTG

AGACAACATGGTTACTTCGTGCCTGAAGATGTGTTTAACAACTTCAAGGAC

AGCAAAGGAACTTTCAAGCAAGTTCTGGGTGAAGACATCAAGGGATTGATG

AGCTTATACGAAGCTTCGCAGCTAGGTACAGAAGGAGAAGATACACTTGTT

GAAGCTGAAAAGTTTAGTGGCCATCTGCTAAAGACTTCTCTGTCACATCTT

GATCGTCATCGAGCCAGAATTGTTGGAAATACATTGAGGAATCCTCATCGC

AAAAGCTTGGCCTCATTCATGGCCAGGAACTTTTTCGTTACTTCTCAAGCC

ACCAATTCATGGTTAAATTTGCTAAAAGAAGTAGCAAAAACAGATTTCAAT

ATGGTCCGGTCTGTGCACCAGAAAGAAATAGTTCAAATTTCCAAATGGTGG

AAGGAGCTTGGATTGGTTAAGGAACTGAAGTTTGCAAGAGATCAACCACTG

AAATGGTACACTTGGTCCATGGCAGGCCTAACAGATCCAAAGTTATCAGAG

GAGAGGGTTGAGCTCACAAAACCCATCTCTTTTGTCTATTTGATAGATGAC

ATTTTCGATGTTTATGGAACCCTTGATGACCTCATTCTCTTCACAGAAGCT

GTTAATAGATGGGAAATTACTGCTATAGACCACTTACCGACTATATGAAG

ATATGCTTCAAGGCTCTCTATGATATGACTAATGAATTCAGCTGCAAGGTC

TATCAGAAGCATGGATGGAACCCCTTACGATCTTTGAAAATTTCGTGGGCG

AGTCTTTGCAATGCGTTTTTGGTGGAAGCAAAATGGTTCGCATCTGGGCAG

CTGCCGAAGTCAGAAGAGTACTTGAAGAACGGCATCGTTTCTTCGGGGTA

AATGTGGGTCTAGTCCACATGTTTTTTCTCTTGGGTCAGAACATAACCAGA

AAGAGTGTGGAGTTGTTGAATGAAACTCCAGCCATGATATCGTCCTCAGCA

GCAATTCTTCGACTCTGGGACGATTTAGGCAGTGCAAAGGATGAGAACCAG

GATGGGAACGATGGGTCGTATGTAAGGTGCTACTTAGAGGAACATGAAGGC

TGTTCCATTGAGGAGGCACGAGAAAAGACGATTAATATGATTTCAGATGAA

TGGAAGAAACTGAACAGAGAACTGCTCTCTCCAAATCCATTTCCAGCAACA

TTCACATCGGCTTCTCTTAATCTCGCAAGAATGATCCCCTTGATGTATAGC

TACGATGGCAACCAATCCCTTCCATCTCTTAAAGAGTATATGAAACTGATG

TTGTATGAGACTGTATCAATGTAATTGATAATAAGACTGCTGGAAGTGGAG

TTGAACA

INFORMATION FOR NO: 4B (H64VES)
SEQUENCE CHARACTERISTICS:
LENGTH: 580
TYPE: Peptide
STRANDNESS: Single
TOPOLOGY: Linear
OTHER INFORMATION: WILD STRAWBERRY LINALOOL/
NEROLIDOL SYNTHASE
SEQUENCE DISCRIPTION FOR NO: 4B
MASSSWAFFKVFNPQIAPKSISHIGQSDLMQLTHKKQLPTFQRRGIAEDSL

LPSSTTPIKPMHVETKHTRTMGDIFVQHSQKLELFRNVLRNAAELDALEGL

NMIDAVQRLGIDYHFQREIDEILHKQMGIVSACDDLYEVALRFRLLRQHGY

FVPEDVFNNFKDSKGTFKQVLGEDIKGLMSLYEASQLGTEGEDTLVEAEKF

SGHLLKTSLSHLDRHRARIVGNTLRNPHRKSLASFMARNFFVTSQATNSWL

NLLKEVAKTDFNMVRSVHQKEIVQISKWWKELGLVKELKFARDQPLKWYTW

SMAGLTDPKLSEERVELTKPISFVYLIDDIFDVYGTLDDLILFTEAVNRWE

ITAIDHLPDYMKICFKALYDMTNEFSCKVYQKHGWNPLRSLKISWASLCNA

FLVEAKWFASGQLPKSEEYLKNGIVSSGVNVGLVHMFFLLGQNITRKSVEL

LNETPAMISSSAAILRLWDDLGSAKDENQDGNDGSYVRCYLEEHEGCSIEE

AREKTINMISDEWKKLNRELLSPNPFPATFTSASLNLARMIPLMYSYDGNQ

SLPSLKEYMKLMLYETVSM

INFORMATION FOR NO: 5A (H64NORD1/W155)
SEQUENCE CHARACTERISTICS:
LENGTH: 333
TYPE: Genomic DNA
STRANDNESS: Single
TOPOLOGY: Linear
OTHER INFORMATION: PCR fragment from the 5' of
cultivated strawberry H64. Includes stop codon
and an intron.
SEQUENCE DISCRIPTION FOR NO: 5A
CTCCCACAGCTTCTTAGTTGCTGATCATAGATCAGATGGCATCGTCTTCTC

GGGCCTTCTTTAAAGTATTCAATCCTCAAATTGCCTGCTACTTTTGAGATA

GCTTGCTTCCCAGTTCTATTACTATAAAGCCGATGAACGTTGAAACCAAGC

ATACTAGAACTATGGTAAAATTCTCGGAGCTTTCTCCGAAGTACATTTCTA

CAAAAGGGTAGAGCTAGCTACTAAACAATAGTTAATTGACTGTGCCTTGCT

TGCAGGGTGACATTTTTGTCCAACATTCTCAGAAGTTGGAACTATTGAAAA

CTGTCTTGAGGAATGTAGCAGAGCTAG

INFORMATION FOR NO: 5B (H64NORD1/W155)
SEQUENCE CHARACTERISTICS:
LENGTH: 240
TYPE: Genomic DNA
STRANDNESS: Single
TOPOLOGY: Linear
OTHER INFORMATION: PCR fragment from the 5' of
cultivated strawberry H64. Stop codon modified
and intron removed.
SEQUENCE DISCRIPTION FOR NO: 5B
CTCCCACAGCTTCTTAGTTGCTGATCATAGATCAGATGGCATCGTCTTCTC

GGGCCTTCTTTAAAGTATTCAATCCTCAAATTGCCTGCTACTTTCTAGATA

GCTTGCTTCCCAGTTCTATTACTATAAAGCCGATGAACGTTGAAACCAAGC

ATACTAGAACTATGGGTGACATTTTTGTCCAACATTCTCAGAAGTTGGAAC

TATTGAAAACTGTCTTGAGGAATGTAGCAGAGCTAG

INFORMATION FOR NO: 5C (H64NORD1/W155)
SEQUENCE CHARACTERISTICS:
LENGTH: 68
TYPE: Peptide
STRANDNESS: Single
TOPOLOGY: Linear -continued
OTHER INFORMATION: PCR fragment from the 5' of
cultivated strawberry H64. Stop codon modified
and intron removed and fragment translated.
SEQUENCE DISCRIPTION FOR NO: 5C
MASSSRAFFKVFNPQIACYFLDSLLPSSITIKPMNVETKHTRTMGDIFVQH

SQKLELLKTVLRNVAEL

INFORMATION FOR NO: 6A (H64NORU1/W151)
SEQUENCE CHARACTERISTICS:
LENGTH: 392
TYPE: Genomic DNA
STRANDNESS: Single
TOPOLOGY: Linear
OTHER INFORMATION: PCR fragment from the 5' of
cultivated strawberry H64. Includes stop codon
and an intron.
SEQUENCE DISCRIPTION FOR NO: 6A
CTCCCACAGCTTCTTAGTTGCTGATCATAGATCAGATGGCATAGTCTTTTC

GGTCCCTCTTTAAAGTATTCAATCAAATTGCTCCAAAAATTATCTCACATG

TTGGCCACTCTAAGAAGCAGCTGCCTGCTACTTTTCAAAGATGGGGCGTTG

CCGAAGATAGCTTGCTTTCCAGTTCTAGTACTATAAAGCTGATGAACGTTG

AAACCAAGCATACTAGAACTATGGTAAAATTCTTGGGCTTTCTCCTACGT

ACATTTCTTCAATGAGGCTAGCTAGCTACTAAACAATAGTTAATTGACTGT

GCCTTACTTGCAGGATGACATTTTTGTCCAACATTCTCGGAAGCTGGAACT

ACTCAGGAATGTCTTGAGGAATGTAGCAGAGCTAG

INFORMATION FOR NO: 6B (H64NORU1/W151)
SEQUENCE CHARACTERISTICS:
LENGTH: 300
TYPE: Genomic DNA
STRANDNESS: Single
TOPOLOGY: Linear
OTHER INFORMATION: PCR fragment from the 5' of
cultivated strawberry H64. Stop codon modified
and intron removed.
SEQUENCE DISCRIPTION FOR NO: 6B
CTCCCACAGCTTCTTAGTTGCTGATCATAGATCAGATGGCAAAGTCTTTTC

GGTCCCTCTTTAAAGTATTCAATCAAATTGCTCCAAAAATTATCTCACATG

TTGGCCACTCTAAGAAGCAGCTGCCTGCTACTTTTCAAAGATGGGGCGTTG

CCGAAGATAGCTTGCTTTCCAGTTCTAGTACTATAAAGCTGATGAACGTTG

AAACCAAGCATACTAGAACTATGGATGACATTTTTGTCCAACATTCTCGGA

AGCTGGAACTACTCAGGAATGTCTTGAGGAATGTAGCAGAGCTAG

INFORMATION FOR NO: 6C (H64NORU1/W151)
SEQUENCE CHARACTERISTICS:
LENGTH: 88
TYPE: Peptide
STRANDNESS: Single
TOPOLOGY: Linear
OTHER INFORMATION: PCR fragment from the 5' of
cultivated strawberry H64. Stop codon modified
and intron removed and fragment translated
SEQUENCE DISCRIPTION FOR NO: 6C
MAKSFRSLFKVFNQIAPKIISHVGHSKKQLPATFQRWGVAEDSLLSSSSTI

KLMNVETKHTRTMDDIFVQHSRKLELLRNVLRNVAEL

INFORMATION FOR NO: 7A (H64NORU2/UP3)
SEQUENCE CHARACTERISTICS:
LENGTH: 350
TYPE: Genomic DNA
STRANDNESS: Single
TOPOLOGY: Linear -continued
OTHER INFORMATION: PCR fragment from the 5' of
cultivated strawberry H64. Includes stop codon
and an intron.
SEQUENCE DISCRIPTION FOR NO: 7A
CTCCCACAGCTTCTTAGTTGCTGATCATAGATCAGATGGCATAGTCTTTTC

GGTCCCTCTTTAAAGTATTCAATCAAATTGCTCCAAAAATTATCTCACATG

TTGGCCACTCTAAGAAGCAGCTGCCTGCTACTTTTCAAAGATGGGGCGTTG

CCGAAGATAGCTTGCTTTCCAGTTCTAGTACTATAAAGCTGATGAACGTTG

AAACCGAGCATACTAGAACTATGGTAAAATTCTTGGGCTTTCTCCTACGT

ACATTTCTTCAATGAGGCTAGCTAGCTACTAAACAATAGTTAATTGACTGT

GCCTTACTTGCAGGATGACATTTTTGTCCAACATTCTCGGAAGC

INFORMATION FOR NO: 7B (H64NORU2/UP3)
SEQUENCE CHARACTERISTICS:
LENGTH: 258
TYPE: Genomic DNA
STRANDNESS: Single
TOPOLOGY: Linear
OTHER INFORMATION: PCR fragment from the 5' of
cultivated strawberry H64. Stop codon modified
and intron removed.
SEQUENCE DISCRIPTION FOR NO: 7B
CTCCCACAGCTTCTTAGTTGCTGATCATAGATCAGATGGCAAAGTCTTTTC

GGTCCCTCTTTAAAGTATTCAATCAAATTGCTCCAAAAATTATCTCACATG

TTGGCCACTCTAAGAAGCAGCTGCCTGCTACTTTTCAAAGATGGGGCGTTG

CCGAAGATAGCTTGCTTTCCAGTTCTAGTACTATAAAGCTGATGAACGTTG

AAACCGAGCATACTAGAACTATGGATGACATTTTTGTCCAACATTCTCGGA

AGC

INFORMATION FOR NO: 7C (H64NORU2/UP3)
SEQUENCE CHARACTERISTICS:
LENGTH: 74
TYPE: Peptide
STRANDNESS: Single
TOPOLOGY: Linear
OTHER INFORMATION: PCR fragment from the 5' of
cultivated strawberry H64. Stop codon modified
and intron removed and fragment translated
SEQUENCE DISCRIPTION FOR NO: 7C
MAKSFRSLFKVFNQIAPKIISHVGHSKKQLPATFQRWGVAEDSLLSSSSTI

KLMNVETEHTRTMDDIFVQHSRK

INFORMATION FOR NO: 8A (H64NORU3/UP16)
SEQUENCE CHARACTERISTICS:
LENGTH: 367
TYPE: Genomic DNA
STRANDNESS: Single
TOPOLOGY: Linear
OTHER INFORMATION: PCR fragment from the 5' of
cultivated strawberry H64. Includes an intron.
SEQUENCE DISCRIPTION FOR NO: 8A
CTCCCACAGCTTCTTAGTTGCTGATCATAGATCAGATGGCATCGTCTTCTC

GGGCCTTCTTTAAAGTATTCAATCCTGCTCCAAAAAGCATCCCACGTATTG

GCCAGTCTAACCTCATGCAGCTTACACATAAGAAGCAGCTGCCTACTTTTC

AAAGACGGGGCATTGCCGAAGATAGCTTGCTTCCCAGTTCTACTACTCCCA

TAAAGCTGATGAACGTTGAAACCAAGCATACTAGAACTATGGTAAAATTCT

CGGAGCTTTCTCCGAAGTACATTTCATCAAGAGGCTAGCTATAGCTACTAC

ACAATAGTTTGACTGTGCCTTGCTTGCAGGGTGACATTTTTGTCCAACATT

GTCAGAAGTT

INFORMATION FOR NO: 8B (H64NORU3/UP16)
SEQUENCE CHARACTERISTICS:

LENGTH: 277
TYPE: Genomic DNA
STRANDNESS: Single
TOPOLOGY: Linear
OTHER INFORMATION: PCR fragment from the 5' of cultivated strawberry H64. Intron removed.
SEQUENCE DISCRIPTION FOR NO: 8B
CTCCCACAGCTTCTTAGTTGCTGATCATAGATCAGATGGCATCGTCTTCTC

GGGCCTTCTTTAAAGTATTCAATCCTGCTCCAAAAAGCATCCCACGTATTG

GCCAGTCTAACCTCATGCAGCTTACACATAAGAAGCAGCTGCCTACTTTTC

AAAGACGGGGCATTGCCGAAGATAGCTTGCTTCCCAGTTCTACTACTCCCA

TAAAGCTGATGAACGTTGAAACCAAGCATACTAGAACTATGGGTGACATTT

TTGTCCAACATTGTCAGAAGTT

INFORMATION FOR NO: 8C (H64NORU3/UP16)
SEQUENCE CHARACTERISTICS:
LENGTH: 80
TYPE: Peptide
STRANDNESS: Single
TOPOLOGY: Linear
OTHER INFORMATION: PCR fragment from the 5' of cultivated strawberry H64. Intron removed and fragment translated
SEQUENCE DISCRIPTION FOR NO: 8C
MASSSRAFFKVFNPAPKSIPRIGQSNLMQLTHKKQLPTFQRRGIAEDSLLP

SSTTPIKLMNVETKHTRTMGDIFVQHCQK

INFORMATION FOR NO: 9A (H64NORU4/UP1)
SEQUENCE CHARACTERISTICS:
LENGTH: 357
TYPE: Genomic DNA
STRANDNESS: Single
TOPOLOGY: Linear
OTHER INFORMATION: PCR fragment from the 5' of cultivated strawberry H64. Includes an intron.
SEQUENCE DISCRIPTION FOR NO: 9A
CTCCCACAGCTTCTTAGTTGCTGATCATAGATCAGATGGCATCGTCTTCTC

GGGCCTTCTTTAAAGTATTCAATCCTGCTCCAAAAAGCATCCCACGTATTG

GCCAGTCTAACCTCATGCAGCTTACACATAAGAAGCAGCTGCCTACTTTTC

AAAGACGGGGCATTGCCGAAGATAGCTTGCTTCCCAGTTCTACTACTCCCA

TAAAGCCGATGAACGTTGAAACCAAGCATACTAGAACTATGGTAAAATTCT

CGGAGCTTTCTCCGAAGTACATTTCATCAAGAGGCTAGCTATAGCTACTAC

ACAATAGTTTGACTGTGCCTTGCTTGCAGGGTGACATTTTTGTCCAACATT

INFORMATION FOR NO: 9B (H64NORU4/UP1)
SEQUENCE CHARACTERISTICS:
LENGTH: 267
TYPE: Genomic DNA
STRANDNESS: Single
TOPOLOGY: Linear
OTHER INFORMATION: PCR fragment from the 5' of cultivated strawberry H64. Intron removed.
SEQUENCE DISCRIPTION FOR NO: 9B
CTCCCACAGCTTCTTAGTTGCTGATCATAGATCAGATGGCATCGTCTTCTC

GGGCCTTCTTTAAAGTATTCAATCCTGCTCCAAAAAGCATCCCACGTATTG

GCCAGTCTAACCTCATGCAGCTTACACATAAGAAGCAGCTGCCTACTTTTC

AAAGACGGGGCATTGCCGAAGATAGCTTGCTTCCCAGTTCTACTACTCCCA

TAAAGCCGATGAACGTTGAAACCAAGCATACTAGAACTATGGGTGACATTT

TTGTCCAACATT

INFORMATION FOR NO: 9C (H64NORU4/UP1)
SEQUENCE CHARACTERISTICS:
LENGTH: 77
TYPE: Peptide
STRANDNESS: Single
TOPOLOGY: Linear
OTHER INFORMATION: PCR fragment from the 5' of cultivated strawberry H64. Intron removed and fragment translated
SEQUENCE DISCRIPTION FOR NO: 9C
MASSSRAFFKVFNPAPKSIPRIGQSNLMQLTHKKQLPTFQRRGIAEDSLLP

SSTTPIKPMNVETKHTRTMGDIFVNI

INFORMATION FOR NO: 10A (SOSA/WS)
SEQUENCE CHARACTERISTICS:
LENGTH: 1672
TYPE: cDNA
STRANDNESS: Single
TOPOLOGY: Linear
OTHER INFORMATION: CULTIVATED STRAWBERRY OLEFIN SYNTHASE.
INCLUDES A STOP CODON.
SEQUENCE DISCRIPTION FOR NO: 10A
ATGCCTGTCCATGCTACTCCAGCAGCTGAATCCCAGATCATCTCTATGCCG

GAAGTTGTTCGGCGCACAGCAAATTTTAAACCTAGCGTTTGGGGAGATCGG

TTTGCTAACTATGCCGAAGACATTATAACTCAAACTCAAATGCAAGAACAA

GTTGAGGAGCTGAAACAAGTGAGGAAGGAAGTATTCACTAATGCTGCTGAT

GATTCTTCACATCAACTGAAGCCAATTGATGAAATCCAGCGCCTCGGTGTG

GCTTACCATTTCGAAAGCGAAATAGATCAAGCCCTGGAACGTATACATGAG

ACATATCAAGATATTCATGATGGTGGTGATCTGTACAATGTTGCTCTTCGT

TTTCGGCTACTCAGGCGACATGGATATAATGTTTCCTGCGATGTATTCAAC

AAGTTCAAAGATACTAATGGTGACTACAAGAAAAGCTTGGTCACTGATCTT

TCTGGTATGCTGAGCTTTTATGAGGCGGCCCATCTGAGGGTGCATGGAGAA

AAATTACTTGAAGAGGCTCTGGTTTTTACCACCACTCATCTCCAGTCAGCA

AGTGCAAAAAGCTCTTTGCTGAAAACACAAATAACTGAAGCCGTAGAGAGA

CTACTAAAAACTATGGAGAGGTTAGGTGCTCGGCGTTACATGTCAATATAT

CAAGATGAAGCTTCATACAGTGAAAATTTACTGAAACTTGCAAAATTAGAT

TTTAATGTTGTTCAGTGTTTACACAAAAAGGAACTCAGTGACATTCCCTAA

GATGGTACAAGGAACTGGACTTTGCAAGGAGGATGCCTTTTGCTCGAGATA

GGATCGTGGAGTTGTTCTTTTGGATAGCAGGAATATATTTCGAACCTGAAT

ACGTCTTTAGGAGACACATTCTGACTAAACTGATTGAGATAACAACAGTAA

TGGATGATATGTATGATGCATTCGGTACATTCGAAGAACTCGTCAACTTGA

CTGAAGCAATTGACAGGTGGGATGCAAGTTGCATGGATCAACTGCCAGACT

ATATGCAACCATTTTATATTACACTTCTGGATGTTATCGATGAAGTTGAAG

AGGAGCTGACAAAGCAAGGAAGATCTTACCGAATTCACTACGCAAAAGAAA

TTATGAAGAATCAAGCCAGGCTCTACTTCGCTGAGGCCAGATGGTTCCACG

AAGGATGCACCCCAAAAATGGATGAGTATATGCGAGTTGCGGCATCTTCTG

TCGGTAACACCATGCTTTCCGTCGTGTCTTTAGTAGGCATGGGAGACATTA

TAACAAAATTTGAATTCGAGTGGCTGACCAATGAGCCTAAAATCCTTAGAG

CTTCGAATACCATATTTAGGCTTATGGATGACATTGCTGGGTACAAGTTTG

AGAAAGAGAGGGCATGTTGCTTCAAGTATTGATTGCTACATGAATGAAT

ACGGGGTTTCAGAGCAAGAGACAATTGATATCTTCAACAAACGAATTGTGG

ATTCGTGGAAGGATATAAACGAAGAGTTTCTGAGACCCACTGCTGCTCCAG

TCCCTGTGCTTAATCGTGTTCTTAACCTAACCCGAGTGGTTGATCTGCTTT

ACAAAAGGGGAGATGCCTTCACGCATGTCGGAAAACTGATGAAAGATTGTA

TTGCTGCAATGTTTATTGATCCAGTGCCACTCTGAACTCA

INFORMATION FOR NO: 10B (SOSA/WS)
SEQUENCE CHARACTERISTICS:
LENGTH: 254
TYPE: Peptide
STRANDNESS: Single
TOPOLOGY: Linear
OTHER INFORMATION: CULTIVATED STRAWBERRY OLEFIN SYNTHASE.
SEQUENCE DISCRIPTION FOR NO: 10B
MPVHATPAAESQIISMPEVVRRTANFKPSVWGDRFANYAEDIITQTQMQEQ

VEELKQVRKEVFTNAADDSSHQLKPIDEIQRLGVAYHFESEIDQALERIHE

TYQDIHDGGDLYNVALRFRLLRRHGYNVSCDVFNKFKDTNGDYKKSLVTDL

SGMLSFYEAAHLRVHGEKLLEEALVFTTTHLQSASAKSSLLKTQITEAVER

LLKTMERLGARRYMSIYQDEASYSENLLKLAKLDFNVVQCLHKKELSDIP

INFORMATION FOR NO: 10C (SOSA/WS)
SEQUENCE CHARACTERISTICS:
LENGTH: 554
TYPE: Peptide
STRANDNESS: Single
TOPOLOGY: Linear
OTHER INFORMATION: CULTIVATED STRAWBERRY OLEFIN SYNTHASE.
Deleting the CC insertion
SEQUENCE DISCRIPTION FOR NO: 10C
MPVHATPAAESQIISMPEVVRRTANFKPSVWGDRFANYAEDIITQTQMQEQ

VEELKQVRKEVFTNAADDSSHQLKPIDEIQRLGVAYHFESEIDQALERIHE

TYQDIHDGGDLYNVALRFRLLRRHGYNVSCDVFNKFKDTNGDYKKSLVTDL

SGMLSFYEAAHLRVHGEKLLEEALVFTTTHLQSASAKSSLLKTQITEAVER

LLKTMERLGARRYMSIYQDEASYSENLLKLAKLDFNVVQCLHKKELSDILR

WYKELDFARRMPFARDRIVELFFWIAGIYFEPEYVFRRHILTKLIEITTVM

DDMYDAFGTFEELVNLTEAIDRWDASCMDQLPDYMQPFYITLLDVIDEVEE

ELTKQGRSYRIHYAKEIMKNQARLYFAEARWFHEGCTPKMDEYMRVAASSV

GNTMLSVVSLVGMGDIITKFEFEWLTNEPKILRASNTIFRLMDDIAGYKFE

KERGHVASSIDCYMNEYGVSEQETIDIFNKRIVDSWKDINEEFLRPTAAPV

PVLNRVLNLTRVVDLLYKRGDAFTHVGKLMKDCIAAMFIDPVPL

INFORMATION FOR NO: 11A (SOSA/MA)
SEQUENCE CHARACTERISTICS:
LENGTH: 2605
TYPE: cDNA
STRANDNESS: Single
TOPOLOGY: Linear
OTHER INFORMATION: CULTIVATED STRAWBERRY OLEFIN SYNTHASE.
INCLUDES A STOP CODON.
SEQUENCE DISCRIPTION FOR NO: 11A
CTAATACGACTCACTATAGGGCAAGCAGTGGTAACAACGCAGAGTACGCGG

GGACATTTGATTCATAGTTATTAGATTGTGTTTTTCCGTCCAGTTAGGTTT

AAGGATTATACACTCGTTTAATGTATTGTTAGAACGGTGATTGTGTGCTTA

GTTAATAGATTTTGCTTTTATTCAAGAGCGTAGGGTTCAATTTGAGTATGC

ATGTTCTTTTATCTTTAGCTTTTATTATGGAATTTTTATAAAATGTTATAA

TATTAATTTCTTAATGAGTAGTTAAATTACGTGATTATTTGATTTTTTTAA

TCTAAAATGTGATATGTAAAATATAGAAGAAAAAAATTTAAAAACTTTCA

GAAATTTTTTAAATTCTTTTAGCCCACCCAAACCTAAAATCCTAGGTCCGC

CGTCGATGCAAAGTACAAATAGAAACATGTCTTTCTCAGTCATGAATCATG

TCATCATGATATTGATAGATGATGTCGTTTAGCAATAAAGGGCTGTTCTGC

GGTTAAAATATAAACATCTTCCGATCTTATTATTTACAACAACAAAAAATC

TTCCAAACTCAATTATCAGCATCTGTATCAGATCTGCATGGAGTCCCCTAT

AAATATATGATCATAGCAGCAATATACTTCATACTTGAAGAAAAAGCTATA

GCTAGTCCACAAGTGCAGAAAGTTAATCATGCCTGTCCATGCTACTCCAGC

AGCTGAATCCCAGATCATCTCTATGCCGGAAGTTGTTCGGCGCACAGCAAA

TTTTAAACCTAGCGTTTGGGGAGATCGGTTTGCTAACTATGCCGAAGACAT

TATAACTCAAACTCAAATGCAAGAACAAGTTGAGGAGCTGAAACAAGTAGT

GAGGAAGGAAGTATTCACTAATGCTGCTGATGATTCTTCACATCAACTGAA

GCTAATTGATGAAATCCAGCGCCTCGGTGTGGCTTACCATTTCGAAAGCGA

AATAGATCAAGCCCTGGAACGTATACATGAGACATATCAAGATATTCATGA

TGGTGGTGATCTGTACAATGTTGCTCTTCGTTTTCGGCTACTCAGGCGACA

TGGATATAATGTTTCCTGCGATGTATTCAACAAGTTCAAAGATACTAATGG

TGACTACAAGAAAAGCTTGGTCACTGATCTTTCTGGTATGCTGAGCTTTTA

TGAGGCGGCCCATCTGAGGGTGCATGGAGAAAAATTACTTGAAGAGGCTCT

GGTTTTTACCACCACTCATCTCCAGTCAGCAAGTGCAAAAGCTCTTTGCT

GAAAACACAAATAACTGAAGCCGTAGAGAGACTACTAAAAACTATGGAGAG

GTTAGGTGCTCGGCGTTACATGTCAATATATCAAGATGAAGCTTCATACAG

TGAAAATTTACTGAAACTTGCAAAATTAGATTTTAATGTTGTTCAGTGTTT

ACACAAAAAGGAACTCAGTGACATTCCCTAAGATGGTACAAGGAACTGGAC

TTTGCAAGGAGGATGCCTTTTGCTCGAGATAGGATCGTGGAGTTGTTCTTT

TGGATAGCAGGAATATATTTCGAACCTGAATACGTCTTTAGGAGACACATT

CTGACTAAACTGATTGAGATAACAACAGTAATGGATGATATGTATGATGCA

TTCGGTACATTCGAAGAACTCGTCAACTTGACTGAAGCAATTGACAGGTGG

GATGCAAGTTGCATGGATCAACTGCCAGACTATATGCAACCATTTTATATT

ACACTTCTGGATGTTATCGATGAAGTTGAAGAGGAGCTGACAAAGCAAGGA

AGATCTTACCGAATTCACTACGCAAAAGAAATTATGAAGAATCAAGCCAGG

CTCTACTTCGCTGAGGCCAGATGGTTCCACGAAGGATGCACCCCAAAAATG

GATGAGTATATGCGAGTTGCGGCATCTTCTGTCGGTAACACCATGCTTTCC

GTCGTGTCTTTAGTAGGCATGGGAGACATTATAACAAAATTTGAATTCGAG

TGGCTGACCAATGAGCCTAAAATCCTTAGAGCTTCGAATACCATATTTAGG

CTTATGGATGACATTGCTGGGTACAAGTTTGAGAAAGAGAGAGGGCATGTT

GCTTCAAGTATTGATTGCTACATGAATGAATACGGGGTTTCAGAGCAAGAG

ACAATTGATATCTTCAACAAACGAATTGTGGATTCGTGGAAGGATATAAAC

GAAGAGTTTCTGAGACCCACTGCTGCTCCAGTCCCTGTGCTTAATCGTGTT

CTTAACCTAACCCGAGTGGTTGATCTGCTTTACAAAAGGGGAGATGCCTTC

ACGCATGTCGGAAAACTGATGAAAGATTGTATTGCTGCAATGTTTATTGAT

CCAGTGCCACTCTGAACTCATCGGATCAGTCATCACATTCAGTCTCCTGAT

GCTAGCGTTTGCTTTTTATTTGAATGTATTCTTGAATAAGACGATGCACCT

```
CGATCAATTTGTGCTTCAGTGTTTCACGTACTGATGAGTCCTATCCTTTCT

AGAAGAGGAACATCAATGTTGGTTTGCTAATAAAGCTTTATTGTTTGAATG

TCGGGTTGATAATTCTTAACTAATTATGTTGTCTAAAAAAAAAAAAAAAAA

AAAA
```

INFORMATION FOR NO: 11B (SOSA/MA)
SEQUENCE CHARACTERISTICS:
LENGTH: 255
TYPE: Peptide
STRANDNESS: Single
TOPOLOGY: Linear
OTHER INFORMATION: CULTIVATED STRAWBERRY OLEFIN SYNTHASE.
SEQUENCE DISCRIPTION FOR NO: 11B

```
MPVHATPAAESQIISMPEVVRRTANFKPSVWGDRFANYAEDIITQTQMQEQ

VEELKQVVRKEVFTNAADDSSHQLKLIDEIQRLGVAYHFESEIDQALERIH

ETYQDIHDGGDLYNVALRFRLLRRHGYNVSCDVFNKFKDTNGDYKKSLVTD

LSGMLSFYEAAHLRVHGEKLLEEALVFTTTHLQSASAKSSLLKTQITEAVE

RLLKTMERLGARRYMSIYQDEASYSENLLKLAKLDFNVVQCLHKKELSDIP
```

INFORMATION FOR NO: 11C (SOSA/MA)
SEQUENCE CHARACTERISTICS:
LENGTH: 555
TYPE: Peptide
STRANDNESS: Single
TOPOLOGY: Linear
OTHER INFORMATION: CULTIVATED STRAWBERRY OLEFIN SYNTHASE.
Deleting the CC insertion.
SEQUENCE DISCRIPTION FOR NO: 11C

```
MPVHATPAAESQIISMPEVVRRTANFKPSVWGDRFANYAEDIITQTQMQEQ

VEELKQVVRKEVFTNAADDSSHQLKLIDEIQRLGVAYHFESEIDQALERIH

ETYQDIHDGGDLYNVALRFRLLRRHGYNVSCDVFNKFKDTNGDYKKSLVTD

LSGMLSFYEAAHLRVHGEKLLEEALVFTTTHLQSASAKSSLLKTQITEAVE

RLLKTMERLGARRYMSIYQDEASYSENLLKLAKLDFNVVQCLHKKELSDIL

RWYKELDFARRMPFARDRIVELFFWIAGIYFEPEYVFRRHILTKLIEITTV

MDDMYDAFGTFEELVNLTEAIDRWDASCMDQLPDYMQPFYITLLDVIDEVE

EELTKQGRSYRIHYAKEIMKNQARLYFAEARWFHEGCTPKMDEYMRVAASS

VGNTMLSVVSLVGMGDIITKFEFEWLTNEPKILRASNTIFRLMDDIAGYKF

EKERGHVASSIDCYMNEYGVSEQETIDIFNKRIVDSWKDINEEFLRPTAAP

VPVLNRVLNLTRVVDLLYKRGDAFTHVGKLMKDCIAAMFIDPVPL
```

INFORMATION FOR NO: 12A (SOSV)
SEQUENCE CHARACTERISTICS:
LENGTH: 1973
TYPE: cDNA
STRANDNESS: Single
TOPOLOGY: Linear
OTHER INFORMATION: WILD STRAWBERRY OLEFIN SYNTHASE
SEQUENCE DISCRIPTION FOR NO: 12A

```
ATGCCTGTCCATGCTACTCCAGCAGCTGAATCCCAGATCATCTCTAAGCCG

GAAGTTGTTCGGCGCACAGCAAATTTTAAACCTAGCGTTTGGGGAGATCGG

TTTGCTAACTATGCCGAAGACATTATAACTCAAACTCAAATGCAAGAACAA

GTTGAGGAGCTGAAACAAGTAGTGAGGAAGGAAGTATTCACTAATGCTGCT

GATGATTCTTCACATCAACTGAAGCTAATTGATGAAATCCAGCGCCTCGGT

GTGGCTTACCATTTCGAAAGCGAAATAGATCAAGCCCTGGAACGTATACAT

GAGACATATCAAGATATTCATGATGGTGGTGATCTGTACAATGTTGCTCTT

CGTTTTCGGCTACTCAGGCGACATGGATATAATGTTTCCTGCGATGTATTC

AACAAGTTCAAAGATACTAATGGTGACTACAAGAAAAGCTTGGTCACTGAT

CTTTCTGGTATGCTGAGCTTTTATGAGGCGGCCCATCTGAGGGTGCATGGA

GAAAAATTACTTGAAGAGGCTCTGGTTTTTACCACCACTCATCTCCAGTCA

GCAAGTGCAAAAAGCTCTTTGCTGAAAACACAAATAACTGAAGCCGTAGAG

AGACCTCTACTAAAAACTATGGAGAGGTTAGGTGCTCGGCGTTACATGTCA

ATATATCAAGATGAAGCTTCATACAGTGAAAATTTACTGAAACTTGCAAAA

TTAGATTTTAATGTTGTTCAGTGTTTACACAAAAAGGAACTCAGTGACATT

CTAAGATGGTACAAGGAACTGGACTTTGCAAGGAGGATGCCTTTTGCTCGA

GATAGGATCGTGGAGTTGTTCTTTTGGATAGCAGGAATATATTTCGAACCT

GAATACGTCTTTGGGAGACACATTCTGACTAAACTGATTGAGATAACAACA

GTAATGGATGATATGTATGATGCATTCGGTACATTCGAAGAACTCGTCATC

TTGACTGAAGCAATTGACAGGTGGGATGCAAGTTGCATGGATCAACTGCCA

GACTATATGCAACCATTTTATATAACACTTCTGGATGTTATCGATGAAGTT

GAAGAGGAGCTGACAAAGCAAGGAAGATCTTACCGAATTCACTACGCAAAA

GAAATTATGAAGAATCAAGCCAGGCTCTACTTCGCTGAGGCCATATGGTTC

CACGAAGGATGCACCCCAAAAATGGATGGGTATATGCGAGTTGCGGCATCT

TCTGTCGGTAACACCATGCTTTCCGTCGTGTCTTTAGTAGGCATGGGAGAC

ATTATAACAAAATTTGAATTCGAGTGGCTGACCAATGAGCCTAAAATCCTT

AGAGCTTCGAATACCATATTTAGGCTTATGGATGACATTGCTGGGTACAAG

TTTGAGAAAGAGAGGGGCATGTTGCTTCTAGTATTGATTGCTACATGAAT

GAATACGGGGTTTCAGAGCAAGAGACAATTGATATCTTCAACAAACGAATT

GTGGATTCGTGGAAGGATATAAACGAAGAGTTTCTGAGACCCACTGCTGCT

CCAGTCCCTGTGCTTAATCGTGTTCTTAACCTAACCCGAGTGGTTGATCTG

CTTTACAAAAGGGGAGATGCCTTCACGCATGTCGGAAAACTGATGAAAGAT

TGTATTGCTGCAATGTTTATTGATCCAGTGCCACTCTGAACTCATCGGATC

AGTCATCACATTCAGTCTCCTGATGCTAGCGTTTGCTTTTTATTTGAATGT

ATTCTTGAATAAGACGATGCACCTCGATCAATTTGTGCTTCAGTGTTTCAC

GTACTGATGAGTCCTATCCTTTCTAGAAGAGGAACATCAATGTTGGTTTGC

TAATAAAGCTTTATTGTTTGAATGTCGGGTTGATAATTCTTAACTAATTAT

GTTGTCTACTTTGTACTTTCAAACTCAATCTCAATACAGAATTTATAGTGT

ACGAACTAAAAAAAAAAAAAAAAAAAAAAAAAAA
```

INFORMATION FOR NO: 12B (SOSV)
SEQUENCE CHARACTERISTICS:
LENGTH: 556
TYPE: Peptide
STRANDNESS: Single
TOPOLOGY: Linear
OTHER INFORMATION: WILD STRAWBERRY OLEFIN SYNTHASE
SEQUENCE DISCRIPTION FOR NO: 12B

```
MPVHATPAAESQIISKPEVVRRTANFKPSVWGDRFANYAEDIITQTQMQEQ

VEELKQVVRKEVFTNAADDSSHQLKLIDEIQRLGVAYHFESEIDQALERIH

ETYQDIHDGGDLYNVALRFRLLRRHGYNVSCDVFNKFKDTNGDYKKSLVTD

LSGMLSFYEAAHLRVHGEKLLEEALVFTTTHLQSASAKSSLLKTQITEAVE
```

RPLLKTMERLGARRYMSIYQDEASYSENLLKLAKLDFNVVQCLHKKELSDI

LRWYKELDFARRMPFARDRIVELFFWIAGIYFEPEYVFGRHILTKLIEITT

VMDDMYDAFGTFEELVILTEAIDRWDASCMDQLPDYMQPFYITLLDVIDEV

EEELTKQGRSYRIHYAKEIMKNQARLYFAEAIWFHEGCTPKMDGYMRVAAS

SVGNTMLSVVSLVGMGDIITKFEFEWLTNEPKILRASNTIFRLMDDIAGYK

FEKERGHVASSIDCYMNEYGVSEQETIDIFNKRIVDSWKDINEEFLRPTAA

PVPVLNRVLNLTRVVDLLYKRGDAFTHVGKLMKDCIAAMFIDPVPL

INFORMATION FOR NO: 13A (SOSV1/W76)
SEQUENCE CHARACTERISTICS:
LENGTH: 289
TYPE: Genomic DNA
STRANDNESS: Single
TOPOLOGY: Linear
OTHER INFORMATION: Fragment from PCR on genomic
DNA of wild strawberry. Including an intron.
SEQUENCE DISCRIPTION FOR NO: 13A
AGAGGTTAGGTGCTCGGCGTTACATGTCAATATATCAAGATGAAGCTTCAT

ACAGTGAAAATTTACTGAAACTTGCAAAATTAGATTTTAATGTTGTTCAGT

GTTTACACAAAAAGGAACTCAGTGACATTCTAAGGTAAATTAAGCCATCGA

TCTTATAGTTAATTAGTATATACATATACAAGATAAGTTATAACCTAATAT

TGTTCTAAATATACTAGATGGTACAAGGAACTGGACTTTGCAAGGAGGATG

CCTTTTGCTCGAGATAGGATCGTGGAGTTGTTCT

INFORMATION FOR NO: 13B (SOSV1/W76)
SEQUENCE CHARACTERISTICS:
LENGTH: 204
TYPE: Genomic DNA
STRANDNESS: Single
TOPOLOGY: Linear
OTHER INFORMATION: Fragment from PCR on genomic
DNA of wild strawberry. Not including an intron.
SEQUENCE DISCRIPTION FOR NO: 13B
AGAGGTTAGGTGCTCGGCGTTACATGTCAATATATCAAGATGAAGCTTCAT

ACAGTGAAAATTTACTGAAACTTGCAAAATTAGATTTTAATGTTGTTCAGT

GTTTACACAAAAAGGAACTCAGTGACATTCTAAGATGGTACAAGGAACTGG

ACTTTGCAAGGAGGATGCCTTTTGCTCGAGATAGGATCGTGGAGTTGTTCT

INFORMATION FOR NO: 13C (SOSV1/W76)
SEQUENCE CHARACTERISTICS:
LENGTH: 67
TYPE: Peptide
STRANDNESS: Single
TOPOLOGY: Linear
OTHER INFORMATION: Translation of fragment from
PCR on genomic DNA of wild strawberry.
SEQUENCE DISCRIPTION FOR NO: 13C
RLGARRYMSIYQDEASYSENLLKLAKLDFNVVQCLHKKELSDILRWYKELD

FARRMPFARDRIVELF

INFORMATION FOR NO: 14A (SOSV2/W93)
SEQUENCE CHARACTERISTICS:
LENGTH: 289
TYPE: Genomic DNA
STRANDNESS: Single
TOPOLOGY: Linear
OTHER INFORMATION: Fragment from PCR on genomic
DNA of wild strawberry. Including an intron.
SEQUENCE DISCRIPTION FOR NO: 14A
AGAGGTTAGGTGCTCGGCGTTACATGTCAATATATCAAGATGAAGCTTCAT

ACAGTGAAAATTTACTGAAACTTGCAAAATTAGATTTTAATGTTGTTCAGT

GTTTACACAAAAAGGAACTCAGTGACATTCTAAGGTAAATTAAGCCATCGA

TCTTATAGTTAATTAGTATATACATATACAAGATAAGTTATAACCTAATAT

TGTTCTAAATATACTAGATGGTACAAGGAACTGGACTTTGCAAGGAGGATG

CCCTTTGCTCGAGATAGGATCGTGGAGTTGTTCT

INFORMATION FOR NO: 14B (SOSV2/W93)
SEQUENCE CHARACTERISTICS:
LENGTH: 204
TYPE: Genomic DNA
STRANDNESS: Single
TOPOLOGY: Linear
OTHER INFORMATION: Fragment from PCR on genomic
DNA of wild strawberry. Not including an intron.
SEQUENCE DISCRIPTION FOR NO: 14B
AGAGGTTAGGTGCTCGGCGTTACATGTCAATATATCAAGATGAAGCTTCAT

ACAGTGAAAATTTACTGAAACTTGCAAAATTAGATTTTAATGTTGTTCAGT

GTTTACACAAAAAGGAACTCAGTGACATTCTAAGATGGTACAAGGAACTGG

ACTTTGCAAGGAGGATGCCCTTTGCTCGAGATAGGATCGTGGAGTTGTTCT

INFORMATION FOR NO: 14C (SOSV2/W93)
SEQUENCE CHARACTERISTICS:
LENGTH: 67
TYPE: Peptide
STRANDNESS: Single
TOPOLOGY: Linear
OTHER INFORMATION: Translation of fragment from
PCR on genomic DNA of wild strawberry.
SEQUENCE DISCRIPTION FOR NO: 14C
RLGARRYMSIYQDEASYSENLLKLAKLDFNVVQCLHKKELSDILRWYKELD

FARRMPFARDRIVELF

INFORMATION FOR NO: 15A (SOSV3/W90)
SEQUENCE CHARACTERISTICS:
LENGTH: 300
TYPE: Genomic DNA
STRANDNESS: Single
TOPOLOGY: Linear
OTHER INFORMATION: Fragment from PCR on genomic
DNA of wild strawberry. Including an intron.
SEQUENCE DISCRIPTION FOR NO: 15A
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAAGGTAAACTAAGCCATCGA

TCTTATAGCTATTAGTTGTATGTATATGTATACAAGATAAGTAATAACCTT

CTAATATTGCTCTATATACTATATATAGATGGTATAAGGAACTGGACTTTG

CAAGGAGGATGCCTTTTGCACGAGATAGGATCGTGGAGTTGTTCT

INFORMATION FOR NO: 15B (SOSV3/W90)
SEQUENCE CHARACTERISTICS:
LENGTH: 204
TYPE: Genomic DNA
STRANDNESS: Single
TOPOLOGY: Linear
OTHER INFORMATION: Fragment from PCR on genomic
DNA of wild strawberry. Not including an intron.
SEQUENCE DISCRIPTION FOR NO: 15B
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAAGATGGTATAAGGAACTGG

ACTTTGCAAGGAGGATGCCTTTTGCACGAGATAGGATCGTGGAGTTGTTCT

INFORMATION FOR NO: 15C (SOSV3/W90)
SEQUENCE CHARACTERISTICS:
LENGTH: 67
TYPE: Peptide
STRANDNESS: Single
TOPOLOGY: Linear
OTHER INFORMATION: Translation of fragment from -continued
PCR on genomic DNA of wild strawberry.
SEQUENCE DISCRIPTION FOR NO: 15C
RLGARRYMSIYQDEASHSENLLKLAKLDFNVVQCLHKKELSDILRWYKELD

FARRMPFARDRIVELF

INFORMATION FOR NO: 16A (SOSV4/W79)
SEQUENCE CHARACTERISTICS:
LENGTH: 289
TYPE:
STRANDNESS: Single
TOPOLOGY: Linear
OTHER INFORMATION: Fragment from PCR on genomic
DNA of wild strawberry. Including an intron.
SEQUENCE DISCRIPTION FOR NO: 16A
AGAGGTTAGGTGCTCGGCGTTACATGTCAATATATCAAGATGAAGCTTCAT

ACAGTGAAAATTTACTGAAACTTGCAAAATTAGATTTTAATGTTGTTCAGT

GTTTACACAAAAAGGAACTCAGTGACATTCTAAGGTAAATTAGGCCATCGA

TCTTATAGTTAATTAGTATATACATATACAAGATAAGTTATAACCTAATAT

TGTTCTAAATATACTAGATGGTACAAGGAACTGGACTTTGCAAGGAGGATG

CCTTTTGCTCGAGATAGGATCGTGGAGTTGTTCT

INFORMATION FOR NO: 16B (SOSV4/W79)
SEQUENCE CHARACTERISTICS:
LENGTH: 204
TYPE: Genomic DNA
STRANDNESS: Single
TOPOLOGY: Linear
OTHER INFORMATION: Fragment from PCR on genomic
DNA of wild strawberry. Not including an intron.
SEQUENCE DISCRIPTION FOR NO: 16B
AGAGGTTAGGTGCTCGGCGTTACATGTCAATATATCAAGATGAAGCTTCAT

ACAGTGAAAATTTACTGAAACTTGCAAAATTAGATTTTAATGTTGTTCAGT

GTTTACACAAAAAGGAACTCAGTGACATTCTAAGATGGTACAAGGAACTGG

ACTTTGCAAGGAGGATGCCTTTTGCTCGAGATAGGATCGTGGAGTTGTTCT

INFORMATION FOR NO: 16C (SOSV4/W79)
SEQUENCE CHARACTERISTICS:
LENGTH: 67
TYPE: Peptide
STRANDNESS: Single
TOPOLOGY: Linear
OTHER INFORMATION: Translation of fragment from
PCR on genomic DNA of wild strawberry.
SEQUENCE DISCRIPTION FOR NO: 16C
RLGARRYMSIYQDEASYSENLLKLAKLDFNVVQCLHKKELSDILRWYKELD

FARRMPFARDRIVELF

INFORMATION FOR NO: 17A (SOSV5/W84)
SEQUENCE CHARACTERISTICS:
LENGTH: 300
TYPE: Genomic DNA
STRANDNESS: Single
TOPOLOGY: Linear
OTHER INFORMATION: Fragment from PCR on genomic
DNA of wild strawberry. Including an intron.
SEQUENCE DISCRIPTION FOR NO: 17A
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAAGGTAAACTAAGCCATCGA

TCTTATAGCTATTAGTTGTATATATATGTATACAAGATAAGTAATAACCTT

CTAATATTGCTCTATATACTATATATAGATGGTATAAGGAACTGGACTTTG

CAAGGAGGATGCCTTTTGCACGAGATAGGATCGTGGAGTTGTTCT

INFORMATION FOR NO: 17B (SOSV5/W84)
SEQUENCE CHARACTERISTICS:
LENGTH: 204
TYPE: Genomic DNA
STRANDNESS: Single
TOPOLOGY: Linear
OTHER INFORMATION: Fragment from PCR on genomic
DNA of wild strawberry. Not including an intron.
SEQUENCE DISCRIPTION FOR NO: 17B
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAAGATGGTATAAGGAACTGG

ACTTTGCAAGGAGGATGCCTTTTGCACGAGATAGGATCGTGGAGTTGTTCT

INFORMATION FOR NO: 17C (SOSV5/W84)
SEQUENCE CHARACTERISTICS:
LENGTH: 67
TYPE: Peptide
STRANDNESS: Single
TOPOLOGY: Linear
OTHER INFORMATION: Translation of fragment from
PCR on genomic DNA of wild strawberry.
SEQUENCE DISCRIPTION FOR NO: 17C
RLGARRYMSIYQDEASHSENLLKLAKLDFNVVQCLHKKELSDILRWYKELD

FARRMPFARDRIVELF

INFORMATION FOR NO: 18A (SOSA1/W66)
SEQUENCE CHARACTERISTICS:
LENGTH: 291
TYPE: Genomic DNA
STRANDNESS: Single
TOPOLOGY: Linear
OTHER INFORMATION: Fragment from PCR on genomic
DNA of cultivated strawberry. Including an intron
and a CC insertion.
SEQUENCE DISCRIPTION FOR NO: 18A
AGAGGTTAGGTGCTCGGCGTTACATGTCAATATATCAAGATGAAGCTTCAT

ACAGTGAAAATTTACTGAAACTTGCAAAATTAGATTTTAATGTTGTTCAGT

GTTTACACAAAAAGGAACTCAGTGACATTCCCTAAGGTAAATTAAGCCATC

GATCTTATAGTTAATTAGTATATACATATACAAGATAAGTTATAACCTAAT

ATTGTTCTAAATATACTAGATGGTACAAGGAACTGGACTTTGCAAGGAGGA

TGCCTTTTGCTCGAGATAGGATCGTGGAGTTGTTCT

INFORMATION FOR NO: 18B (SOSA1/W66)
SEQUENCE CHARACTERISTICS:
LENGTH: 206
TYPE: Genomic DNA
STRANDNESS: Single
TOPOLOGY: Linear
OTHER INFORMATION: Fragment from PCR on genomic
DNA of cultivated strawberry. Not including an
intron. Including a CC insertion.
SEQUENCE DISCRIPTION FOR NO: 18B
AGAGGTTAGGTGCTCGGCGTTACATGTCAATATATCAAGATGAAGCTTCAT

ACAGTGAAAATTTACTGAAACTTGCAAAATTAGATTTTAATGTTGTTCAGT

GTTTACACAAAAAGGAACTCAGTGACATTCCCTAAGATGGTACAAGGAACT

GGACTTTGCAAGGAGGATGCCTTTTGCTCGAGATAGGATCGTGGAGTTGTT

CT

INFORMATION FOR NO: 18C (SOSA1/W66)
SEQUENCE CHARACTERISTICS:
LENGTH: 67
TYPE: Peptide
STRANDNESS: Single
TOPOLOGY: Linear
OTHER INFORMATION: Translation of fragment from
PCR on genomic DNA of cultivated strawberry.

-continued
Deleted CC insertion
SEQUENCE DISCRIPTION FOR NO: 18C
RLGARRYMSIYQDEASYSENLLKLAKLDFNVVQCLHKKELSDILRWYKELD

FARRMPFARDRIVELF

INFORMATION FOR NO: 19A (SOSA2/W68)
SEQUENCE CHARACTERISTICS:
LENGTH: 296
TYPE: Genomic DNA
STRANDNESS: Single
TOPOLOGY: Linear
OTHER INFORMATION: Fragment from PCR on genomic
DNA of cultivated strawberry. Including an intron.
SEQUENCE DISCRIPTION FOR NO: 19A
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAAGGTAAACTAAACAATCGA

TCTTATAGTTATTAGTTGTGTATGTATACAAGATACGCAATAACCATCTAA

TATTGCTCTATATATGTACTATAGATGGTATAAGGAACTGGACTTTGCAAG

GAGGATGCCTTTTGCTCGAGATAGGATCGTGGAGTTGTTCT

INFORMATION FOR NO: 19B (SOSA2/W68)
SEQUENCE CHARACTERISTICS:
LENGTH: 204
TYPE: Genomic DNA
STRANDNESS: Single
TOPOLOGY: Linear
OTHER INFORMATION: Fragment from PCR on genomic
DNA of cultivated strawberry. Not including an
intron.
SEQUENCE DISCRIPTION FOR NO: 19B
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAAGATGGTATAAGGAACTGG

ACTTTGCAAGGAGGATGCCTTTTGCTCGAGATAGGATCGTGGAGTTGTTCT

INFORMATION FOR NO: 19C (SOSA2/W68)
SEQUENCE CHARACTERISTICS:
LENGTH: 67
TYPE: Peptide
STRANDNESS: Single
TOPOLOGY: Linear
OTHER INFORMATION: Translation of fragment from
PCR on genomic DNA of cultivated strawberry.
SEQUENCE DISCRIPTION FOR NO: 19C
RLGARRYMSIYQDEASHSENLLKLAKLDFNVVQCLHKKELSDILRWYKELD

FARRMPFARDRIVELF

INFORMATION FOR NO: 20A (SOSA3/W46)
SEQUENCE CHARACTERISTICS:
LENGTH: 298
TYPE: Genomic DNA
STRANDNESS: Single
TOPOLOGY: Linear
OTHER INFORMATION: Fragment from PCR on genomic
DNA of cultivated strawberry. Including an intron.
SEQUENCE DISCRIPTION FOR NO: 20A
AGAGGTTAGGTGCTCGGCGTTACATGTCAATATATCAAGATGAAGCTTCAC

ACAGTGNAAATTTACTCGAAACTTGCAAAATTAGATTTTAATGTTGTTCA

GTGTTTACACAAAAAGGAACTCAGTGACATTCTAAGGTAAACTAAACAATC

GATCTTATAGTTATTAGTTGTGTATGTATACAAGATACGCAATAACCATCT

AATATTGCTCTATATATGTACTATAGATGGTATAAGGAACTGGACTTTGCA

AGGAGGATGCCTTTTGCCCGAGATAGGATCGTGGAGTTGTTCT

INFORMATION FOR NO: 20B (SOSA3/W46)
SEQUENCE CHARACTERISTICS:
LENGTH: 204
TYPE: Genomic DNA
STRANDNESS: Single
TOPOLOGY: Linear
OTHER INFORMATION: Fragment from PCR on genomic
DNA of cultivated strawberry. Not including an
intron.
SEQUENCE DISCRIPTION FOR NO: 20B
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAAGATGGTATAAGGAACTGG

ACTTTGCAAGGAGGATGCCTTTTGCCCGAGATAGGATCGTGGAGTTGTTCT

INFORMATION FOR NO: 20C (SOSA3/W46)
SEQUENCE CHARACTERISTICS:
LENGTH: 67
TYPE: Peptide
STRANDNESS: Single
TOPOLOGY: Linear
OTHER INFORMATION: Translation of fragment from
PCR on genomic DNA of cultivated strawberry.
SEQUENCE DISCRIPTION FOR NO: 20C
RLGARRYMSIYQDEASHSENLLKLAKLDFNVVQCLHKKELSDILRWYKELD

FARRMPFARDRIVELF

INFORMATION FOR NO: 21A (SOSA4/W59)
SEQUENCE CHARACTERISTICS:
LENGTH: 296
TYPE: Genomic DNA
STRANDNESS: Single
TOPOLOGY: Linear
OTHER INFORMATION: Fragment from PCR on genomic
DNA of cultivated strawberry. Including an intron.
SEQUENCE DISCRIPTION FOR NO: 21A
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAGGGTAAACTAAACAATCGA

TCTTATAGTTATTAGTTGTGTATGTATACAAGATACGCAATAACCATCTAA

TATTGCTCTATATATGTACTATAGATGGTATAAGGAACTGGACTTTGCAAG

GAGGATGCCTTTTGCTCGAGATAGGATCGTGGAGTTGTTCT

INFORMATION FOR NO: 21B (SOSA4/W59)
SEQUENCE CHARACTERISTICS:
LENGTH: 204
TYPE: Genomic DNA
STRANDNESS: Single
TOPOLOGY: Linear
OTHER INFORMATION: Fragment from PCR on genomic
DNA of cultivated strawberry. Not including an
intron.
SEQUENCE DISCRIPTION FOR NO: 21B
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAGGATGGTATAAGGAACTGG

ACTTTGCAAGGAGGATGCCTTTTGCTCGAGATAGGATCGTGGAGTTGTTCT

INFORMATION FOR NO: 21C (SOSA4/W59)
SEQUENCE CHARACTERISTICS:
LENGTH: 67
TYPE: Peptide
STRANDNESS: Single
TOPOLOGY: Linear -continued OTHER INFORMATION: Translation of fragment from
PCR on genomic DNA of cultivated strawberry.
SEQUENCE DISCRIPTION FOR NO: 21C
RLGARRYMSIYQDEASHSENLLKLAKLDFNVVQCLHKKELSDILGWYKELD

FARRMPFARDRIVELF

INFORMATION FOR NO: 22A (SOSA5/W74)
SEQUENCE CHARACTERISTICS:
LENGTH: 296
TYPE: Genomic DNA
STRANDNESS: Single
TOPOLOGY: Linear
OTHER INFORMATION: Fragment from PCR on genomic
DNA of cultivated strawberry. Including an intron.
SEQUENCE DISCRIPTION FOR NO: 22A
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAAGGTAAACTAAACAATCGA

TCTTATAGTTATTAGTTGTGTATGTATACAAGATACGCAATAGCCATCTAA

TATTGCTCTATATATGTACTATAGATGGTATAAGGAACTGGACTTTGCAAG

GAGGATGCCTTTTGCTCGAGATAGGATCGTGGAGTTGTTCT

INFORMATION FOR NO: 22B (SOSA5/W74)
SEQUENCE CHARACTERISTICS:
LENGTH: 204
TYPE: Genomic DNA
STRANDNESS: Single
TOPOLOGY: Linear
OTHER INFORMATION: Fragment from PCR on genomic
DNA of cultivated strawberry. Not including an
intron.
SEQUENCE DISCRIPTION FOR NO: 22B
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAAGATGGTATAAGGAACTGG

ACTTTGCAAGGAGGATGCCTTTTGCTCGAGATAGGATCGTGGAGTTGTTCT

INFORMATION FOR NO: 22C (SOSA5/W74)
SEQUENCE CHARACTERISTICS:
LENGTH: 67
TYPE: Peptide
STRANDNESS: Single
TOPOLOGY: Linear
OTHER INFORMATION: Translation of fragment from
PCR on genomic DNA of cultivated strawberry.
SEQUENCE DISCRIPTION FOR NO: 22C
RLGARRYMSIYQDEASHSENLLKLAKLDFNVVQCLHKKELSDILRWYKELD

FARRMPFARDRIVELF

INFORMATION FOR NO: 23A (SOSA6/W56)
SEQUENCE CHARACTERISTICS:
LENGTH: 302
TYPE: Genomic DNA
STRANDNESS: Single
TOPOLOGY: Linear
OTHER INFORMATION: Fragment from PCR on genomic
DNA of cultivated strawberry. Including an intron.
SEQUENCE DISCRIPTION FOR NO: 23A
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGATATTCTAAGGTAAACTAAGCCATCGA

TCTTATAGCTATTAGTTGTATATATATGTATACAAGATAAGTAATAACCTT

TTAATATTGCTCTATATATACTATATATAGATGGTATAAGGAACTGGACTT

TGCAAAGAGGATGCCTTTTGCTCGAGATAGGATCGTGGAGTTGTTCT

INFORMATION FOR NO: 23B (SOSA6/W56)
SEQUENCE CHARACTERISTICS:
LENGTH: 204
TYPE: Genomic DNA
STRANDNESS: Single
TOPOLOGY: Linear
OTHER INFORMATION: Fragment from PCR on genomic
DNA of cultivated strawberry. Not including an
intron.
SEQUENCE DISCRIPTION FOR NO: 23B
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGATATTCTAAGATGGTATAAGGAACTGG

ACTTTGCAAAGAGGATGCCTTTTGCTCGAGATAGGATCGTGGAGTTGTTCT

INFORMATION FOR NO: 23C (SOSA6/W56)
SEQUENCE CHARACTERISTICS:
LENGTH: 67
TYPE: Peptide
STRANDNESS: Single
TOPOLOGY: Linear
OTHER INFORMATION: Translation of fragment from
PCR on genomic DNA of cultivated strawberry. Not
including an intron.
SEQUENCE DISCRIPTION FOR NO: 23C
RLGARRYMSIYQDEASHSENLLKLAKLDFNVVQCLHKKELSDILRWYKELD

FAKRMPFARDRIVELF

INFORMATION FOR NO: 24A (SOSA7/W61)
SEQUENCE CHARACTERISTICS:
LENGTH: 302
TYPE: Genomic DNA
STRANDNESS: Single
TOPOLOGY: Linear
OTHER INFORMATION: Fragment from PCR on genomic
DNA of cultivated strawberry. Including an intron.
SEQUENCE DISCRIPTION FOR NO: 24A
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAAGGTAAACTAAGCCATCGA

TCTTATAGCTATTAGTTGTATATATATGTATACAAGATAAGTAATAACCTT

CTAATATTGCTCTATATATACTATATATAGATGGTATAAGGAACTGGACTT

TGCAAGGAGGATGCCTTTTGCTCGAGATAGGATCGTGGAGTTGTTCT

INFORMATION FOR NO: 24B (SOSA7/W61)
SEQUENCE CHARACTERISTICS:
LENGTH: 204
TYPE: Genomic DNA
STRANDNESS: Single
TOPOLOGY: Linear
OTHER INFORMATION: Fragment from PCR on genomic
DNA of cultivated strawberry. Not including an
intron.
SEQUENCE DISCRIPTION FOR NO: 24B
AGAGGTTAGGTGCTCGGCGTTACATGTCAATATATCAAGATGAAGCTTCAC

ACAGTGAAAATTTACTGAAACTTGCAAAATTAGATTTTAATGTTGTTCAGT

GTTTACACAAAAAGGAACTCAGTGACATTCTAAGATGGTATAAGGAACTGG

ACTTTGCAAGGAGGATGCCTTTTGCTCGAGATAGGATCGTGGAGTTGTTCT

INFORMATION FOR NO: 24C (SOSA7/W61)
SEQUENCE CHARACTERISTICS:
LENGTH: 67
TYPE: Peptide
STRANDNESS: Single
TOPOLOGY: Linear OTHER INFORMATION: Translation of fragment from
PCR on genomic DNA of cultivated strawberry.
SEQUENCE DISCRIPTION FOR NO: 24C
RLGARRYMSIYQDEASHSENLLKLAKLDFNVVQCLHKKELSDILRWYKELD

FARRMPFARDRIVELF

INFORMATION FOR NO: 25A (H64TAR2)
SEQUENCE CHARACTERISTICS:
LENGTH: 1665
TYPE: cDNA
STRANDNESS: Single
TOPOLOGY: Linear
OTHER INFORMATION: CULTIVATED STRAWBERRY
LINALOOL/NEROLIDOL SYNTHASE WITH TARGET SIGNAL
SEQUENCE DISCRIPTION FOR NO: 25A
TCTAACCTCATGCAGCTTACACATAAGAAGCAGCTGCCTACTTTTCAAAGA

CGGGGCATTGCCGAAGATAGCTTGCTTCCCAGTTCTACTACTCCCATAAAG

CCGATGAACGTTGAAACCAAGCATACTAGAACTATGGGTGACATTTTTGTC

CAACATTGTCAGAAGTTGGAACTATTCAGAAATGTCTTAAGGAATGTAGCA

GAGCTAGATGCCCTTGAAGGTTTGAATATGATCGATGCTGTTCAAAGGCTA

GGCATTGATTTCCACTTTCAACGAGAAATCGATGAAATTCTGCACAAGCAA

ATGAGTAATGTATCTGCCTCTGATGATCTTCATGAGGTTGCACTTCGCTTT

CGACTACTGAGGCAACATGGTTACTTCGTGCCTGAAGATGTGTTTAACAAC

TTCAAGGACAGCAAAGGAACGTTCAAGCAAGTTCTGGGTGAAGACATCAAG

GGATTGATGAGCTTATACGGAGCTTCGCAGCTAGGTACAGAAGGAGAAGAT

ACACTTGTTGAAGCTGAAAAGTTTAGTGGCCATCTGCTAAAGACTTCTCTG

TCACATCTTGATCATCATCATGCCAGAATTGTTGGCAATACATTGAGGAAT

CCTCATCACAAAAGCTTGGCCTCATTCATGGCCAGGAACTTTTTCGTTACT

TCTCAAGCCACCAATTCATGGTTAAATTTGCTAAAAGACGTAGCAAAAACA

GATTTCAATATGGTCCGGTCTCTGCATCAGAATGAAATAGTTCAAATTTCC

AAATGGTGGAAGGAGCTTGGATTGGCTAAGGAACTGAAGTTTGCAAGAGAT

CAACCACAGAAATGGTACATTTGGTCCATGGCATGCCTAACAGATCCAAAG

TTATCAGAGGAGAGGGTTGAGCTCACAAAACCCATTTCTTTTGTCTATTTG

ATAGATGACATTTTCGATGTTTATGGAACTCTTGATGACCTCATTCTCTTC

ACAGAAGCTGTTAATAGATGGGAAATTACTGCTATAGACCACTTACCAGAC

TATATGAAGATATGCTTCAAGGCTCTCTATGATATGACTAATGAAATCAGC

TGCAAGGTCTATCAGAAGCATGGATGGAACCCCTTACAATCTTTGAAAATT

TCGTGGGCGAGTCTTTGCAATGCATTTTTGGTGGAAGCAAAATGGTTCGCA

TCTGGGCAGCTGCCGAAGTCAGAAGAGTACTTGAAGAACGGCATCGTTTCT

TCTGGGGTTAATGTGGTTCTAGTCCACATGTTTTTTATCTTGGGTCAAAAC

ATAACCAGAAAGAGTGTGGAGTTGTTAATGAAACTCCAGCCATGATATCG

TCCTCAGCAGCAATTCTTCGACTCTGGGACGATTAGGCAGTGCAAAGGAT

GAGAACCAGGATGGGAACGATGGGTCGTATGTAAGGTGCTACTTAGAGGAA

CATGAAGGCTGTTCCATTGAGGAGGCACGAGAAAAGACGATTAATATGATT

TCAGATGAATGGAAGAAACTGAACAGAGAACTGCTCTCTCCAAATCCATTT

CCAGCAACAATCACATTGGCTTCTCTTAATCTCGCAAGAATGATCCCCTTG

ATGTATAGCTACGATGGCAACCAATACCTTCCATCTCTTAAAGAGTATATG

AAACTGATGTTGTATGAGACTGTATCAATGTAA

INFORMATION FOR NO: 25B (H64TAR2)
SEQUENCE CHARACTERISTICS:
LENGTH: 554
TYPE: Peptide
STRANDNESS: Single
TOPOLOGY: Linear
OTHER INFORMATION: CULTIVATED STRAWBERRY
LINALOOL/NEROLIDOL SYNTHASE WITH TARGET SIGNAL
SEQUENCE DISCRIPTION FOR NO: 25B
SNLMQLTHKKQLPTFQRRGIAEDSLLPSSTTPIKPMNVETKHTRTMGDIFV

QHCQKLELFRNVLRNVAELDALEGLNMIDAVQRLGIDFHFQREIDEILHKQ

MSNVSASDDLHEVALRFRLLRQHGYFVPEDVFNNFKDSKGTFKQVLGEDIK

GLMSLYGASQLGTEGEDTLVEAEKFSGHLLKTSLSHLDHHHARIVGNTLRN

PHHKSLASFMARNFFVTSQATNSWLNLLKDVAKTDFNMVRSLHQNEIVQIS

KWWKELGLAKELKFARDQPQKWYIWSMACLTDPKLSEERVELTKPISFVYL

IDDIFDVYGTLDDLILFTEAVNRWEITAIDHLPDYMKICFKALYDMTNEIS

CKVYQKHGWNPLQSLKISWASLCNAFLVEAKWFASGQLPKSEEYLKNGIVS

SGVNVVLVHMFFILGQNITRKSVELLNETPAMISSSAAILRLWDDLGSAKD

ENQDGNDGSYVRCYLEEHEGCSIEEAREKTINMISDEWKKLNRELLSPNPF

PATITLASLNLARMIPLMYSYDGNQYLPSLKEYMKLMLYETVSM

INFORMATION FOR NO: 26A (H64TAR6)
SEQUENCE CHARACTERISTICS:
LENGTH: 1665
TYPE: cDNA
STRANDNESS: Single
TOPOLOGY: Linear
OTHER INFORMATION: CULTIVATED STRAWBERRY
LINALOOL/NEROLIDOL SYNTHASE WITH TARGET SIGNAL
SEQUENCE DISCRIPTION FOR NO: 26A
TCTAACCTCATGCAGCTTACACAAAAGAAGCAGCTTCCTACTTTTCAAAGA

CGGGGCATTGCCGAAGATAGCTTGCTTCCCAGTTCTACTACTCCCATAAAG

CCGATGAACGTTGAAACCAAGCATACTAGAACTATGGGTGACATTTTTGTC

CAACATTCTCAGAAGTTGGAACTATTGAAAACTGTCTTGAGGAATGTAGCA

GAGCTAGATGCCCTTGAAGGTTTGAATATGATCGATGCTGTTCAAAGGCTA

GGCATCGATTACAACTTTCAACGAGAAATCGACGAAATTCTGCACAAGCAA

ATGAGTATTGTGTCTGCCTGTGATGATCTTCATGAGGTTGCACTTCGCTTT

CGACTACTGAGACAACATGGTTACTTCGTGCCTGAAGATGTGTTTAACAAC

TTCAAGGACAGCAAAGGAATGTTCAAGCAAGTTCTGGGTGAAGACATCAAG

GGATTGATGAGCTTATACGAAGCTTCGCAGCTAGGTACAGAAGGAGAAGAT

ACACTTGTTGAAGCTGAAAAGTTTAGCGGCCATCTGCTAAAGACTTCTCTG

TCACATCTTGATCATCATCGAGCCAGAATTGTTGCAAATACATTGAGGAAT

CCTCATCACAAAAGCTTGGCCCCATTCATGGCCAGGAACTTTTTCGTTACT

TCTCAAGCCACCAATTCATGGTTAAATTTGCTAAAAGAAGTAGCAAAAACA

GATTTCAATATGGTCCGGTCTCTGCACCAGAATGAAATAGTTCAAATTTCC

AAATGGTGGAAGGAGCTTGGATTGGCTAAGGAACTGAAGTTTGCAAGAGAT

CAACCACTGAAATGGTACATTTGGTCCATGGCATGCCTGACAGATCCAAAG

TTATCAGAGGAGAGGGTTGAGCTCACAAAACCCGTCTCTTTTGTCTATTTG

ATAGATGACATTTTCGATGTTTATGGAACCCTTGATGAACTCATTCTCTTC

ACAGAAGCTGTTAATAGATGGGAAATTACTGCTATAGACCACTTACCAGAC

```
TACATGAAGATATGCTTCAAGGCTCTCTACGATATGACTAATGAATTCAGC

AGCAAGGTCTATCTGAAGCATGGATGGAACCCCTTACAATCTTTGAAAATT

TCGTGGGCGAGTCTTTGCAATGCATTTTTGGTGGAAGCAAAATGGTTCGCA

TCTGGGCAGCTGCCGAAGTCAGAAGAGTACTTGAAGAACGGCATCGTTTCT

TCTGGGGTACATGTGGGTCTAGTCCACATGTTTTTTCTCTTGGGTCAAAAC

ATAACCACAAAGAGTGTGGAGTTGTTGAATGAAACTCCAGCCATGATATCG

TCCTCAGCAGCAATTCTTCGACTCTGGGACGATTTAGGAAGTGCAAAGGAT

GAGAACCAGGATGGAACGATGGGTCGTATATAAGGTGCTACTTAGAGGAA

CATGAAGGCTGTTCCATCGAGGAGGCACGAGAAAGACGATTAATATGATT

TCAGATGAATGGAAGAAACTGAACAGAGAACTGCTCTCTCCAAATCCATTT

TCAGCAACATTCACATTGGCTTCTCTTAATCTCGCTAGAATGATCCCCATG

ATGTATAGCTACGATGGCAACCGATGCCTTCCTGATCTTAAAGAGTATGTG

AAACTGATGTTGTATGAGACTGTATCAATGTAA

INFORMATION FOR NO: 26B (H64TAR6)
SEQUENCE CHARACTERISTICS:
LENGTH: 554
TYPE: Peptide
STRANDNESS: Single
TOPOLOGY: Linear
OTHER INFORMATION: CULTIVATED STRAWBERRY
LINALOOL/NEROLIDOL SYNTHASE WITH TARGET SIGNAL
SEQUENCE DISCRIPTION FOR NO: 26B
SNLMQLTQKKQLPTFQRRGIAEDSLLPSSTTPIKPMNVETKHTRTMGDIFV

QHSQKLELLKTVLRNVAELDALEGLNMIDAVQRLGIDYNFQREIDEILHKQ

MSIVSACDDLHEVALRFRLLRQHGYFVPEDVFNNFKDSKGMFKQVLGEDIK

GLMSLYEASQLGTEGEDTLVEAEKFSGHLLKTSLSHLDHHRARIVANTLRN

PHHKSLAPFMARNFFVTSQATNSWLNLLKEVAKTDFNMVRSLHQNEIVQIS

KWWKELGLAKELKFARDQPLKWYIWSMACLTDPKLSEERVELTKPVSFVYL

IDDIFDVYGTLDELILFTEAVNRWEITAIDHLPDYMKICFKALYDMTNEFS

SKVYLKHGWNPLQSLKISWASLCNAFLVEAKWFASGQLPKSEEYLKNGIVS

SGVHVGLVHMFFLLGQNITTKSVELLNETPAMISSSAAILRLWDDLGSAKD

ENQDGNDGSYIRCYLEEHEGCSIEEAREKTINMISDEWKKLNRELLSPNPF

SATFTLASLNLARMIPMMYSYDGNRCLPDLKEYVKLMLYETVSM

INFORMATION FOR 27A (H64TAR4)
SEQUENCE CHARACTERISTICS:
LENGTH: 1865 bases
TYPE: cDNA
STRANDNESS: Single
TOPOLOGY: Linear
OTHER INFORMATION: CULTIVATED STRAWBERRY
LINALOOL/NEROLIDOL SYNTHASE WITH TARGET SIGNAL
SEQUENCE DISCRIPTION FOR: 27A
CTCCCACAGCTTCTTAGTTGCTGATCATGATCAGATGGCATCGTCTTCTC

GGGCCTTCTTTAAAGTATTCAATCCTGCTCCAAAAAGCATCCCACGTATTG

GCCAGTCTAACCTCATGCAGCTTACACATAAGAAGCAGCTGCCTACTTTTC

AAAGACGGGCATTGCCGAAGATAGCTTGCTTCCCAGTTCTACTACTCCCA

TAAAGCCGATGAACGTTGAAACCAAGCATACTAGAACTATGGGTGACATTT

TTGTCCAACATTGTCAGAAGTTGGAACTATTCAGAAATGTCTTAAGGAATG

TAGCAGAGCTAGATGCCCTTGAAGGTTTGAATATGATCGATGCTGTTCAAA

GGCTAGGCATTGATTTCCACTTTCAACGAGAAATCGATGAAATTCTGCACA

AGCAAATGAGTAATGTATCTGCCTCTGATGATCTTCATGAGGTTGCACTTC

GCTTTCGACTACTGAGACAACATGGTTACTTCGTGCCTGAAGATGTGTTTA

ACAACTTCAAGGACAGCAAAGGAACGTTCAAGCAAGTTCTGGGTGAAGACA

TCAAGGGATTGATGAGCTTATACGAAGCTTCGCAGCTAGGTACAGAAGGAG

AAGATACACTTGTTGAAGCTGAAAAGTTTAGTGGCCATCTGCTAAAGACTT

CTCTGTCACATCTTGATCATCATCATGCCAGAATTGTTGGCAATACATTGA

GGAATCCTCATCACAAAGCTTGGCCTCATTCATGGCAAGGAACTTTTTCG

TTACTACTCAAGCCACCAATTCATGGTTAAATTTGCTAAAAGACGTAGCAA

AAACAGATTTCAATATGGTCCGGTCTCTGCATCAGAATGAAATAGTTCAAA

TTTCCAAATGGTGGAAGGAGCTTGGACTGGCTAAGGAACTGAAGTTTGCAA

GAGATCAACCACAGAAATGGTACATTTGGTCCATGGCATGCCTAACAGATC

CAAAGTTATCAGAGGAGAGGGTTGAGCTCACAAAACCCATTTCTTTTGTCT

ATTTGATAGATGACATTTTCGATGTTTATGGAACTCTTGATGACCTCATTC

TCTTCACAGAAGCTGTTAATAGATGGGAAATTACTGCTATAGACCACTTAC

CAGACTATATGAAGATATGCTTCAAGGCTCTCTATGATATGACTAATGAAA

TCAGCTGCAAGGTCTATCAGAAGCATGGATGAACCCCTTACAATCTTTGA

AAATTTCGTGGGCGAGTCTTTGCAATGCATTTTTGGTGGAAGCAAAATGGT

TCGCATCTGGGCAGCTGCCGAAGTCAAAAGAGTACTTGAAGAACGGCATCG

TTTCTTCTGGGGTTAATGTGGTTCTAGTCCACATGTTTTTTATCTTGGGTC

AAAACATAACCACAAAGAGTGTGGAGTTGTTGAATGAAACTCCAGCCATGA

TATCGTCCTCAGCAGCAATTCTTCGACTCTGGGACGATTTAGGAAGTGCAA

AGGATGAGAACCAGGATGGGAACGATGGGTCGTATGTAAGGTGCTACTTAG

AGGAACATGAAGGCTGTTCCATTGAGGAGGCACGAGAAAAGACGATTAATA

TGATTTCAGATGAATGGAAGAAACTGAACAGAGAACTGCTCTCTCCAAATC

CATTTCCAGCAACAATCACATTGGCTTCTCTTAATCTCGCAAGAATGATCC

CCTTGATGTATAGCTACGATGGCAACCAATGCCTTCCATCTCTTAAAGAGT

ATATGAAACTGATGTTGTATGAGACTGTATCAATGTAATAATAATGACACT

ACTGGAAGTGGAGTTGAACTTCAAAGGTGGTCAAGAGAAACAAGAAGCCTA

AGCTGTGTCAGTGAGCTGTGACTTGGTTG

INFORMATION FOR 27B (H64TAR4)
SEQUENCE CHARACTERISTICS:
LENGTH: 578 amino acids
TYPE: Peptide
STRANDNESS: Single
TOPOLOGY: Linear
OTHER INFORMATION: CULTIVATED STRAWBERRY
LINALOOL/NEROLIDOL SYNTHASE WITH TARGET SIGNAL
SEQUENCE DISCRIPTION FOR: 27B
MASSSRAFFKVFNPAPKSIPRIGQSNLMQLTHKKQLPTFQRRGIAEDSLLP

SSTTPIKPMNVETKHTRTMGDIFVQHCQKLELFRNVLRNVAELDALEGLNM

IDAVQRLGIDFHFQREIDEILHKQMSNVSASDDLHEVALRFRLLRQHGYFV

PEDVFNNFKDSKGTFKQVLGEDIKGLMSLYEASQLGTEGEDTLVEAEKFSG

HLLKTSLSHLDHHHARIVGNTLRNPHHKSLASFMARNFFVTTQATNSWLNL

LKDVAKTDFNMVRSLHQNEIVQISKWWKELGLAKELKFARDQPKWYIWSM

ACLTDPKLSEERVELTKPISFVYLIDDIFDVYGTLDDLILFTEAVNRWEIT
```

AIDHLPDYMKICFKALYDMTNEISCKVYQKHGWNPLQSLKISWASLCNAFL

VEAKWFASGQLPKSKEYLKNGIVSSGVNVVLVHMFFILGQNITTKSVELLN

ETPAMISSSAAILRLWDDLGSAKDENQDGNDGSYVRCYLEEHEGCSIEEAR

EKTINMISDEWKKLNRELLSPNPFPATITLASLNLARMIPLMYSYDGNQCL

PSLKEYMKLMLYETVSM

INFORMATION FOR: 28A (H64NORL)
SEQUENCE CHARACTERISTICS:
LENGTH: 2277 bases
TYPE: Genomic DNA
STRANDNESS: Single
TOPOLOGY: Linear
OTHER INFORMATION: CULTIVATED STRAWBERRY
LINALOOL/NEROLIDOL SYNTHASE GENOMIC DNA FRAGMENT
SEQUENCE DISCRIPTION FOR: 28A
CTCCCACAGCTTCTTAGTTGCTGATCATAGATCAGATGGCATCGTCTTCTC

GGGCCTTCTTTAAAGTATTCAATCCTCAAATTGCCTGCTACTTTTGAGATA

GCTTGCTTCCCAGTTCTATTACTATAAAGCCGATGAACGTTGAAACCAAGC

ATACTAGAACTATGGTAAAATTCTCGGAGCTTTCTCCGAAGTACATTTCTA

CAAAAGGGTAGAGCTAGCTACTAAACAATAGTTAATTGACTGTGCCTTGCT

TGCAGGGTGACATTTTTGTCCAACATTCTCAGAAGTTGGAACTATTGAAAA

CTGTCTTGAGGAATGTAGCAGAGCTAGATGCCCTTGAAGGTTTGAATATGA

TCGATGCTGTTCAAAGGCTAGGCATCGATTACAACTTTCAACGAGAAATCG

ACGAAATCCTGCACAAGCAAATGAGTATTGTGTCTGCCCGTGATGATCTTC

ATGAGGTTGCACTTCGCTTTCGACTACTGAGACAACATGGTTACTTCGTGC

CTGAAGGTAAGTTTAATCACACGTATTATTTTTCGTTCGCTAAACGATATG

AAACTATTTCATTCATAAACAGTTGTAAAACTTGTGTAGTAATACATATTT

CTACGTGTTTGTTACAGATGTGTTTAACAACTTCAAGGACAGCAAAGGAAC

GTTCAAGCAAGTTCTGGGTGAAGACATCAAGGGATTGATGAGCTTATACGA

AGCTTCGCAGCTAGGTACAGAAGGAGAAGATATACTTGTTGAAGCTGAAAA

GTTTAGCGGCCATCTGCTAAAGACTTCTCTGTCACATCTTGATCATCATCG

AGTCAGAATTGTTGCAAATACATTGAGGAATCCTCATCACAAAAGCTTGGC

CCCATTCATGGCCAGGAACTTTTTCGTTACTTCTCAAGCCACCAATTCATG

GTTAAATTTGCTAAAAGAAGTAGCAAAAACAGATTTCAATATGGTCCGGTC

TCTGCACCAGAATGAAATAGTTCAAATGTCCAAGTAAGTTTGACAATGACT

TCACCAGTGTCAGGACATTGATACTTTAATTCACACAGGAGATACTTAGTG

TAATTATGTGTATTTTTGACATTGTAGATGGTGGAAGGAGCTTGGATTGGC

TAAGGAACTGAAGTTTGCAAGAGATCAACCACTGAAATGGTACATTTGGTC

CATGGCATGCCTGACAGATCCAAAGTTATCAGAGGAGAGGGTTGAGCTCAC

AAAACCCATCTCTTTTGTCTATTTGATAGATGACATTTTCGATGTTTATGG

AACCCTTGATGACCTCATTCTCTTCACAGAAGCTGTTAATCGGTATATATG

AATTATATGCGTCAGTGATGAAATATAATCAGACTTGTTACCAATTTATGA

TTGATCAACAACCTATTGCATACATACAGATGGGAAATTACTGCTATAGAC

CACTTACCAGACTATAtGAAGATATGCTTCAAGGCTCTCTATGATATGACT

AATGAATTCAGCAGCAAGGTCTATCTGAAGCATGGATGGAACCCCTTACAA

TCTTTGAAAATTTCGGTACATAACTATATATACAAACTGTGACTAATCTAT

CACATTTAACTTGATTATCGTTAAAATCGTGAGCTTGGATTACAAGGTTTA

CATTGAGACCATTCATTCTGTAACTTCTGTTGCAGTGGGCGAGTCTTTGCA

ATGCATTTTTGGTGGAAGCAAAAATGGTTCGCCTCTGGGAAGCTGCCGAAG

TCAGAAGAGTACTTGAAGAATGGCATCGTTTCTTCTGGGGTAAATGTGGTT

CTAGTCCACATGTTTTTCTCTTGGTCAGAACAAACCAGAAAGAGTGTGGA

GTTGTTGAATGAAACTCCAGCCATTATATCGTCCTCAGCAGCAATTCTTCG

ACTCTGGGACGATTTAGGAAGTGCAAAGGATGAGAACCAGGATGGGAACGA

TGGGTCGTATGTAAGGTGCTACTTAGAGGAACATGAAGGCTGTTCCATTGA

GGAGGCACGAGAAAAGACGATTAATATGATTTCAGATGAATGGAAGAAACT

GAACAGAGAACTGCTCTCTCCAAATCCATTTCCAGCATCATTCACATTGGC

TTCTCTTAATCTCGCAAGAATGATCCCCTTGATGTATAGCTACGATGGCAA

CCAATGCCTTCCATCTCTTAAAGAGTATATGAAACTGATGTTGTATGAGAC

TGTATCAATGTAATTAATAATAAGACTACCGGAAGTGGAGTTGAACTTCAA

AGGTGGGTGGTCAAGAGAAACAAGAAGCCTAAG

INFORMATION FOR 29 (E1)
SEQUENCE CHARACTERISTICS:
LENGTH: 227 bases
TYPE: Genomic DNA
STRANDNESS: Single
TOPOLOGY: Linear
OTHER INFORMATION: Fragment from PCR on genomic
DNA from both sides of the methionine residues
SEQUENCE DISCRIPTION FOR: 29A
GGCCGCGGGAATTCTATTCGCTGATCATAGATCAGATGGCATTGTCTACTC

GGGCCTTCTTTAAAGTATTCAATCCCCAAATTACTCCAAACAGTATCTCAC

ATATTGGCCAGTCTAACCTCATGCAGCTTACACAAAAGAAGCAGCTTCCTA

CTTTTCAAAGACGGGCATTGCCGAAGATAGCTTGCTTCCCAGTTCTACTA

CTCCCATAAAGCCGATGCACGTT

INFORMATION FOR: 29B (E1)
SEQUENCE CHARACTERISTICS:
LENGTH: 64 amino acids
TYPE: Peptide
STRANDNESS: Single
TOPOLOGY: Linear
OTHER INFORMATION: Fragment from PCR on genomic
DNA from both sides of the methionine residues
SEQUENCE DISCRIPTION FOR: 29B
MALSTRAFFKVFNPQITPNSISHIGQSNLMQLTQKKQLPTFQRRGIAEDSL

LPSSTTPIKPMHV

INFORMATION FOR: 30A (E2)
SEQUENCE CHARACTERISTICS:
LENGTH: 201 bases
TYPE: Genomic DNA
STRANDNESS: Single
TOPOLOGY: Linear
OTHER INFORMATION: Fragment from PCR on genomic
DNA from both sides of the methionine residues
SEQUENCE DISCRIPTION FOR: 30A
CCGCGGGAATTCGATTTGCTGATCATAGATCAGATGGCTAGTCTTTTCGG

TCCCTCTTTAAAGTATTCAATCAAATTGCTCCAAAAATTAACTCACATGTT

GGCCACTCTAAGAAGCAGCTGCCTGCTACTTTTCAAAGATGGGGCGTTGCC

GAAGATAGCTTGCTTTCCAGTTCTAGTACTATAAAGCTGATGCACGTT

INFORMATION FOR: 31A (E3)
SEQUENCE CHARACTERISTICS:
LENGTH: 141 bases

-continued

TYPE: Genomic DNA
STRANDNESS: Single
TOPOLOGY: Linear
OTHER INFORMATION: Fragment from PCR on genomic DNA from both sides of the methionine residues
SEQUENCE DISCRIPTION FOR: 31A -continued

CCGCGGGAATTCGATTTGCTGATCATAGATCAGATGGCATCGTCTTCTCGG

GCCTTCTTTAAAGTATTCAATCCTCAAATTGCCTGCTACTTTTGAGAAAGC

TTGCTTCCCAGTTCTATTACTATAAAGCCGATGCACGTT

---

The invention claimed is:

1. A method for enhancing fungal resistance of a plant comprising providing the plant with an increased amount of linalool, nerolidol or farnesol, wherein the providing comprises transforming said plant with a gene encoding the proteinaceous molecule of SEQ ID NO: 19 or 21, or a variant of said proteinaceous molecule that is at least 95% identical thereto so as to cause expression of said proteinaceous molecule by the plant.

2. Method according to claim 1, wherein said amount is increased by expression or overexpression of a gene encoding the proteinaceous molecule that is at least 95% identical thereto.

* * * * *

UNITED STATES PATENT AND TRADEMARK OFFICE
CERTIFICATE OF CORRECTION

PATENT NO.        : 8,338,663 B2
APPLICATION NO.   : 12/272329
DATED             : December 25, 2012
INVENTOR(S)       : Aharoni et al.

It is certified that error appears in the above-identified patent and that said Letters Patent is hereby corrected as shown below:

On the title page, Item [73] Assignee should read:

Monsanto Invest N.V., Amstelveen (NL)
Enza Zaden Beheer B.V., Enkhuizen (NL)

Signed and Sealed this
Twenty-fifth Day of March, 2014

Michelle K. Lee
*Deputy Director of the United States Patent and Trademark Office*

SEQUENCE LISTING

<160> NUMBER OF SEQ ID NOS: 93

<210> SEQ ID NO 1
<211> LENGTH: 12
<212> TYPE: PRT
<213> ORGANISM: Artificial
<220> FEATURE:
<223> OTHER INFORMATION: RR MOTIF

<400> SEQUENCE: 1

Asp Ser Leu Leu Pro Ser Ser Ile Thr Ile Lys Pro
1               5                   10

<210> SEQ ID NO 2
<211> LENGTH: 20
<212> TYPE: DNA
<213> ORGANISM: Artificial
<220> FEATURE:
<223> OTHER INFORMATION: OLIGONUCLEOTIDE AAP 291

<400> SEQUENCE: 2
cttcatgagg ttgcacttcg                                              20

<210> SEQ ID NO 3
<211> LENGTH: 24
<212> TYPE: DNA
<213> ORGANISM: Artificial
<220> FEATURE:
<223> OTHER INFORMATION: OLIGONUCLEOTIDE AAP 293

<400> SEQUENCE: 3
aatggtggaa ggagcttgga ttgg                                         24

<210> SEQ ID NO 4
<211> LENGTH: 23
<212> TYPE: DNA
<213> ORGANISM: Artificial Sequence
<220> FEATURE:
<223> OTHER INFORMATION: OLIGONUCLEOTIDE ON THE 3' UNTRANSLATED REGION

<400> SEQUENCE: 4
gttcaactcc acttccagca gtc                                          23

<210> SEQ ID NO 5
<211> LENGTH: 34
<212> TYPE: DNA
<213> ORGANISM: Artificial
<220> FEATURE:
<223> OTHER INFORMATION: OLIGONUCLEOTIDE FOR SITE DIRECTED MUTAGENESIS

<400> SEQUENCE: 5
gggaagcaag ctatctagaa agtagcaggc aatt                              34

<210> SEQ ID NO 6
<211> LENGTH: 21
<212> TYPE: DNA
<213> ORGANISM: Artificial

```
<220> FEATURE:
<223> OTHER INFORMATION: UPSTREAM OLIGONUCLEOTIDE FOR PCR ON G DNA

<400> SEQUENCE: 6
ctcccacagc ttcttagttg c                                          21

<210> SEQ ID NO 7
<211> LENGTH: 25
<212> TYPE: DNA
<213> ORGANISM: Artificial
<220> FEATURE:
<223> OTHER INFORMATION: DOWNSTREAM OLIGONUCLEOTIDE FOR PCR ON G DNA

<400> SEQUENCE: 7
ctagctctgc tacattcctc aagac                                      25

<210> SEQ ID NO 8
<211> LENGTH: 25
<212> TYPE: DNA
<213> ORGANISM: Artificial
<220> FEATURE:
<223> OTHER INFORMATION: OLIGONUCLEOTIDE AAP 339

<400> SEQUENCE: 8
cggatccggc atcgtcttct cgggc                                      25

<210> SEQ ID NO 9
<211> LENGTH: 27
<212> TYPE: DNA
<213> ORGANISM: Artificial
<220> FEATURE:
<223> OTHER INFORMATION: OLIGONUCLEOTIDE AAP 334

<400> SEQUENCE: 9
cgtcgaccaa ctccacttcc ggtagtc                                    27

<210> SEQ ID NO 10
<211> LENGTH: 23
<212> TYPE: DNA
<213> ORGANISM: Artificial
<220> FEATURE:
<223> OTHER INFORMATION: OLIGONUCLEOTIDE AAP 272

<400> SEQUENCE: 10
gatgatatgt atgatgcatt cgg                                        23

<210> SEQ ID NO 11
<211> LENGTH: 25
<212> TYPE: DNA
<213> ORGANISM: Artificial Sequence
<220> FEATURE:
<223> OTHER INFORMATION: OLIGONUCLEOTIDE AAP 283

<400> SEQUENCE: 11
gaaaggatag gctcatcagt acgtg                                      25

<210> SEQ ID NO 12
<211> LENGTH: 25
<212> TYPE: DNA
<213> ORGANISM: Artificial
<220> FEATURE:
<223> OTHER INFORMATION: OLIGONUCLEOTIDE AAP 325

<400> SEQUENCE: 12
cggatccgcc tgtccatgct actcc                                      25
```

-continued

```
<210> SEQ ID NO 13
<211> LENGTH: 27
<212> TYPE: DNA
<213> ORGANISM: Artificial
<220> FEATURE:
<223> OTHER INFORMATION: OLIGONUCLEOTIDE AAP 341

<400> SEQUENCE: 13
cgtcgactga gttcagagtg gcactgg                                        27

<210> SEQ ID NO 14
<211> LENGTH: 23
<212> TYPE: DNA
<213> ORGANISM: Artificial
<220> FEATURE:
<223> OTHER INFORMATION: OLIGONUCLEOTIDE AAP 345

<400> SEQUENCE: 14
agaggttagg tgctcggcgt tac                                            23

<210> SEQ ID NO 15
<211> LENGTH: 23
<212> TYPE: DNA
<213> ORGANISM: Artificial
<220> FEATURE:
<223> OTHER INFORMATION: OLIGONUCLEOTIDE AAP 346

<400> SEQUENCE: 15
gaacaactcc acgatcctat ctc                                            23

<210> SEQ ID NO 16
<211> LENGTH: 1874
<212> TYPE: DNA
<213> ORGANISM: CULTIVATED STRAWBERRY ELSANTA
<220> FEATURE:
<221> NAME/KEY: CDS
<222> LOCATION: (244)..(1800)

<400> SEQUENCE: 16
ctaatacgac tcactatagg gcaagcagtg gtaacaacgc agagtacgcg gggacaactt    60
aagttcttaa ttcgcaaaca agatcaaga agagcgaaaa aaatatcatc tcccacagct   120
tcttagttgc tgatcataga tcagatggca tcgtcttctc gggccttctt taaagtattc   180
aatcctcaaa ttgcctgcta cttttgagat agcttgcttc ccagttctat tactataaag   240 ccg atg aac gtt gaa acc aag cat act aga act atg ggt gac att ttt    288
    Met Asn Val Glu Thr Lys His Thr Arg Thr Met Gly Asp Ile Phe
    1               5                  10                  15 gtc caa cat tct cag aag ttg gaa cta ttg aaa act gtc ttg agg aat    336
Val Gln His Ser Gln Lys Leu Glu Leu Leu Lys Thr Val Leu Arg Asn
                20                  25                  30 gta gca gag cta gat gcc ctt gaa ggt ttg aat atg atc gat gct gtt    384
Val Ala Glu Leu Asp Ala Leu Glu Gly Leu Asn Met Ile Asp Ala Val
            35                  40                  45 caa agg cta ggc atc gat tac aac ttt caa cga gaa atc gac gaa atc    432
Gln Arg Leu Gly Ile Asp Tyr Asn Phe Gln Arg Glu Ile Asp Glu Ile
        50                  55                  60 ctg cac aag caa atg agt att gtg tct gcc cgt gat gat ctt cat gag    480
Leu His Lys Gln Met Ser Ile Val Ser Ala Arg Asp Asp Leu His Glu
    65                  70                  75 gtt gca ctt cgc ttt cga cta ctg aga caa cat ggt tac ttc gtg cct    528
Val Ala Leu Arg Phe Arg Leu Leu Arg Gln His Gly Tyr Phe Val Pro
80                  85                  90                  95 gaa gat gtg ttt aac aac ttc aag gac agc aaa gga acg ttc aag caa    576
Glu Asp Val Phe Asn Asn Phe Lys Asp Ser Lys Gly Thr Phe Lys Gln
```

-continued

|  |  |  |
|---|---|---|
| 100 | 105 | 110 |

| | | |
|---|---|---|
| gtt ctg ggt gaa gac atc aag gga ttg atg agc tta tac gaa gct tcg<br>Val Leu Gly Glu Asp Ile Lys Gly Leu Met Ser Leu Tyr Glu Ala Ser<br>115                           120                       125 | 624 |
| cag cta ggt aca gaa gga gaa gat ata ctt gtt gaa gct gaa aag ttt<br>Gln Leu Gly Thr Glu Gly Glu Asp Ile Leu Val Glu Ala Glu Lys Phe<br>           130                        135                       140 | 672 |
| agc ggc cat ctg cta aag act tct ctg tca cat ctt gat cat cat cga<br>Ser Gly His Leu Leu Lys Thr Ser Leu Ser His Leu Asp His His Arg<br>145                           150                       155 | 720 |
| gtc aga att gtt gca aat aca ttg agg aat cct cat cac aaa agc ttg<br>Val Arg Ile Val Ala Asn Thr Leu Arg Asn Pro His His Lys Ser Leu<br>160                         165                       170                       175 | 768 |
| gcc cca ttc atg gcc agg aac ttt ttc gtt act tct caa gcc acc aat<br>Ala Pro Phe Met Ala Arg Asn Phe Phe Val Thr Ser Gln Ala Thr Asn<br>           180                        185                       190 | 816 |
| tca tgg tta aat ttg cta aaa gaa gta gca aaa aca gat ttc aat atg<br>Ser Trp Leu Asn Leu Leu Lys Glu Val Ala Lys Thr Asp Phe Asn Met<br>195                           200                       205 | 864 |
| gtc cgg tct ctg cac cag aat gaa ata gtt caa atg tcc aaa tgg tgg<br>Val Arg Ser Leu His Gln Asn Glu Ile Val Gln Met Ser Lys Trp Trp<br>210                         215                       220 | 912 |
| aag gag ctt gga ttg gct aag gaa ctg aag ttt gca aga gat caa cca<br>Lys Glu Leu Gly Leu Ala Lys Glu Leu Lys Phe Ala Arg Asp Gln Pro<br>225                           230                       235 | 960 |
| ctg aaa tgg tac att tgg tcc atg gca tgc ctg aca gat cca aag tta<br>Leu Lys Trp Tyr Ile Trp Ser Met Ala Cys Leu Thr Asp Pro Lys Leu<br>240                         245                       250                       255 | 1008 |
| tca gag gag agg gtt gag ctc aca aaa ccc atc tct ttt gtc tat ttg<br>Ser Glu Glu Arg Val Glu Leu Thr Lys Pro Ile Ser Phe Val Tyr Leu<br>           260                        265                       270 | 1056 |
| ata gac gac att ttc gat gtt tat gga acc ctt gat gac ctc att ctc<br>Ile Asp Asp Ile Phe Asp Val Tyr Gly Thr Leu Asp Asp Leu Ile Leu<br>275                         280                       285 | 1104 |
| ttc aca gaa gct gtt aat cga tgg gaa att act gct ata gac cac tta<br>Phe Thr Glu Ala Val Asn Arg Trp Glu Ile Thr Ala Ile Asp His Leu<br>           290                        295                       300 | 1152 |
| cca gac tat atg aag ata tgc ttc aag gct ctc tat gat atg act aat<br>Pro Asp Tyr Met Lys Ile Cys Phe Lys Ala Leu Tyr Asp Met Thr Asn<br>305                         310                       315 | 1200 |
| gaa ttc agc agc aag gtc tat ctg aag cat gga tgg aac ccc tta caa<br>Glu Phe Ser Ser Lys Val Tyr Leu Lys His Gly Trp Asn Pro Leu Gln<br>320                         325                       330                       335 | 1248 |
| tct ttg aaa att tcg tgg gcg agt ctt tgc aat gca ttt ttg gtg gaa<br>Ser Leu Lys Ile Ser Trp Ala Ser Leu Cys Asn Ala Phe Leu Val Glu<br>           340                        345                       350 | 1296 |
| gca aaa tgg ttc gcc tct ggg aag ctg ccg aag tca gaa gag tac ttg<br>Ala Lys Trp Phe Ala Ser Gly Lys Leu Pro Lys Ser Glu Glu Tyr Leu<br>355                         360                       365 | 1344 |
| aag aat ggc atc gtt tct tct ggg gta aat gtg gtt cta gtc cac atg<br>Lys Asn Gly Ile Val Ser Ser Gly Val Asn Val Val Leu Val His Met<br>           370                        375                       380 | 1392 |
| ttt ttt ctc ttg ggt cag aac ata acc aga aag agt gtg gag ttg ttg<br>Phe Phe Leu Leu Gly Gln Asn Ile Thr Arg Lys Ser Val Glu Leu Leu<br>385                           390                       395 | 1440 |
| aat gaa act cca gcc att ata tcg tcc tca gca gca att ctt cga ctc<br>Asn Glu Thr Pro Ala Ile Ile Ser Ser Ser Ala Ala Ile Leu Arg Leu<br>400                         405                       410                       415 | 1488 |
| tgg gac gat tta gga agt gca aag gat gag aac cag gat ggg aac gat<br>Trp Asp Asp Leu Gly Ser Ala Lys Asp Glu Asn Gln Asp Gly Asn Asp | 1536 |

-continued

```
                  420              425              430
ggg tcg tat gta agg tgc tac tta gag gaa cat gaa ggc tgt tcc att    1584
Gly Ser Tyr Val Arg Cys Tyr Leu Glu Glu His Glu Gly Cys Ser Ile
        435              440              445 gag gag gca cga gaa aag acg att aat atg att tca gat gaa tgg aag    1632
Glu Glu Ala Arg Glu Lys Thr Ile Asn Met Ile Ser Asp Glu Trp Lys
            450              455              460 aaa ctg aac aga gaa ctg ctc tct cca aat cca ttt cca gca tca ttc    1680
Lys Leu Asn Arg Glu Leu Leu Ser Pro Asn Pro Phe Pro Ala Ser Phe
465              470              475 aca ttg gct tct ctt aat ctc gca aga atg atc ccc ttg atg tat agc    1728
Thr Leu Ala Ser Leu Asn Leu Ala Arg Met Ile Pro Leu Met Tyr Ser
480              485              490              495 tac gat ggc aac caa tgc ctt cca tct ctt aaa gag tat atg aaa ctg    1776
Tyr Asp Gly Asn Gln Cys Leu Pro Ser Leu Lys Glu Tyr Met Lys Leu
                500              505              510 atg ttg tat gag act gta tca atg taattaataa taagactacc ggaagtggag   1830
Met Leu Tyr Glu Thr Val Ser Met
                515 ttgaacttca aggtgggtg gtcaagagaa acaagaagcc taag                    1874

<210> SEQ ID NO 17
<211> LENGTH: 519
<212> TYPE: PRT
<213> ORGANISM: CULTIVATED STRAWBERRY ELSANTA

<400> SEQUENCE: 17

Met Asn Val Glu Thr Lys His Thr Arg Thr Met Gly Asp Ile Phe Val
1               5                   10                  15

Gln His Ser Gln Lys Leu Glu Leu Leu Lys Thr Val Leu Arg Asn Val
            20                  25                  30

Ala Glu Leu Asp Ala Leu Glu Gly Leu Asn Met Ile Asp Ala Val Gln
        35                  40                  45

Arg Leu Gly Ile Asp Tyr Asn Phe Gln Arg Glu Ile Asp Glu Ile Leu
    50                  55                  60

His Lys Gln Met Ser Ile Val Ser Ala Arg Asp Asp Leu His Glu Val
65                  70                  75                  80

Ala Leu Arg Phe Arg Leu Leu Arg Gln His Gly Tyr Phe Val Pro Glu
                85                  90                  95

Asp Val Phe Asn Asn Phe Lys Asp Ser Lys Gly Thr Phe Lys Gln Val
            100                 105                 110

Leu Gly Glu Asp Ile Lys Gly Leu Met Ser Leu Tyr Glu Ala Ser Gln
        115                 120                 125

Leu Gly Thr Glu Gly Glu Asp Ile Leu Val Glu Ala Glu Lys Phe Ser
    130                 135                 140

Gly His Leu Leu Lys Thr Ser Leu Ser His Leu Asp His His Arg Val
145                 150                 155                 160

Arg Ile Val Ala Asn Thr Leu Arg Asn Pro His His Lys Ser Leu Ala
                165                 170                 175

Pro Phe Met Ala Arg Asn Phe Phe Val Thr Ser Gln Ala Thr Asn Ser
            180                 185                 190

Trp Leu Asn Leu Leu Lys Glu Val Ala Lys Thr Asp Phe Asn Met Val
        195                 200                 205

Arg Ser Leu His Gln Asn Glu Ile Val Gln Met Ser Lys Trp Trp Lys
    210                 215                 220

Glu Leu Gly Leu Ala Lys Glu Leu Lys Phe Ala Arg Asp Gln Pro Leu
225                 230                 235                 240
```

```
Lys Trp Tyr Ile Trp Ser Met Ala Cys Leu Thr Asp Pro Lys Leu Ser
                245                 250                 255

Glu Glu Arg Val Glu Leu Thr Lys Pro Ile Ser Phe Val Tyr Leu Ile
            260                 265                 270

Asp Asp Ile Phe Asp Val Tyr Gly Thr Leu Asp Asp Leu Ile Leu Phe
        275                 280                 285

Thr Glu Ala Val Asn Arg Trp Glu Ile Thr Ala Ile Asp His Leu Pro
    290                 295                 300

Asp Tyr Met Lys Ile Cys Phe Lys Ala Leu Tyr Asp Met Thr Asn Glu
305                 310                 315                 320

Phe Ser Ser Lys Val Tyr Leu Lys His Gly Trp Asn Pro Leu Gln Ser
                325                 330                 335

Leu Lys Ile Ser Trp Ala Ser Leu Cys Asn Ala Phe Leu Val Glu Ala
            340                 345                 350

Lys Trp Phe Ala Ser Gly Lys Leu Pro Lys Ser Glu Glu Tyr Leu Lys
        355                 360                 365

Asn Gly Ile Val Ser Ser Gly Val Asn Val Val Leu Val His Met Phe
    370                 375                 380

Phe Leu Leu Gly Gln Asn Ile Thr Arg Lys Ser Val Glu Leu Leu Asn
385                 390                 395                 400

Glu Thr Pro Ala Ile Ile Ser Ser Ser Ala Ala Ile Leu Arg Leu Trp
                405                 410                 415

Asp Asp Leu Gly Ser Ala Lys Asp Glu Asn Gln Asp Gly Asn Asp Gly
            420                 425                 430

Ser Tyr Val Arg Cys Tyr Leu Glu Glu His Glu Gly Cys Ser Ile Glu
        435                 440                 445

Glu Ala Arg Glu Lys Thr Ile Asn Met Ile Ser Asp Gly Trp Lys Lys
    450                 455                 460

Leu Asn Arg Glu Leu Leu Ser Pro Asn Pro Phe Pro Ala Ser Phe Thr
465                 470                 475                 480

Leu Ala Ser Leu Asn Leu Ala Arg Met Ile Pro Leu Met Tyr Ser Tyr
                485                 490                 495

Asp Gly Asn Gln Cys Leu Pro Ser Leu Lys Glu Tyr Met Lys Leu Met
            500                 505                 510

Leu Tyr Glu Thr Val Ser Met
        515

<210> SEQ ID NO 18
<211> LENGTH: 1631
<212> TYPE: DNA
<213> ORGANISM: CULTIVATED STRAWBERRY ELSANTA
<220> FEATURE:
<221> NAME/KEY: CDS
<222> LOCATION: (1)..(1557)

<400> SEQUENCE: 18 atg aac gtt gaa acc aag cat act aga act atg ggt gac att ttt gtc      48
Met Asn Val Glu Thr Lys His Thr Arg Thr Met Gly Asp Ile Phe Val
1               5                   10                  15 caa cat tct cag aag ttg gaa cta ttg aaa act gtc ttg agg aat gta      96
Gln His Ser Gln Lys Leu Glu Leu Leu Lys Thr Val Leu Arg Asn Val
            20                  25                  30 gca gag cta gat gcc ctt gaa ggt ttg aat atg atc gat gct gtt caa     144
Ala Glu Leu Asp Ala Leu Glu Gly Leu Asn Met Ile Asp Ala Val Gln
        35                  40                  45 agg cta ggc atc gat tac aac ttt caa cga gaa atc gac gaa atc ctg     192
Arg Leu Gly Ile Asp Tyr Asn Phe Gln Arg Glu Ile Asp Glu Ile Leu
```

```
                    50                    55                     60
cac aag caa atg agt att gtg tct gcc cgt gat gat ctt cat gag gtt     240
His Lys Gln Met Ser Ile Val Ser Ala Arg Asp Asp Leu His Glu Val
 65                  70                      75                  80 gca ctt cgc ttt cga cta ctg aga caa cat ggt tac ttc gtg cct gaa     288
Ala Leu Arg Phe Arg Leu Leu Arg Gln His Gly Tyr Phe Val Pro Glu
                     85                      90                  95 gat gtg ttt aac aac ttc aag gac agc aaa gga acg ttc aag caa gtt     336
Asp Val Phe Asn Asn Phe Lys Asp Ser Lys Gly Thr Phe Lys Gln Val
                100                     105                 110 ctg ggt gaa gac atc aag gga ttg atg agc tta tac gaa gct tcg cag     384
Leu Gly Glu Asp Ile Lys Gly Leu Met Ser Leu Tyr Glu Ala Ser Gln
            115                     120                 125 cta ggt aca gaa gga gaa gat ata ctt gtt gaa gct gaa aag ttt agc     432
Leu Gly Thr Glu Gly Glu Asp Ile Leu Val Glu Ala Glu Lys Phe Ser
 130                 135                     140 ggc cat ctg cta aag act tct ctg tca cat ctt gat cat cat cga gtc     480
Gly His Leu Leu Lys Thr Ser Leu Ser His Leu Asp His His Arg Val
 145                 150                     155                 160 aga att gtt gca aat aca ttg agg aat cct cat cac aaa agc ttg gcc     528
Arg Ile Val Ala Asn Thr Leu Arg Asn Pro His His Lys Ser Leu Ala
                     165                     170                 175 cca ttc atg gcc agg aac ttt ttc gtt act tct caa gcc acc aat tca     576
Pro Phe Met Ala Arg Asn Phe Phe Val Thr Ser Gln Ala Thr Asn Ser
                180                     185                 190 tgg tta aat ttg cta aaa gaa gta gca aaa aca gat ttc aat atg gtc     624
Trp Leu Asn Leu Leu Lys Glu Val Ala Lys Thr Asp Phe Asn Met Val
            195                     200                 205 cgg tct ctg cac cag aat gaa ata gtt caa atg tcc aaa tgg tgg aag     672
Arg Ser Leu His Gln Asn Glu Ile Val Gln Met Ser Lys Trp Trp Lys
 210                 215                     220 gag ctt gga ttg gct aag gaa ctg aag ttt gca aga gat caa cca ctg     720
Glu Leu Gly Leu Ala Lys Glu Leu Lys Phe Ala Arg Asp Gln Pro Leu
 225                 230                     235                 240 aaa tgg tac att tgg tcc atg gca tgc ctg aca gat cca aag tta tca     768
Lys Trp Tyr Ile Trp Ser Met Ala Cys Leu Thr Asp Pro Lys Leu Ser
                     245                     250                 255 gag gag agg gtt gag ctc aca aaa ccc atc tct ttt gtc tat ttg ata     816
Glu Glu Arg Val Glu Leu Thr Lys Pro Ile Ser Phe Val Tyr Leu Ile
                260                     265                 270 gat gac att ttc gat gtt tat gga acc ctt gat gac ctc att ctc ttc     864
Asp Asp Ile Phe Asp Val Tyr Gly Thr Leu Asp Asp Leu Ile Leu Phe
            275                     280                 285 aca gaa gct gtt aat cga tgg gaa att act gct ata gac cac tta cca     912
Thr Glu Ala Val Asn Arg Trp Glu Ile Thr Ala Ile Asp His Leu Pro
 290                 295                     300 gac tat atg aag ata tgc ttc aag gct ctc tat gat atg act aat gaa     960
Asp Tyr Met Lys Ile Cys Phe Lys Ala Leu Tyr Asp Met Thr Asn Glu
 305                 310                     315                 320 ttc agc agc aag gtc tat ctg aag cat gga tgg aac ccc tta caa tct    1008
Phe Ser Ser Lys Val Tyr Leu Lys His Gly Trp Asn Pro Leu Gln Ser
                     325                     330                 335 ttg aaa att tcg tgg gcg agt ctt tgc aat gca ttt ttg gtg gaa gca    1056
Leu Lys Ile Ser Trp Ala Ser Leu Cys Asn Ala Phe Leu Val Glu Ala
                340                     345                 350 aaa tgg ttc gcc tct ggg aag ctg ccg aag tca gaa gag tac ttg aag    1104
Lys Trp Phe Ala Ser Gly Lys Leu Pro Lys Ser Glu Glu Tyr Leu Lys
            355                     360                 365 aat ggc atc gtt tct tct ggg gta aat gtg gtt cta gtc cac atg ttt    1152
Asn Gly Ile Val Ser Ser Gly Val Asn Val Val Leu Val His Met Phe
```

|  |  |  |  |  |  |  |  |  |  |  |  |  |  |  |  |
|---|---|---|---|---|---|---|---|---|---|---|---|---|---|---|---|
|  | 370 |  |  |  | 375 |  |  |  |  | 380 |  |  |  |  |  |
| ttt | ctc | ttg | ggt | cag | aac | ata | acc | aga | aag | agt | gtg | gag | ttg | ttg | aat | 1200 |
| Phe | Leu | Leu | Gly | Gln | Asn | Ile | Thr | Arg | Lys | Ser | Val | Glu | Leu | Leu | Asn |  |
| 385 |  |  |  |  | 390 |  |  |  |  | 395 |  |  |  |  | 400 |  |
| gaa | act | cca | gcc | att | ata | tcg | tcc | tca | gca | gca | att | ctt | cga | ctc | tgg | 1248 |
| Glu | Thr | Pro | Ala | Ile | Ile | Ser | Ser | Ser | Ala | Ala | Ile | Leu | Arg | Leu | Trp |  |
|  |  |  |  | 405 |  |  |  |  | 410 |  |  |  |  | 415 |  |  |
| gac | gat | tta | gga | agt | gca | aag | gat | gag | aac | cag | gat | ggg | aac | gat | ggg | 1296 |
| Asp | Asp | Leu | Gly | Ser | Ala | Lys | Asp | Glu | Asn | Gln | Asp | Gly | Asn | Asp | Gly |  |
|  |  |  | 420 |  |  |  |  | 425 |  |  |  |  | 430 |  |  |  |
| tcg | tat | gta | agg | tgc | tac | tta | gag | gaa | cat | gaa | ggc | tgt | tcc | att | gag | 1344 |
| Ser | Tyr | Val | Arg | Cys | Tyr | Leu | Glu | Glu | His | Glu | Gly | Cys | Ser | Ile | Glu |  |
|  |  | 435 |  |  |  |  | 440 |  |  |  |  | 445 |  |  |  |  |
| gag | gca | cga | gaa | aag | acg | att | aat | atg | att | tca | gat | gaa | tgg | aag | aaa | 1392 |
| Glu | Ala | Arg | Glu | Lys | Thr | Ile | Asn | Met | Ile | Ser | Asp | Glu | Trp | Lys | Lys |  |
|  | 450 |  |  |  |  | 455 |  |  |  |  | 460 |  |  |  |  |  |
| ctg | aac | aga | gaa | ctg | ctc | tct | cca | aat | cca | ttt | cca | gca | tca | ttc | aca | 1440 |
| Leu | Asn | Arg | Glu | Leu | Leu | Ser | Pro | Asn | Pro | Phe | Pro | Ala | Ser | Phe | Thr |  |
| 465 |  |  |  |  | 470 |  |  |  |  | 475 |  |  |  |  | 480 |  |
| ttg | gct | tct | ctt | aat | ctc | gca | aga | atg | atc | ccc | ttg | atg | tat | agc | tac | 1488 |
| Leu | Ala | Ser | Leu | Asn | Leu | Ala | Arg | Met | Ile | Pro | Leu | Met | Tyr | Ser | Tyr |  |
|  |  |  |  | 485 |  |  |  |  | 490 |  |  |  |  | 495 |  |  |
| gat | ggc | aac | caa | tgc | ctt | cca | tct | ctt | aaa | gag | tat | atg | aaa | ctg | atg | 1536 |
| Asp | Gly | Asn | Gln | Cys | Leu | Pro | Ser | Leu | Lys | Glu | Tyr | Met | Lys | Leu | Met |  |
|  |  |  | 500 |  |  |  |  | 505 |  |  |  |  | 510 |  |  |  |
| ttg | tat | gag | act | gta | tca | atg | taattaataa | taagactacc | ggaagtggag |  |  |  |  |  |  | 1587 |
| Leu | Tyr | Glu | Thr | Val | Ser | Met |  |  |  |  |  |  |  |  |  |  |
|  |  |  | 515 |  |  |  |  |  |  |  |  |  |  |  |  |  |
| ttgaacttca | aaggtgggtg | gtcaagagaa | acaagaagcc | taag |  |  |  |  |  |  |  |  |  |  |  | 1631 |

<210> SEQ ID NO 19
<211> LENGTH: 519
<212> TYPE: PRT
<213> ORGANISM: CULTIVATED STRAWBERRY ELSANTA

<400> SEQUENCE: 19

| Met | Asn | Val | Glu | Thr | Lys | His | Thr | Arg | Thr | Met | Gly | Asp | Ile | Phe | Val |
|---|---|---|---|---|---|---|---|---|---|---|---|---|---|---|---|
| 1 |  |  |  | 5 |  |  |  |  | 10 |  |  |  |  | 15 |  |
| Gln | His | Ser | Gln | Lys | Leu | Glu | Leu | Leu | Lys | Thr | Val | Leu | Arg | Asn | Val |
|  |  |  | 20 |  |  |  |  | 25 |  |  |  |  | 30 |  |  |
| Ala | Glu | Leu | Asp | Ala | Leu | Glu | Gly | Leu | Asn | Met | Ile | Asp | Ala | Val | Gln |
|  |  | 35 |  |  |  |  | 40 |  |  |  |  | 45 |  |  |  |
| Arg | Leu | Gly | Ile | Asp | Tyr | Asn | Phe | Gln | Arg | Glu | Ile | Asp | Glu | Ile | Leu |
|  | 50 |  |  |  |  | 55 |  |  |  |  | 60 |  |  |  |  |
| His | Lys | Gln | Met | Ser | Ile | Val | Ser | Ala | Arg | Asp | Asp | Leu | His | Glu | Val |
| 65 |  |  |  |  | 70 |  |  |  |  | 75 |  |  |  |  | 80 |
| Ala | Leu | Arg | Phe | Arg | Leu | Leu | Arg | Gln | His | Gly | Tyr | Phe | Val | Pro | Glu |
|  |  |  |  | 85 |  |  |  |  | 90 |  |  |  |  | 95 |  |
| Asp | Val | Phe | Asn | Asn | Phe | Lys | Asp | Ser | Lys | Gly | Thr | Phe | Lys | Gln | Val |
|  |  |  | 100 |  |  |  |  | 105 |  |  |  |  | 110 |  |  |
| Leu | Gly | Glu | Asp | Ile | Lys | Gly | Leu | Met | Ser | Leu | Tyr | Glu | Ala | Ser | Gln |
|  |  | 115 |  |  |  |  | 120 |  |  |  |  | 125 |  |  |  |
| Leu | Gly | Thr | Glu | Gly | Glu | Asp | Ile | Leu | Val | Glu | Ala | Glu | Lys | Phe | Ser |
|  | 130 |  |  |  |  | 135 |  |  |  |  | 140 |  |  |  |  |
| Gly | His | Leu | Leu | Lys | Thr | Ser | Leu | Ser | His | Leu | Asp | His | His | Arg | Val |
| 145 |  |  |  |  | 150 |  |  |  |  | 155 |  |  |  |  | 160 |
| Arg | Ile | Val | Ala | Asn | Thr | Leu | Arg | Asn | Pro | His | His | Lys | Ser | Leu | Ala |
|  |  |  |  | 165 |  |  |  |  | 170 |  |  |  |  | 175 |  |

Pro Phe Met Ala Arg Asn Phe Val Thr Ser Gln Ala Thr Asn Ser
                180                 185                 190

Trp Leu Asn Leu Leu Lys Glu Val Ala Lys Thr Asp Phe Asn Met Val
        195                 200                 205

Arg Ser Leu His Gln Asn Glu Ile Val Gln Met Ser Lys Trp Trp Lys
        210                 215                 220

Glu Leu Gly Leu Ala Lys Glu Leu Lys Phe Ala Arg Asp Gln Pro Leu
225                 230                 235                 240

Lys Trp Tyr Ile Trp Ser Met Ala Cys Leu Thr Asp Pro Lys Leu Ser
                245                 250                 255

Glu Glu Arg Val Glu Leu Thr Lys Pro Ile Ser Phe Val Tyr Leu Ile
                260                 265                 270

Asp Asp Ile Phe Asp Val Tyr Gly Thr Leu Asp Asp Leu Ile Leu Phe
                275                 280                 285

Thr Glu Ala Val Asn Arg Trp Glu Ile Thr Ala Ile Asp His Leu Pro
            290                 295                 300

Asp Tyr Met Lys Ile Cys Phe Lys Ala Leu Tyr Asp Met Thr Asn Glu
305                 310                 315                 320

Phe Ser Ser Lys Val Tyr Leu Lys His Gly Trp Asn Pro Leu Gln Ser
                325                 330                 335

Leu Lys Ile Ser Trp Ala Ser Leu Cys Asn Ala Phe Leu Val Glu Ala
            340                 345                 350

Lys Trp Phe Ala Ser Gly Lys Leu Pro Lys Ser Glu Glu Tyr Leu Lys
                355                 360                 365

Asn Gly Ile Val Ser Ser Gly Val Asn Val Val Leu Val His Met Phe
        370                 375                 380

Phe Leu Leu Gly Gln Asn Ile Thr Arg Lys Ser Val Glu Leu Leu Asn
385                 390                 395                 400

Glu Thr Pro Ala Ile Ile Ser Ser Ser Ala Ala Ile Leu Arg Leu Trp
                405                 410                 415

Asp Asp Leu Gly Ser Ala Lys Asp Glu Asn Gln Asp Gly Asn Asp Gly
                420                 425                 430

Ser Tyr Val Arg Cys Tyr Leu Glu Glu His Glu Gly Cys Ser Ile Glu
            435                 440                 445

Glu Ala Arg Glu Lys Thr Ile Asn Met Ile Ser Asp Glu Trp Lys Lys
        450                 455                 460

Leu Asn Arg Glu Leu Leu Ser Pro Asn Pro Phe Pro Ala Ser Phe Thr
465                 470                 475                 480

Leu Ala Ser Leu Asn Leu Ala Arg Met Ile Pro Leu Met Tyr Ser Tyr
                485                 490                 495

Asp Gly Asn Gln Cys Leu Pro Ser Leu Lys Glu Tyr Met Lys Leu Met
            500                 505                 510

Leu Tyr Glu Thr Val Ser Met
        515

<210> SEQ ID NO 20
<211> LENGTH: 1874
<212> TYPE: DNA
<213> ORGANISM: Cultivated strawberry Elsanta
<220> FEATURE:
<221> NAME/KEY: CDS
<222> LOCATION: (145)..(1800)

<400> SEQUENCE: 20
ctaatacgac tcactatagg gcaagcagtg gtaacaacgc agagtacgcg gggacaactt        60

| | | |
|---|---|---|
| aagttcttaa ttcgcaaaca aagatcaaga agagcgaaag aaatatcatc tcccacagct | | 120 |
| tcttagttgc tgatcataga tcag atg gca tcg tct tct cgg gcc ttc ttt<br>                                     Met Ala Ser Ser Ser Arg Ala Phe Phe<br>                                     1                5 | | 171 |
| aaa gta ttc aat cct caa att gcc tgc tac ttt cta gat agc ttg ctt<br>Lys Val Phe Asn Pro Gln Ile Ala Cys Tyr Phe Leu Asp Ser Leu Leu<br>10                      15                    20                   25 | | 219 |
| ccc agt tct att act ata aag ccg atg aac gtt gaa acc aag cat act<br>Pro Ser Ser Ile Thr Ile Lys Pro Met Asn Val Glu Thr Lys His Thr<br>                  30                    35                    40 | | 267 |
| aga act atg ggt gac att ttt gtc caa cat tct cag aag ttg gaa cta<br>Arg Thr Met Gly Asp Ile Phe Val Gln His Ser Gln Lys Leu Glu Leu<br>            45                    50                    55 | | 315 |
| ttg aaa act gtc ttg agg aat gta gca gag cta gat gcc ctt gaa ggt<br>Leu Lys Thr Val Leu Arg Asn Val Ala Glu Leu Asp Ala Leu Glu Gly<br>    60                    65                    70 | | 363 |
| ttg aat atg atc gat gct gtt caa agg cta ggc atc gat tac aac ttt<br>Leu Asn Met Ile Asp Ala Val Gln Arg Leu Gly Ile Asp Tyr Asn Phe<br>75                      80                    85 | | 411 |
| caa cga gaa atc gac gaa atc ctg cac aag caa atg agt att gtg tct<br>Gln Arg Glu Ile Asp Glu Ile Leu His Lys Gln Met Ser Ile Val Ser<br>90                      95                   100              105 | | 459 |
| gcc cgt gat gat ctt cat gag gtt gca ctt cgc ttt cga cta ctg aga<br>Ala Arg Asp Asp Leu His Glu Val Ala Leu Arg Phe Arg Leu Leu Arg<br>                  110                   115               120 | | 507 |
| caa cat ggt tac ttc gtg cct gaa gat gtg ttt aac aac ttc aag gac<br>Gln His Gly Tyr Phe Val Pro Glu Asp Val Phe Asn Asn Phe Lys Asp<br>            125                   130                 135 | | 555 |
| agc aaa gga acg ttc aag caa gtt ctg ggt gaa gac atc aag gga ttg<br>Ser Lys Gly Thr Phe Lys Gln Val Leu Gly Glu Asp Ile Lys Gly Leu<br>        140                   145                 150 | | 603 |
| atg agc tta tac gaa gct tcg cag cta ggt aca gaa gga gaa gat ata<br>Met Ser Leu Tyr Glu Ala Ser Gln Leu Gly Thr Glu Gly Glu Asp Ile<br>155                    160                   165 | | 651 |
| ctt gtt gaa gct gaa aag ttt agc ggc cat ctg cta aag act tct ctg<br>Leu Val Glu Ala Glu Lys Phe Ser Gly His Leu Leu Lys Thr Ser Leu<br>170                    175                 180              185 | | 699 |
| tca cat ctt gat cat cat cga gtc aga att gtt gca aat aca ttg agg<br>Ser His Leu Asp His His Arg Val Arg Ile Val Ala Asn Thr Leu Arg<br>                  190                   195               200 | | 747 |
| aat cct cat cac aaa agc ttg gcc cca ttc atg gcc agg aac ttt ttc<br>Asn Pro His His Lys Ser Leu Ala Pro Phe Met Ala Arg Asn Phe Phe<br>            205                   210                 215 | | 795 |
| gtt act tct caa gcc acc aat tca tgg tta aat ttg cta aaa gaa gta<br>Val Thr Ser Gln Ala Thr Asn Ser Trp Leu Asn Leu Leu Lys Glu Val<br>        220                   225                 230 | | 843 |
| gca aaa aca gat ttc aat atg gtc cgg tct ctg cac cag aat gaa ata<br>Ala Lys Thr Asp Phe Asn Met Val Arg Ser Leu His Gln Asn Glu Ile<br>235                    240                 245 | | 891 |
| gtt caa atg tcc aaa tgg tgg aag gag ctt gga ttg gct aag gaa ctg<br>Val Gln Met Ser Lys Trp Trp Lys Glu Leu Gly Leu Ala Lys Glu Leu<br>250                    255                 260              265 | | 939 |
| aag ttt gca aga gat caa cca ctg aaa tgg tac att tgg tcc atg gca<br>Lys Phe Ala Arg Asp Gln Pro Leu Lys Trp Tyr Ile Trp Ser Met Ala<br>            270                   275                 280 | | 987 |
| tgc ctg aca gat cca aag tta tca gag gag agg gtt gag ctc aca aaa<br>Cys Leu Thr Asp Pro Lys Leu Ser Glu Glu Arg Val Glu Leu Thr Lys<br>            285                   290                 295 | | 1035 |
| ccc atc tct ttt gtc tat ttg ata gat gac att ttc gat gtt tat gga<br>Pro Ile Ser Phe Val Tyr Leu Ile Asp Asp Ile Phe Asp Val Tyr Gly | | 1083 |

```
                 300                 305                 310
acc ctt gat gac ctc att ctc ttc aca gaa gct gtt aat cga tgg gaa      1131
Thr Leu Asp Asp Leu Ile Leu Phe Thr Glu Ala Val Asn Arg Trp Glu
315                 320                 325 att act gct ata gac cac tta cca gac tat atg aag ata tgc ttc aag      1179
Ile Thr Ala Ile Asp His Leu Pro Asp Tyr Met Lys Ile Cys Phe Lys
330                 335                 340                 345 gct ctc tat gat atg act aat gaa ttc agc agc aag gtc tat ctg aag      1227
Ala Leu Tyr Asp Met Thr Asn Glu Phe Ser Ser Lys Val Tyr Leu Lys
                350                 355                 360 cat gga tgg aac ccc tta caa tct ttg aaa att tcg tgg gcg agt ctt      1275
His Gly Trp Asn Pro Leu Gln Ser Leu Lys Ile Ser Trp Ala Ser Leu
            365                 370                 375 tgc aat gca ttt ttg gtg gaa gca aaa tgg ttc gcc tct ggg aag ctg      1323
Cys Asn Ala Phe Leu Val Glu Ala Lys Trp Phe Ala Ser Gly Lys Leu
        380                 385                 390 ccg aag tca gaa gag tac ttg aag aat ggc atc gtt tct tct ggg gta      1371
Pro Lys Ser Glu Glu Tyr Leu Lys Asn Gly Ile Val Ser Ser Gly Val
    395                 400                 405 aat gtg gtt cta gtc cac atg ttt ttt ctc ttg ggt cag aac ata acc      1419
Asn Val Val Leu Val His Met Phe Phe Leu Leu Gly Gln Asn Ile Thr
410                 415                 420                 425 aga aag agt gtg gag ttg ttg aat gaa act cca gcc att ata tcg tcc      1467
Arg Lys Ser Val Glu Leu Leu Asn Glu Thr Pro Ala Ile Ile Ser Ser
                430                 435                 440 tca gca gca att ctt cga ctc tgg gac gat tta gga agt gca aag gat      1515
Ser Ala Ala Ile Leu Arg Leu Trp Asp Asp Leu Gly Ser Ala Lys Asp
            445                 450                 455 gag aac cag gat ggg aac gat ggg tcg tat gta agg tgc tac tta gag      1563
Glu Asn Gln Asp Gly Asn Asp Gly Ser Tyr Val Arg Cys Tyr Leu Glu
        460                 465                 470 gaa cat gaa ggc tgt tcc att gag gag gca cga gaa aag acg att aat      1611
Glu His Glu Gly Cys Ser Ile Glu Glu Ala Arg Glu Lys Thr Ile Asn
    475                 480                 485 atg att tca gat gaa tgg aag aaa ctg aac aga gaa ctg ctc tct cca      1659
Met Ile Ser Asp Glu Trp Lys Lys Leu Asn Arg Glu Leu Leu Ser Pro
490                 495                 500                 505 aat cca ttt cca gca tca ttc aca ttg gct tct ctt aat ctc gca aga      1707
Asn Pro Phe Pro Ala Ser Phe Thr Leu Ala Ser Leu Asn Leu Ala Arg
                510                 515                 520 atg atc ccc ttg atg tat agc tac gat ggc aac caa tgc ctt cca tct      1755
Met Ile Pro Leu Met Tyr Ser Tyr Asp Gly Asn Gln Cys Leu Pro Ser
            525                 530                 535 ctt aaa gag tat atg aaa ctg atg ttg tat gag act gta tca atg          1800
Leu Lys Glu Tyr Met Lys Leu Met Leu Tyr Glu Thr Val Ser Met
        540                 545                 550 taattaataa taagactacc ggaagtggag ttgaacttca aggtgggtg gtcaagagaa    1860 acaagaagcc taag                                                     1874

<210> SEQ ID NO 21
<211> LENGTH: 552
<212> TYPE: PRT
<213> ORGANISM: Cultivated strawberry Elsanta

<400> SEQUENCE: 21

Met Ala Ser Ser Ser Arg Ala Phe Phe Lys Val Phe Asn Pro Gln Ile
1               5                   10                  15

Ala Cys Tyr Phe Leu Asp Ser Leu Leu Pro Ser Ser Ile Thr Ile Lys
            20                  25                  30
```

-continued

Pro Met Asn Val Glu Thr Lys His Thr Arg Thr Met Gly Asp Ile Phe
        35                  40                  45

Val Gln His Ser Gln Lys Leu Glu Leu Leu Lys Thr Val Leu Arg Asn
 50                  55                  60

Val Ala Glu Leu Asp Ala Leu Glu Gly Leu Asn Met Ile Asp Ala Val
 65                  70                  75                  80

Gln Arg Leu Gly Ile Asp Tyr Asn Phe Gln Arg Glu Ile Asp Glu Ile
                 85                  90                  95

Leu His Lys Gln Met Ser Ile Val Ser Ala Arg Asp Asp Leu His Glu
                100                 105                 110

Val Ala Leu Arg Phe Arg Leu Leu Arg Gln His Gly Tyr Phe Val Pro
                115                 120                 125

Glu Asp Val Phe Asn Asn Phe Lys Asp Ser Lys Gly Thr Phe Lys Gln
130                 135                 140

Val Leu Gly Glu Asp Ile Lys Gly Leu Met Ser Leu Tyr Glu Ala Ser
145                 150                 155                 160

Gln Leu Gly Thr Glu Gly Glu Asp Ile Leu Val Glu Ala Glu Lys Phe
                165                 170                 175

Ser Gly His Leu Leu Lys Thr Ser Leu Ser His Leu Asp His His Arg
                180                 185                 190

Val Arg Ile Val Ala Asn Thr Leu Arg Asn Pro His His Lys Ser Leu
                195                 200                 205

Ala Pro Phe Met Ala Arg Asn Phe Phe Val Thr Ser Gln Ala Thr Asn
210                 215                 220

Ser Trp Leu Asn Leu Leu Lys Glu Val Ala Lys Thr Asp Phe Asn Met
225                 230                 235                 240

Val Arg Ser Leu His Gln Asn Glu Ile Val Gln Met Ser Lys Trp Trp
                245                 250                 255

Lys Glu Leu Gly Leu Ala Lys Glu Leu Lys Phe Ala Arg Asp Gln Pro
                260                 265                 270

Leu Lys Trp Tyr Ile Trp Ser Met Ala Cys Leu Thr Asp Pro Lys Leu
                275                 280                 285

Ser Glu Glu Arg Val Glu Leu Thr Lys Pro Ile Ser Phe Val Tyr Leu
                290                 295                 300

Ile Asp Asp Ile Phe Asp Val Tyr Gly Thr Leu Asp Asp Leu Ile Leu
305                 310                 315                 320

Phe Thr Glu Ala Val Asn Arg Trp Glu Ile Thr Ala Ile Asp His Leu
                325                 330                 335

Pro Asp Tyr Met Lys Ile Cys Phe Lys Ala Leu Tyr Asp Met Thr Asn
                340                 345                 350

Glu Phe Ser Ser Lys Val Tyr Leu Lys His Gly Trp Asn Pro Leu Gln
                355                 360                 365

Ser Leu Lys Ile Ser Trp Ala Ser Leu Cys Asn Ala Phe Leu Val Glu
370                 375                 380

Ala Lys Trp Phe Ala Ser Gly Lys Leu Pro Lys Ser Glu Glu Tyr Leu
385                 390                 395                 400

Lys Asn Gly Ile Val Ser Ser Gly Val Asn Val Val Leu Val His Met
                405                 410                 415

Phe Phe Leu Leu Gly Gln Asn Ile Thr Arg Lys Ser Val Glu Leu Leu
                420                 425                 430

Asn Glu Thr Pro Ala Ile Ile Ser Ser Ser Ala Ala Ile Leu Arg Leu
                435                 440                 445

Trp Asp Asp Leu Gly Ser Ala Lys Asp Glu Asn Gln Asp Gly Asn Asp
450                 455                 460

```
Gly Ser Tyr Val Arg Cys Tyr Leu Glu Glu His Glu Gly Cys Ser Ile
465                 470                 475                 480

Glu Glu Ala Arg Glu Lys Thr Ile Asn Met Ile Ser Asp Glu Trp Lys
                485                 490                 495

Lys Leu Asn Arg Glu Leu Leu Ser Pro Asn Pro Phe Pro Ala Ser Phe
            500                 505                 510

Thr Leu Ala Ser Leu Asn Leu Ala Arg Met Ile Pro Leu Met Tyr Ser
        515                 520                 525

Tyr Asp Gly Asn Gln Cys Leu Pro Ser Leu Lys Glu Tyr Met Lys Leu
530                 535                 540

Met Leu Tyr Glu Thr Val Ser Met
545                 550

<210> SEQ ID NO 22
<211> LENGTH: 1894
<212> TYPE: DNA
<213> ORGANISM: Wild strawberry
<220> FEATURE:
<221> NAME/KEY: CDS
<222> LOCATION: (118)..(1857)

<400> SEQUENCE: 22
aagcagtggt aacaacgcag agtacgcggg gacaactgaa gttcttaatt cgcaaacaaa      60
gatcaagaag agcgaaagaa gtatcatctc ccgccttagg tgctgatcat agatcag       117 atg gca tcg tct tct tgg gcc ttc ttt aaa gta ttc aat ccc caa att      165
Met Ala Ser Ser Ser Trp Ala Phe Phe Lys Val Phe Asn Pro Gln Ile
1               5                   10                  15 gct cca aaa agt atc tca cat att ggc cag tct gac ctc atg cag ctt      213
Ala Pro Lys Ser Ile Ser His Ile Gly Gln Ser Asp Leu Met Gln Leu
            20                  25                  30 aca cat aag aag cag ctg cct act ttt caa aga cgg ggc att gcc gaa      261
Thr His Lys Lys Gln Leu Pro Thr Phe Gln Arg Arg Gly Ile Ala Glu
        35                  40                  45 gat agc ttg ctt ccc agt tct act act ccc ata aag ccg atg cac gtt      309
Asp Ser Leu Leu Pro Ser Ser Thr Thr Pro Ile Lys Pro Met His Val
50                  55                  60 gaa acc aag cat act aga act atg ggt gac att ttt gtc caa cat tct      357
Glu Thr Lys His Thr Arg Thr Met Gly Asp Ile Phe Val Gln His Ser
65                  70                  75                  80 cag aag ttg gaa cta ttc aga aat gtc ttg agg aat gca gca gag cta      405
Gln Lys Leu Glu Leu Phe Arg Asn Val Leu Arg Asn Ala Ala Glu Leu
                85                  90                  95 gat gcc ctt gaa ggt ttg aat atg atc gat gcc gtt caa agg cta ggc      453
Asp Ala Leu Glu Gly Leu Asn Met Ile Asp Ala Val Gln Arg Leu Gly
            100                 105                 110 atc gat tac cac ttt caa cga gaa atc gac gaa att ctg cac aag caa      501
Ile Asp Tyr His Phe Gln Arg Glu Ile Asp Glu Ile Leu His Lys Gln
        115                 120                 125 atg ggt att gta tct gcc tgt gat gat ctt tat gag gtt gca ctt cgt      549
Met Gly Ile Val Ser Ala Cys Asp Asp Leu Tyr Glu Val Ala Leu Arg
    130                 135                 140 ttt cga cta ctg aga caa cat ggt tac ttc gtg cct gaa gat gtg ttt      597
Phe Arg Leu Leu Arg Gln His Gly Tyr Phe Val Pro Glu Asp Val Phe
145                 150                 155                 160 aac aac ttc aag gac agc aaa gga act ttc aag caa gtt ctg ggt gaa      645
Asn Asn Phe Lys Asp Ser Lys Gly Thr Phe Lys Gln Val Leu Gly Glu
                165                 170                 175 gac atc aag gga ttg atg agc tta tac gaa gct tcg cag cta ggt aca      693
Asp Ile Lys Gly Leu Met Ser Leu Tyr Glu Ala Ser Gln Leu Gly Thr
```

|     |     |     |     |     |     |     |     |     |     |     |     |     |     |     |     |      |
|---|---|---|---|---|---|---|---|---|---|---|---|---|---|---|---|---|
|     |     |     | 180 |     |     |     | 185 |     |     |     | 190 |     |     |     |     |      |
| gaa | gga | gaa | gat | aca | ctt | gtt | gaa | gct | gaa | aag | ttt | agt | ggc | cat | ctg | 741  |
| Glu | Gly | Glu | Asp | Thr | Leu | Val | Glu | Ala | Glu | Lys | Phe | Ser | Gly | His | Leu |      |
|     |     | 195 |     |     |     |     | 200 |     |     |     |     | 205 |     |     |     |      |
| cta | aag | act | tct | ctg | tca | cat | ctt | gat | cgt | cat | cga | gcc | aga | att | gtt | 789  |
| Leu | Lys | Thr | Ser | Leu | Ser | His | Leu | Asp | Arg | His | Arg | Ala | Arg | Ile | Val |      |
| 210 |     |     |     |     |     | 215 |     |     |     |     | 220 |     |     |     |     |      |
| gga | aat | aca | ttg | agg | aat | cct | cat | cgc | aaa | agc | ttg | gcc | tca | ttc | atg | 837  |
| Gly | Asn | Thr | Leu | Arg | Asn | Pro | His | Arg | Lys | Ser | Leu | Ala | Ser | Phe | Met |      |
| 225 |     |     |     |     | 230 |     |     |     |     | 235 |     |     |     |     | 240 |      |
| gcc | agg | aac | ttt | ttc | gtt | act | tct | caa | gcc | acc | aat | tca | tgg | tta | aat | 885  |
| Ala | Arg | Asn | Phe | Phe | Val | Thr | Ser | Gln | Ala | Thr | Asn | Ser | Trp | Leu | Asn |      |
|     |     |     |     | 245 |     |     |     |     | 250 |     |     |     |     | 255 |     |      |
| ttg | cta | aaa | gaa | gta | gca | aaa | aca | gat | ttc | aat | atg | gtc | cgg | tct | gtg | 933  |
| Leu | Leu | Lys | Glu | Val | Ala | Lys | Thr | Asp | Phe | Asn | Met | Val | Arg | Ser | Val |      |
|     |     |     | 260 |     |     |     |     | 265 |     |     |     |     | 270 |     |     |      |
| cac | cag | aaa | gaa | ata | gtt | caa | att | tcc | aaa | tgg | tgg | aag | gag | ctt | gga | 981  |
| His | Gln | Lys | Glu | Ile | Val | Gln | Ile | Ser | Lys | Trp | Trp | Lys | Glu | Leu | Gly |      |
|     |     | 275 |     |     |     |     | 280 |     |     |     |     | 285 |     |     |     |      |
| ttg | gtt | aag | gaa | ctg | aag | ttt | gca | aga | gat | caa | cca | ctg | aaa | tgg | tac | 1029 |
| Leu | Val | Lys | Glu | Leu | Lys | Phe | Ala | Arg | Asp | Gln | Pro | Leu | Lys | Trp | Tyr |      |
|     | 290 |     |     |     |     | 295 |     |     |     |     | 300 |     |     |     |     |      |
| act | tgg | tcc | atg | gca | ggc | cta | aca | gat | cca | aag | tta | tca | gag | gag | agg | 1077 |
| Thr | Trp | Ser | Met | Ala | Gly | Leu | Thr | Asp | Pro | Lys | Leu | Ser | Glu | Glu | Arg |      |
| 305 |     |     |     |     | 310 |     |     |     |     | 315 |     |     |     |     | 320 |      |
| gtt | gag | ctc | aca | aaa | ccc | atc | tct | ttt | gtc | tat | ttg | ata | gat | gac | att | 1125 |
| Val | Glu | Leu | Thr | Lys | Pro | Ile | Ser | Phe | Val | Tyr | Leu | Ile | Asp | Asp | Ile |      |
|     |     |     |     | 325 |     |     |     |     | 330 |     |     |     |     | 335 |     |      |
| ttc | gat | gtt | tat | gga | acc | ctt | gat | gac | ctc | att | ctc | ttc | aca | gaa | gct | 1173 |
| Phe | Asp | Val | Tyr | Gly | Thr | Leu | Asp | Asp | Leu | Ile | Leu | Phe | Thr | Glu | Ala |      |
|     |     |     | 340 |     |     |     |     | 345 |     |     |     |     | 350 |     |     |      |
| gtt | aat | aga | tgg | gaa | att | act | gct | ata | gac | cac | tta | cca | gac | tat | atg | 1221 |
| Val | Asn | Arg | Trp | Glu | Ile | Thr | Ala | Ile | Asp | His | Leu | Pro | Asp | Tyr | Met |      |
|     |     | 355 |     |     |     |     | 360 |     |     |     |     | 365 |     |     |     |      |
| aag | ata | tgc | ttc | aag | gct | ctc | tat | gat | atg | act | aat | gaa | ttc | agc | tgc | 1269 |
| Lys | Ile | Cys | Phe | Lys | Ala | Leu | Tyr | Asp | Met | Thr | Asn | Glu | Phe | Ser | Cys |      |
|     | 370 |     |     |     |     | 375 |     |     |     |     | 380 |     |     |     |     |      |
| aag | gtc | tat | cag | aag | cat | gga | tgg | aac | ccc | tta | cga | tct | ttg | aaa | att | 1317 |
| Lys | Val | Tyr | Gln | Lys | His | Gly | Trp | Asn | Pro | Leu | Arg | Ser | Leu | Lys | Ile |      |
| 385 |     |     |     |     | 390 |     |     |     |     | 395 |     |     |     |     | 400 |      |
| tcg | tgg | gcg | agt | ctt | tgc | aat | gcg | ttt | ttg | gtg | gaa | gca | aaa | tgg | ttc | 1365 |
| Ser | Trp | Ala | Ser | Leu | Cys | Asn | Ala | Phe | Leu | Val | Glu | Ala | Lys | Trp | Phe |      |
|     |     |     |     | 405 |     |     |     |     | 410 |     |     |     |     | 415 |     |      |
| gca | tct | ggg | cag | ctg | ccg | aag | tca | gaa | gag | tac | ttg | aag | aac | ggc | atc | 1413 |
| Ala | Ser | Gly | Gln | Leu | Pro | Lys | Ser | Glu | Glu | Tyr | Leu | Lys | Asn | Gly | Ile |      |
|     |     |     | 420 |     |     |     |     | 425 |     |     |     |     | 430 |     |     |      |
| gtt | tct | tct | ggg | gta | aat | gtg | ggt | cta | gtc | cac | atg | ttt | ttt | ctc | ttg | 1461 |
| Val | Ser | Ser | Gly | Val | Asn | Val | Gly | Leu | Val | His | Met | Phe | Phe | Leu | Leu |      |
|     |     | 435 |     |     |     |     | 440 |     |     |     |     | 445 |     |     |     |      |
| ggt | cag | aac | ata | acc | aga | aag | agt | gtg | gag | ttg | ttg | aat | gaa | act | cca | 1509 |
| Gly | Gln | Asn | Ile | Thr | Arg | Lys | Ser | Val | Glu | Leu | Leu | Asn | Glu | Thr | Pro |      |
|     | 450 |     |     |     |     | 455 |     |     |     |     | 460 |     |     |     |     |      |
| gcc | atg | ata | tcg | tcc | tca | gca | gca | att | ctt | cga | ctc | tgg | gac | gat | tta | 1557 |
| Ala | Met | Ile | Ser | Ser | Ser | Ala | Ala | Ile | Leu | Arg | Leu | Trp | Asp | Asp | Leu |      |
| 465 |     |     |     |     | 470 |     |     |     |     | 475 |     |     |     |     | 480 |      |
| ggc | agt | gca | aag | gat | gag | aac | cag | gat | ggg | aac | gat | ggg | tcg | tat | gta | 1605 |
| Gly | Ser | Ala | Lys | Asp | Glu | Asn | Gln | Asp | Gly | Asn | Asp | Gly | Ser | Tyr | Val |      |
|     |     |     |     | 485 |     |     |     |     | 490 |     |     |     |     | 495 |     |      |
| agg | tgc | tac | tta | gag | gaa | cat | gaa | ggc | tgt | tcc | att | gag | gag | gca | cga | 1653 |
| Arg | Cys | Tyr | Leu | Glu | Glu | His | Glu | Gly | Cys | Ser | Ile | Glu | Glu | Ala | Arg |      |

```
                       500             505             510
gaa aag acg att aat atg att tca gat gaa tgg aag aaa ctg aac aga        1701
Glu Lys Thr Ile Asn Met Ile Ser Asp Glu Trp Lys Lys Leu Asn Arg
        515             520             525 gaa ctg ctc tct cca aat cca ttt cca gca aca ttc aca tcg gct tct        1749
Glu Leu Leu Ser Pro Asn Pro Phe Pro Ala Thr Phe Thr Ser Ala Ser
    530             535             540 ctt aat ctc gca aga atg atc ccc ttg atg tat agc tac gat ggc aac        1797
Leu Asn Leu Ala Arg Met Ile Pro Leu Met Tyr Ser Tyr Asp Gly Asn
545             550             555             560 caa tcc ctt cca tct ctt aaa gag tat atg aaa ctg atg ttg tat gag        1845
Gln Ser Leu Pro Ser Leu Lys Glu Tyr Met Lys Leu Met Leu Tyr Glu
        565             570             575 act gta tca atg taattgataa taagactgct ggaagtggag ttgaaca              1894
Thr Val Ser Met
        580

<210> SEQ ID NO 23
<211> LENGTH: 580
<212> TYPE: PRT
<213> ORGANISM: Wild strawberry

<400> SEQUENCE: 23

Met Ala Ser Ser Trp Ala Phe Phe Lys Val Phe Asn Pro Gln Ile
1               5                   10                  15

Ala Pro Lys Ser Ile Ser His Ile Gly Gln Ser Asp Leu Met Gln Leu
            20                  25                  30

Thr His Lys Lys Gln Leu Pro Thr Phe Gln Arg Arg Gly Ile Ala Glu
        35                  40                  45

Asp Ser Leu Leu Pro Ser Ser Thr Thr Pro Ile Lys Pro Met His Val
    50                  55                  60

Glu Thr Lys His Thr Arg Thr Met Gly Asp Ile Phe Val Gln His Ser
65                  70                  75                  80

Gln Lys Leu Glu Leu Phe Arg Asn Val Leu Arg Asn Ala Ala Glu Leu
                85                  90                  95

Asp Ala Leu Glu Gly Leu Asn Met Ile Asp Ala Val Gln Arg Leu Gly
            100                 105                 110

Ile Asp Tyr His Phe Gln Arg Glu Ile Asp Glu Ile Leu His Lys Gln
        115                 120                 125

Met Gly Ile Val Ser Ala Cys Asp Asp Leu Tyr Glu Val Ala Leu Arg
130                 135                 140

Phe Arg Leu Leu Arg Gln His Gly Tyr Phe Val Pro Glu Asp Val Phe
145                 150                 155                 160

Asn Asn Phe Lys Asp Ser Lys Gly Thr Phe Lys Gln Val Leu Gly Glu
                165                 170                 175

Asp Ile Lys Gly Leu Met Ser Leu Tyr Glu Ala Ser Gln Leu Gly Thr
            180                 185                 190

Glu Gly Glu Asp Thr Leu Val Glu Ala Glu Lys Phe Ser Gly His Leu
        195                 200                 205

Leu Lys Thr Ser Leu Ser His Leu Asp Arg His Arg Ala Arg Ile Val
    210                 215                 220

Gly Asn Thr Leu Arg Asn Pro His Arg Lys Ser Leu Ala Ser Phe Met
225                 230                 235                 240

Ala Arg Asn Phe Phe Val Thr Ser Gln Ala Thr Asn Ser Trp Leu Asn
                245                 250                 255

Leu Leu Lys Glu Val Ala Lys Thr Asp Phe Asn Met Val Arg Ser Val
            260                 265                 270
```

```
His Gln Lys Glu Ile Val Gln Ile Ser Lys Trp Trp Lys Glu Leu Gly
            275                 280                 285

Leu Val Lys Glu Leu Lys Phe Ala Arg Asp Gln Pro Leu Lys Trp Tyr
            290                 295                 300

Thr Trp Ser Met Ala Gly Leu Thr Asp Pro Lys Leu Ser Glu Glu Arg
305                 310                 315                 320

Val Glu Leu Thr Lys Pro Ile Ser Phe Val Tyr Leu Ile Asp Asp Ile
                    325                 330                 335

Phe Asp Val Tyr Gly Thr Leu Asp Asp Leu Ile Leu Phe Thr Glu Ala
                340                 345                 350

Val Asn Arg Trp Glu Ile Thr Ala Ile Asp His Leu Pro Asp Tyr Met
            355                 360                 365

Lys Ile Cys Phe Lys Ala Leu Tyr Asp Met Thr Asn Glu Phe Ser Cys
            370                 375                 380

Lys Val Tyr Gln Lys His Gly Trp Asn Pro Leu Arg Ser Leu Lys Ile
385                 390                 395                 400

Ser Trp Ala Ser Leu Cys Asn Ala Phe Leu Val Glu Ala Lys Trp Phe
                    405                 410                 415

Ala Ser Gly Gln Leu Pro Lys Ser Glu Tyr Leu Lys Asn Gly Ile
                420                 425                 430

Val Ser Ser Gly Val Asn Val Gly Leu Val His Met Phe Phe Leu Leu
            435                 440                 445

Gly Gln Asn Ile Thr Arg Lys Ser Val Glu Leu Leu Asn Glu Thr Pro
            450                 455                 460

Ala Met Ile Ser Ser Ser Ala Ala Ile Leu Arg Leu Trp Asp Asp Leu
465                 470                 475                 480

Gly Ser Ala Lys Asp Glu Asn Gln Asp Gly Asn Asp Gly Ser Tyr Val
                    485                 490                 495

Arg Cys Tyr Leu Glu Glu His Glu Gly Cys Ser Ile Glu Glu Ala Arg
                500                 505                 510

Glu Lys Thr Ile Asn Met Ile Ser Asp Glu Trp Lys Lys Leu Asn Arg
            515                 520                 525

Glu Leu Leu Ser Pro Asn Pro Phe Pro Ala Thr Phe Thr Ser Ala Ser
            530                 535                 540

Leu Asn Leu Ala Arg Met Ile Pro Leu Met Tyr Ser Tyr Asp Gly Asn
545                 550                 555                 560

Gln Ser Leu Pro Ser Leu Lys Glu Tyr Met Lys Leu Met Leu Tyr Glu
                    565                 570                 575

Thr Val Ser Met
            580

<210> SEQ ID NO 24
<211> LENGTH: 333
<212> TYPE: DNA
<213> ORGANISM: Cultivated strawberry Elsanta

<400> SEQUENCE: 24
ctcccacagc ttcttagttg ctgatcatag atcagatggc atcgtcttct cgggccttct      60
ttaaagtatt caatcctcaa attgcctgct acttttgaga tagcttgctt cccagttcta     120
ttactataaa gccgatgaac gttgaaacca agcatactag aactatggta aaattctcgg     180
agctttctcc gaagtacatt tctacaaaag ggtagagcta gctactaaac aatagttaat     240
tgactgtgcc ttgcttgcag ggtgacattt ttgtccaaca ttctcagaag ttggaactat     300
tgaaaactgt cttgaggaat gtagcagagc tag                                   333
```

```
<210> SEQ ID NO 25
<211> LENGTH: 240
<212> TYPE: DNA
<213> ORGANISM: Cultivated strawberry Elsanta
<220> FEATURE:
<221> NAME/KEY: CDS
<222> LOCATION: (36)..(239)

<400> SEQUENCE: 25
ctcccacagc ttcttagttg ctgatcatag atcag atg gca tcg tct tct cgg         53
                                      Met Ala Ser Ser Ser Arg
                                       1               5 gcc ttc ttt aaa gta ttc aat cct caa att gcc tgc tac ttt cta gat       101
Ala Phe Phe Lys Val Phe Asn Pro Gln Ile Ala Cys Tyr Phe Leu Asp
                10                  15                  20 agc ttg ctt ccc agt tct att act ata aag ccg atg aac gtt gaa acc       149
Ser Leu Leu Pro Ser Ser Ile Thr Ile Lys Pro Met Asn Val Glu Thr
             25                  30                  35 aag cat act aga act atg ggt gac att ttt gtc caa cat tct cag aag       197
Lys His Thr Arg Thr Met Gly Asp Ile Phe Val Gln His Ser Gln Lys
         40                  45                  50 ttg gaa cta ttg aaa act gtc ttg agg aat gta gca gag cta g             240
Leu Glu Leu Leu Lys Thr Val Leu Arg Asn Val Ala Glu Leu
 55                  60                  65

<210> SEQ ID NO 26
<211> LENGTH: 68
<212> TYPE: PRT
<213> ORGANISM: Cultivated strawberry Elsanta

<400> SEQUENCE: 26

Met Ala Ser Ser Ser Arg Ala Phe Phe Lys Val Phe Asn Pro Gln Ile
 1               5                  10                  15

Ala Cys Tyr Phe Leu Asp Ser Leu Leu Pro Ser Ser Ile Thr Ile Lys
            20                  25                  30

Pro Met Asn Val Glu Thr Lys His Thr Arg Thr Met Gly Asp Ile Phe
         35                  40                  45

Val Gln His Ser Gln Lys Leu Glu Leu Leu Lys Thr Val Leu Arg Asn
     50                  55                  60

Val Ala Glu Leu
 65

<210> SEQ ID NO 27
<211> LENGTH: 392
<212> TYPE: DNA
<213> ORGANISM: Cultivated strawberry Elsanta
<220> FEATURE:
<221> NAME/KEY: misc_feature
<222> LOCATION: (1)..(392)
<223> OTHER INFORMATION: /NOTE="PCR FRAGMENT FROM THE 5'END OF
      CULTIVATED STRAWBERRY ELSANTA H64, INCLUDES STOP CODON AND INTRON"

<400> SEQUENCE: 27
ctcccacagc ttcttagttg ctgatcatag atcagatggc atagtctttt cggtccctct        60
ttaaagtatt caatcaaatt gctccaaaaa ttatctcaca tgttggccac tctaagaagc       120
agctgcctgc tactttttcaa agatggggcg ttgccgaaga tagcttgctt tccagttcta      180
gtactataaa gctgatgaac gttgaaacca agcatactag aactatggta aaattcttgg      240
ggctttctcc tacgtacatt tcttcaatga ggctagctag ctactaaaca atagttaatt       300
gactgtgcct tacttgcagg atgacatttt tgtccaacat tctcggaagc tggaactact       360
```

```
caggaatgtc ttgaggaatg tagcagagct ag                               392
```

<210> SEQ ID NO 28
<211> LENGTH: 300
<212> TYPE: DNA
<213> ORGANISM: Cultivated strawberry Elsanta
<220> FEATURE:
<221> NAME/KEY: misc_feature
<222> LOCATION: (1)..(300)
<223> OTHER INFORMATION: PCR FRAGMENT FROM THR 5' END OF CULTIVATED
      STRAWBERRY ELSANTA H64 WITH TRANSLATION
<220> FEATURE:
<221> NAME/KEY: CDS
<222> LOCATION: (36)..(299)

<400> SEQUENCE: 28

```
ctcccacagc ttcttagttg ctgatcatag atcag atg gca aag tct ttt cgg      53
                                      Met Ala Lys Ser Phe Arg
                                       1               5 tcc ctc ttt aaa gta ttc aat caa att gct cca aaa att atc tca cat    101
Ser Leu Phe Lys Val Phe Asn Gln Ile Ala Pro Lys Ile Ile Ser His
         10                  15                  20 gtt ggc cac tct aag aag cag ctg cct gct act ttt caa aga tgg ggc    149
Val Gly His Ser Lys Lys Gln Leu Pro Ala Thr Phe Gln Arg Trp Gly
     25                  30                  35 gtt gcc gaa gat agc ttg ctt tcc agt tct agt act ata aag ctg atg    197
Val Ala Glu Asp Ser Leu Leu Ser Ser Ser Ser Thr Ile Lys Leu Met
 40                  45                  50 aac gtt gaa acc aag cat act aga act atg gat gac att ttt gtc caa    245
Asn Val Glu Thr Lys His Thr Arg Thr Met Asp Asp Ile Phe Val Gln
 55                  60                  65                  70 cat tct cgg aag ctg gaa cta ctc agg aat gtc ttg agg aat gta gca    293
His Ser Arg Lys Leu Glu Leu Leu Arg Asn Val Leu Arg Asn Val Ala
                 75                  80                  85 gag cta g                                                          300
Glu Leu
```

<210> SEQ ID NO 29
<211> LENGTH: 88
<212> TYPE: PRT
<213> ORGANISM: Cultivated strawberry Elsanta

<400> SEQUENCE: 29

```
Met Ala Lys Ser Phe Arg Ser Leu Phe Lys Val Phe Asn Gln Ile Ala
 1               5                  10                  15

Pro Lys Ile Ile Ser His Val Gly His Ser Lys Lys Gln Leu Pro Ala
             20                  25                  30

Thr Phe Gln Arg Trp Gly Val Ala Glu Asp Ser Leu Leu Ser Ser Ser
         35                  40                  45

Ser Thr Ile Lys Leu Met Asn Val Glu Thr Lys His Thr Arg Thr Met
 50                  55                  60

Asp Asp Ile Phe Val Gln His Ser Arg Lys Leu Glu Leu Leu Arg Asn
 65                  70                  75                  80

Val Leu Arg Asn Val Ala Glu Leu
             85
```

<210> SEQ ID NO 30
<211> LENGTH: 350
<212> TYPE: DNA
<213> ORGANISM: Cultivated strawberry Elsanta
<220> FEATURE:
<221> NAME/KEY: misc_feature
<222> LOCATION: (1)..(350)
<223> OTHER INFORMATION: /NOTE="PCR FRAGMENT FROM THE 5'END OF

CULTIVATED STRAWBERRY ELSANTA H64, INCLUDES STOP CODON AND INTRON"

<400> SEQUENCE: 30

```
ctcccacagc ttcttagttg ctgatcatag atcagatggc atagtctttt cggtccctct      60
ttaaagtatt caatcaaatt gctccaaaaa ttatctcaca tgttggccac tctaagaagc     120
agctgcctgc tacttttcaa agatggggcg ttgccgaaga tagcttgctt tccagttcta     180
gtactataaa gctgatgaac gttgaaaccg agcatactag aactatggta aaattcttgg     240
ggctttctcc tacgtacatt tcttcaatga ggctagctag ctactaaaca atagttaatt     300
gactgtgcct tacttgcagg atgacatttt tgtccaacat tctcggaagc                350
```

<210> SEQ ID NO 31
<211> LENGTH: 258
<212> TYPE: DNA
<213> ORGANISM: Cultivated strawberry Elsanta
<220> FEATURE:
<221> NAME/KEY: misc_feature
<222> LOCATION: (1)..(258)
<223> OTHER INFORMATION: PCR FRAGMENT FROM THR 5' END OF CULTIVATED STRAWBERRY ELSANTA H64 WITH TRANSLATION
<220> FEATURE:
<221> NAME/KEY: CDS
<222> LOCATION: (36)..(257)

<400> SEQUENCE: 31

```
ctcccacagc ttcttagttg ctgatcatag atcag atg gca aag tct ttt cgg        53
                                       Met Ala Lys Ser Phe Arg
                                       1               5 tcc ctc ttt aaa gta ttc aat caa att gct cca aaa att atc tca cat      101
Ser Leu Phe Lys Val Phe Asn Gln Ile Ala Pro Lys Ile Ile Ser His
            10                  15                  20 gtt ggc cac tct aag aag cag ctg cct gct act ttt caa aga tgg ggc      149
Val Gly His Ser Lys Lys Gln Leu Pro Ala Thr Phe Gln Arg Trp Gly
        25                  30                  35 gtt gcc gaa gat agc ttg ctt tcc agt tct agt act ata aag ctg atg      197
Val Ala Glu Asp Ser Leu Leu Ser Ser Ser Ser Thr Ile Lys Leu Met
40                  45                  50 aac gtt gaa acc gag cat act aga act atg gat gac att ttt gtc caa      245
Asn Val Glu Thr Glu His Thr Arg Thr Met Asp Asp Ile Phe Val Gln
55                  60                  65                  70 cat tct cgg aag c                                                     258
His Ser Arg Lys
```

<210> SEQ ID NO 32
<211> LENGTH: 74
<212> TYPE: PRT
<213> ORGANISM: Cultivated strawberry Elsanta

<400> SEQUENCE: 32

```
Met Ala Lys Ser Phe Arg Ser Leu Phe Lys Val Phe Asn Gln Ile Ala
1               5                   10                  15

Pro Lys Ile Ile Ser His Val Gly His Ser Lys Lys Gln Leu Pro Ala
            20                  25                  30

Thr Phe Gln Arg Trp Gly Val Ala Glu Asp Ser Leu Leu Ser Ser Ser
        35                  40                  45

Ser Thr Ile Lys Leu Met Asn Val Glu Thr Glu His Thr Arg Thr Met
    50                  55                  60

Asp Asp Ile Phe Val Gln His Ser Arg Lys
65                  70
```

<210> SEQ ID NO 33

<211> LENGTH: 367
<212> TYPE: DNA
<213> ORGANISM: Cultivated strawberry Elsanta
<220> FEATURE:
<221> NAME/KEY: misc_feature
<222> LOCATION: (1)..(367)
<223> OTHER INFORMATION: /NOTE="PCR FRAGMENT FROM THE 5'END OF CULTIVATED STRAWBERRY ELSANTA H64, INCLUDES STOP CODON AND INTRON"

<400> SEQUENCE: 33

```
ctcccacagc ttcttagttg ctgatcatag atcagatggc atcgtcttct cgggccttct      60
ttaaagtatt caatcctgct ccaaaaagca tcccacgtat tggccagtct aacctcatgc     120
agcttacaca taagaagcag ctgcctactt ttcaaagacg gggcattgcc gaagatagct     180
tgcttcccag ttctactact cccataaagc tgatgaacgt tgaaaccaag catactagaa     240
ctatggtaaa attctcggag ctttctccga agtacatttc atcaagaggc tagctatagc     300
tactacacaa tagtttgact gtgccttgct tgcagggtga catttttgtc caacattgtc     360
agaagtt                                                                367
```

<210> SEQ ID NO 34
<211> LENGTH: 277
<212> TYPE: DNA
<213> ORGANISM: Cultivated strawberry Elsanta
<220> FEATURE:
<221> NAME/KEY: misc_feature
<222> LOCATION: (1)..(277)
<223> OTHER INFORMATION: PCR FRAGMENT FROM THR 5' END OF CULTIVATED STRAWBERRY ELSANTA H64 WITH TRANSLATION
<220> FEATURE:
<221> NAME/KEY: CDS
<222> LOCATION: (36)..(275)

<400> SEQUENCE: 34

```
ctcccacagc ttcttagttg ctgatcatag atcag atg gca tcg tct tct cgg        53
                                      Met Ala Ser Ser Ser Arg
                                      1               5 gcc ttc ttt aaa gta ttc aat cct gct cca aaa agc atc cca cgt att      101
Ala Phe Phe Lys Val Phe Asn Pro Ala Pro Lys Ser Ile Pro Arg Ile
         10                  15                  20 ggc cag tct aac ctc atg cag ctt aca cat aag aag cag ctg cct act      149
Gly Gln Ser Asn Leu Met Gln Leu Thr His Lys Lys Gln Leu Pro Thr
     25                  30                  35 ttt caa aga cgg ggc att gcc gaa gat agc ttg ctt ccc agt tct act      197
Phe Gln Arg Arg Gly Ile Ala Glu Asp Ser Leu Leu Pro Ser Ser Thr
 40                  45                  50 act ccc ata aag ctg atg aac gtt gaa acc aag cat act aga act atg      245
Thr Pro Ile Lys Leu Met Asn Val Glu Thr Lys His Thr Arg Thr Met
55                  60                  65                  70 ggt gac att ttt gtc caa cat tgt cag aag tt                           277
Gly Asp Ile Phe Val Gln His Cys Gln Lys
                 75                  80
```

<210> SEQ ID NO 35
<211> LENGTH: 80
<212> TYPE: PRT
<213> ORGANISM: Cultivated strawberry Elsanta

<400> SEQUENCE: 35

```
Met Ala Ser Ser Ser Arg Ala Phe Phe Lys Val Phe Asn Pro Ala Pro
1               5                   10                  15

Lys Ser Ile Pro Arg Ile Gly Gln Ser Asn Leu Met Gln Leu Thr His
            20                  25                  30

Lys Lys Gln Leu Pro Thr Phe Gln Arg Arg Gly Ile Ala Glu Asp Ser
```

Leu Leu Pro Ser Ser Thr Thr Pro Ile Lys Leu Met Asn Val Glu Thr
         50                  55                  60

Lys His Thr Arg Thr Met Gly Asp Ile Phe Val Gln His Cys Gln Lys
 65                  70                  75                  80

<210> SEQ ID NO 36
<211> LENGTH: 357
<212> TYPE: DNA
<213> ORGANISM: Cultivated strawberry Elsanta
<220> FEATURE:
<221> NAME/KEY: misc_feature
<222> LOCATION: (1)..(357)
<223> OTHER INFORMATION: /NOTE="PCR FRAGMENT FROM THE 5'END OF
      CULTIVATED STRAWBERRY ELSANTA H64, INCLUDES STOP CODON AND INTRON"

<400> SEQUENCE: 36
ctcccacagc ttcttagttg ctgatcatag atcagatggc atcgtcttct cgggccttct      60
ttaaagtatt caatcctgct ccaaaaagca tcccacgtat tggccagtct aacctcatgc     120
agcttacaca taagaagcag ctgcctactt tcaaagacg gggcattgcc gaagatagct      180
tgcttcccag ttctactact cccataaagc cgatgaacgt tgaaaccaag catactagaa     240
ctatggtaaa attctcggag ctttctccga agtacatttc atcaagaggc tagctatagc    300
tactacacaa tagtttgact gtgccttgct tgcagggtga cattttgtc caacatt        357

<210> SEQ ID NO 37
<211> LENGTH: 267
<212> TYPE: DNA
<213> ORGANISM: Cultivated strawberry Elsanta
<220> FEATURE:
<221> NAME/KEY: misc_feature
<222> LOCATION: (1)..(267)
<223> OTHER INFORMATION: PCR FRAGMENT FROM THR 5' END OF CULTIVATED
      STRAWBERRY ELSANTA H64 WITH TRANSLATION
<220> FEATURE:
<221> NAME/KEY: CDS
<222> LOCATION: (36)..(266)

<400> SEQUENCE: 37
ctcccacagc ttcttagttg ctgatcatag atcag atg gca tcg tct tct cgg         53
                                      Met Ala Ser Ser Ser Arg
                                        1               5 gcc ttc ttt aaa gta ttc aat cct gct cca aaa agc atc cca cgt att       101
Ala Phe Phe Lys Val Phe Asn Pro Ala Pro Lys Ser Ile Pro Arg Ile
             10                  15                  20 ggc cag tct aac ctc atg cag ctt aca cat aag aag cag ctg cct act       149
Gly Gln Ser Asn Leu Met Gln Leu Thr His Lys Lys Gln Leu Pro Thr
         25                  30                  35 ttt caa aga cgg ggc att gcc gaa gat agc ttg ctt ccc agt tct act       197
Phe Gln Arg Arg Gly Ile Ala Glu Asp Ser Leu Leu Pro Ser Ser Thr
     40                  45                  50 act ccc ata aag ccg atg aac gtt gaa acc aag cat act aga act atg       245
Thr Pro Ile Lys Pro Met Asn Val Glu Thr Lys His Thr Arg Thr Met
 55                  60                  65                  70 ggt gac att ttt gtc caa cat t                                          267
Gly Asp Ile Phe Val Gln His
                 75

<210> SEQ ID NO 38
<211> LENGTH: 77
<212> TYPE: PRT
<213> ORGANISM: Cultivated strawberry Elsanta

<400> SEQUENCE: 38

```
Met Ala Ser Ser Arg Ala Phe Phe Lys Val Phe Asn Pro Ala Pro
1               5                   10                  15

Lys Ser Ile Pro Arg Ile Gly Gln Ser Asn Leu Met Gln Leu Thr His
            20                  25                  30

Lys Lys Gln Leu Pro Thr Phe Gln Arg Arg Gly Ile Ala Glu Asp Ser
            35                  40                  45

Leu Leu Pro Ser Ser Thr Thr Pro Ile Lys Pro Met Asn Val Glu Thr
    50                  55                  60

Lys His Thr Arg Thr Met Gly Asp Ile Phe Val Gln His
65              70                  75

<210> SEQ ID NO 39
<211> LENGTH: 1672
<212> TYPE: DNA
<213> ORGANISM: Cultivated strawberry Elsanta
<220> FEATURE:
<221> NAME/KEY: CDS
<222> LOCATION: (1)..(762)
<220> FEATURE:
<221> NAME/KEY: misc_feature
<222> LOCATION: (1)..(762)
<223> OTHER INFORMATION: OLEFIN SYNTHASE, INCLUDES A STOP CODON

<400> SEQUENCE: 39 atg cct gtc cat gct act cca gca gct gaa tcc cag atc atc tct atg        48
Met Pro Val His Ala Thr Pro Ala Ala Glu Ser Gln Ile Ile Ser Met
1               5                   10                  15 ccg gaa gtt gtt cgg cgc aca gca aat ttt aaa cct agc gtt tgg gga        96
Pro Glu Val Val Arg Arg Thr Ala Asn Phe Lys Pro Ser Val Trp Gly
            20                  25                  30 gat cgg ttt gct aac tat gcc gaa gac att ata act caa act caa atg       144
Asp Arg Phe Ala Asn Tyr Ala Glu Asp Ile Ile Thr Gln Thr Gln Met
        35                  40                  45 caa gaa caa gtt gag gag ctg aaa caa gtg agg aag gaa gta ttc act       192
Gln Glu Gln Val Glu Glu Leu Lys Gln Val Arg Lys Glu Val Phe Thr
    50                  55                  60 aat gct gct gat gat tct tca cat caa ctg aag cca att gat gaa atc       240
Asn Ala Ala Asp Asp Ser Ser His Gln Leu Lys Pro Ile Asp Glu Ile
65                  70                  75                  80 cag cgc ctc ggt gtg gct tac cat ttc gaa agc gaa ata gat caa gcc       288
Gln Arg Leu Gly Val Ala Tyr His Phe Glu Ser Glu Ile Asp Gln Ala
                85                  90                  95 ctg gaa cgt ata cat gag aca tat caa gat att cat gat ggt ggt gat       336
Leu Glu Arg Ile His Glu Thr Tyr Gln Asp Ile His Asp Gly Gly Asp
            100                 105                 110 ctg tac aat gtt gct ctt cgt ttt cgg cta ctc agg cga cat gga tat       384
Leu Tyr Asn Val Ala Leu Arg Phe Arg Leu Leu Arg Arg His Gly Tyr
        115                 120                 125 aat gtt tcc tgc gat gta ttc aac aag ttc aaa gat act aat ggt gac       432
Asn Val Ser Cys Asp Val Phe Asn Lys Phe Lys Asp Thr Asn Gly Asp
    130                 135                 140 tac aag aaa agc ttg gtc act gat ctt tct ggt atg ctg agc ttt tat       480
Tyr Lys Lys Ser Leu Val Thr Asp Leu Ser Gly Met Leu Ser Phe Tyr
145                 150                 155                 160 gag gcg gcc cat ctg agg gtg cat gga gaa aaa tta ctt gaa gag gct       528
Glu Ala Ala His Leu Arg Val His Gly Glu Lys Leu Leu Glu Glu Ala
                165                 170                 175 ctg gtt ttt acc acc act cat ctc cag tca gca agt gca aaa agc tct       576
Leu Val Phe Thr Thr Thr His Leu Gln Ser Ala Ser Ala Lys Ser Ser
            180                 185                 190 ttg ctg aaa aca caa ata act gaa gcc gta gag aga cta cta aaa act       624
```

```
                    Leu Leu Lys Thr Gln Ile Thr Glu Ala Val Glu Arg Leu Leu Lys Thr
                            195                 200                 205 atg gag agg tta ggt gct cgg cgt tac atg tca ata tat caa gat gaa          672
Met Glu Arg Leu Gly Ala Arg Arg Tyr Met Ser Ile Tyr Gln Asp Glu
    210                 215                 220 gct tca tac agt gaa aat tta ctg aaa ctt gca aaa tta gat ttt aat          720
Ala Ser Tyr Ser Glu Asn Leu Leu Lys Leu Ala Lys Leu Asp Phe Asn
225                 230                 235                 240 gtt gtt cag tgt tta cac aaa aag gaa ctc agt gac att ccc                  762
Val Val Gln Cys Leu His Lys Lys Glu Leu Ser Asp Ile Pro
                245                 250 taagatggta caaggaactg gactttgcaa ggaggatgcc ttttgctcga gataggatcg         822
tggagttgtt cttttggata gcaggaatat atttcgaacc tgaatacgtc tttaggagac         882
acattctgac taaactgatt gagataacaa cagtaatgga tgatatgtat gatgcattcg         942
gtacattcga agaactcgtc aacttgactg aagcaattga caggtgggat gcaagttgca        1002
tggatcaact gccagactat atgcaaccat tttatattac acttctggat gttatcgatg        1062
aagttgaaga ggagctgaca aagcaaggaa gatcttaccg aattcactac gcaaaagaaa        1122
ttatgaagaa tcaagccagg ctctacttcg ctgaggccag atggttccac gaaggatgca        1182
ccccaaaaat ggatgagtat atgcgagttg cggcatcttc tgtcggtaac accatgcttt        1242
ccgtcgtgtc tttagtaggc atgggagaca ttataacaaa atttgaattc gagtggctga        1302
ccaatgagcc taaaatcctt agagcttcga ataccatatt taggcttatg gatgacattg        1362
ctgggtacaa gttgagaaaa gagagagggc atgttgcttc aagtattgat tgctacatga        1422
atgaatacgg ggtttcagag caagagacaa ttgatatctt caacaaacga attgtggatt        1482
cgtggaagga tataaacgaa gagtttctga gacccactgc tgctccagtc cctgtgctta        1542
atcgtgttct taacctaacc cgagtggttg atctgcttta caaaggggga gatgccttca        1602
cgcatgtcgg aaaactgatg aaagattgta ttgctgcaat gtttattgat ccagtgccac        1662
tctgaactca                                                              1672

<210> SEQ ID NO 40
<211> LENGTH: 254
<212> TYPE: PRT
<213> ORGANISM: Cultivated strawberry Elsanta

<400> SEQUENCE: 40

Met Pro Val His Ala Thr Pro Ala Ala Glu Ser Gln Ile Ile Ser Met
1               5                   10                  15

Pro Glu Val Val Arg Arg Thr Ala Asn Phe Lys Pro Ser Val Trp Gly
            20                  25                  30

Asp Arg Phe Ala Asn Tyr Ala Glu Asp Ile Ile Thr Gln Thr Gln Met
        35                  40                  45

Gln Glu Gln Val Glu Glu Leu Lys Gln Val Arg Lys Glu Val Phe Thr
    50                  55                  60

Asn Ala Ala Asp Asp Ser Ser His Gln Leu Lys Pro Ile Asp Glu Ile
65                  70                  75                  80

Gln Arg Leu Gly Val Ala Tyr His Phe Glu Ser Glu Ile Asp Gln Ala
                85                  90                  95

Leu Glu Arg Ile His Glu Thr Tyr Gln Asp Ile His Asp Gly Gly Asp
            100                 105                 110

Leu Tyr Asn Val Ala Leu Arg Phe Arg Leu Leu Arg Arg His Gly Tyr
        115                 120                 125

Asn Val Ser Cys Asp Val Phe Asn Lys Phe Lys Asp Thr Asn Gly Asp
```

```
                130                 135                 140
Tyr Lys Lys Ser Leu Val Thr Asp Leu Ser Gly Met Leu Ser Phe Tyr
145                 150                 155                 160

Glu Ala Ala His Leu Arg Val His Gly Glu Lys Leu Leu Glu Ala
                165                 170                 175

Leu Val Phe Thr Thr Thr His Leu Gln Ser Ala Ser Ala Lys Ser Ser
                180                 185                 190

Leu Leu Lys Thr Gln Ile Thr Glu Ala Val Glu Arg Leu Leu Lys Thr
                195                 200                 205

Met Glu Arg Leu Gly Ala Arg Arg Tyr Met Ser Ile Tyr Gln Asp Glu
                210                 215                 220

Ala Ser Tyr Ser Glu Asn Leu Leu Lys Leu Ala Lys Leu Asp Phe Asn
225                 230                 235                 240

Val Val Gln Cys Leu His Lys Lys Glu Leu Ser Asp Ile Pro
                245                 250

<210> SEQ ID NO 41
<211> LENGTH: 554
<212> TYPE: PRT
<213> ORGANISM: Cultivated strawberry Elsanta

<400> SEQUENCE: 41

Met Pro Val His Ala Thr Pro Ala Ala Glu Ser Gln Ile Ile Ser Met
1               5                   10                  15

Pro Glu Val Val Arg Arg Thr Ala Asn Phe Lys Pro Ser Val Trp Gly
                20                  25                  30

Asp Arg Phe Ala Asn Tyr Ala Glu Asp Ile Ile Thr Gln Thr Gln Met
                35                  40                  45

Gln Glu Gln Val Glu Glu Leu Lys Gln Val Arg Lys Glu Val Phe Thr
50                  55                  60

Asn Ala Ala Asp Asp Ser Ser His Gln Leu Lys Pro Ile Asp Glu Ile
65                  70                  75                  80

Gln Arg Leu Gly Val Ala Tyr His Phe Glu Ser Glu Ile Asp Gln Ala
                85                  90                  95

Leu Glu Arg Ile His Glu Thr Tyr Gln Asp Ile His Asp Gly Gly Asp
                100                 105                 110

Leu Tyr Asn Val Ala Leu Arg Phe Arg Leu Leu Arg Arg His Gly Tyr
                115                 120                 125

Asn Val Ser Cys Asp Val Phe Asn Lys Phe Lys Asp Thr Asn Gly Asp
                130                 135                 140

Tyr Lys Lys Ser Leu Val Thr Asp Leu Ser Gly Met Leu Ser Phe Tyr
145                 150                 155                 160

Glu Ala Ala His Leu Arg Val His Gly Glu Lys Leu Leu Glu Ala
                165                 170                 175

Leu Val Phe Thr Thr Thr His Leu Gln Ser Ala Ser Ala Lys Ser Ser
                180                 185                 190

Leu Leu Lys Thr Gln Ile Thr Glu Ala Val Glu Arg Leu Leu Lys Thr
                195                 200                 205

Met Glu Arg Leu Gly Ala Arg Arg Tyr Met Ser Ile Tyr Gln Asp Glu
                210                 215                 220

Ala Ser Tyr Ser Glu Asn Leu Leu Lys Leu Ala Lys Leu Asp Phe Asn
225                 230                 235                 240

Val Val Gln Cys Leu His Lys Lys Glu Leu Ser Asp Ile Leu Arg Trp
                245                 250                 255

Tyr Lys Glu Leu Asp Phe Ala Arg Arg Met Pro Phe Ala Arg Asp Arg
```

```
        260                 265                 270
Ile Val Glu Leu Phe Phe Trp Ile Ala Gly Ile Tyr Phe Glu Pro Glu
            275                 280                 285

Tyr Val Phe Arg Arg His Ile Leu Thr Lys Leu Ile Glu Ile Thr Thr
        290                 295                 300

Val Met Asp Asp Met Tyr Asp Ala Phe Gly Thr Phe Glu Glu Leu Val
305                 310                 315                 320

Asn Leu Thr Glu Ala Ile Asp Arg Trp Asp Ala Ser Cys Met Asp Gln
            325                 330                 335

Leu Pro Asp Tyr Met Gln Pro Phe Tyr Ile Thr Leu Leu Asp Val Ile
        340                 345                 350

Asp Glu Val Glu Glu Glu Leu Thr Lys Gln Gly Arg Ser Tyr Arg Ile
        355                 360                 365

His Tyr Ala Lys Glu Ile Met Lys Asn Gln Ala Arg Leu Tyr Phe Ala
        370                 375                 380

Glu Ala Arg Trp Phe His Glu Gly Cys Thr Pro Lys Met Asp Glu Tyr
385                 390                 395                 400

Met Arg Val Ala Ala Ser Ser Val Gly Asn Thr Met Leu Ser Val Val
                405                 410                 415

Ser Leu Val Gly Met Gly Asp Ile Ile Thr Lys Phe Glu Phe Glu Trp
            420                 425                 430

Leu Thr Asn Glu Pro Lys Ile Leu Arg Ala Ser Asn Thr Ile Phe Arg
        435                 440                 445

Leu Met Asp Asp Ile Ala Gly Tyr Lys Phe Lys Glu Arg Gly His
        450                 455                 460

Val Ala Ser Ser Ile Asp Cys Tyr Met Asn Glu Tyr Gly Val Ser Glu
465                 470                 475                 480

Gln Glu Thr Ile Asp Ile Phe Asn Lys Arg Ile Val Asp Ser Trp Lys
                485                 490                 495

Asp Ile Asn Glu Glu Phe Leu Arg Pro Thr Ala Ala Pro Val Pro Val
            500                 505                 510

Leu Asn Arg Val Leu Asn Leu Thr Arg Val Val Asp Leu Leu Tyr Lys
        515                 520                 525

Arg Gly Asp Ala Phe Thr His Val Gly Lys Leu Met Lys Asp Cys Ile
        530                 535                 540

Ala Ala Met Phe Ile Asp Pro Val Pro Leu
545                 550

<210> SEQ ID NO 42
<211> LENGTH: 2605
<212> TYPE: DNA
<213> ORGANISM: Cultivated strawberry Elsanta
<220> FEATURE:
<221> NAME/KEY: CDS
<222> LOCATION: (692)..(1456)
<220> FEATURE:
<221> NAME/KEY: misc_feature
<222> LOCATION: (692)..(1456)
<223> OTHER INFORMATION: /NOTE="SEQUENCE WITH THE CC INSERTION LEFT IN"

<400> SEQUENCE: 42
ctaatacgac tcactatagg gcaagcagtg gtaacaacgc agagtacgcg gggacatttg      60
attcatagtt attagattgt gtttttccgt ccagttaggt ttaaggatta tacactcgtt     120
taatgtattg ttagaacggg gattgtgtgc ttagttaata gattttgctt ttattcaaga     180
gcgtagggtt caatttgagt atgcatgttc tttatctttt agcttttatt atggaatttt     240
tataaaatgt tataatatta atttcttaat gagtagttaa attacgtgat tatttgattt     300
```

```
ttttaatcta aaatgtgata tgtaaaatat agaagaaaaa aaatttaaaa actttcagaa    360
attttttaaa ttcttttagc ccacccaaac ctaaaatcct aggtccgccg tcgatgcaaa    420
gtacaaatag aaacatgtct ttctcagtca tgaatcatgt catcatgata ttgatagatg    480
atgtcgttta gcaataaagg gctgttctgc ggttaaaata taaacatctt ccgatcttat    540
tatttacaac aacaaaaaat cttccaaact caattatcag catctgtatc agatctgcat    600
ggagtcccct ataaatatat gatcatagca gcaatatact tcatacttga agaaaaagct    660
atagctagtc cacaagtgca gaaagttaat c atg cct gtc cat gct act cca       712
                                  Met Pro Val His Ala Thr Pro
                                  1               5
```

```
gca gct gaa tcc cag atc atc tct atg ccg gaa gtt gtt cgg cgc aca      760
Ala Ala Glu Ser Gln Ile Ile Ser Met Pro Glu Val Val Arg Arg Thr
        10                  15                  20 gca aat ttt aaa cct agc gtt tgg gga gat cgg ttt gct aac tat gcc      808
Ala Asn Phe Lys Pro Ser Val Trp Gly Asp Arg Phe Ala Asn Tyr Ala
 25                  30                  35 gaa gac att ata act caa act caa atg caa gaa caa gtt gag gag ctg      856
Glu Asp Ile Ile Thr Gln Thr Gln Met Gln Glu Gln Val Glu Glu Leu
40                  45                  50                  55 aaa caa gta gtg agg aag gaa gta ttc act aat gct gct gat gat tct      904
Lys Gln Val Val Arg Lys Glu Val Phe Thr Asn Ala Ala Asp Asp Ser
                60                  65                  70 tca cat caa ctg aag cta att gat gaa atc cag cgc ctc ggt gtg gct      952
Ser His Gln Leu Lys Leu Ile Asp Glu Ile Gln Arg Leu Gly Val Ala
            75                  80                  85 tac cat ttc gaa agc gaa ata gat caa gcc ctg gaa cgt ata cat gag     1000
Tyr His Phe Glu Ser Glu Ile Asp Gln Ala Leu Glu Arg Ile His Glu
        90                  95                 100 aca tat caa gat att cat gat ggt ggt gat ctg tac aat gtt gct ctt     1048
Thr Tyr Gln Asp Ile His Asp Gly Gly Asp Leu Tyr Asn Val Ala Leu
105                 110                 115 cgt ttt cgg cta ctc agg cga cat gga tat aat gtt tcc tgc gat gta     1096
Arg Phe Arg Leu Leu Arg Arg His Gly Tyr Asn Val Ser Cys Asp Val
120                 125                 130                 135 ttc aac aag ttc aaa gat act aat ggt gac tac aag aaa agc ttg gtc     1144
Phe Asn Lys Phe Lys Asp Thr Asn Gly Asp Tyr Lys Lys Ser Leu Val
                140                 145                 150 act gat ctt tct ggt atg ctg agc ttt tat gag gcg gcc cat ctg agg     1192
Thr Asp Leu Ser Gly Met Leu Ser Phe Tyr Glu Ala Ala His Leu Arg
            155                 160                 165 gtg cat gga gaa aaa tta ctt gaa gag gct ctg gtt ttt acc acc act     1240
Val His Gly Glu Lys Leu Leu Glu Glu Ala Leu Val Phe Thr Thr Thr
        170                 175                 180 cat ctc cag tca gca agt gca aaa agc tct ttg ctg aaa aca caa ata     1288
His Leu Gln Ser Ala Ser Ala Lys Ser Ser Leu Leu Lys Thr Gln Ile
185                 190                 195 act gaa gcc gta gag aga cta cta aaa act atg gag agg tta ggt gct     1336
Thr Glu Ala Val Glu Arg Leu Leu Lys Thr Met Glu Arg Leu Gly Ala
200                 205                 210                 215 cgg cgt tac atg tca ata tat caa gat gaa gct tca tac agt gaa aat     1384
Arg Arg Tyr Met Ser Ile Tyr Gln Asp Glu Ala Ser Tyr Ser Glu Asn
                220                 225                 230 tta ctg aaa ctt gca aaa tta gat ttt aat gtt gtt cag tgt tta cac     1432
Leu Leu Lys Leu Ala Lys Leu Asp Phe Asn Val Val Gln Cys Leu His
            235                 240                 245 aaa aag gaa ctc agt gac att ccc taagatggta caaggaactg gactttgcaa    1486
Lys Lys Glu Leu Ser Asp Ile Pro
        250                 255
```

-continued

```
ggaggatgcc ttttgctcga gataggatcg tggagttgtt cttttggata gcaggaatat   1546
atttcgaacc tgaatacgtc tttaggagac acattctgac taaactgatt gagataacaa   1606
cagtaatgga tgtatatgtat gatgcattcg gtacattcga agaactcgtc aacttgactg   1666
aagcaattga caggtgggat gcaagttgca tggatcaact gccagactat atgcaaccat   1726
tttatattac acttctggat gttatcgatg aagttgaaga ggagctgaca agcaaggaa    1786 gatcttaccg aattcactac gcaaaagaaa ttatgaagaa tcaagccagg ctctacttcg   1846
ctgaggccag atggttccac gaaggatgca ccccaaaaat ggatgagtat atgcgagttg   1906
cggcatcttc tgtcggtaac accatgcttt ccgtcgtgtc tttagtaggc atgggagaca   1966
ttataacaaa atttgaattc gagtggctga ccaatgagcc taaaatcctt agagcttcga   2026
ataccatatt taggcttatg gatgacattg ctgggtacaa gtttgagaaa gagagagggc   2086
atgttgcttc aagtattgat tgctacatga atgaatacgg ggtttcagag caagagacaa   2146
ttgatatctt caacaaacga attgtggatt cgtggaagga tataaacgaa gagtttctga   2206
gacccactgc tgctccagtc cctgtgctta atcgtgttct taacctaacc cgagtggttg   2266
atctgcttta caaagggga gatgccttca cgcatgtcgg aaaactgatg aaagattgta   2326
ttgctgcaat gtttattgat ccagtgccac tctgaactca tcggatcagt catcacattc   2386
agtctcctga tgctagcgtt tgcttttat ttgaatgtat tcttgaataa gacgatgcac   2446
ctcgatcaat ttgtgcttca gtgtttcacg tactgatgag tcctatcctt tctagaagag   2506
gaacatcaat gttggtttgc taataaagct ttattgtttg aatgtcgggt tgataattct   2566
taactaatta tgttgtctaa aaaaaaaaaa aaaaaaaa                           2605
```

<210> SEQ ID NO 43
<211> LENGTH: 255
<212> TYPE: PRT
<213> ORGANISM: Cultivated strawberry Elsanta

<400> SEQUENCE: 43

```
Met Pro Val His Ala Thr Pro Ala Ala Glu Ser Gln Ile Ile Ser Met
1               5                   10                  15

Pro Glu Val Val Arg Arg Thr Ala Asn Phe Lys Pro Ser Val Trp Gly
            20                  25                  30

Asp Arg Phe Ala Asn Tyr Ala Glu Asp Ile Ile Thr Gln Thr Gln Met
        35                  40                  45

Gln Glu Gln Val Glu Glu Leu Lys Gln Val Val Arg Lys Glu Val Phe
    50                  55                  60

Thr Asn Ala Ala Asp Asp Ser Ser His Gln Leu Lys Leu Ile Asp Glu
65                  70                  75                  80

Ile Gln Arg Leu Gly Val Ala Tyr His Phe Glu Ser Glu Ile Asp Gln
                85                  90                  95

Ala Leu Glu Arg Ile His Glu Thr Tyr Gln Asp Ile His Asp Gly Gly
            100                 105                 110

Asp Leu Tyr Asn Val Ala Leu Arg Phe Arg Leu Leu Arg Arg His Gly
        115                 120                 125

Tyr Asn Val Ser Cys Asp Val Phe Asn Lys Phe Lys Asp Thr Asn Gly
    130                 135                 140

Asp Tyr Lys Lys Ser Leu Val Thr Asp Leu Ser Gly Met Leu Ser Phe
145                 150                 155                 160

Tyr Glu Ala Ala His Leu Arg Val His Gly Glu Lys Leu Leu Glu Glu
                165                 170                 175
```

```
Ala Leu Val Phe Thr Thr Thr His Leu Gln Ser Ala Ser Ala Lys Ser
            180                 185                 190

Ser Leu Leu Lys Thr Gln Ile Thr Glu Ala Val Glu Arg Leu Leu Lys
            195                 200                 205

Thr Met Glu Arg Leu Gly Ala Arg Arg Tyr Met Ser Ile Tyr Gln Asp
        210                 215                 220

Glu Ala Ser Tyr Ser Glu Asn Leu Leu Lys Leu Ala Lys Leu Asp Phe
225                 230                 235                 240

Asn Val Val Gln Cys Leu His Lys Lys Glu Leu Ser Asp Ile Pro
                245                 250                 255

<210> SEQ ID NO 44
<211> LENGTH: 555
<212> TYPE: PRT
<213> ORGANISM: Cultivated strawberry Elsanta
<220> FEATURE:
<221> NAME/KEY: SITE
<222> LOCATION: (1)..(555)
<223> OTHER INFORMATION: /NOTE="TRANSLATION OF SEQUENCE NO. 42 WITH THE
      CC INSERTION REMOVED

<400> SEQUENCE: 44

Met Pro Val His Ala Thr Pro Ala Ala Glu Ser Gln Ile Ile Ser Met
1               5                   10                  15

Pro Glu Val Val Arg Arg Thr Ala Asn Phe Lys Pro Ser Val Trp Gly
            20                  25                  30

Asp Arg Phe Ala Asn Tyr Ala Glu Asp Ile Ile Thr Gln Thr Gln Met
        35                  40                  45

Gln Glu Gln Val Glu Glu Leu Lys Gln Val Val Arg Lys Glu Val Phe
    50                  55                  60

Thr Asn Ala Ala Asp Asp Ser Ser His Gln Leu Lys Leu Ile Asp Glu
65                  70                  75                  80

Ile Gln Arg Leu Gly Val Ala Tyr His Phe Glu Ser Glu Ile Asp Gln
                85                  90                  95

Ala Leu Glu Arg Ile His Glu Thr Tyr Gln Asp Ile His Asp Gly Gly
            100                 105                 110

Asp Leu Tyr Asn Val Ala Leu Arg Phe Arg Leu Leu Arg His Gly
        115                 120                 125

Tyr Asn Val Ser Cys Asp Val Phe Asn Lys Phe Lys Asp Thr Asn Gly
    130                 135                 140

Asp Tyr Lys Lys Ser Leu Val Thr Asp Leu Ser Gly Met Leu Ser Phe
145                 150                 155                 160

Tyr Glu Ala Ala His Leu Arg Val His Gly Glu Lys Leu Leu Glu Glu
                165                 170                 175

Ala Leu Val Phe Thr Thr Thr His Leu Gln Ser Ala Ser Ala Lys Ser
            180                 185                 190

Ser Leu Leu Lys Thr Gln Ile Thr Glu Ala Val Glu Arg Leu Leu Lys
            195                 200                 205

Thr Met Glu Arg Leu Gly Ala Arg Arg Tyr Met Ser Ile Tyr Gln Asp
        210                 215                 220

Glu Ala Ser Tyr Ser Glu Asn Leu Leu Lys Leu Ala Lys Leu Asp Phe
225                 230                 235                 240

Asn Val Val Gln Cys Leu His Lys Lys Glu Leu Ser Asp Ile Leu Arg
                245                 250                 255

Trp Tyr Lys Glu Leu Asp Phe Ala Arg Arg Met Pro Phe Ala Arg Asp
            260                 265                 270

Arg Ile Val Glu Leu Phe Phe Trp Ile Ala Gly Ile Tyr Phe Glu Pro
```

```
                    275                 280                 285
Glu Tyr Val Phe Arg Arg His Ile Leu Thr Lys Leu Ile Glu Ile Thr
290                 295                 300

Thr Val Met Asp Asp Met Tyr Asp Ala Phe Gly Thr Phe Glu Leu
305                 310                 315                 320

Val Asn Leu Thr Glu Ala Ile Asp Arg Trp Asp Ala Ser Cys Met Asp
                325                 330                 335

Gln Leu Pro Asp Tyr Met Gln Pro Phe Tyr Ile Thr Leu Leu Asp Val
                340                 345                 350

Ile Asp Glu Val Glu Glu Glu Leu Thr Lys Gln Gly Arg Ser Tyr Arg
                355                 360                 365

Ile His Tyr Ala Lys Glu Ile Met Lys Asn Gln Ala Arg Leu Tyr Phe
370                 375                 380

Ala Glu Ala Arg Trp Phe His Glu Gly Cys Thr Pro Lys Met Asp Glu
385                 390                 395                 400

Tyr Met Arg Val Ala Ala Ser Ser Val Gly Asn Thr Met Leu Ser Val
                405                 410                 415

Val Ser Leu Val Gly Met Gly Asp Ile Ile Thr Lys Phe Glu Phe Glu
                420                 425                 430

Trp Leu Thr Asn Glu Pro Lys Ile Leu Arg Ala Ser Asn Thr Ile Phe
                435                 440                 445

Arg Leu Met Asp Asp Ile Ala Gly Tyr Lys Phe Lys Glu Arg Gly
450                 455                 460

His Val Ala Ser Ser Ile Asp Cys Tyr Met Asn Glu Tyr Gly Val Ser
465                 470                 475                 480

Glu Gln Glu Thr Ile Asp Ile Phe Asn Lys Arg Ile Val Asp Ser Trp
                485                 490                 495

Lys Asp Ile Asn Glu Glu Phe Leu Arg Pro Thr Ala Ala Pro Val Pro
                500                 505                 510

Val Leu Asn Arg Val Leu Asn Leu Thr Arg Val Val Asp Leu Leu Tyr
                515                 520                 525

Lys Arg Gly Asp Ala Phe Thr His Val Gly Lys Leu Met Lys Asp Cys
530                 535                 540

Ile Ala Ala Met Phe Ile Asp Pro Val Pro Leu
545                 550                 555

<210> SEQ ID NO 45
<211> LENGTH: 1973
<212> TYPE: DNA
<213> ORGANISM: Wild Strawberry Vesca
<220> FEATURE:
<221> NAME/KEY: CDS
<222> LOCATION: (1)..(1668)

<400> SEQUENCE: 45 atg cct gtc cat gct act cca gca gct gaa tcc cag atc atc tct aag     48
Met Pro Val His Ala Thr Pro Ala Ala Glu Ser Gln Ile Ile Ser Lys
1               5                   10                  15 ccg gaa gtt gtt cgg cgc aca gca aat ttt aaa cct agc gtt tgg gga     96
Pro Glu Val Val Arg Arg Thr Ala Asn Phe Lys Pro Ser Val Trp Gly
            20                  25                  30 gat cgg ttt gct aac tat gcc gaa gac att ata act caa act caa atg    144
Asp Arg Phe Ala Asn Tyr Ala Glu Asp Ile Ile Thr Gln Thr Gln Met
        35                  40                  45 caa gaa caa gtt gag gag ctg aaa caa gta gtg agg aag gaa gta ttc    192
Gln Glu Gln Val Glu Glu Leu Lys Gln Val Val Arg Lys Glu Val Phe
50                  55                  60
```

```
act aat gct gct gat gat tct tca cat caa ctg aag cta att gat gaa      240
Thr Asn Ala Ala Asp Asp Ser Ser His Gln Leu Lys Leu Ile Asp Glu
 65                  70                  75                  80 atc cag cgc ctc ggt gtg gct tac cat ttc gaa agc gaa ata gat caa      288
Ile Gln Arg Leu Gly Val Ala Tyr His Phe Glu Ser Glu Ile Asp Gln
                 85                  90                  95 gcc ctg gaa cgt ata cat gag aca tat caa gat att cat gat ggt ggt      336
Ala Leu Glu Arg Ile His Glu Thr Tyr Gln Asp Ile His Asp Gly Gly
            100                 105                 110 gat ctg tac aat gtt gct ctt cgt ttt cgg cta ctc agg cga cat gga      384
Asp Leu Tyr Asn Val Ala Leu Arg Phe Arg Leu Leu Arg Arg His Gly
        115                 120                 125 tat aat gtt tcc tgc gat gta ttc aac aag ttc aaa gat act aat ggt      432
Tyr Asn Val Ser Cys Asp Val Phe Asn Lys Phe Lys Asp Thr Asn Gly
130                 135                 140 gac tac aag aaa agc ttg gtc act gat ctt tct ggt atg ctg agc ttt      480
Asp Tyr Lys Lys Ser Leu Val Thr Asp Leu Ser Gly Met Leu Ser Phe
145                 150                 155                 160 tat gag gcg gcc cat ctg agg gtg cat gga gaa aaa tta ctt gaa gag      528
Tyr Glu Ala Ala His Leu Arg Val His Gly Glu Lys Leu Leu Glu Glu
                165                 170                 175 gct ctg gtt ttt acc acc act cat ctc cag tca gca agt gca aaa agc      576
Ala Leu Val Phe Thr Thr Thr His Leu Gln Ser Ala Ser Ala Lys Ser
            180                 185                 190 tct ttg ctg aaa aca caa ata act gaa gcc gta gag aga cct cta cta      624
Ser Leu Leu Lys Thr Gln Ile Thr Glu Ala Val Glu Arg Pro Leu Leu
        195                 200                 205 aaa act atg gag agg tta ggt gct cgg cgt tac atg tca ata tat caa      672
Lys Thr Met Glu Arg Leu Gly Ala Arg Arg Tyr Met Ser Ile Tyr Gln
    210                 215                 220 gat gaa gct tca tac agt gaa aat tta ctg aaa ctt gca aaa tta gat      720
Asp Glu Ala Ser Tyr Ser Glu Asn Leu Leu Lys Leu Ala Lys Leu Asp
225                 230                 235                 240 ttt aat gtt gtt cag tgt tta cac aaa aag gaa ctc agt gac att cta      768
Phe Asn Val Val Gln Cys Leu His Lys Lys Glu Leu Ser Asp Ile Leu
                245                 250                 255 aga tgg tac aag gaa ctg gac ttt gca agg agg atg cct ttt gct cga      816
Arg Trp Tyr Lys Glu Leu Asp Phe Ala Arg Arg Met Pro Phe Ala Arg
            260                 265                 270 gat agg atc gtg gag ttg ttc ttt tgg ata gca gga ata tat ttc gaa      864
Asp Arg Ile Val Glu Leu Phe Phe Trp Ile Ala Gly Ile Tyr Phe Glu
        275                 280                 285 cct gaa tac gtc ttt ggg aga cac att ctg act aaa ctg att gag ata      912
Pro Glu Tyr Val Phe Gly Arg His Ile Leu Thr Lys Leu Ile Glu Ile
    290                 295                 300 aca aca gta atg gat gat atg tat gat gca ttc ggt aca ttc gaa gaa      960
Thr Thr Val Met Asp Asp Met Tyr Asp Ala Phe Gly Thr Phe Glu Glu
305                 310                 315                 320 ctc gtc atc ttg act gaa gca att gac agg tgg gat gca agt tgc atg     1008
Leu Val Ile Leu Thr Glu Ala Ile Asp Arg Trp Asp Ala Ser Cys Met
                325                 330                 335 gat caa ctg cca gac tat atg caa cca ttt tat ata aca ctt ctg gat     1056
Asp Gln Leu Pro Asp Tyr Met Gln Pro Phe Tyr Ile Thr Leu Leu Asp
            340                 345                 350 gtt atc gat gaa gtt gaa gag gag ctg aca aag caa gga aga tct tac     1104
Val Ile Asp Glu Val Glu Glu Glu Leu Thr Lys Gln Gly Arg Ser Tyr
        355                 360                 365 cga att cac tac gca aaa gaa att atg aag aat caa gcc agg ctc tac     1152
Arg Ile His Tyr Ala Lys Glu Ile Met Lys Asn Gln Ala Arg Leu Tyr
    370                 375                 380
```

| | | | | | | | | | | | | | | | | |
|---|---|---|---|---|---|---|---|---|---|---|---|---|---|---|---|---|
|ttc|gct|gag|gcc|ata|tgg|ttc|cac|gaa|gga|tgc|acc|cca|aaa|atg|gat| 1200 |
|Phe|Ala|Glu|Ala|Ile|Trp|Phe|His|Glu|Gly|Cys|Thr|Pro|Lys|Met|Asp| |
|385| | | | |390| | | | |395| | | | |400| |

| | | | | | | | | | | | | | | | | |
|---|---|---|---|---|---|---|---|---|---|---|---|---|---|---|---|---|
|ggg|tat|atg|cga|gtt|gcg|gca|tct|tct|gtc|ggt|aac|acc|atg|ctt|tcc| 1248 |
|Gly|Tyr|Met|Arg|Val|Ala|Ala|Ser|Ser|Val|Gly|Asn|Thr|Met|Leu|Ser| |
| | | | |405| | | | |410| | | | |415| | |

| | | | | | | | | | | | | | | | | |
|---|---|---|---|---|---|---|---|---|---|---|---|---|---|---|---|---|
|gtc|gtg|tct|tta|gta|ggc|atg|gga|gac|att|ata|aca|aaa|ttt|gaa|ttc| 1296 |
|Val|Val|Ser|Leu|Val|Gly|Met|Gly|Asp|Ile|Ile|Thr|Lys|Phe|Glu|Phe| |
| | | |420| | | | |425| | | | |430| | | |

| | | | | | | | | | | | | | | | | |
|---|---|---|---|---|---|---|---|---|---|---|---|---|---|---|---|---|
|gag|tgg|ctg|acc|aat|gag|cct|aaa|atc|ctt|aga|gct|tcg|aat|acc|ata| 1344 |
|Glu|Trp|Leu|Thr|Asn|Glu|Pro|Lys|Ile|Leu|Arg|Ala|Ser|Asn|Thr|Ile| |
| | |435| | | | |440| | | | |445| | | | |

| | | | | | | | | | | | | | | | | |
|---|---|---|---|---|---|---|---|---|---|---|---|---|---|---|---|---|
|ttt|agg|ctt|atg|gat|gac|att|gct|ggg|tac|aag|ttt|gag|aaa|gag|aga| 1392 |
|Phe|Arg|Leu|Met|Asp|Asp|Ile|Ala|Gly|Tyr|Lys|Phe|Glu|Lys|Glu|Arg| |
|450| | | | |455| | | | |460| | | | | | |

| | | | | | | | | | | | | | | | | |
|---|---|---|---|---|---|---|---|---|---|---|---|---|---|---|---|---|
|ggg|cat|gtt|gct|tct|agt|att|gat|tgc|tac|atg|aat|gaa|tac|ggg|gtt| 1440 |
|Gly|His|Val|Ala|Ser|Ser|Ile|Asp|Cys|Tyr|Met|Asn|Glu|Tyr|Gly|Val| |
|465| | | | |470| | | | |475| | | | |480| |

| | | | | | | | | | | | | | | | | |
|---|---|---|---|---|---|---|---|---|---|---|---|---|---|---|---|---|
|tca|gag|caa|gag|aca|att|gat|atc|ttc|aac|aaa|cga|att|gtg|gat|tcg| 1488 |
|Ser|Glu|Gln|Glu|Thr|Ile|Asp|Ile|Phe|Asn|Lys|Arg|Ile|Val|Asp|Ser| |
| | | | |485| | | | |490| | | | |495| | |

| | | | | | | | | | | | | | | | | |
|---|---|---|---|---|---|---|---|---|---|---|---|---|---|---|---|---|
|tgg|aag|gat|ata|aac|gaa|gag|ttt|ctg|aga|ccc|act|gct|gct|cca|gtc| 1536 |
|Trp|Lys|Asp|Ile|Asn|Glu|Glu|Phe|Leu|Arg|Pro|Thr|Ala|Ala|Pro|Val| |
| | | |500| | | | |505| | | | |510| | | |

| | | | | | | | | | | | | | | | | |
|---|---|---|---|---|---|---|---|---|---|---|---|---|---|---|---|---|
|cct|gtg|ctt|aat|cgt|gtt|ctt|aac|cta|acc|cga|gtg|gtt|gat|ctg|ctt| 1584 |
|Pro|Val|Leu|Asn|Arg|Val|Leu|Asn|Leu|Thr|Arg|Val|Val|Asp|Leu|Leu| |
| | |515| | | | |520| | | | |525| | | | |

| | | | | | | | | | | | | | | | | |
|---|---|---|---|---|---|---|---|---|---|---|---|---|---|---|---|---|
|tac|aaa|agg|gga|gat|gcc|ttc|acg|cat|gtc|gga|aaa|ctg|atg|aaa|gat| 1632 |
|Tyr|Lys|Arg|Gly|Asp|Ala|Phe|Thr|His|Val|Gly|Lys|Leu|Met|Lys|Asp| |
|530| | | | |535| | | | |540| | | | | | |

| | | | | | | | | | | | |
|---|---|---|---|---|---|---|---|---|---|---|---|
|tgt|att|gct|gca|atg|ttt|att|gat|cca|gtg|cca|ctc tgaactcatc| 1678 |
|Cys|Ile|Ala|Ala|Met|Phe|Ile|Asp|Pro|Val|Pro|Leu| |
|545| | | | |550| | | | |555| | |

| | |
|---|---|
|ggatcagtca tcacattcag tctcctgatg ctagcgtttg cttttatttt gaatgtattc| 1738 |
|ttgaataaga cgatgcacct cgatcaattt gtgcttcagt gtttcacgta ctgatgagtc| 1798 |
|ctatcctttc tagaagagga acatcaatgt tggtttgcta ataaagcttt attgtttgaa| 1858 |
|tgtcggggttg ataattctta actaattatg ttgtctactt tgtactttca aactcaatct| 1918 |
|caatacagaa tttatagtgt acgaactaaa aaaaaaaaaa aaaaaaaaaa aaaaa| 1973 |

<210> SEQ ID NO 46
<211> LENGTH: 556
<212> TYPE: PRT
<213> ORGANISM: Wild Strawberry Vesca

<400> SEQUENCE: 46

Met Pro Val His Ala Thr Pro Ala Ala Glu Ser Gln Ile Ile Ser Lys
1               5                   10                  15

Pro Glu Val Val Arg Arg Thr Ala Asn Phe Lys Pro Ser Val Trp Gly
                20                  25                  30

Asp Arg Phe Ala Asn Tyr Ala Glu Asp Ile Ile Thr Gln Thr Gln Met
            35                  40                  45

Gln Glu Gln Val Glu Glu Leu Lys Gln Val Val Arg Lys Glu Val Phe
        50                  55                  60

Thr Asn Ala Ala Asp Ser Ser His Gln Leu Lys Leu Ile Asp Glu
65                  70                  75                  80

Ile Gln Arg Leu Gly Val Ala Tyr His Phe Glu Ser Glu Ile Asp Gln
                85                  90                  95

-continued

```
Ala Leu Glu Arg Ile His Glu Thr Tyr Gln Asp Ile His Asp Gly Gly
            100                 105                 110

Asp Leu Tyr Asn Val Ala Leu Arg Phe Arg Leu Leu Arg His Gly
            115                 120                 125

Tyr Asn Val Ser Cys Asp Val Phe Asn Lys Phe Lys Asp Thr Asn Gly
130                 135                 140

Asp Tyr Lys Lys Ser Leu Val Thr Asp Leu Ser Gly Met Leu Ser Phe
145                 150                 155                 160

Tyr Glu Ala Ala His Leu Arg Val His Gly Glu Lys Leu Leu Glu Glu
                165                 170                 175

Ala Leu Val Phe Thr Thr Thr His Leu Gln Ser Ala Ser Ala Lys Ser
            180                 185                 190

Ser Leu Leu Lys Thr Gln Ile Thr Glu Ala Val Glu Arg Pro Leu Leu
            195                 200                 205

Lys Thr Met Glu Arg Leu Gly Ala Arg Arg Tyr Met Ser Ile Tyr Gln
210                 215                 220

Asp Glu Ala Ser Tyr Ser Glu Asn Leu Leu Lys Leu Ala Lys Leu Asp
225                 230                 235                 240

Phe Asn Val Val Gln Cys Leu His Lys Lys Glu Leu Ser Asp Ile Leu
                245                 250                 255

Arg Trp Tyr Lys Glu Leu Asp Phe Ala Arg Arg Met Pro Phe Ala Arg
            260                 265                 270

Asp Arg Ile Val Glu Leu Phe Phe Trp Ile Ala Gly Ile Tyr Phe Glu
            275                 280                 285

Pro Glu Tyr Val Phe Gly Arg His Ile Leu Thr Lys Leu Ile Glu Ile
            290                 295                 300

Thr Thr Val Met Asp Asp Met Tyr Asp Ala Phe Gly Thr Phe Glu Glu
305                 310                 315                 320

Leu Val Ile Leu Thr Glu Ala Ile Asp Arg Trp Asp Ala Ser Cys Met
                325                 330                 335

Asp Gln Leu Pro Asp Tyr Met Gln Pro Phe Tyr Ile Thr Leu Leu Asp
            340                 345                 350

Val Ile Asp Glu Val Glu Glu Glu Leu Thr Lys Gln Gly Arg Ser Tyr
            355                 360                 365

Arg Ile His Tyr Ala Lys Glu Ile Met Lys Asn Gln Ala Arg Leu Tyr
370                 375                 380

Phe Ala Glu Ala Ile Trp Phe His Glu Gly Cys Thr Pro Lys Met Asp
385                 390                 395                 400

Gly Tyr Met Arg Val Ala Ala Ser Ser Val Gly Asn Thr Met Leu Ser
                405                 410                 415

Val Val Ser Leu Val Gly Met Gly Asp Ile Ile Thr Lys Phe Glu Phe
            420                 425                 430

Glu Trp Leu Thr Asn Glu Pro Lys Ile Leu Arg Ala Ser Asn Thr Ile
            435                 440                 445

Phe Arg Leu Met Asp Asp Ile Ala Gly Tyr Lys Phe Glu Lys Glu Arg
450                 455                 460

Gly His Val Ala Ser Ser Ile Asp Cys Tyr Met Asn Glu Tyr Gly Val
465                 470                 475                 480

Ser Glu Gln Glu Thr Ile Asp Ile Phe Asn Lys Arg Ile Val Asp Ser
                485                 490                 495

Trp Lys Asp Ile Asn Glu Glu Phe Leu Arg Pro Thr Ala Ala Pro Val
            500                 505                 510

Pro Val Leu Asn Arg Val Leu Asn Leu Thr Arg Val Val Asp Leu Leu
            515                 520                 525
```

```
Tyr Lys Arg Gly Asp Ala Phe Thr His Val Gly Lys Leu Met Lys Asp
    530                 535                 540

Cys Ile Ala Ala Met Phe Ile Asp Pro Val Pro Leu
545                 550                 555

<210> SEQ ID NO 47
<211> LENGTH: 289
<212> TYPE: DNA
<213> ORGANISM: Wild strawberry Vesca
<220> FEATURE:
<221> NAME/KEY: misc_feature
<222> LOCATION: (1)..(289)
<223> OTHER INFORMATION: /NOTE="PCR FRAGMENT OF GENOMIC DNA OF WILD
      STRAWBERRY VESCA, INCLUDING AN INTRON"

<400> SEQUENCE: 47
agaggttagg tgctcggcgt tacatgtcaa tatatcaaga tgaagcttca tacagtgaaa       60
atttactgaa acttgcaaaa ttagatttta atgttgttca gtgtttacac aaaaaggaac      120
tcagtgacat tctaaggtaa attaagccat cgatcttata gttaattagt atatacatat      180
acaagataag ttataaccta atattgttct aaatatacta gatggtacaa ggaactggac      240
tttgcaagga ggatgccttt tgctcgagat aggatcgtgg agttgttct                  289

<210> SEQ ID NO 48
<211> LENGTH: 204
<212> TYPE: DNA
<213> ORGANISM: Wild strawberry Vesca
<220> FEATURE:
<221> NAME/KEY: CDS
<222> LOCATION: (3)..(203)
<220> FEATURE:
<221> NAME/KEY: misc_feature
<222> LOCATION: (3)..(203)
<223> OTHER INFORMATION: PCR FRAGMENT OF GENOMIC DNA OF WILD STRAWBERRY
      VESCA WITH TRANSLATION

<400> SEQUENCE: 48 ag agg tta ggt gct cgg cgt tac atg tca ata tat caa gat gaa gct         47
   Arg Leu Gly Ala Arg Arg Tyr Met Ser Ile Tyr Gln Asp Glu Ala
   1               5                   10                  15 tca tac agt gaa aat tta ctg aaa ctt gca aaa tta gat ttt aat gtt         95
Ser Tyr Ser Glu Asn Leu Leu Lys Leu Ala Lys Leu Asp Phe Asn Val
            20                  25                  30 gtt cag tgt tta cac aaa aag gaa ctc agt gac att cta aga tgg tac        143
Val Gln Cys Leu His Lys Lys Glu Leu Ser Asp Ile Leu Arg Trp Tyr
        35                  40                  45 aag gaa ctg gac ttt gca agg agg atg cct ttt gct cga gat agg atc        191
Lys Glu Leu Asp Phe Ala Arg Arg Met Pro Phe Ala Arg Asp Arg Ile
    50                  55                  60 gtg gag ttg ttc t                                                      204
Val Glu Leu Phe
    65

<210> SEQ ID NO 49
<211> LENGTH: 67
<212> TYPE: PRT
<213> ORGANISM: Wild strawberry Vesca

<400> SEQUENCE: 49

Arg Leu Gly Ala Arg Arg Tyr Met Ser Ile Tyr Gln Asp Glu Ala Ser
1               5                   10                  15

Tyr Ser Glu Asn Leu Leu Lys Leu Ala Lys Leu Asp Phe Asn Val Val
            20                  25                  30
```

```
Gln Cys Leu His Lys Lys Glu Leu Ser Asp Ile Leu Arg Trp Tyr Lys
        35                  40                  45

Glu Leu Asp Phe Ala Arg Arg Met Pro Phe Ala Arg Asp Arg Ile Val
 50                  55                  60

Glu Leu Phe
 65

<210> SEQ ID NO 50
<211> LENGTH: 289
<212> TYPE: DNA
<213> ORGANISM: Wild strawberry Vesca
<220> FEATURE:
<221> NAME/KEY: misc_feature
<222> LOCATION: (1)..(289)
<223> OTHER INFORMATION: /NOTE="PCR FRAGMENT ON GENOMIC DNA OF WILD
      STRAWBERRY VESCA, INCLUDING AN INTRON"

<400> SEQUENCE: 50
agaggttagg tgctcggcgt tacatgtcaa tatatcaaga tgaagcttca tacagtgaaa      60
atttactgaa acttgcaaaa ttagatttta atgttgttca gtgtttacac aaaaaggaac    120
tcagtgacat tctaaggtaa attaagccat cgatcttata gttaattagt atatacatat    180
acaagataag ttataaccta atattgttct aaatatacta gatggtacaa ggaactggac    240
tttgcaagga ggatgccctt tgctcgagat aggatcgtgg agttgttct                289

<210> SEQ ID NO 51
<211> LENGTH: 204
<212> TYPE: DNA
<213> ORGANISM: Wild strawberry Vesca
<220> FEATURE:
<221> NAME/KEY: CDS
<222> LOCATION: (3)..(203)
<220> FEATURE:
<221> NAME/KEY: misc_feature
<222> LOCATION: (3)..(203)
<223> OTHER INFORMATION: PCR FRAGMENT ON GENOMIC DNA OF WILD STRAWBERRY
      VESCA WITH TRANSLATION

<400> SEQUENCE: 51 ag agg tta ggt gct cgg cgt tac atg tca ata tat caa gat gaa gct        47
   Arg Leu Gly Ala Arg Arg Tyr Met Ser Ile Tyr Gln Asp Glu Ala
   1               5                   10                  15 tca tac agt gaa aat tta ctg aaa ctt gca aaa tta gat ttt aat gtt       95
Ser Tyr Ser Glu Asn Leu Leu Lys Leu Ala Lys Leu Asp Phe Asn Val
                 20                  25                  30 gtt cag tgt tta cac aaa aag gaa ctc agt gac att cta aga tgg tac      143
Val Gln Cys Leu His Lys Lys Glu Leu Ser Asp Ile Leu Arg Trp Tyr
            35                  40                  45 aag gaa ctg gac ttt gca agg agg atg ccc ttt gct cga gat agg atc      191
Lys Glu Leu Asp Phe Ala Arg Arg Met Pro Phe Ala Arg Asp Arg Ile
 50                  55                  60 gtg gag ttg ttc t                                                    204
Val Glu Leu Phe
     65

<210> SEQ ID NO 52
<211> LENGTH: 67
<212> TYPE: PRT
<213> ORGANISM: Wild strawberry Vesca

<400> SEQUENCE: 52

Arg Leu Gly Ala Arg Arg Tyr Met Ser Ile Tyr Gln Asp Glu Ala Ser
1               5                   10                  15

Tyr Ser Glu Asn Leu Leu Lys Leu Ala Lys Leu Asp Phe Asn Val Val
```

```
                    20                  25                  30

Gln Cys Leu His Lys Lys Glu Leu Ser Asp Ile Leu Arg Trp Tyr Lys
        35                  40                  45

Glu Leu Asp Phe Ala Arg Arg Met Pro Phe Ala Arg Asp Arg Ile Val
    50                  55                  60

Glu Leu Phe
65

<210> SEQ ID NO 53
<211> LENGTH: 300
<212> TYPE: DNA
<213> ORGANISM: Wild strawberry Vesca
<220> FEATURE:
<221> NAME/KEY: misc_feature
<222> LOCATION: (1)..(300)
<223> OTHER INFORMATION: /NOTE="PCR FRAGMENT ON GENOMIC DNA OF WILD
      STRAWBERRY VESCA, INCLUDING AN INTRON"

<400> SEQUENCE: 53
agaggttagg tgctcggcgt tacatgtcaa tatatcaaga tgaagcttca cacagtgaaa      60
atttactgaa acttgcaaaa ttagatttta atgttgttca gtgtttacac aaaaaggaac    120
tcagtgacat tctaaggtaa actaagccat cgatcttata gctattagtt gtatgtatat    180
gtatacaaga taagtaataa ccttctaata ttgctctata tactatatat agatggtata    240
aggaactgga ctttgcaagg aggatgcctt ttgcacgaga taggatcgtg gagttgttct    300

<210> SEQ ID NO 54
<211> LENGTH: 204
<212> TYPE: DNA
<213> ORGANISM: Wild strawberry Vesca
<220> FEATURE:
<221> NAME/KEY: CDS
<222> LOCATION: (3)..(203)

<400> SEQUENCE: 54 ag agg tta ggt gct cgg cgt tac atg tca ata tat caa gat gaa gct       47
   Arg Leu Gly Ala Arg Arg Tyr Met Ser Ile Tyr Gln Asp Glu Ala
   1               5                  10                  15 tca cac agt gaa aat tta ctg aaa ctt gca aaa tta gat ttt aat gtt      95
Ser His Ser Glu Asn Leu Leu Lys Leu Ala Lys Leu Asp Phe Asn Val
                20                  25                  30 gtt cag tgt tta cac aaa aag gaa ctc agt gac att cta aga tgg tat     143
Val Gln Cys Leu His Lys Lys Glu Leu Ser Asp Ile Leu Arg Trp Tyr
            35                  40                  45 aag gaa ctg gac ttt gca agg agg atg cct ttt gca cga gat agg atc     191
Lys Glu Leu Asp Phe Ala Arg Arg Met Pro Phe Ala Arg Asp Arg Ile
        50                  55                  60 gtg gag ttg ttc t                                                    204
Val Glu Leu Phe
    65

<210> SEQ ID NO 55
<211> LENGTH: 67
<212> TYPE: PRT
<213> ORGANISM: Wild strawberry Vesca

<400> SEQUENCE: 55

Arg Leu Gly Ala Arg Arg Tyr Met Ser Ile Tyr Gln Asp Glu Ala Ser
1               5                  10                  15

His Ser Glu Asn Leu Leu Lys Leu Ala Lys Leu Asp Phe Asn Val Val
                20                  25                  30

Gln Cys Leu His Lys Lys Glu Leu Ser Asp Ile Leu Arg Trp Tyr Lys
```

```
                35                  40                  45
Glu Leu Asp Phe Ala Arg Arg Met Pro Phe Ala Arg Asp Arg Ile Val
         50                  55                  60

Glu Leu Phe
65

<210> SEQ ID NO 56
<211> LENGTH: 289
<212> TYPE: DNA
<213> ORGANISM: Wild strawberry Vesca

<400> SEQUENCE: 56
agaggttagg tgctcggcgt acatgtcaa tatatcaaga tgaagcttca tacagtgaaa     60
atttactgaa acttgcaaaa ttagatttta atgttgttca gtgtttacac aaaaaggaac   120
tcagtgacat tctaaggtaa attaggccat cgatcttata gttaattagt atatacatat   180
acaagataag ttataaccta atattgttct aaatatacta gatggtacaa ggaactggac   240
tttgcaagga ggatgccttt tgctcgagat aggatcgtgg agttgttct                289

<210> SEQ ID NO 57
<211> LENGTH: 204
<212> TYPE: DNA
<213> ORGANISM: Wild strawberry Vesca
<220> FEATURE:
<221> NAME/KEY: CDS
<222> LOCATION: (3)..(203)

<400> SEQUENCE: 57 ag agg tta ggt gct cgg cgt tac atg tca ata tat caa gat gaa gct      47
   Arg Leu Gly Ala Arg Arg Tyr Met Ser Ile Tyr Gln Asp Glu Ala
   1               5                  10                  15 tca tac agt gaa aat tta ctg aaa ctt gca aaa tta gat ttt aat gtt    95
Ser Tyr Ser Glu Asn Leu Leu Lys Leu Ala Lys Leu Asp Phe Asn Val
                 20                  25                  30 gtt cag tgt tta cac aaa aag gaa ctc agt gac att cta aga tgg tac   143
Val Gln Cys Leu His Lys Lys Glu Leu Ser Asp Ile Leu Arg Trp Tyr
             35                  40                  45 aag gaa ctg gac ttt gca agg agg atg cct ttt gct cga gat agg atc   191
Lys Glu Leu Asp Phe Ala Arg Arg Met Pro Phe Ala Arg Asp Arg Ile
         50                  55                  60 gtg gag ttg ttc t                                                   204
Val Glu Leu Phe
     65

<210> SEQ ID NO 58
<211> LENGTH: 67
<212> TYPE: PRT
<213> ORGANISM: Wild strawberry Vesca

<400> SEQUENCE: 58

Arg Leu Gly Ala Arg Arg Tyr Met Ser Ile Tyr Gln Asp Glu Ala Ser
1               5                  10                  15

Tyr Ser Glu Asn Leu Leu Lys Leu Ala Lys Leu Asp Phe Asn Val Val
            20                  25                  30

Gln Cys Leu His Lys Lys Glu Leu Ser Asp Ile Leu Arg Trp Tyr Lys
        35                  40                  45

Glu Leu Asp Phe Ala Arg Arg Met Pro Phe Ala Arg Asp Arg Ile Val
    50                  55                  60

Glu Leu Phe
65
```

```
<210> SEQ ID NO 59
<211> LENGTH: 300
<212> TYPE: DNA
<213> ORGANISM: Wild strawberry Vesca

<400> SEQUENCE: 59
agaggttagg tgctcggcgt tacatgtcaa tatatcaaga tgaagcttca cacagtgaaa      60
atttactgaa acttgcaaaa ttagatttta atgttgttca gtgtttacac aaaaaggaac     120
tcagtgacat tctaaggtaa actaagccat cgatcttata gctattagtt gtatatatat     180
gtatacaaga taagtaataa ccttctaata ttgctctata tactatatat agatggtata     240
aggaactgga ctttgcaagg aggatgcctt ttgcacgaga taggatcgtg gagttgttct     300

<210> SEQ ID NO 60
<211> LENGTH: 204
<212> TYPE: DNA
<213> ORGANISM: Wild strawberry Vesca
<220> FEATURE:
<221> NAME/KEY: CDS
<222> LOCATION: (3)..(203)

<400> SEQUENCE: 60 ag agg tta ggt gct cgg cgt tac atg tca ata tat caa gat gaa gct        47
   Arg Leu Gly Ala Arg Arg Tyr Met Ser Ile Tyr Gln Asp Glu Ala
   1               5                  10                  15 tca cac agt gaa aat tta ctg aaa ctt gca aaa tta gat ttt aat gtt       95
Ser His Ser Glu Asn Leu Leu Lys Leu Ala Lys Leu Asp Phe Asn Val
                20                  25                  30 gtt cag tgt tta cac aaa aag gaa ctc agt gac att cta aga tgg tat      143
Val Gln Cys Leu His Lys Lys Glu Leu Ser Asp Ile Leu Arg Trp Tyr
            35                  40                  45 aag gaa ctg gac ttt gca agg agg atg cct ttt gca cga gat agg atc      191
Lys Glu Leu Asp Phe Ala Arg Arg Met Pro Phe Ala Arg Asp Arg Ile
        50                  55                  60 gtg gag ttg ttc t                                                    204
Val Glu Leu Phe
    65

<210> SEQ ID NO 61
<211> LENGTH: 67
<212> TYPE: PRT
<213> ORGANISM: Wild strawberry Vesca

<400> SEQUENCE: 61

Arg Leu Gly Ala Arg Arg Tyr Met Ser Ile Tyr Gln Asp Glu Ala Ser
1               5                   10                  15

His Ser Glu Asn Leu Leu Lys Leu Ala Lys Leu Asp Phe Asn Val Val
                20                  25                  30

Gln Cys Leu His Lys Lys Glu Leu Ser Asp Ile Leu Arg Trp Tyr Lys
            35                  40                  45

Glu Leu Asp Phe Ala Arg Arg Met Pro Phe Ala Arg Asp Arg Ile Val
        50                  55                  60

Glu Leu Phe
65

<210> SEQ ID NO 62
<211> LENGTH: 291
<212> TYPE: DNA
<213> ORGANISM: Cultivated strawberry Elsanta

<400> SEQUENCE: 62
```

```
agaggttagg tgctcggcgt tacatgtcaa tatatcaaga tgaagcttca tacagtgaaa    60
atttactgaa acttgcaaaa ttagatttta atgttgttca gtgtttacac aaaaaggaac   120
tcagtgacat tccctaaggt aaattaagcc atcgatctta tagttaatta gtatatacat   180
atacaagata agttataacc taatattgtt ctaaatatac tagatggtac aaggaactgg   240
actttgcaag gaggatgcct tttgctcgag ataggatcgt ggagttgttc t            291

<210> SEQ ID NO 63
<211> LENGTH: 206
<212> TYPE: DNA
<213> ORGANISM: Cultivated strawberry Elsanta

<400> SEQUENCE: 63
agaggttagg tgctcggcgt tacatgtcaa tatatcaaga tgaagcttca tacagtgaaa    60
atttactgaa acttgcaaaa ttagatttta atgttgttca gtgtttacac aaaaaggaac   120
tcagtgacat tccctaagat ggtacaagga actggacttt gcaaggagga tgccttttgc   180
tcgagatagg atcgtggagt tgttct                                        206

<210> SEQ ID NO 64
<211> LENGTH: 67
<212> TYPE: PRT
<213> ORGANISM: Cultivated strawberry Elsanta

<400> SEQUENCE: 64

Arg Leu Gly Ala Arg Arg Tyr Met Ser Ile Tyr Gln Asp Glu Ala Ser
1               5                   10                  15

Tyr Ser Glu Asn Leu Leu Lys Leu Ala Lys Leu Asp Phe Asn Val Val
                20                  25                  30

Gln Cys Leu His Lys Lys Glu Leu Ser Asp Ile Leu Arg Trp Tyr Lys
            35                  40                  45

Glu Leu Asp Phe Ala Arg Arg Met Pro Phe Ala Arg Asp Arg Ile Val
        50                  55                  60

Glu Leu Phe
65

<210> SEQ ID NO 65
<211> LENGTH: 296
<212> TYPE: DNA
<213> ORGANISM: Cultivated strawberry Elsanta

<400> SEQUENCE: 65
agaggttagg tgctcggcgt tacatgtcaa tatatcaaga tgaagcttca cacagtgaaa    60
atttactgaa acttgcaaaa ttagatttta atgttgttca gtgtttacac aaaaaggaac   120
tcagtgacat tctaaggtaa actaaacaat cgatcttata gttattagtt gtgtatgtat   180
acaagatacg caataaccat ctaatattgc tctatatatg tactatagat ggtataagga   240
actggacttt gcaaggagga tgccttttgc tcgagatagg atcgtggagt tgttct       296

<210> SEQ ID NO 66
<211> LENGTH: 204
<212> TYPE: DNA
<213> ORGANISM: Cultivated strawberry Elsanta
<220> FEATURE:
<221> NAME/KEY: CDS
<222> LOCATION: (3)..(203)

<400> SEQUENCE: 66 ag agg tta ggt gct cgg cgt tac atg tca ata tat caa gat gaa gct      47
   Arg Leu Gly Ala Arg Arg Tyr Met Ser Ile Tyr Gln Asp Glu Ala
```

```
                   1               5                  10                 15
tca cac agt gaa aat tta ctg aaa ctt gca aaa tta gat ttt aat gtt        95
Ser His Ser Glu Asn Leu Leu Lys Leu Ala Lys Leu Asp Phe Asn Val
                    20                  25                  30 gtt cag tgt tta cac aaa aag gaa ctc agt gac att cta aga tgg tat       143
Val Gln Cys Leu His Lys Lys Glu Leu Ser Asp Ile Leu Arg Trp Tyr
         35                  40                  45 aag gaa ctg gac ttt gca agg agg atg cct ttt gct cga gat agg atc       191
Lys Glu Leu Asp Phe Ala Arg Arg Met Pro Phe Ala Arg Asp Arg Ile
     50                  55                  60 gtg gag ttg ttc t                                                      204
Val Glu Leu Phe
     65

<210> SEQ ID NO 67
<211> LENGTH: 67
<212> TYPE: PRT
<213> ORGANISM: Cultivated strawberry Elsanta

<400> SEQUENCE: 67

Arg Leu Gly Ala Arg Arg Tyr Met Ser Ile Tyr Gln Asp Glu Ala Ser
1               5                   10                  15

His Ser Glu Asn Leu Leu Lys Leu Ala Lys Leu Asp Phe Asn Val Val
            20                  25                  30

Gln Cys Leu His Lys Lys Glu Leu Ser Asp Ile Leu Arg Trp Tyr Lys
        35                  40                  45

Glu Leu Asp Phe Ala Arg Arg Met Pro Phe Ala Arg Asp Arg Ile Val
    50                  55                  60

Glu Leu Phe
65

<210> SEQ ID NO 68
<211> LENGTH: 298
<212> TYPE: DNA
<213> ORGANISM: Cultivated strawberry Elsanta
<220> FEATURE:
<221> NAME/KEY: misc_feature
<222> LOCATION: (58)..(58)
<223> OTHER INFORMATION: n is a, c, g, or t

<400> SEQUENCE: 68
agaggttagg tgctcggcgt tacatgtcaa tatatcaaga tgaagcttca cacagtgnaa     60
aatttactcg aaacttgcaa aattagattt taatgttgtt cagtgtttac acaaaaagga   120
actcagtgac attctaaggt aaactaaaca atcgatctta tagttattag ttgtgtatgt   180
atacaagata cgcaataacc atctaatatt gctctatata tgtactatag atggtataag   240
gaactggact ttgcaaggag gatgcctttt gcccgagata ggatcgtgga gttgttct      298

<210> SEQ ID NO 69
<211> LENGTH: 204
<212> TYPE: DNA
<213> ORGANISM: Cultivated strawberry Elsanta
<220> FEATURE:
<221> NAME/KEY: CDS
<222> LOCATION: (3)..(203)

<400> SEQUENCE: 69 ag agg tta ggt gct cgg cgt tac atg tca ata tat caa gat gaa gct        47
   Arg Leu Gly Ala Arg Arg Tyr Met Ser Ile Tyr Gln Asp Glu Ala
   1               5                   10                  15 tca cac agt gaa aat tta ctg aaa ctt gca aaa tta gat ttt aat gtt       95
Ser His Ser Glu Asn Leu Leu Lys Leu Ala Lys Leu Asp Phe Asn Val
```

```
                    20                  25                  30 gtt cag tgt tta cac aaa aag gaa ctc agt gac att cta aga tgg tat     143
Val Gln Cys Leu His Lys Lys Glu Leu Ser Asp Ile Leu Arg Trp Tyr
        35                  40                  45 aag gaa ctg gac ttt gca agg agg atg cct ttt gcc cga gat agg atc     191
Lys Glu Leu Asp Phe Ala Arg Arg Met Pro Phe Ala Arg Asp Arg Ile
    50                  55                  60 gtg gag ttg ttc t                                                   204
Val Glu Leu Phe
    65

<210> SEQ ID NO 70
<211> LENGTH: 67
<212> TYPE: PRT
<213> ORGANISM: Cultivated strawberry Elsanta

<400> SEQUENCE: 70

Arg Leu Gly Ala Arg Arg Tyr Met Ser Ile Tyr Gln Asp Glu Ala Ser
1               5                   10                  15

His Ser Glu Asn Leu Leu Lys Leu Ala Lys Leu Asp Phe Asn Val Val
            20                  25                  30

Gln Cys Leu His Lys Lys Glu Leu Ser Asp Ile Leu Arg Trp Tyr Lys
        35                  40                  45

Glu Leu Asp Phe Ala Arg Arg Met Pro Phe Ala Arg Asp Arg Ile Val
    50                  55                  60

Glu Leu Phe
65

<210> SEQ ID NO 71
<211> LENGTH: 296
<212> TYPE: DNA
<213> ORGANISM: Cultivated strawberry Elsanta

<400> SEQUENCE: 71
agaggttagg tgctcggcgt tacatgtcaa tatatcaaga tgaagcttca cacagtgaaa      60
atttactgaa acttgcaaaa ttagatttta atgttgttca gtgtttacac aaaaaggaac     120
tcagtgacat tctagggtaa actaaacaat cgatcttata gttattagtt gtgtatgtat     180
acaagatacg caataaccat ctaatattgc tctatatatg tactatagat ggtataagga     240
actggacttt gcaaggagga tgcctttgc tcgagatagg atcgtggagt tgttct          296

<210> SEQ ID NO 72
<211> LENGTH: 204
<212> TYPE: DNA
<213> ORGANISM: Cultivated strawberry Elsanta
<220> FEATURE:
<221> NAME/KEY: CDS
<222> LOCATION: (3)..(203)

<400> SEQUENCE: 72 ag agg tta ggt gct cgg cgt tac atg tca ata tat caa gat gaa gct         47
   Arg Leu Gly Ala Arg Arg Tyr Met Ser Ile Tyr Gln Asp Glu Ala
   1               5                   10                  15 tca cac agt gaa aat tta ctg aaa ctt gca aaa tta gat ttt aat gtt        95
Ser His Ser Glu Asn Leu Leu Lys Leu Ala Lys Leu Asp Phe Asn Val
            20                  25                  30 gtt cag tgt tta cac aaa aag gaa ctc agt gac att cta gga tgg tat       143
Val Gln Cys Leu His Lys Lys Glu Leu Ser Asp Ile Leu Gly Trp Tyr
        35                  40                  45 aag gaa ctg gac ttt gca agg agg atg cct ttt gct cga gat agg atc       191
Lys Glu Leu Asp Phe Ala Arg Arg Met Pro Phe Ala Arg Asp Arg Ile
```

```
                    50                  55                  60
gtg gag ttg ttc t                                                      204
Val Glu Leu Phe
    65

<210> SEQ ID NO 73
<211> LENGTH: 67
<212> TYPE: PRT
<213> ORGANISM: Cultivated strawberry Elsanta

<400> SEQUENCE: 73

Arg Leu Gly Ala Arg Arg Tyr Met Ser Ile Tyr Gln Asp Glu Ala Ser
1               5                   10                  15

His Ser Glu Asn Leu Leu Lys Leu Ala Lys Leu Asp Phe Asn Val Val
            20                  25                  30

Gln Cys Leu His Lys Lys Glu Leu Ser Asp Ile Leu Gly Trp Tyr Lys
        35                  40                  45

Glu Leu Asp Phe Ala Arg Arg Met Pro Phe Ala Arg Asp Arg Ile Val
    50                  55                  60

Glu Leu Phe
65

<210> SEQ ID NO 74
<211> LENGTH: 296
<212> TYPE: DNA
<213> ORGANISM: Cultivated strawberry Elsanta

<400> SEQUENCE: 74
agaggttagg tgctcggcgt tacatgtcaa tatatcaaga tgaagcttca cacagtgaaa      60
atttactgaa acttgcaaaa ttagatttta atgttgttca gtgtttacac aaaaaggaac    120
tcagtgacat tctaaggtaa actaaacaat cgatcttata gttattagtt gtgtatgtat    180
acaagatacg caatagccat ctaatattgc tctatatatg tactatagat ggtataagga    240
actggacttt gcaaggagga tgcctttgc tcgagatagg atcgtggagt tgttct         296

<210> SEQ ID NO 75
<211> LENGTH: 204
<212> TYPE: DNA
<213> ORGANISM: Cultivated strawberry Elsanta
<220> FEATURE:
<221> NAME/KEY: CDS
<222> LOCATION: (3)..(203)

<400> SEQUENCE: 75 ag agg tta ggt gct cgg cgt tac atg tca ata tat caa gat gaa gct       47
   Arg Leu Gly Ala Arg Arg Tyr Met Ser Ile Tyr Gln Asp Glu Ala
   1               5                   10                  15 tca cac agt gaa aat tta ctg aaa ctt gca aaa tta gat ttt aat gtt      95
Ser His Ser Glu Asn Leu Leu Lys Leu Ala Lys Leu Asp Phe Asn Val
                20                  25                  30 gtt cag tgt tta cac aaa aag gaa ctc agt gac att cta aga tgg tat     143
Val Gln Cys Leu His Lys Lys Glu Leu Ser Asp Ile Leu Arg Trp Tyr
            35                  40                  45 aag gaa ctg gac ttt gca agg agg atg cct ttt gct cga gat agg atc     191
Lys Glu Leu Asp Phe Ala Arg Arg Met Pro Phe Ala Arg Asp Arg Ile
        50                  55                  60 gtg gag ttg ttc t                                                    204
Val Glu Leu Phe
    65

<210> SEQ ID NO 76
```

```
<211> LENGTH: 67
<212> TYPE: PRT
<213> ORGANISM: Cultivated strawberry Elsanta

<400> SEQUENCE: 76

Arg Leu Gly Ala Arg Arg Tyr Met Ser Ile Tyr Gln Asp Glu Ala Ser
1               5                   10                  15

His Ser Glu Asn Leu Leu Lys Leu Ala Lys Leu Asp Phe Asn Val Val
            20                  25                  30

Gln Cys Leu His Lys Lys Glu Leu Ser Asp Ile Leu Arg Trp Tyr Lys
        35                  40                  45

Glu Leu Asp Phe Ala Arg Arg Met Pro Phe Ala Arg Asp Arg Ile Val
    50                  55                  60

Glu Leu Phe
65

<210> SEQ ID NO 77
<211> LENGTH: 302
<212> TYPE: DNA
<213> ORGANISM: Cultivated strawberry Elsanta

<400> SEQUENCE: 77
agaggttagg tgctcggcgt tacatgtcaa tatatcaaga tgaagcttca cacagtgaaa      60
atttactgaa acttgcaaaa ttagatttta atgttgttca gtgttacac aaaaaggaac     120 tcagtgatat tctaaggtaa actaagccat cgatcttata gctattagtt gtatatatat     180
gtatacaaga taagtaataa ccttttaata ttgctctata tatactatat atagatggta     240
taaggaactg gactttgcaa agaggatgcc ttttgctcga gataggatcg tggagttgtt     300
ct                                                                    302

<210> SEQ ID NO 78
<211> LENGTH: 204
<212> TYPE: DNA
<213> ORGANISM: Cultivated strawberry Elsanta
<220> FEATURE:
<221> NAME/KEY: CDS
<222> LOCATION: (3)..(203)

<400> SEQUENCE: 78 ag agg tta ggt gct cgg cgt tac atg tca ata tat caa gat gaa gct          47
   Arg Leu Gly Ala Arg Arg Tyr Met Ser Ile Tyr Gln Asp Glu Ala
   1               5                   10                  15 tca cac agt gaa aat tta ctg aaa ctt gca aaa tta gat ttt aat gtt         95
Ser His Ser Glu Asn Leu Leu Lys Leu Ala Lys Leu Asp Phe Asn Val
                20                  25                  30 gtt cag tgt tta cac aaa aag gaa ctc agt gat att cta aga tgg tat        143
Val Gln Cys Leu His Lys Lys Glu Leu Ser Asp Ile Leu Arg Trp Tyr
            35                  40                  45 aag gaa ctg gac ttt gca aag agg atg cct ttt gct cga gat agg atc        191
Lys Glu Leu Asp Phe Ala Lys Arg Met Pro Phe Ala Arg Asp Arg Ile
        50                  55                  60 gtg gag ttg ttc t                                                      204
Val Glu Leu Phe
    65

<210> SEQ ID NO 79
<211> LENGTH: 67
<212> TYPE: PRT
<213> ORGANISM: Cultivated strawberry Elsanta

<400> SEQUENCE: 79
```

```
Arg Leu Gly Ala Arg Arg Tyr Met Ser Ile Tyr Gln Asp Glu Ala Ser
1               5                   10                  15

His Ser Glu Asn Leu Leu Lys Leu Ala Lys Leu Asp Phe Asn Val Val
            20                  25                  30

Gln Cys Leu His Lys Lys Glu Leu Ser Asp Ile Leu Arg Trp Tyr Lys
        35                  40                  45

Glu Leu Asp Phe Ala Lys Arg Met Pro Phe Ala Arg Asp Arg Ile Val
    50                  55                  60

Glu Leu Phe
65

<210> SEQ ID NO 80
<211> LENGTH: 302
<212> TYPE: DNA
<213> ORGANISM: Cultivated strawberry Elsanta

<400> SEQUENCE: 80
agaggttagg tgctcggcgt tacatgtcaa tatatcaaga tgaagcttca cacagtgaaa      60
atttactgaa acttgcaaaa ttagatttta atgttgttca gtgtttacac aaaaaggaac    120
tcagtgacat tctaaggtaa actaagccat cgatcttata gctattagtt gtatatatat    180
gtatacaaga taagtaataa ccttctaata ttgctctata tatactatat atagatggta    240
taaggaactg gactttgcaa ggaggatgcc ttttgctcga gataggatcg tggagttgtt    300
ct                                                                   302

<210> SEQ ID NO 81
<211> LENGTH: 204
<212> TYPE: DNA
<213> ORGANISM: Cultivated strawberry Elsanta
<220> FEATURE:
<221> NAME/KEY: CDS
<222> LOCATION: (3)..(203)

<400> SEQUENCE: 81 ag agg tta ggt gct cgg cgt tac atg tca ata tat caa gat gaa gct         47
   Arg Leu Gly Ala Arg Arg Tyr Met Ser Ile Tyr Gln Asp Glu Ala
   1               5                   10                  15 tca cac agt gaa aat tta ctg aaa ctt gca aaa tta gat ttt aat gtt        95
Ser His Ser Glu Asn Leu Leu Lys Leu Ala Lys Leu Asp Phe Asn Val
            20                  25                  30 gtt cag tgt tta cac aaa aag gaa ctc agt gac att cta aga tgg tat       143
Val Gln Cys Leu His Lys Lys Glu Leu Ser Asp Ile Leu Arg Trp Tyr
        35                  40                  45 aag gaa ctg gac ttt gca agg agg atg cct ttt gct cga gat agg atc       191
Lys Glu Leu Asp Phe Ala Arg Arg Met Pro Phe Ala Arg Asp Arg Ile
    50                  55                  60 gtg gag ttg ttc t                                                     204
Val Glu Leu Phe
65

<210> SEQ ID NO 82
<211> LENGTH: 67
<212> TYPE: PRT
<213> ORGANISM: Cultivated strawberry Elsanta

<400> SEQUENCE: 82

Arg Leu Gly Ala Arg Arg Tyr Met Ser Ile Tyr Gln Asp Glu Ala Ser
1               5                   10                  15

His Ser Glu Asn Leu Leu Lys Leu Ala Lys Leu Asp Phe Asn Val Val
            20                  25                  30
```

```
                     Gln Cys Leu His Lys Lys Glu Leu Ser Asp Ile Leu Arg Trp Tyr Lys
                                  35                  40                  45

Glu Leu Asp Phe Ala Arg Arg Met Pro Phe Ala Arg Asp Arg Ile Val
                      50                  55                  60

Glu Leu Phe
                      65

<210> SEQ ID NO 83
<211> LENGTH: 1665
<212> TYPE: DNA
<213> ORGANISM: Cultivated strawberry Elsanta
<220> FEATURE:
<221> NAME/KEY: CDS
<222> LOCATION: (1)..(1665)

<400> SEQUENCE: 83 tct aac ctc atg cag ctt aca cat aag aag cag ctg cct act ttt caa       48
Ser Asn Leu Met Gln Leu Thr His Lys Lys Gln Leu Pro Thr Phe Gln
1               5                   10                  15 aga cgg ggc att gcc gaa gat agc ttg ctt ccc agt tct act act ccc       96
Arg Arg Gly Ile Ala Glu Asp Ser Leu Leu Pro Ser Ser Thr Thr Pro
            20                  25                  30 ata aag ccg atg aac gtt gaa acc aag cat act aga act atg ggt gac      144
Ile Lys Pro Met Asn Val Glu Thr Lys His Thr Arg Thr Met Gly Asp
        35                  40                  45 att ttt gtc caa cat tgt cag aag ttg gaa cta ttc aga aat gtc tta      192
Ile Phe Val Gln His Cys Gln Lys Leu Glu Leu Phe Arg Asn Val Leu
    50                  55                  60 agg aat gta gca gag cta gat gcc ctt gaa ggt ttg aat atg atc gat      240
Arg Asn Val Ala Glu Leu Asp Ala Leu Glu Gly Leu Asn Met Ile Asp
65                  70                  75                  80 gct gtt caa agg cta ggc att gat ttc cac ttt caa cga gaa atc gat      288
Ala Val Gln Arg Leu Gly Ile Asp Phe His Phe Gln Arg Glu Ile Asp
                85                  90                  95 gaa att ctg cac aag caa atg agt aat gta tct gcc tct gat gat ctt      336
Glu Ile Leu His Lys Gln Met Ser Asn Val Ser Ala Ser Asp Asp Leu
            100                 105                 110 cat gag gtt gca ctt cgc ttt cga cta ctg agg caa cat ggt tac ttc      384
His Glu Val Ala Leu Arg Phe Arg Leu Leu Arg Gln His Gly Tyr Phe
        115                 120                 125 gtg cct gaa gat gtg ttt aac aac ttc aag gac agc aaa gga acg ttc      432
Val Pro Glu Asp Val Phe Asn Asn Phe Lys Asp Ser Lys Gly Thr Phe
    130                 135                 140 aag caa gtt ctg ggt gaa gac atc aag gga ttg atg agc tta tac gga      480
Lys Gln Val Leu Gly Glu Asp Ile Lys Gly Leu Met Ser Leu Tyr Gly
145                 150                 155                 160 gct tcg cag cta ggt aca gaa gga gaa gat aca ctt gtt gaa gct gaa      528
Ala Ser Gln Leu Gly Thr Glu Gly Glu Asp Thr Leu Val Glu Ala Glu
                165                 170                 175 aag ttt agt ggc cat ctg cta aag act tct ctg tca cat ctt gat cat      576
Lys Phe Ser Gly His Leu Leu Lys Thr Ser Leu Ser His Leu Asp His
            180                 185                 190 cat cat gcc aga att gtt ggc aat aca ttg agg aat cct cat cac aaa      624
His His Ala Arg Ile Val Gly Asn Thr Leu Arg Asn Pro His His Lys
        195                 200                 205 agc ttg gcc tca ttc atg gcc agg aac ttt ttc gtt act tct caa gcc      672
Ser Leu Ala Ser Phe Met Ala Arg Asn Phe Phe Val Thr Ser Gln Ala
    210                 215                 220 acc aat tca tgg tta aat ttg cta aaa gac gta gca aaa aca gat ttc      720
Thr Asn Ser Trp Leu Asn Leu Leu Lys Asp Val Ala Lys Thr Asp Phe
225                 230                 235                 240
```

```
aat atg gtc cgg tct ctg cat cag aat gaa ata gtt caa att tcc aaa      768
Asn Met Val Arg Ser Leu His Gln Asn Glu Ile Val Gln Ile Ser Lys
            245                 250                 255 tgg tgg aag gag ctt gga ttg gct aag gaa ctg aag ttt gca aga gat      816
Trp Trp Lys Glu Leu Gly Leu Ala Lys Glu Leu Lys Phe Ala Arg Asp
            260                 265                 270 caa cca cag aaa tgg tac att tgg tcc atg gca tgc cta aca gat cca      864
Gln Pro Gln Lys Trp Tyr Ile Trp Ser Met Ala Cys Leu Thr Asp Pro
        275                 280                 285 aag tta tca gag gag agg gtt gag ctc aca aaa ccc att tct ttt gtc      912
Lys Leu Ser Glu Glu Arg Val Glu Leu Thr Lys Pro Ile Ser Phe Val
        290                 295                 300 tat ttg ata gat gac att ttc gat gtt tat gga act ctt gat gac ctc      960
Tyr Leu Ile Asp Asp Ile Phe Asp Val Tyr Gly Thr Leu Asp Asp Leu
305                 310                 315                 320 att ctc ttc aca gaa gct gtt aat aga tgg gaa att act gct ata gac     1008
Ile Leu Phe Thr Glu Ala Val Asn Arg Trp Glu Ile Thr Ala Ile Asp
                325                 330                 335 cac tta cca gac tat atg aag ata tgc ttc aag gct ctc tat gat atg     1056
His Leu Pro Asp Tyr Met Lys Ile Cys Phe Lys Ala Leu Tyr Asp Met
                340                 345                 350 act aat gaa atc agc tgc aag gtc tat cag aag cat gga tgg aac ccc     1104
Thr Asn Glu Ile Ser Cys Lys Val Tyr Gln Lys His Gly Trp Asn Pro
            355                 360                 365 tta caa tct ttg aaa att tcg tgg gcg agt ctt tgc aat gca ttt ttg     1152
Leu Gln Ser Leu Lys Ile Ser Trp Ala Ser Leu Cys Asn Ala Phe Leu
        370                 375                 380 gtg gaa gca aaa tgg ttc gca tct ggg cag ctg ccg aag tca gaa gag     1200
Val Glu Ala Lys Trp Phe Ala Ser Gly Gln Leu Pro Lys Ser Glu Glu
385                 390                 395                 400 tac ttg aag aac ggc atc gtt tct tct ggg gtt aat gtg gtt cta gtc     1248
Tyr Leu Lys Asn Gly Ile Val Ser Ser Gly Val Asn Val Val Leu Val
                405                 410                 415 cac atg ttt ttt atc ttg ggt caa aac ata acc aga aag agt gtg gag     1296
His Met Phe Phe Ile Leu Gly Gln Asn Ile Thr Arg Lys Ser Val Glu
                420                 425                 430 ttg ttg aat gaa act cca gcc atg ata tcg tcc tca gca gca att ctt     1344
Leu Leu Asn Glu Thr Pro Ala Met Ile Ser Ser Ser Ala Ala Ile Leu
            435                 440                 445 cga ctc tgg gac gat tta ggc agt gca aag gat gag aac cag gat ggg     1392
Arg Leu Trp Asp Asp Leu Gly Ser Ala Lys Asp Glu Asn Gln Asp Gly
        450                 455                 460 aac gat ggg tcg tat gta agg tgc tac tta gag gaa cat gaa ggc tgt     1440
Asn Asp Gly Ser Tyr Val Arg Cys Tyr Leu Glu Glu His Glu Gly Cys
465                 470                 475                 480 tcc att gag gag gca cga gaa aag acg att aat atg att tca gat gaa     1488
Ser Ile Glu Glu Ala Arg Glu Lys Thr Ile Asn Met Ile Ser Asp Glu
                485                 490                 495 tgg aag aaa ctg aac aga gaa ctg ctc tct cca aat cca ttt cca gca     1536
Trp Lys Lys Leu Asn Arg Glu Leu Leu Ser Pro Asn Pro Phe Pro Ala
            500                 505                 510 aca atc aca ttg gct tct ctt aat ctc gca aga atg atc ccc ttg atg     1584
Thr Ile Thr Leu Ala Ser Leu Asn Leu Ala Arg Met Ile Pro Leu Met
            515                 520                 525 tat agc tac gat ggc aac caa tac ctt cca tct ctt aaa gag tat atg     1632
Tyr Ser Tyr Asp Gly Asn Gln Tyr Leu Pro Ser Leu Lys Glu Tyr Met
        530                 535                 540 aaa ctg atg ttg tat gag act gta tca atg taa                         1665
Lys Leu Met Leu Tyr Glu Thr Val Ser Met
545                 550
```

```
<210> SEQ ID NO 84
<211> LENGTH: 554
<212> TYPE: PRT
<213> ORGANISM: Cultivated strawberry Elsanta

<400> SEQUENCE: 84
```

| | | | | | | | | | | | | | | | |
|---|---|---|---|---|---|---|---|---|---|---|---|---|---|---|---|
| Ser | Asn | Leu | Met | Gln | Leu | Thr | His | Lys | Lys | Gln | Leu | Pro | Thr | Phe | Gln |
| 1 | | | | 5 | | | | | 10 | | | | | 15 | |
| Arg | Arg | Gly | Ile | Ala | Glu | Asp | Ser | Leu | Leu | Pro | Ser | Thr | Thr | Pro | |
| | | | 20 | | | | | 25 | | | | | 30 | | |
| Ile | Lys | Pro | Met | Asn | Val | Glu | Thr | Lys | His | Thr | Arg | Thr | Met | Gly | Asp |
| | | | 35 | | | | | 40 | | | | | 45 | | |
| Ile | Phe | Val | Gln | His | Cys | Gln | Lys | Leu | Glu | Leu | Phe | Arg | Asn | Val | Leu |
| | | | 50 | | | | | 55 | | | | | 60 | | |
| Arg | Asn | Val | Ala | Glu | Leu | Asp | Ala | Leu | Glu | Gly | Leu | Asn | Met | Ile | Asp |
| 65 | | | | | 70 | | | | | 75 | | | | | 80 |
| Ala | Val | Gln | Arg | Leu | Gly | Ile | Asp | Phe | His | Phe | Gln | Arg | Glu | Ile | Asp |
| | | | | 85 | | | | | 90 | | | | | 95 | |
| Glu | Ile | Leu | His | Lys | Gln | Met | Ser | Asn | Val | Ser | Ala | Ser | Asp | Asp | Leu |
| | | | 100 | | | | | 105 | | | | | 110 | | |
| His | Glu | Val | Ala | Leu | Arg | Phe | Arg | Leu | Leu | Arg | Gln | His | Gly | Tyr | Phe |
| | | | 115 | | | | | 120 | | | | | 125 | | |
| Val | Pro | Glu | Asp | Val | Phe | Asn | Asn | Phe | Lys | Asp | Ser | Lys | Gly | Thr | Phe |
| | | | 130 | | | | | 135 | | | | | 140 | | |
| Lys | Gln | Val | Leu | Gly | Glu | Asp | Ile | Lys | Gly | Leu | Met | Ser | Leu | Tyr | Gly |
| 145 | | | | | 150 | | | | | 155 | | | | | 160 |
| Ala | Ser | Gln | Leu | Gly | Thr | Glu | Gly | Glu | Asp | Thr | Leu | Val | Glu | Ala | Glu |
| | | | | 165 | | | | | 170 | | | | | 175 | |
| Lys | Phe | Ser | Gly | His | Leu | Leu | Lys | Thr | Ser | Leu | Ser | His | Leu | Asp | His |
| | | | | 180 | | | | | 185 | | | | | 190 | |
| His | His | Ala | Arg | Ile | Val | Gly | Asn | Thr | Leu | Arg | Asn | Pro | His | His | Lys |
| | | | 195 | | | | | 200 | | | | | 205 | | |
| Ser | Leu | Ala | Ser | Phe | Met | Ala | Arg | Asn | Phe | Phe | Val | Thr | Ser | Gln | Ala |
| | | 210 | | | | | 215 | | | | | 220 | | | |
| Thr | Asn | Ser | Trp | Leu | Asn | Leu | Leu | Lys | Asp | Val | Ala | Lys | Thr | Asp | Phe |
| 225 | | | | | 230 | | | | | 235 | | | | | 240 |
| Asn | Met | Val | Arg | Ser | Leu | His | Gln | Asn | Glu | Ile | Val | Gln | Ile | Ser | Lys |
| | | | | 245 | | | | | 250 | | | | | 255 | |
| Trp | Trp | Lys | Glu | Leu | Gly | Leu | Ala | Lys | Glu | Leu | Lys | Phe | Ala | Arg | Asp |
| | | | 260 | | | | | 265 | | | | | 270 | | |
| Gln | Pro | Gln | Lys | Trp | Tyr | Ile | Trp | Ser | Met | Ala | Cys | Leu | Thr | Asp | Pro |
| | | | 275 | | | | | 280 | | | | | 285 | | |
| Lys | Leu | Ser | Glu | Glu | Arg | Val | Glu | Leu | Thr | Lys | Pro | Ile | Ser | Phe | Val |
| | | 290 | | | | | 295 | | | | | 300 | | | |
| Tyr | Leu | Ile | Asp | Asp | Ile | Phe | Asp | Val | Tyr | Gly | Thr | Leu | Asp | Asp | Leu |
| 305 | | | | | 310 | | | | | 315 | | | | | 320 |
| Ile | Leu | Phe | Thr | Glu | Ala | Val | Asn | Arg | Trp | Glu | Ile | Thr | Ala | Ile | Asp |
| | | | | 325 | | | | | 330 | | | | | 335 | |
| His | Leu | Pro | Asp | Tyr | Met | Lys | Ile | Cys | Phe | Lys | Ala | Leu | Tyr | Asp | Met |
| | | | | 340 | | | | | 345 | | | | | 350 | |
| Thr | Asn | Glu | Ile | Ser | Cys | Lys | Val | Tyr | Gln | Lys | His | Gly | Trp | Asn | Pro |
| | | | 355 | | | | | 360 | | | | | 365 | | |
| Leu | Gln | Ser | Leu | Lys | Ile | Ser | Trp | Ala | Ser | Leu | Cys | Asn | Ala | Phe | Leu |
| | | 370 | | | | | 375 | | | | | 380 | | | |

| | | | | | | | | | | | | |
|---|---|---|---|---|---|---|---|---|---|---|---|---|
|Val|Glu|Ala|Lys|Trp|Phe|Ala|Ser|Gly|Gln|Leu|Pro|Lys|Ser|Glu|Glu|
|385| | | |390| | | |395| | | |400|

Tyr Leu Lys Asn Gly Ile Val Ser Ser Gly Val Asn Val Val Leu Val
                405                 410                 415

His Met Phe Phe Ile Leu Gly Gln Asn Ile Thr Arg Lys Ser Val Glu
            420                 425                 430

Leu Leu Asn Glu Thr Pro Ala Met Ile Ser Ser Ala Ala Ile Leu
        435                 440                 445

Arg Leu Trp Asp Asp Leu Gly Ser Ala Lys Asp Glu Asn Gln Asp Gly
    450                 455                 460

Asn Asp Gly Ser Tyr Val Arg Cys Tyr Leu Glu His Glu Gly Cys
465                 470                 475                 480

Ser Ile Glu Glu Ala Arg Glu Lys Thr Ile Asn Met Ile Ser Asp Glu
                485                 490                 495

Trp Lys Lys Leu Asn Arg Glu Leu Leu Ser Pro Asn Pro Phe Pro Ala
            500                 505                 510

Thr Ile Thr Leu Ala Ser Leu Asn Leu Ala Arg Met Ile Pro Leu Met
        515                 520                 525

Tyr Ser Tyr Asp Gly Asn Gln Tyr Leu Pro Ser Leu Lys Glu Tyr Met
    530                 535                 540

Lys Leu Met Leu Tyr Glu Thr Val Ser Met
545                 550

<210> SEQ ID NO 85
<211> LENGTH: 1665
<212> TYPE: DNA
<213> ORGANISM: Cultivated strawberry Elsanta
<220> FEATURE:
<221> NAME/KEY: CDS
<222> LOCATION: (1)..(1662)

<400> SEQUENCE: 85

```
tct aac ctc atg cag ctt aca caa aag aag cag ctt cct act ttt caa      48
Ser Asn Leu Met Gln Leu Thr Gln Lys Lys Gln Leu Pro Thr Phe Gln
1               5                   10                  15 aga cgg ggc att gcc gaa gat agc ttg ctt ccc agt tct act act ccc      96
Arg Arg Gly Ile Ala Glu Asp Ser Leu Leu Pro Ser Ser Thr Thr Pro
            20                  25                  30 ata aag ccg atg aac gtt gaa acc aag cat act aga act atg ggt gac     144
Ile Lys Pro Met Asn Val Glu Thr Lys His Thr Arg Thr Met Gly Asp
        35                  40                  45 att ttt gtc caa cat tct cag aag ttg gaa cta ttg aaa act gtc ttg     192
Ile Phe Val Gln His Ser Gln Lys Leu Glu Leu Leu Lys Thr Val Leu
    50                  55                  60 agg aat gta gca gag cta gat gcc ctt gaa ggt ttg aat atg atc gat     240
Arg Asn Val Ala Glu Leu Asp Ala Leu Glu Gly Leu Asn Met Ile Asp
65                  70                  75                  80 gct gtt caa agg cta ggc atc gat tac aac ttt caa cga gaa atc gac     288
Ala Val Gln Arg Leu Gly Ile Asp Tyr Asn Phe Gln Arg Glu Ile Asp
                85                  90                  95 gaa att ctg cac aag caa atg agt att gtg tct gcc tgt gat gat ctt     336
Glu Ile Leu His Lys Gln Met Ser Ile Val Ser Ala Cys Asp Asp Leu
            100                 105                 110 cat gag gtt gca ctt cgc ttt cga cta ctg aga caa cat ggt tac ttc     384
His Glu Val Ala Leu Arg Phe Arg Leu Leu Arg Gln His Gly Tyr Phe
        115                 120                 125 gtg cct gaa gat gtg ttt aac aac ttc aag gac agc aaa gga atg ttc     432
Val Pro Glu Asp Val Phe Asn Asn Phe Lys Asp Ser Lys Gly Met Phe
    130                 135                 140
```

```
aag caa gtt ctg ggt gaa gac atc aag gga ttg atg agc tta tac gaa    480
Lys Gln Val Leu Gly Glu Asp Ile Lys Gly Leu Met Ser Leu Tyr Glu
145                 150                 155                 160 gct tcg cag cta ggt aca gaa gga gaa gat aca ctt gtt gaa gct gaa    528
Ala Ser Gln Leu Gly Thr Glu Gly Glu Asp Thr Leu Val Glu Ala Glu
                165                 170                 175 aag ttt agc ggc cat ctg cta aag act tct ctg tca cat ctt gat cat    576
Lys Phe Ser Gly His Leu Leu Lys Thr Ser Leu Ser His Leu Asp His
    180                 185                 190 cat cga gcc aga att gtt gca aat aca ttg agg aat cct cat cac aaa    624
His Arg Ala Arg Ile Val Ala Asn Thr Leu Arg Asn Pro His His Lys
195                 200                 205 agc ttg gcc cca ttc atg gcc agg aac ttt ttc gtt act tct caa gcc    672
Ser Leu Ala Pro Phe Met Ala Arg Asn Phe Phe Val Thr Ser Gln Ala
    210                 215                 220 acc aat tca tgg tta aat ttg cta aaa gaa gta gca aaa aca gat ttc    720
Thr Asn Ser Trp Leu Asn Leu Leu Lys Glu Val Ala Lys Thr Asp Phe
225                 230                 235                 240 aat atg gtc cgg tct ctg cac cag aat gaa ata gtt caa att tcc aaa    768
Asn Met Val Arg Ser Leu His Gln Asn Glu Ile Val Gln Ile Ser Lys
                245                 250                 255 tgg tgg aag gag ctt gga ttg gct aag gaa ctg aag ttt gca aga gat    816
Trp Trp Lys Glu Leu Gly Leu Ala Lys Glu Leu Lys Phe Ala Arg Asp
            260                 265                 270 caa cca ctg aaa tgg tac att tgg tcc atg gca tgc ctg aca gat cca    864
Gln Pro Leu Lys Trp Tyr Ile Trp Ser Met Ala Cys Leu Thr Asp Pro
        275                 280                 285 aag tta tca gag gag agg gtt gag ctc aca aaa ccc gtc tct ttt gtc    912
Lys Leu Ser Glu Glu Arg Val Glu Leu Thr Lys Pro Val Ser Phe Val
    290                 295                 300 tat ttg ata gat gac att ttc gat gtt tat gga acc ctt gat gaa ctc    960
Tyr Leu Ile Asp Asp Ile Phe Asp Val Tyr Gly Thr Leu Asp Glu Leu
305                 310                 315                 320 att ctc ttc aca gaa gct gtt aat aga tgg gaa att act gct ata gac   1008
Ile Leu Phe Thr Glu Ala Val Asn Arg Trp Glu Ile Thr Ala Ile Asp
                325                 330                 335 cac tta cca gac tac atg aag ata tgc ttc aag gct ctc tac gat atg   1056
His Leu Pro Asp Tyr Met Lys Ile Cys Phe Lys Ala Leu Tyr Asp Met
            340                 345                 350 act aat gaa ttc agc agc aag gtc tat ctg aag cat gga tgg aac ccc   1104
Thr Asn Glu Phe Ser Ser Lys Val Tyr Leu Lys His Gly Trp Asn Pro
        355                 360                 365 tta caa tct ttg aaa att tcg tgg gcg agt ctt tgc aat gca ttt ttg   1152
Leu Gln Ser Leu Lys Ile Ser Trp Ala Ser Leu Cys Asn Ala Phe Leu
    370                 375                 380 gtg gaa gca aaa tgg ttc gca tct ggg cag ctg ccg aag tca gaa gag   1200
Val Glu Ala Lys Trp Phe Ala Ser Gly Gln Leu Pro Lys Ser Glu Glu
385                 390                 395                 400 tac ttg aag aac ggc atc gtt tct tct ggg gta cat gtg ggt cta gtc   1248
Tyr Leu Lys Asn Gly Ile Val Ser Ser Gly Val His Val Gly Leu Val
                405                 410                 415 cac atg ttt ttt ctc ttg ggt caa aac ata acc aca aag agt gtg gag   1296
His Met Phe Phe Leu Leu Gly Gln Asn Ile Thr Thr Lys Ser Val Glu
            420                 425                 430 ttg ttg aat gaa act cca gcc atg ata tcg tcc tca gca gca att ctt   1344
Leu Leu Asn Glu Thr Pro Ala Met Ile Ser Ser Ser Ala Ala Ile Leu
        435                 440                 445 cga ctc tgg gac gat tta gga agt gca aag gat gag aac cag gat ggg   1392
Arg Leu Trp Asp Asp Leu Gly Ser Ala Lys Asp Glu Asn Gln Asp Gly
    450                 455                 460
```

```
aac gat ggg tcg tat ata agg tgc tac tta gag gaa cat gaa ggc tgt    1440
Asn Asp Gly Ser Tyr Ile Arg Cys Tyr Leu Glu Glu His Glu Gly Cys
465                 470                 475                 480 tcc atc gag gag gca cga gaa aag acg att aat atg att tca gat gaa    1488
Ser Ile Glu Glu Ala Arg Glu Lys Thr Ile Asn Met Ile Ser Asp Glu
                485                 490                 495 tgg aag aaa ctg aac aga gaa ctg ctc tct cca aat cca ttt tca gca    1536
Trp Lys Lys Leu Asn Arg Glu Leu Leu Ser Pro Asn Pro Phe Ser Ala
        500                 505                 510 aca ttc aca ttg gct tct ctt aat ctc gct aga atg atc ccc atg atg    1584
Thr Phe Thr Leu Ala Ser Leu Asn Leu Ala Arg Met Ile Pro Met Met
    515                 520                 525 tat agc tac gat ggc aac cga tgc ctt cct gat ctt aaa gag tat gtg    1632
Tyr Ser Tyr Asp Gly Asn Arg Cys Leu Pro Asp Leu Lys Glu Tyr Val
530                 535                 540 aaa ctg atg ttg tat gag act gta tca atg taa                        1665
Lys Leu Met Leu Tyr Glu Thr Val Ser Met
545                 550

<210> SEQ ID NO 86
<211> LENGTH: 554
<212> TYPE: PRT
<213> ORGANISM: Cultivated strawberry Elsanta

<400> SEQUENCE: 86

Ser Asn Leu Met Gln Leu Thr Gln Lys Lys Gln Leu Pro Thr Phe Gln
1               5                   10                  15

Arg Arg Gly Ile Ala Glu Asp Ser Leu Leu Pro Ser Ser Thr Thr Pro
            20                  25                  30

Ile Lys Pro Met Asn Val Glu Thr Lys His Thr Arg Thr Met Gly Asp
        35                  40                  45

Ile Phe Val Gln His Ser Gln Lys Leu Glu Leu Leu Lys Thr Val Leu
    50                  55                  60

Arg Asn Val Ala Glu Leu Asp Ala Leu Glu Gly Leu Asn Met Ile Asp
65                  70                  75                  80

Ala Val Gln Arg Leu Gly Ile Asp Tyr Asn Phe Gln Arg Glu Ile Asp
                85                  90                  95

Glu Ile Leu His Lys Gln Met Ser Ile Val Ser Ala Cys Asp Asp Leu
            100                 105                 110

His Glu Val Ala Leu Arg Phe Arg Leu Leu Arg Gln His Gly Tyr Phe
        115                 120                 125

Val Pro Glu Asp Val Phe Asn Asn Phe Lys Asp Ser Lys Gly Met Phe
    130                 135                 140

Lys Gln Val Leu Gly Glu Asp Ile Lys Gly Leu Met Ser Leu Tyr Glu
145                 150                 155                 160

Ala Ser Gln Leu Gly Thr Glu Gly Glu Asp Thr Leu Val Glu Ala Glu
                165                 170                 175

Lys Phe Ser Gly His Leu Leu Lys Thr Ser Leu Ser His Leu Asp His
            180                 185                 190

His Arg Ala Arg Ile Val Ala Asn Thr Leu Arg Asn Pro His His Lys
        195                 200                 205

Ser Leu Ala Pro Phe Met Ala Arg Asn Phe Phe Val Thr Ser Gln Ala
    210                 215                 220

Thr Asn Ser Trp Leu Asn Leu Leu Lys Glu Val Ala Lys Thr Asp Phe
225                 230                 235                 240

Asn Met Val Arg Ser Leu His Gln Asn Glu Ile Val Gln Ile Ser Lys
                245                 250                 255
```

-continued

```
Trp Trp Lys Glu Leu Gly Leu Ala Lys Glu Leu Lys Phe Ala Arg Asp
        260                 265                 270
Gln Pro Leu Lys Trp Tyr Ile Trp Ser Met Ala Cys Leu Thr Asp Pro
    275                 280                 285
Lys Leu Ser Glu Glu Arg Val Glu Leu Thr Lys Pro Val Ser Phe Val
290                 295                 300
Tyr Leu Ile Asp Asp Ile Phe Asp Val Tyr Gly Thr Leu Asp Glu Leu
305                 310                 315                 320
Ile Leu Phe Thr Glu Ala Val Asn Arg Trp Glu Ile Thr Ala Ile Asp
                325                 330                 335
His Leu Pro Asp Tyr Met Lys Ile Cys Phe Lys Ala Leu Tyr Asp Met
            340                 345                 350
Thr Asn Glu Phe Ser Ser Lys Val Tyr Leu Lys His Gly Trp Asn Pro
        355                 360                 365
Leu Gln Ser Leu Lys Ile Ser Trp Ala Ser Leu Cys Asn Ala Phe Leu
    370                 375                 380
Val Glu Ala Lys Trp Phe Ala Ser Gly Gln Leu Pro Lys Ser Glu Glu
385                 390                 395                 400
Tyr Leu Lys Asn Gly Ile Val Ser Ser Gly Val His Val Gly Leu Val
                405                 410                 415
His Met Phe Phe Leu Leu Gly Gln Asn Ile Thr Thr Lys Ser Val Glu
            420                 425                 430
Leu Leu Asn Glu Thr Pro Ala Met Ile Ser Ser Ala Ala Ile Leu
        435                 440                 445
Arg Leu Trp Asp Asp Leu Gly Ser Ala Lys Asp Glu Asn Gln Asp Gly
    450                 455                 460
Asn Asp Gly Ser Tyr Ile Arg Cys Tyr Leu Glu Glu His Glu Gly Cys
465                 470                 475                 480
Ser Ile Glu Glu Ala Arg Glu Lys Thr Ile Asn Met Ile Ser Asp Glu
                485                 490                 495
Trp Lys Lys Leu Asn Arg Glu Leu Leu Ser Pro Asn Pro Phe Ser Ala
            500                 505                 510
Thr Phe Thr Leu Ala Ser Leu Asn Leu Ala Arg Met Ile Pro Met Met
        515                 520                 525
Tyr Ser Tyr Asp Gly Asn Arg Cys Leu Pro Asp Leu Lys Glu Tyr Val
    530                 535                 540
Lys Leu Met Leu Tyr Glu Thr Val Ser Met
545                 550

<210> SEQ ID NO 87
<211> LENGTH: 1865
<212> TYPE: DNA
<213> ORGANISM: Cultivated strawberry Elsanta
<220> FEATURE:
<221> NAME/KEY: CDS
<222> LOCATION: (36)..(1769)

<400> SEQUENCE: 87
ctcccacagc ttcttagttg ctgatcatag atcag atg gca tcg tct tct cgg      53
                                    Met Ala Ser Ser Ser Arg
                                      1               5 gcc ttc ttt aaa gta ttc aat cct gct cca aaa agc atc cca cgt att    101
Ala Phe Phe Lys Val Phe Asn Pro Ala Pro Lys Ser Ile Pro Arg Ile
         10                  15                  20 ggc cag tct aac ctc atg cag ctt aca cat aag aag cag ctg cct act    149
Gly Gln Ser Asn Leu Met Gln Leu Thr His Lys Lys Gln Leu Pro Thr
     25                  30                  35
```

| | | | | | | | | | | | | | | | | |
|---|---|---|---|---|---|---|---|---|---|---|---|---|---|---|---|---|
| ttt | caa | aga | cgg | ggc | att | gcc | gaa | gat | agc | ttg | ctt | ccc | agt | tct | act | 197 |
| Phe | Gln | Arg | Arg | Gly | Ile | Ala | Glu | Asp | Ser | Leu | Leu | Pro | Ser | Ser | Thr | |
| | 40 | | | | 45 | | | | | 50 | | | | | | |
| act | ccc | ata | aag | ccg | atg | aac | gtt | gaa | acc | aag | cat | act | aga | act | atg | 245 |
| Thr | Pro | Ile | Lys | Pro | Met | Asn | Val | Glu | Thr | Lys | His | Thr | Arg | Thr | Met | |
| 55 | | | | | 60 | | | | | 65 | | | | | 70 | |
| ggt | gac | att | ttt | gtc | caa | cat | tgt | cag | aag | ttg | gaa | cta | ttc | aga | aat | 293 |
| Gly | Asp | Ile | Phe | Val | Gln | His | Cys | Gln | Lys | Leu | Glu | Leu | Phe | Arg | Asn | |
| | | | | 75 | | | | | 80 | | | | | 85 | | |
| gtc | tta | agg | aat | gta | gca | gag | cta | gat | gcc | ctt | gaa | ggt | ttg | aat | atg | 341 |
| Val | Leu | Arg | Asn | Val | Ala | Glu | Leu | Asp | Ala | Leu | Glu | Gly | Leu | Asn | Met | |
| | | 90 | | | | | 95 | | | | | 100 | | | | |
| atc | gat | gct | gtt | caa | agg | cta | ggc | att | gat | ttc | cac | ttt | caa | cga | gaa | 389 |
| Ile | Asp | Ala | Val | Gln | Arg | Leu | Gly | Ile | Asp | Phe | His | Phe | Gln | Arg | Glu | |
| | | 105 | | | | | 110 | | | | | 115 | | | | |
| atc | gat | gaa | att | ctg | cac | aag | caa | atg | agt | aat | gta | tct | gcc | tct | gat | 437 |
| Ile | Asp | Glu | Ile | Leu | His | Lys | Gln | Met | Ser | Asn | Val | Ser | Ala | Ser | Asp | |
| 120 | | | | | 125 | | | | | 130 | | | | | | |
| gat | ctt | cat | gag | gtt | gca | ctt | cgc | ttt | cga | cta | ctg | aga | caa | cat | ggt | 485 |
| Asp | Leu | His | Glu | Val | Ala | Leu | Arg | Phe | Arg | Leu | Leu | Arg | Gln | His | Gly | |
| 135 | | | | 140 | | | | | 145 | | | | | 150 | | |
| tac | ttc | gtg | cct | gaa | gat | gtg | ttt | aac | aac | ttc | aag | gac | agc | aaa | gga | 533 |
| Tyr | Phe | Val | Pro | Glu | Asp | Val | Phe | Asn | Asn | Phe | Lys | Asp | Ser | Lys | Gly | |
| | | | | 155 | | | | | 160 | | | | | 165 | | |
| acg | ttc | aag | caa | gtt | ctg | ggt | gaa | gac | atc | aag | gga | ttg | atg | agc | tta | 581 |
| Thr | Phe | Lys | Gln | Val | Leu | Gly | Glu | Asp | Ile | Lys | Gly | Leu | Met | Ser | Leu | |
| | | | 170 | | | | | 175 | | | | | 180 | | | |
| tac | gaa | gct | tcg | cag | cta | ggt | aca | gaa | gga | gaa | gat | aca | ctt | gtt | gaa | 629 |
| Tyr | Glu | Ala | Ser | Gln | Leu | Gly | Thr | Glu | Gly | Glu | Asp | Thr | Leu | Val | Glu | |
| | | 185 | | | | | 190 | | | | | 195 | | | | |
| gct | gaa | aag | ttt | agt | ggc | cat | ctg | cta | aag | act | tct | ctg | tca | cat | ctt | 677 |
| Ala | Glu | Lys | Phe | Ser | Gly | His | Leu | Leu | Lys | Thr | Ser | Leu | Ser | His | Leu | |
| 200 | | | | | 205 | | | | | 210 | | | | | | |
| gat | cat | cat | cat | gcc | aga | att | gtt | ggc | aat | aca | ttg | agg | aat | cct | cat | 725 |
| Asp | His | His | His | Ala | Arg | Ile | Val | Gly | Asn | Thr | Leu | Arg | Asn | Pro | His | |
| 215 | | | | 220 | | | | | 225 | | | | | 230 | | |
| cac | aaa | agc | ttg | gcc | tca | ttc | atg | gca | agg | aac | ttt | ttc | gtt | act | act | 773 |
| His | Lys | Ser | Leu | Ala | Ser | Phe | Met | Ala | Arg | Asn | Phe | Phe | Val | Thr | Thr | |
| | | | | 235 | | | | | 240 | | | | | 245 | | |
| caa | gcc | acc | aat | tca | tgg | tta | aat | ttg | cta | aaa | gac | gta | gca | aaa | aca | 821 |
| Gln | Ala | Thr | Asn | Ser | Trp | Leu | Asn | Leu | Leu | Lys | Asp | Val | Ala | Lys | Thr | |
| | | | 250 | | | | | 255 | | | | | 260 | | | |
| gat | ttc | aat | atg | gtc | cgg | tct | ctg | cat | cag | aat | gaa | ata | gtt | caa | att | 869 |
| Asp | Phe | Asn | Met | Val | Arg | Ser | Leu | His | Gln | Asn | Glu | Ile | Val | Gln | Ile | |
| | | 265 | | | | | 270 | | | | | 275 | | | | |
| tcc | aaa | tgg | tgg | aag | gag | ctt | gga | ctg | gct | aag | gaa | ctg | aag | ttt | gca | 917 |
| Ser | Lys | Trp | Trp | Lys | Glu | Leu | Gly | Leu | Ala | Lys | Glu | Leu | Lys | Phe | Ala | |
| | 280 | | | | | 285 | | | | | 290 | | | | | |
| aga | gat | caa | cca | cag | aaa | tgg | tac | att | tgg | tcc | atg | gca | tgc | cta | aca | 965 |
| Arg | Asp | Gln | Pro | Gln | Lys | Trp | Tyr | Ile | Trp | Ser | Met | Ala | Cys | Leu | Thr | |
| 295 | | | | 300 | | | | | 305 | | | | | 310 | | |
| gat | cca | aag | tta | tca | gag | gag | agg | gtt | gag | ctc | aca | aaa | ccc | att | tct | 1013 |
| Asp | Pro | Lys | Leu | Ser | Glu | Glu | Arg | Val | Glu | Leu | Thr | Lys | Pro | Ile | Ser | |
| | | | | 315 | | | | | 320 | | | | | 325 | | |
| ttt | gtc | tat | ttg | ata | gat | gac | att | ttc | gat | gtt | tat | gga | act | ctt | gat | 1061 |
| Phe | Val | Tyr | Leu | Ile | Asp | Asp | Ile | Phe | Asp | Val | Tyr | Gly | Thr | Leu | Asp | |
| | | | 330 | | | | | 335 | | | | | 340 | | | |
| gac | ctc | att | ctc | ttc | aca | gaa | gct | gtt | aat | aga | tgg | gaa | att | act | gct | 1109 |
| Asp | Leu | Ile | Leu | Phe | Thr | Glu | Ala | Val | Asn | Arg | Trp | Glu | Ile | Thr | Ala | |
| | | 345 | | | | | 350 | | | | | 355 | | | | |

```
ata gac cac tta cca gac tat atg aag ata tgc ttc aag gct ctc tat      1157
Ile Asp His Leu Pro Asp Tyr Met Lys Ile Cys Phe Lys Ala Leu Tyr
    360                 365                 370 gat atg act aat gaa atc agc tgc aag gtc tat cag aag cat gga tgg      1205
Asp Met Thr Asn Glu Ile Ser Cys Lys Val Tyr Gln Lys His Gly Trp
375                 380                 385                 390 aac ccc tta caa tct ttg aaa att tcg tgg gcg agt ctt tgc aat gca      1253
Asn Pro Leu Gln Ser Leu Lys Ile Ser Trp Ala Ser Leu Cys Asn Ala
                395                 400                 405 ttt ttg gtg gaa gca aaa tgg ttc gca tct ggg cag ctg ccg aag tca      1301
Phe Leu Val Glu Ala Lys Trp Phe Ala Ser Gly Gln Leu Pro Lys Ser
            410                 415                 420 aaa gag tac ttg aag aac ggc atc gtt tct tct ggg gtt aat gtg gtt      1349
Lys Glu Tyr Leu Lys Asn Gly Ile Val Ser Ser Gly Val Asn Val Val
        425                 430                 435 cta gtc cac atg ttt ttt atc ttg ggt caa aac ata acc aca aag agt      1397
Leu Val His Met Phe Phe Ile Leu Gly Gln Asn Ile Thr Thr Lys Ser
    440                 445                 450 gtg gag ttg ttg aat gaa act cca gcc atg ata tcg tcc tca gca gca      1445
Val Glu Leu Leu Asn Glu Thr Pro Ala Met Ile Ser Ser Ser Ala Ala
455                 460                 465                 470 att ctt cga ctc tgg gac gat tta gga agt gca aag gat gag aac cag      1493
Ile Leu Arg Leu Trp Asp Asp Leu Gly Ser Ala Lys Asp Glu Asn Gln
                475                 480                 485 gat ggg aac gat ggg tcg tat gta agg tgc tac tta gag gaa cat gaa      1541
Asp Gly Asn Asp Gly Ser Tyr Val Arg Cys Tyr Leu Glu Glu His Glu
            490                 495                 500 ggc tgt tcc att gag gag gca cga gaa aag acg att aat atg att tca      1589
Gly Cys Ser Ile Glu Glu Ala Arg Glu Lys Thr Ile Asn Met Ile Ser
        505                 510                 515 gat gaa tgg aag aaa ctg aac aga gaa ctg ctc tct cca aat cca ttt      1637
Asp Glu Trp Lys Lys Leu Asn Arg Glu Leu Leu Ser Pro Asn Pro Phe
    520                 525                 530 cca gca aca atc aca ttg gct tct ctt aat ctc gca aga atg atc ccc      1685
Pro Ala Thr Ile Thr Leu Ala Ser Leu Asn Leu Ala Arg Met Ile Pro
535                 540                 545                 550 ttg atg tat agc tac gat ggc aac caa tgc ctt cca tct ctt aaa gag      1733
Leu Met Tyr Ser Tyr Asp Gly Asn Gln Cys Leu Pro Ser Leu Lys Glu
                555                 560                 565 tat atg aaa ctg atg ttg tat gag act gta tca atg taataataat           1779
Tyr Met Lys Leu Met Leu Tyr Glu Thr Val Ser Met
            570                 575 gacactactg gaagtggagt tgaacttcaa aggtggtcaa gagaaacaag aagcctaagc    1839
tgtgtcagtg agctgtgact tggttg                                         1865

<210> SEQ ID NO 88
<211> LENGTH: 578
<212> TYPE: PRT
<213> ORGANISM: Cultivated strawberry Elsanta

<400> SEQUENCE: 88

Met Ala Ser Ser Arg Ala Phe Phe Lys Val Phe Asn Pro Ala Pro
1               5                   10                  15

Lys Ser Ile Pro Arg Ile Gly Gln Ser Asn Leu Met Gln Leu Thr His
            20                  25                  30

Lys Lys Gln Leu Pro Thr Phe Gln Arg Arg Gly Ile Ala Glu Asp Ser
        35                  40                  45

Leu Leu Pro Ser Ser Thr Thr Pro Ile Lys Pro Met Asn Val Glu Thr
    50                  55                  60
```

```
Lys His Thr Arg Thr Met Gly Asp Ile Phe Val Gln His Cys Gln Lys
 65                  70                  75                  80

Leu Glu Leu Phe Arg Asn Val Leu Arg Asn Val Ala Glu Leu Asp Ala
                 85                  90                  95

Leu Glu Gly Leu Asn Met Ile Asp Ala Val Gln Arg Leu Gly Ile Asp
                100                 105                 110

Phe His Phe Gln Arg Glu Ile Asp Glu Ile Leu His Lys Gln Met Ser
            115                 120                 125

Asn Val Ser Ala Ser Asp Asp Leu His Glu Val Ala Leu Arg Phe Arg
            130                 135                 140

Leu Leu Arg Gln His Gly Tyr Phe Val Pro Glu Asp Val Phe Asn Asn
145                 150                 155                 160

Phe Lys Asp Ser Lys Gly Thr Phe Lys Gln Val Leu Gly Glu Asp Ile
                165                 170                 175

Lys Gly Leu Met Ser Leu Tyr Glu Ala Ser Gln Leu Gly Thr Glu Gly
                180                 185                 190

Glu Asp Thr Leu Val Glu Ala Glu Lys Phe Ser Gly His Leu Leu Lys
            195                 200                 205

Thr Ser Leu Ser His Leu Asp His His Ala Arg Ile Val Gly Asn
210                 215                 220

Thr Leu Arg Asn Pro His His Lys Ser Leu Ala Ser Phe Met Ala Arg
225                 230                 235                 240

Asn Phe Phe Val Thr Thr Gln Ala Thr Asn Ser Trp Leu Asn Leu Leu
                245                 250                 255

Lys Asp Val Ala Lys Thr Asp Phe Asn Met Val Arg Ser Leu His Gln
                260                 265                 270

Asn Glu Ile Val Gln Ile Ser Lys Trp Trp Lys Glu Leu Gly Leu Ala
            275                 280                 285

Lys Glu Leu Lys Phe Ala Arg Asp Gln Pro Gln Lys Trp Tyr Ile Trp
290                 295                 300

Ser Met Ala Cys Leu Thr Asp Pro Lys Leu Ser Glu Glu Arg Val Glu
305                 310                 315                 320

Leu Thr Lys Pro Ile Ser Phe Val Tyr Leu Ile Asp Asp Ile Phe Asp
                325                 330                 335

Val Tyr Gly Thr Leu Asp Asp Leu Ile Leu Phe Thr Glu Ala Val Asn
            340                 345                 350

Arg Trp Glu Ile Thr Ala Ile Asp His Leu Pro Asp Tyr Met Lys Ile
            355                 360                 365

Cys Phe Lys Ala Leu Tyr Asp Met Thr Asn Glu Ile Ser Cys Lys Val
370                 375                 380

Tyr Gln Lys His Gly Trp Asn Pro Leu Gln Ser Leu Lys Ile Ser Trp
385                 390                 395                 400

Ala Ser Leu Cys Asn Ala Phe Leu Val Glu Ala Lys Trp Phe Ala Ser
                405                 410                 415

Gly Gln Leu Pro Lys Ser Lys Glu Tyr Leu Lys Asn Gly Ile Val Ser
            420                 425                 430

Ser Gly Val Asn Val Val Leu His Met Phe Phe Ile Leu Gly Gln
            435                 440                 445

Asn Ile Thr Thr Lys Ser Val Glu Leu Leu Asn Glu Thr Pro Ala Met
            450                 455                 460

Ile Ser Ser Ser Ala Ala Ile Leu Arg Leu Trp Asp Asp Leu Gly Ser
465                 470                 475                 480

Ala Lys Asp Glu Asn Gln Asp Gly Asn Asp Gly Ser Tyr Val Arg Cys
                485                 490                 495
```

```
Tyr Leu Glu Glu His Glu Gly Cys Ser Ile Glu Glu Ala Arg Glu Lys
            500                 505                 510

Thr Ile Asn Met Ile Ser Asp Glu Trp Lys Lys Leu Asn Arg Glu Leu
        515                 520                 525

Leu Ser Pro Asn Pro Phe Pro Ala Thr Ile Thr Leu Ala Ser Leu Asn
    530                 535                 540

Leu Ala Arg Met Ile Pro Leu Met Tyr Ser Tyr Asp Gly Asn Gln Cys
545                 550                 555                 560

Leu Pro Ser Leu Lys Glu Tyr Met Lys Leu Met Leu Tyr Glu Thr Val
                565                 570                 575

Ser Met

<210> SEQ ID NO 89
<211> LENGTH: 2277
<212> TYPE: DNA
<213> ORGANISM: Cultivated strawberry Elsanta

<400> SEQUENCE: 89
```

| | | | | |
|---|---|---|---|---|
| ctcccacagc ttcttagttg ctgatcatag atcagatggc atcgtcttct cgggccttct | 60 |
| ttaaagtatt caatcctcaa attgcctgct acttttgaga tagcttgctt cccagttcta | 120 |
| ttactataaa gccgatgaac gttgaaacca agcatactag aactatggta aaattctcgg | 180 |
| agctttctcc gaagtacatt tctacaaaag ggtagagcta gctactaaac aatagttaat | 240 |
| tgactgtgcc ttgcttgcag ggtgacattt ttgtccaaca ttctcagaag ttggaactat | 300 |
| tgaaaactgt cttgaggaat gtagcagagc tagatgccct tgaaggtttg aatatgatcg | 360 |
| atgctgttca aaggctaggc atcgattaca actttcaacg agaaatcgac gaaatcctgc | 420 |
| acaagcaaat gagtattgtg tctgcccgtg atgatcttca tgaggttgca cttcgctttc | 480 |
| gactactgag acaacatggt tacttcgtgc ctgaaggtaa gtttaatcac acgtattatt | 540 |
| tttcgttcgc taaacgatat gaaactattt cattcataaa cagttgtaaa acttgtgtag | 600 |
| taatacatat ttctacgtgt ttgttacaga tgtgtttaac aacttcaagg acagcaaagg | 660 |
| aacgttcaag caagttctgg gtgaagacat caagggattg atgagcttat acgaagcttc | 720 |
| gcagctaggt acagaaggag aagatatact tgttgaagct gaaaagttta gcggccatct | 780 |
| gctaaagact tctctgtcac atcttgatca tcatcgagtc agaattgttg caaatacatt | 840 |
| gaggaatcct catcacaaaa gcttggcccc attcatggcc aggaactttt tcgttacttc | 900 |
| tcaagccacc aattcatggt taaatttgct aaaagaagta gcaaaaacag atttcaatat | 960 |
| ggtccggtct ctgcaccaga atgaaatagt tcaaatgtcc aagtaagttt gacaatgact | 1020 |
| tcaccagtgt caggacattg atactttaat tcacacagga gatacttagt gtaattatgt | 1080 |
| gtattttga cattgtagat ggtggaagga gcttggattg gctaaggaac tgaagtttgc | 1140 |
| aagagatcaa ccactgaaat ggtacatttg gtccatggca tgcctgacag atccaaagtt | 1200 |
| atcagaggag agggttgagc tcacaaaacc catctctttt gtctatttga tagatgacat | 1260 |
| tttcgatgtt tatggaaccc ttgatgacct cattctcttc acagaagctg ttaatcggta | 1320 |
| tatatgaatt atatgcgtca gtgatgaaat ataatcagac ttgttaccaa tttatgattg | 1380 |
| atcaacaacc tattgcatac atacagatgg gaaattactg ctatagacca cttaccagac | 1440 |
| tatatgaaga tatgcttcaa ggctctctat gatatgacta atgaattcag cagcaaggtc | 1500 |
| tatctgaagc atggatggaa ccccttacaa tctttgaaaa tttcggtaca taactatata | 1560 |
| tacaaactgt gactaatcta tcacatttaa cttgattatc gttaaaatcg tgagcttgga | 1620 |

```
ttacaaggtt tacattgaga ccattcattc tgtaacttct gttgcagtgg gcgagtcttt    1680
gcaatgcatt tttggtggaa gcaaaaatgg ttcgcctctg ggaagctgcc gaagtcagaa    1740
gagtacttga agaatggcat cgtttcttct ggggtaaatg tggttctagt ccacatgttt    1800
tttctcttgg tcagaacaaa ccagaaagag tgtggagttg ttgaatgaaa ctccagccat    1860
tatatcgtcc tcagcagcaa ttcttcgact ctgggacgat ttaggaagtg caaaggatga    1920
gaaccaggat gggaacgatg ggtcgtatgt aaggtgctac ttagaggaac atgaaggctg    1980
ttccattgag gaggcacgag aaaagacgat taatatgatt tcagatgaat ggaagaaact    2040
gaacagagaa ctgctctctc caaatccatt tccagcatca ttcacattgg cttctcttaa    2100
tctcgcaaga atgatcccct tgatgtatag ctacgatggc aaccaatgcc ttccatctct    2160
taaagagtat atgaaactga tgttgtatga gactgtatca atgtaattaa taataagact    2220
accggaagtg gagttgaact tcaaaggtgg gtggtcaaga gaaacaagaa gcctaag       2277
```

<210> SEQ ID NO 90
<211> LENGTH: 227
<212> TYPE: DNA
<213> ORGANISM: Artificial Sequence
<220> FEATURE:
<223> OTHER INFORMATION: FRAGMENT FROM PCR ON GENOMIC DNA FROM BOTH
      SIDES OF THE METHIONINE RESIDUES
<220> FEATURE:
<221> NAME/KEY: CDS
<222> LOCATION: (36)..(227)

<400> SEQUENCE: 90

```
ggccgcggga attctattcg ctgatcatag atcag atg gca ttg tct act cgg          53
                                      Met Ala Leu Ser Thr Arg
                                      1               5 gcc ttc ttt aaa gta ttc aat ccc caa att act cca aac agt atc tca        101
Ala Phe Phe Lys Val Phe Asn Pro Gln Ile Thr Pro Asn Ser Ile Ser
        10                  15                  20 cat att ggc cag tct aac ctc atg cag ctt aca caa aag aag cag ctt        149
His Ile Gly Gln Ser Asn Leu Met Gln Leu Thr Gln Lys Lys Gln Leu
                25                  30                  35 cct act ttt caa aga cgg ggc att gcc gaa gat agc ttg ctt ccc agt        197
Pro Thr Phe Gln Arg Arg Gly Ile Ala Glu Asp Ser Leu Leu Pro Ser
    40                  45                  50 tct act act ccc ata aag ccg atg cac gtt                                227
Ser Thr Thr Pro Ile Lys Pro Met His Val
55                  60
```

<210> SEQ ID NO 91
<211> LENGTH: 64
<212> TYPE: PRT
<213> ORGANISM: Artificial Sequence
<220> FEATURE:
<223> OTHER INFORMATION: FRAGMENT FROM PCR ON GENOMIC DNA FROM BOTH
      SIDES OF THE METHIONINE RESIDUES

<400> SEQUENCE: 91

```
Met Ala Leu Ser Thr Arg Ala Phe Phe Lys Val Phe Asn Pro Gln Ile
1               5                   10                  15

Thr Pro Asn Ser Ile Ser His Ile Gly Gln Ser Asn Leu Met Gln Leu
            20                  25                  30

Thr Gln Lys Lys Gln Leu Pro Thr Phe Gln Arg Arg Gly Ile Ala Glu
        35                  40                  45

Asp Ser Leu Leu Pro Ser Ser Thr Thr Pro Ile Lys Pro Met His Val
    50                  55                  60
```

```
<210> SEQ ID NO 92
<211> LENGTH: 201
<212> TYPE: DNA
<213> ORGANISM: Artificial Sequence
<220> FEATURE:
<223> OTHER INFORMATION: FRAGMENT FROM PCR ON GENOMIC DNA FROM BOTH
      SIDES OF THE METHIONEN RESIDUES

<400> SEQUENCE: 92
ccgcgggaat tcgatttgct gatcatagat cagatggcat agtctttcg gtccctcttt      60 aaagtattca atcaaattgc tccaaaaatt aactcacatg ttggccactc taagaagcag    120
ctgcctgcta cttttcaaag atggggcgtt gccgaagata gcttgctttc cagttctagt    180
actataaagc tgatgcacgt t                                              201

<210> SEQ ID NO 93
<211> LENGTH: 141
<212> TYPE: DNA
<213> ORGANISM: Artificial Sequence
<220> FEATURE:
<223> OTHER INFORMATION: FRAGMENT FROM PCR ON GENOMIC DNA FROM BOTH
      SIDES OF THE METHIONINE RESIDUES

<400> SEQUENCE: 93
ccgcgggaat tcgatttgct gatcatagat cagatggcat cgtcttctcg ggccttcttt     60
aaagtattca atcctcaaat tgcctgctac ttttgagaaa gcttgcttcc cagttctatt    120
actataaagc cgatgcacgt t                                              141
```